US011110096B2

(12) United States Patent
Kutok et al.

(10) Patent No.: US 11,110,096 B2
(45) Date of Patent: Sep. 7, 2021

(54) COMBINATION THERAPIES

(71) Applicant: Infinity Pharmaceuticals, Inc., Cambridge, MA (US)

(72) Inventors: Jeffery L. Kutok, Natick, MA (US); Howard M. Stern, Waban, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/587,208

(22) Filed: May 4, 2017

(65) Prior Publication Data

US 2018/0055847 A1 Mar. 1, 2018

Related U.S. Application Data

(63) Continuation of application No. 14/687,768, filed on Apr. 15, 2015, now abandoned.

(60) Provisional application No. 62/042,681, filed on Aug. 27, 2014, provisional application No. 62/042,691, filed on Aug. 27, 2014, provisional application No. 61/980,549, filed on Apr. 16, 2014.

(51) Int. Cl.
| A61K 31/52 | (2006.01) |
| A61K 31/5377 | (2006.01) |
| A61K 45/06 | (2006.01) |
| A61K 31/437 | (2006.01) |
| A61K 31/496 | (2006.01) |

(52) U.S. Cl.
CPC ............ *A61K 31/52* (2013.01); *A61K 31/437* (2013.01); *A61K 31/496* (2013.01); *A61K 31/5377* (2013.01); *A61K 45/06* (2013.01)

(58) Field of Classification Search
None
See application file for complete search history.

(56) References Cited

U.S. PATENT DOCUMENTS

| 4,547,508 A | 10/1985 | Konz et al. |
| 4,656,159 A | 4/1987 | McPherson et al. |
| 4,704,381 A | 11/1987 | Schaumann et al. |
| 4,795,627 A | 1/1989 | Fisher et al. |
| 5,240,941 A | 8/1993 | Bruneau |
| 5,294,612 A | 3/1994 | Bacon et al. |
| 5,310,731 A | 5/1994 | Olsson et al. |
| 5,364,862 A | 11/1994 | Spada et al. |
| 5,409,930 A | 4/1995 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,480,883 A | 1/1996 | Spada et al. |
| 5,504,103 A | 4/1996 | Bonjouklian et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,646,153 A | 7/1997 | Spada et al. |
| 5,652,366 A | 7/1997 | Spada et al. |
| 5,654,307 A | 8/1997 | Bridges et al. |
| 5,656,643 A | 8/1997 | Spada et al. |
| 5,665,721 A | 9/1997 | Bhagwat et al. |
| 5,674,998 A | 10/1997 | Boyer et al. |
| 5,686,455 A | 11/1997 | Adams et al. |
| 5,710,158 A | 1/1998 | Myers et al. |
| 5,714,493 A | 2/1998 | Myers et al. |
| 5,721,237 A | 2/1998 | Myers et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,811,454 A | 9/1998 | Springer |
| 5,824,492 A | 10/1998 | Hiles et al. |
| 5,858,753 A | 1/1999 | Chantry et al. |
| 5,914,488 A | 6/1999 | Sone |
| RE36,256 E | 7/1999 | Spada et al. |
| 5,919,808 A | 7/1999 | Petrie et al. |
| 5,922,753 A | 7/1999 | Petrie et al. |
| 5,948,776 A | 9/1999 | Petrie et al. |
| 5,962,457 A | 10/1999 | Chenard et al. |
| 5,965,573 A | 10/1999 | Petrie et al. |
| 5,977,061 A | 11/1999 | Holy et al. |

(Continued)

FOREIGN PATENT DOCUMENTS

| CA | 1338379 C | 6/1996 |
| CN | 101602768 A | 12/2009 |

(Continued)

OTHER PUBLICATIONS

Kakkola et al. Cell Death and Disease (2013) 4, e742; (Year: 2013).*
Vaillant et al. Cancer Cell 24, 120-129, Jul. 8, 2013; (Year: 2013).*
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 11, 2011.
International Preliminary Report on Patentability and Written Opinion for PCT/US2009/060985 dated Apr. 19, 2011.
International Preliminary Report on Patentability for PCT/US2009/000038 dated Jul. 6, 2010.

(Continued)

*Primary Examiner* — Jeffrey S Lundgren
*Assistant Examiner* — Michael J Schmitt
(74) *Attorney, Agent, or Firm* — Cooley LLP

(57) ABSTRACT

Provided herein are pharmaceutical compositions comprising a phosphatidylinositol 3-kinase inhibitor or a pharmaceutically acceptable form thereof, and a Bcl-2 inhibitor or a pharmaceutically acceptable form thereof. Also provided herein are methods for treating cancer comprising administration the compositions, and uses of the compositions, e.g., for the treatment of cancer.

16 Claims, 17 Drawing Sheets

(56) References Cited

U.S. PATENT DOCUMENTS

| | | |
|---|---|---|
| 5,981,533 A | 11/1999 | Traxler et al. |
| 5,985,589 A | 11/1999 | Chantry et al. |
| 5,990,109 A | 11/1999 | Chen et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,057,320 A | 5/2000 | Spada et al. |
| 6,057,371 A | 5/2000 | Glennon |
| 6,084,095 A | 7/2000 | Bridges et al. |
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,242,453 B1 | 6/2001 | Cirillo et al. |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,358,945 B1 | 3/2002 | Breitfelder et al. |
| 6,362,216 B1 | 3/2002 | Burgess et al. |
| RE37,650 E | 4/2002 | Myers et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,472,562 B1 | 10/2002 | Klingler et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,969 B1 | 11/2003 | Myers et al. |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,664,393 B2 | 12/2003 | Klingler et al. |
| 6,667,300 B2 | 12/2003 | Sadhu et al. |
| 6,667,398 B2 | 12/2003 | Dunn et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,825,219 B2 | 11/2004 | Cywin et al. |
| 6,849,420 B2 | 2/2005 | Vanhaesebroeck et al. |
| 6,849,637 B2 | 2/2005 | Andrianjara et al. |
| 6,849,713 B2 | 2/2005 | Zhang et al. |
| 6,852,727 B2 | 2/2005 | Goulet et al. |
| 6,858,756 B2 | 2/2005 | Rampf et al. |
| 6,906,103 B2 | 6/2005 | Zhang et al. |
| 6,916,949 B2 | 7/2005 | Springer et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,005,520 B2 | 2/2006 | Dunn et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,087,597 B1 | 8/2006 | Miwa et al. |
| 7,102,046 B2 | 9/2006 | Rampf et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,493 B2 | 4/2007 | Wrasidlo et al. |
| 7,208,601 B2 | 4/2007 | Mjalli et al. |
| 7,217,794 B2 | 5/2007 | Abdel-Meguid et al. |
| 7,223,780 B2 | 5/2007 | Nazare et al. |
| 7,235,585 B2 | 6/2007 | Springer et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,317,027 B2 | 1/2008 | Nazare et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,088 B2 | 4/2008 | Nazare et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon |
| 7,459,472 B2 | 12/2008 | Mjalli et al. |
| 7,465,806 B2 | 12/2008 | Bauer et al. |
| 7,470,721 B2 | 12/2008 | Durden |
| 7,501,538 B2 | 3/2009 | Mjalli et al. |
| 7,514,445 B2 | 4/2009 | Freyne et al. |
| 7,534,797 B2 | 5/2009 | Arnold |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,642,272 B2 | 1/2010 | Shankar et al. |
| 7,678,803 B2 | 3/2010 | Huang et al. |
| 7,700,552 B2 | 4/2010 | Wahling et al. |
| 7,700,607 B2 | 4/2010 | Hu et al. |
| 7,705,018 B2 | 4/2010 | Chen et al. |
| 7,745,485 B2 | 6/2010 | Durden |
| 7,829,590 B2 | 11/2010 | Brenchley et al. |
| 7,919,046 B2 | 4/2011 | Delapierre et al. |
| 7,932,260 B2 | 4/2011 | Fowler et al. |
| 8,053,445 B2 | 11/2011 | Yamamori et al. |
| 8,053,603 B2 | 11/2011 | Shao et al. |
| 8,088,385 B2 | 1/2012 | Chesney et al. |
| 8,101,637 B2 | 1/2012 | Bessis et al. |
| 8,106,146 B2 | 1/2012 | Benz et al. |
| 8,124,625 B2 | 2/2012 | Yamamori et al. |
| 8,188,134 B2 | 5/2012 | Brenchley et al. |
| 8,193,182 B2 | 6/2012 | Ren et al. |
| 8,399,483 B2 | 3/2013 | Allen et al. |
| 8,557,823 B2 | 10/2013 | Tapolsky et al. |
| 8,569,323 B2 | 10/2013 | Ren et al. |
| 8,703,777 B2 | 4/2014 | Ren et al. |
| 8,703,778 B2 | 4/2014 | Ren et al. |
| 8,785,456 B2 | 7/2014 | Ren et al. |
| 2001/0019829 A1 | 9/2001 | Nelson et al. |

(56) References Cited

U.S. PATENT DOCUMENTS

| | | |
|---|---|---|
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0107245 A1 | 8/2002 | Wagle et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156073 A1 | 10/2002 | Wagle et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2002/0193377 A1 | 12/2002 | Andrianjara et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0029875 A1 | 2/2004 | Fauchere et al. |
| 2004/0039035 A1 | 2/2004 | Collins et al. |
| 2004/0043959 A1 | 3/2004 | Bloom et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0072871 A1 | 4/2004 | Dublanchet et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0146941 A1 | 7/2004 | Zhang et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0235849 A1 | 11/2004 | Beyreuther et al. |
| 2004/0266780 A1 | 12/2004 | Sadhu et al. |
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0214310 A1 | 9/2005 | Toki et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2005/0282814 A1 | 12/2005 | Wrasidlo et al. |
| 2006/0019967 A1 | 1/2006 | Wu |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0205694 A1 | 9/2006 | Alonso et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2006/0293274 A1 | 12/2006 | Wu |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0179122 A1 | 8/2007 | Urmann et al. |
| 2007/0179151 A1 | 8/2007 | Chen et al. |
| 2007/0224672 A1 | 9/2007 | Leban et al. |
| 2007/0249598 A1 | 10/2007 | Wang et al. |
| 2007/0254318 A1 | 11/2007 | Sebti et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetli et al. |
| 2008/0119461 A1 | 5/2008 | Sin et al. |
| 2008/0125432 A1 | 5/2008 | Blom et al. |
| 2008/0200461 A1 | 8/2008 | Anderson et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0023729 A1 | 1/2009 | Nakamura et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | Chua et al. |
| 2009/0270426 A1 | 10/2009 | Knight et al. |
| 2009/0270567 A1 | 10/2009 | Small et al. |
| 2009/0312319 A1* | 12/2009 | Ren .............. C07D 487/04 514/234.2 |
| 2009/0312406 A1 | 12/2009 | Hsieh et al. |

(56) References Cited

U.S. PATENT DOCUMENTS

| | | |
|---|---|---|
| 2009/0318411 A1 | 12/2009 | Castanedo et al. |
| 2009/0318503 A1 | 12/2009 | Crooks et al. |
| 2009/0325967 A1 | 12/2009 | Fairhurst et al. |
| 2010/0009963 A1 | 1/2010 | Knight et al. |
| 2010/0022531 A1 | 1/2010 | Kincaid et al. |
| 2010/0022585 A1 | 1/2010 | deLong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0063047 A1 | 3/2010 | Borchardt et al. |
| 2010/0105630 A1 | 4/2010 | Blagg |
| 2010/0168153 A1 | 7/2010 | Stowasser et al. |
| 2010/0179167 A1 | 7/2010 | Xu et al. |
| 2010/0190749 A1 | 7/2010 | Ren et al. |
| 2010/0202963 A1 | 8/2010 | Gallatin et al. |
| 2010/0216791 A1 | 8/2010 | Aquila et al. |
| 2010/0278811 A1 | 11/2010 | Wrasidlo et al. |
| 2010/0280067 A1 | 11/2010 | Sarma et al. |
| 2010/0280255 A1 | 11/2010 | Moniz et al. |
| 2010/0298290 A1 | 11/2010 | Anand et al. |
| 2011/0009378 A1 | 1/2011 | Lange et al. |
| 2011/0046165 A1 | 2/2011 | Ren |
| 2011/0112137 A1 | 5/2011 | Eissenstat et al. |
| 2011/0124641 A1 | 5/2011 | Ren et al. |
| 2011/0135655 A1 | 6/2011 | Katsikis et al. |
| 2011/0144134 A1 | 6/2011 | Shokat et al. |
| 2011/0160463 A1 | 6/2011 | Moniz et al. |
| 2011/0172228 A1 | 7/2011 | Ren et al. |
| 2011/0172335 A1 | 7/2011 | Deshpande |
| 2011/0190157 A1 | 8/2011 | Kipps et al. |
| 2011/0212975 A1 | 9/2011 | Kao et al. |
| 2011/0224223 A1 | 9/2011 | Shokat et al. |
| 2011/0251182 A1 | 10/2011 | Sun et al. |
| 2011/0269779 A1 | 11/2011 | Wilson et al. |
| 2011/0275803 A1 | 11/2011 | Remenar et al. |
| 2011/0281866 A1 | 11/2011 | Ren et al. |
| 2011/0301144 A1 | 12/2011 | Knight et al. |
| 2011/0306622 A1 | 12/2011 | Lannutti et al. |
| 2012/0004198 A1 | 1/2012 | Liao et al. |
| 2012/0046307 A1 | 2/2012 | Engel et al. |
| 2012/0059000 A1 | 3/2012 | Ren et al. |
| 2012/0065154 A1 | 3/2012 | Tanaka et al. |
| 2012/0094997 A1 | 4/2012 | England et al. |
| 2012/0122838 A1 | 5/2012 | Ren et al. |
| 2012/0149701 A1 | 6/2012 | Ren et al. |
| 2012/0149715 A1 | 6/2012 | Kao et al. |
| 2012/0157696 A1 | 6/2012 | Chopra et al. |
| 2012/0177749 A1 | 7/2012 | Tapolsky et al. |
| 2012/0183535 A1 | 7/2012 | Buggy et al. |
| 2012/0184568 A1 | 7/2012 | Ren et al. |
| 2012/0196905 A1 | 8/2012 | Cashman |
| 2012/0202784 A1 | 8/2012 | Aronov et al. |
| 2012/0220575 A1 | 8/2012 | Chang et al. |
| 2012/0225851 A1 | 9/2012 | Cardone et al. |
| 2012/0238549 A1 | 9/2012 | Cusack et al. |
| 2012/0238559 A1 | 9/2012 | Baldwin et al. |
| 2012/0245169 A1 | 9/2012 | Ren et al. |
| 2012/0258953 A1 | 10/2012 | Aay et al. |
| 2012/0293063 A1 | 11/2012 | Kang et al. |
| 2012/0322769 A1 | 12/2012 | Yang et al. |
| 2012/0329776 A1 | 12/2012 | Ren et al. |
| 2013/0029982 A1 | 1/2013 | Castro et al. |
| 2013/0029984 A1 | 1/2013 | Castro et al. |
| 2013/0039945 A1 | 2/2013 | Iadonato et al. |
| 2013/0045229 A1 | 2/2013 | Iadonato et al. |
| 2013/0053362 A1 | 2/2013 | Castro et al. |
| 2013/0064812 A1 * | 3/2013 | Gallatin .............. A61K 39/3955 424/133.1 |
| 2013/0102608 A1 | 4/2013 | Hoelzemann et al. |
| 2013/0109713 A1 | 5/2013 | Lavoie et al. |
| 2013/0158003 A1 | 6/2013 | Campbell et al. |
| 2013/0172388 A1 | 7/2013 | Xie et al. |
| 2013/0344061 A1 | 12/2013 | Palombella et al. |
| 2013/0345216 A1 | 12/2013 | Ren et al. |
| 2014/0024637 A1 | 1/2014 | Rice |
| 2014/0031547 A1 | 1/2014 | Sheridan et al. |
| 2014/0037622 A1 | 2/2014 | Boshoff et al. |
| 2014/0120060 A1 | 5/2014 | Palombella et al. |
| 2014/0120083 A1 | 5/2014 | Stern et al. |
| 2014/0206684 A1 | 7/2014 | Ren et al. |
| 2014/0371246 A1 | 12/2014 | Evarts et al. |
| 2014/0377258 A1 | 12/2014 | Stern et al. |
| 2015/0065431 A1 | 3/2015 | Xu et al. |
| 2015/0184249 A1 | 7/2015 | Chang et al. |
| 2016/0113932 A1 | 4/2016 | Stern et al. |

FOREIGN PATENT DOCUMENTS

| | | | |
|---|---|---|---|
| CN | 102206172 A | 10/2011 | |
| CN | 102731492 A | 10/2012 | |
| DE | 2139107 A1 | 2/1973 | |
| DE | WO 2012136549 A1 * | 10/2012 | ........... A61K 31/517 |
| EP | 773023 A1 | 5/1997 | |
| EP | 1020445 B1 | 7/2000 | |
| EP | 1262176 A1 | 12/2002 | |
| GB | 812366 A | 4/1959 | |
| GB | 937725 A | 9/1963 | |
| JP | 61109797 A | 5/1986 | |
| JP | H04211063 A | 8/1992 | |
| JP | 08295667 A | 11/1996 | |
| JP | 09143163 A | 6/1997 | |
| JP | 10206995 A | 8/1998 | |
| JP | 2000072773 A | 3/2000 | |
| JP | 2002131859 A | 5/2002 | |
| JP | 2003073357 A | 3/2003 | |
| JP | 2004161716 A | 6/2004 | |
| JP | 4834699 B2 | 12/2011 | |
| JP | 4846769 B2 | 12/2011 | |
| JP | 05256693 A | 8/2013 | |
| WO | 1983001446 A1 | 4/1983 | |
| WO | 1991017161 A1 | 11/1991 | |
| WO | 1992014733 A1 | 9/1992 | |
| WO | 1993016091 A1 | 8/1993 | |
| WO | 1993016092 A1 | 8/1993 | |
| WO | 1993018035 A1 | 9/1993 | |
| WO | 1993019767 A1 | 10/1993 | |
| WO | 1993022443 A1 | 11/1993 | |
| WO | 1994013677 A1 | 6/1994 | |
| WO | 1994017803 A1 | 8/1994 | |
| WO | 1994029436 A1 | 12/1994 | |
| WO | 1995010628 A2 | 4/1995 | |
| WO | 1995012588 A1 | 5/1995 | |
| WO | 1995019774 A1 | 7/1995 | |
| WO | 1995029673 A1 | 11/1995 | |
| WO | 1995032984 A1 | 12/1995 | |
| WO | 1995010628 A3 | 9/1996 | |
| WO | 1996040706 A1 | 12/1996 | |
| WO | 1997028133 A1 | 8/1997 | |
| WO | 1997028161 A1 | 8/1997 | |
| WO | 1998041525 A1 | 9/1998 | |
| WO | 1998052611 A1 | 11/1998 | |
| WO | 1998057952 A1 | 12/1998 | |
| WO | 2000017202 A1 | 3/2000 | |
| WO | 2001002369 A2 | 1/2001 | |
| WO | 2001016114 A2 | 3/2001 | |
| WO | 2001019829 A3 | 3/2001 | |
| WO | 2001021160 A2 | 3/2001 | |
| WO | 2001025238 A2 | 4/2001 | |
| WO | 2001031063 A1 | 5/2001 | |
| WO | 2001038584 A2 | 5/2001 | |
| WO | 2001016114 A3 | 8/2001 | |
| WO | 2001055140 A1 | 8/2001 | |
| WO | 2001056988 A1 | 8/2001 | |
| WO | 2001060824 A1 | 8/2001 | |
| WO | 2001019829 A3 | 9/2001 | |
| WO | 2001025238 A3 | 10/2001 | |
| WO | 2001038584 A3 | 10/2001 | |
| WO | 2001081346 A2 | 11/2001 | |
| WO | 2002006192 A1 | 1/2002 | |
| WO | 2001081346 A3 | 3/2002 | |
| WO | 2001002369 A3 | 4/2002 | |
| WO | 2002028853 A1 | 4/2002 | |

(56) References Cited

FOREIGN PATENT DOCUMENTS

| | | |
|---|---|---|
| WO | 2002030944 A2 | 4/2002 |
| WO | 2002057425 A2 | 7/2002 |
| WO | 2002076986 A1 | 10/2002 |
| WO | 2002080926 A1 | 10/2002 |
| WO | 2002083143 A1 | 10/2002 |
| WO | 2002088025 A1 | 11/2002 |
| WO | 2002090334 A1 | 11/2002 |
| WO | 2002030944 A3 | 1/2003 |
| WO | 2003000187 A2 | 1/2003 |
| WO | 2003016275 A1 | 2/2003 |
| WO | 2003020880 A2 | 3/2003 |
| WO | 2003024969 A1 | 3/2003 |
| WO | 2003028341 A2 | 4/2003 |
| WO | 2003035075 A1 | 5/2003 |
| WO | 2003059884 A1 | 7/2003 |
| WO | 2003020880 A3 | 10/2003 |
| WO | 2003082341 A1 | 10/2003 |
| WO | 2003106426 A1 | 12/2003 |
| WO | 2004006906 A2 | 1/2004 |
| WO | 2004006906 A3 | 3/2004 |
| WO | 2004018058 A2 | 3/2004 |
| WO | 2004031177 A1 | 4/2004 |
| WO | 2004039774 A2 | 5/2004 |
| WO | 2004046128 A1 | 6/2004 |
| WO | 2004039774 A3 | 7/2004 |
| WO | 2004058717 A1 | 7/2004 |
| WO | 2003000187 A3 | 8/2004 |
| WO | 2004075917 A1 | 9/2004 |
| WO | 2004087053 A2 | 10/2004 |
| WO | 2004087679 A1 | 10/2004 |
| WO | 2004089877 A1 | 10/2004 |
| WO | 2004111014 A1 | 12/2004 |
| WO | 2005002585 A1 | 1/2005 |
| WO | 2005007085 A2 | 1/2005 |
| WO | 2005012323 A2 | 2/2005 |
| WO | 2005016348 A1 | 2/2005 |
| WO | 2005016349 A1 | 2/2005 |
| WO | 2005016528 A2 | 2/2005 |
| WO | 2005021533 A1 | 3/2005 |
| WO | 2002057425 A3 | 4/2005 |
| WO | 2005016528 A3 | 5/2005 |
| WO | 2005044181 A2 | 5/2005 |
| WO | 2005047289 A1 | 5/2005 |
| WO | 2005061460 A1 | 7/2005 |
| WO | 2005063258 A1 | 7/2005 |
| WO | 2005067901 A2 | 7/2005 |
| WO | 2005074603 A2 | 8/2005 |
| WO | 2005007085 A3 | 9/2005 |
| WO | 2005097800 A1 | 10/2005 |
| WO | 2005105760 A1 | 11/2005 |
| WO | 2005067901 A3 | 12/2005 |
| WO | 2005112935 A1 | 12/2005 |
| WO | 2005113556 A1 | 12/2005 |
| WO | 2005117889 A1 | 12/2005 |
| WO | 2005120511 A1 | 12/2005 |
| WO | 2006015279 A1 | 2/2006 |
| WO | 2005044181 A3 | 3/2006 |
| WO | 2006030032 A1 | 3/2006 |
| WO | 2006038865 A1 | 4/2006 |
| WO | 2006050501 A2 | 5/2006 |
| WO | 2006050946 A1 | 5/2006 |
| WO | 2006068760 A2 | 6/2006 |
| WO | 2004087053 A3 | 8/2006 |
| WO | 2006108107 A1 | 10/2006 |
| WO | 2006112666 A1 | 10/2006 |
| WO | 2005074603 A3 | 11/2006 |
| WO | 2006068760 A3 | 12/2006 |
| WO | 2006089106 A2 | 12/2006 |
| WO | 2006089106 A3 | 12/2006 |
| WO | 2007002293 A2 | 1/2007 |
| WO | 2007006547 A1 | 1/2007 |
| WO | 2007020046 A1 | 2/2007 |
| WO | 2007002293 A3 | 3/2007 |
| WO | 2007025090 A2 | 3/2007 |
| WO | 2007029121 A2 | 3/2007 |
| WO | 2006050501 A3 | 5/2007 |
| WO | 2007061737 A2 | 5/2007 |
| WO | 2006114064 A2 | 6/2007 |
| WO | 2006114064 A3 | 6/2007 |
| WO | 2006114065 A2 | 6/2007 |
| WO | 2006114065 A3 | 6/2007 |
| WO | 2007025090 A3 | 6/2007 |
| WO | 2007075554 A2 | 7/2007 |
| WO | 2007112005 A2 | 7/2007 |
| WO | 2007079164 A2 | 9/2007 |
| WO | 2007079164 A3 | 9/2007 |
| WO | 2007103308 A2 | 9/2007 |
| WO | 2007114926 A2 | 10/2007 |
| WO | 2007121453 A1 | 10/2007 |
| WO | 2007121920 A2 | 11/2007 |
| WO | 2007121924 A2 | 11/2007 |
| WO | 2007124854 A1 | 11/2007 |
| WO | 2007125310 A2 | 11/2007 |
| WO | 2007125315 A2 | 11/2007 |
| WO | 2007126841 A2 | 11/2007 |
| WO | 2007134828 A1 | 11/2007 |
| WO | 2007135380 A2 | 11/2007 |
| WO | 2007135398 A1 | 11/2007 |
| WO | 2007061737 A3 | 12/2007 |
| WO | 2007125315 A3 | 12/2007 |
| WO | 2007121453 A3 | 1/2008 |
| WO | 2007121920 A3 | 1/2008 |
| WO | 2008001236 A2 | 1/2008 |
| WO | 2008012326 A1 | 1/2008 |
| WO | 2007103308 A3 | 2/2008 |
| WO | 2007112005 A3 | 2/2008 |
| WO | 2007125310 A3 | 3/2008 |
| WO | 2008025755 A1 | 3/2008 |
| WO | 2008047821 A1 | 4/2008 |
| WO | 2008063625 A2 | 5/2008 |
| WO | 2008064018 A1 | 5/2008 |
| WO | 2008070507 A2 | 6/2008 |
| WO | 2008079028 A1 | 7/2008 |
| WO | 2007121924 A3 | 9/2008 |
| WO | 2008112715 A2 | 9/2008 |
| WO | 2007114926 A3 | 10/2008 |
| WO | 2008117050 A1 | 10/2008 |
| WO | 2008118455 A1 | 10/2008 |
| WO | 2008118468 A1 | 10/2008 |
| WO | 2008125014 A1 | 10/2008 |
| WO | 2008125207 A1 | 10/2008 |
| WO | 20080127226 A3 | 10/2008 |
| WO | 2007126841 A3 | 11/2008 |
| WO | 2008112715 A3 | 11/2008 |
| WO | 2008118454 A2 | 11/2008 |
| WO | 2008136457 A1 | 11/2008 |
| WO | 2008082487 A2 | 12/2008 |
| WO | 2008082487 A3 | 12/2008 |
| WO | 2008127226 A3 | 12/2008 |
| WO | 2009000412 A1 | 12/2008 |
| WO | 2009004621 A1 | 1/2009 |
| WO | 2009010925 A2 | 1/2009 |
| WO | 2009019531 A2 | 2/2009 |
| WO | 2008094737 A2 | 3/2009 |
| WO | 2008094737 A3 | 3/2009 |
| WO | 2009029617 A1 | 3/2009 |
| WO | 2009023718 A2 | 4/2009 |
| WO | 2009023718 A3 | 4/2009 |
| WO | 2009044707 A1 | 4/2009 |
| WO | 2009010925 A3 | 7/2009 |
| WO | 2009064802 A2 | 7/2009 |
| WO | 2009064802 A3 | 7/2009 |
| WO | 2009088986 A1 | 7/2009 |
| WO | 2009088990 A1 | 7/2009 |
| WO | 2009103022 A1 | 8/2009 |
| WO | 20090100406 A2 | 8/2009 |
| WO | 2009117157 A1 | 9/2009 |
| WO | 2009118765 A2 | 10/2009 |
| WO | 2009050506 A2 | 11/2009 |
| WO | 2009050506 A3 | 11/2009 |
| WO | 2009100406 A3 | 11/2009 |
| WO | 2010006086 A2 | 1/2010 |
| WO | 2010009207 A1 | 1/2010 |
| WO | 2010036380 A1 | 4/2010 |

(56) References Cited

FOREIGN PATENT DOCUMENTS

| | | |
|---|---|---|
| WO | 2010019210 A2 | 5/2010 |
| WO | 2010019210 A3 | 5/2010 |
| WO | 2010053998 A1 | 5/2010 |
| WO | 2010057048 A1 | 5/2010 |
| WO | 2010065923 A2 | 6/2010 |
| WO | 2010070032 A1 | 6/2010 |
| WO | 2010039534 A2 | 8/2010 |
| WO | 2010039534 A3 | 8/2010 |
| WO | 2010092340 A1 | 8/2010 |
| WO | 2010133836 A1 | 11/2010 |
| WO | 2011008302 A1 | 1/2011 |
| WO | 2011058108 A1 | 5/2011 |
| WO | 2011058109 A1 | 5/2011 |
| WO | 2011058110 A1 | 5/2011 |
| WO | 2011075628 A1 | 6/2011 |
| WO | 2011094890 A1 | 8/2011 |
| WO | 2011111880 A1 | 9/2011 |
| WO | 2011146882 A1 | 11/2011 |
| WO | 2012009452 A1 | 1/2012 |
| WO | 2012032334 A1 | 3/2012 |
| WO | 2012037204 A1 | 3/2012 |
| WO | 2012052540 A1 | 4/2012 |
| WO | 2012061696 A1 | 5/2012 |
| WO | 2012064973 A2 | 5/2012 |
| WO | 2012068096 A2 | 5/2012 |
| WO | 2012068106 A2 | 5/2012 |
| WO | 2012071519 A1 | 5/2012 |
| WO | 2012097000 A1 | 7/2012 |
| WO | 2012121953 A1 | 9/2012 |
| WO | 2012129562 A2 | 9/2012 |
| WO | 2012135750 A1 | 10/2012 |
| WO | 2013006532 A1 | 1/2013 |
| WO | 2013012915 A1 | 1/2013 |
| WO | 2013012918 A1 | 1/2013 |
| WO | 2013013504 A1 | 1/2013 |
| WO | 2013013505 A1 | 1/2013 |
| WO | 2013025498 A1 | 2/2013 |
| WO | 2013044169 A1 | 3/2013 |
| WO | 2013059738 A2 | 4/2013 |
| WO | 2013066483 A1 | 5/2013 |
| WO | 2013074583 A1 | 5/2013 |
| WO | 2013086131 A1 | 6/2013 |
| WO | 2013090725 A1 | 6/2013 |
| WO | 2013113838 A1 | 8/2013 |
| WO | 2013113841 A1 | 8/2013 |
| WO | 2013188763 A1 | 12/2013 |
| WO | 2014004470 A1 | 1/2014 |
| WO | 2014018567 A1 | 1/2014 |
| WO | 2014046617 A1 | 3/2014 |
| WO | 2014071105 A1 | 5/2014 |
| WO | 2014071109 A1 | 5/2014 |
| WO | 2014071125 A1 | 5/2014 |
| WO | 2014072937 A1 | 5/2014 |
| WO | 2014075393 A1 | 5/2014 |
| WO | 2014124458 A1 | 8/2014 |
| WO | 2014141165 A1 | 9/2014 |
| WO | 2014168975 A1 | 10/2014 |
| WO | 2014175267 A1 | 10/2014 |
| WO | 2014194254 A1 | 12/2014 |
| WO | 2014203959 A1 | 12/2014 |
| WO | 2015002729 A2 | 1/2015 |
| WO | 2015010641 A1 | 1/2015 |
| WO | 2015037005 A1 | 3/2015 |
| WO | 2015051252 A1 | 4/2015 |
| WO | 2015054099 A1 | 4/2015 |
| WO | 2015054355 A1 | 4/2015 |
| WO | 2015081127 A2 | 6/2015 |
| WO | 2015083008 A1 | 6/2015 |
| WO | 2015095807 A1 | 6/2015 |
| WO | 2015095819 A2 | 6/2015 |
| WO | 2015095825 A1 | 6/2015 |
| WO | 2015095829 A1 | 6/2015 |
| WO | 2015095831 A1 | 6/2015 |
| WO | 2015095834 A2 | 6/2015 |
| WO | 2015095838 A2 | 6/2015 |
| WO | 2015095840 A1 | 6/2015 |
| WO | 2015095842 A2 | 6/2015 |
| WO | 2015109286 A1 | 7/2015 |
| WO | 2015143382 A1 | 9/2015 |
| WO | 2015160975 A2 | 10/2015 |
| WO | 2015160986 A2 | 10/2015 |
| WO | 2015175966 A1 | 11/2015 |
| WO | 2015179772 A1 | 11/2015 |
| WO | 2015181053 A1 | 12/2015 |
| WO | 2015181055 A1 | 12/2015 |
| WO | 2015188119 A1 | 12/2015 |

OTHER PUBLICATIONS

International Preliminary Report on Patentability for PCT/US2009/000042 dated Jul. 6, 2010.
International Preliminary Report on Patentability for PCT/US2009/005380 dated Apr. 7, 2011.
International Preliminary Report on Patentability for PCT/US2010/002020 dated Jan. 26, 2012.
International Search Report & Written Opinion for PCT/US2011/060212 dated Jun. 1, 2012.
International Search Report & Written Opinion issued after Submission of Request for Additional Search for PCT/US2011/060212 dated Jul. 6, 2012.
International Search Report and Written Opinion for PCT/US2009/005380 dated Nov. 20, 2009.
International Search Report and Written Opinion for PCT/US2009/049969 dated Mar. 15, 2010.
International Search Report and Written Opinion for PCT/US2010/033939 dated Nov. 5, 2010.
International Search Report and Written Opinion for PCT/US2012/020831 dated May 2, 2012.
International Search Report and Written Opinion for PCT/US2012/047190 dated Oct. 2, 2012.
International Search Report for PCT/US1995/005213 dated Aug. 21, 1995.
International Search Report for PCT/US2005/042524 (7 Pages) dated Oct. 2, 2006.
International Search Report for PCT/US2007/008355 dated Sep. 25, 2008.
International Search Report for PCT/US2007/008395 (4 Pages) dated Aug. 27, 2008.
International Search Report for PCT/US2009/000038 dated Mar. 11, 2009.
International Search Report for PCT/US2009/000042 dated Mar. 23, 2009.
International Search Report for PCT/US2009/060985 dated Jun. 28, 2010.
International Search Report for PCT/US2010/002020 dated Nov. 2, 2010.
International Search Report for PCT/US2011/037412 dated Aug. 22, 2011.
Ishiyama et al., "A Stoichiometric Aromatic C—H Borylation Catalyzed by Iridium(I)/2,2'-Bipyridine Complexes at Room Temperature," Agnew. Chem. Int. Ed. Engl. 41 (16): 3056-3057 (2002).
Ishiyama et al., "Mild Iridium-Catalyzed Borylation of Arenes. High Turnover Numbers, Room Temperature Reactions, and Isolation of a Potential Intermediate," J. Am. Chem. Soc. 124 (3): 390-391 (2002).
Jackson et al., "PI 3-kinase p110beta: a new target for antithrombotic therapy," Nat. Med. 11: 507-514 (2005).
Jimeno et al., "Phase I Trial of PX-866, a Novel Phosphoinositide-3-Kinase (PI-3K) Inhibitor," J. Clin. Oncol. 27: 15s (Suppl: Abstract 3542) (2009).
Johnson et al., "Accessory cell-derived signals required for T cell activation," Immunol. Res. 12 (1): 48-64 (1993).
Jou et al., "Essential, nonredundant role for the phosphoinositide 3-kinase p110delta in signaling by the B-cell receptor complex," Mol. Cell. Biol. 22 (24): 8580-8591 (2002).
June et al., "Evidence for the involvement of three distinct signals in the induction of IL-2 gene expression in human T lymphocytes," J. Immunol. 143 (1): 153-161 (1989).

(56) References Cited

OTHER PUBLICATIONS

June et al., "Inhibition of tyrosine phosphorylation prevents T-cell receptor-mediated signal transduction," Proc. Natl. Acad. Sci. U.S.A. 87 (19): 7722-7726 (1990).
June et al., "Role of CD28 receptor in T-cell activation," Immunol. Today 11 (6): 211-216 (1990).
June, C.H., "Signaling transduction in T cells," Curr. Opin. Immunol. 3 (3): 287-293 (1991).
Kajita et al., "Nickel-Catalyzed Decarbonylative Addition of Phthalimides to Alkynes," J. Chem. Soc. 130 (19): 6058-6059 (2008).
Kallberg et al., "Short-chain dehydrogenase/reductase (SDR) relationships: A large family with eight clusters common to human, animal, and plant genomes" Protein Sci. 11 (3): 636-641 (2002).
Kallberg et al., "Short-Chain Dehydrogenases/Reducatses (SDRs)—Coenzyme-Based Functional Assignments in Completed Genomes," Eur. J. Biochem. 269 (18): 4409-4417 (2002).
Kang et al., "Oncogenic transformation induced by the p110beta, -gamma, and -delta isoforms of class I phosphoinositide 3-kinase," PNAS 103 (5): 1289-1294 (2006).
Karpeiskii et al., "Pyridoxal-5'-Derivatives of Nucleobases," Bioorganicheskaya Khimiya 11 (8): 1097-1104 (1985).
Kassern, "Top Ten Bone Diseases," LiveStrong.com, Apr. 29, 2011. <http://www.livestrong.com/article/119479-top-ten-bone-diseases/>.
Kavanagh, Sean. Patient. Mylodysplastic syndromes. 2012. www.patient.co.uk/doctor/myelodysplastic-syndromes-pro.
Khwaja, A., "PI3K as a Target for Therapy in Haematological Malignancies," Curr. Top. Microbiol. Immunol. 347: 169-188 (2010).
Kiefer, Lymphoma Prevention. Healthline. 2011. <http://www.healthline.com/health/lymphoma/prevention>.
Kim et al., "Activation and Function of the mTORC1 Pathway in Mast Cells,"J. Immunol. 180 (7): 4586-4595 (2008).
Knight et al., "A Pharmacological Map of the PI3-K Family Defines a Role for p110alpha in Insulin Signaling," Cell 125 (4): 733-747 (2006).
Kong, D. and Yamori, T., "Advances in Development of Phosphatidylinositol 3-Kinase inhibitors," Curr. Med. Chem. 16 (22): 2839-2854 (2009).
Kost et al., "Recyclization of 3-Alkyl- and 1,3-Dialkylisoquinolinium Salts to Naphthylamines," Chemistry of Heterocyclic Compounds 16 (9): 965-970 (1980).
Kraybill et al., "Inhibitor scaffolds as new allele specific kinase substrates," J. Am. Chem. Soc. 124 (41): 12118-12128 (2002).
Kreutzberger et al., "5-Substituierte 4-Aminopyrmidine durch Aminomethinylierung von Acetonitrilen," Liebigs Ann. Chem. 1977 (4): 537-544 (1977).
Camps et al., "Blockade of PI3Kgamma suppresses joint inflammation and damage in mouse models of rheumatoid arthritis," Nat. Med. 11(9): 936-943 (2005).
Castor et al, "PI3Kg controls leukocyte recruitment, tissue injury, and lethality in a model of draft-versus-host disease in mice," J. Leukocyte Biol. 89: 955-964 (2011).
Chaisuparat et al., "Dual inhibition of PI3Kalpha and mTOR as an alternative treatment for Kaposi's Sarcoma," Cancer Res. 68: 8361-8368 (2008).
Chang et al., "The Bruton tyrosine kinase inhibitor PCI-32765 ameliorates autoimmune arthritis by inhibition of multiple effector cells," Arthritis Research & Therapy 13(4): R115 (2011).
Chappelow et al., "Neovascular age-related macular degeneration: potential therapies," Drugs 68(8): 1029-1036 (2008).
Chapuis et al., "Dual inhibition of PI3K and mTORC1/2 Signaling by NVP-BE7235 as a New Therapeutic Strategy for Acute Myeloid Leukemia," Clin. Cancer Res. 16(22): 5425-5435 (2010).
Chawla et al., "Challenges in Polymorphism of Pharmaceuticals," Current Research & Information on Pharmaceutical Science 5(1): 9-12 (2004).

Chen et al., "Characterization of Structurally Distinct, Isoform-Selective Phosphoinositide 3'-Kinase Inhibitors in Combination with Radiation in the Treatment of Glioblastoma," Mol. Cancer Ther. 7(4): 841-850 (2008).
Cheson et al., "Bendamustine: Rebirth of an Old Drug," J. Clin. Oncol. 27(9): 1492-1501 (2009).
Cheson et al., "Novel Targeted Agents and the Need to Refine Clinical End Points in Chronic Lymphocytic Leukemia", Journal of Clinical Oncology, vol. 30, No. 23, pp. 2820-2822, Aug. 10, 2012.
Cheung et al., "Genome-wide profiling of follicular lymphoma by array comparative genomic hybridization reveals prognostically significant DNAcopy number imbalances," Blood 113(1): 137-148 (2009).
Cheung et al., "High resolution analysis of follicular lymphoma genomes reveals somatic recurrent sites of copy-neutral loss of heterozygosity and copy number alterations that target single genes," Genes, Chromosomes & Cancer 49: 669-681 (2010).
Chiarini et al., "Activity of the Novel Dual Phosphatidylinositol 3-Kinase/Mammalian Target of Rapamycin Inhibitor NVP-BEZ235 against T-Cell Acute Lymphoblastic Leukemia," Cancer Res. 70(20): 8097-8107 (2010).
Chiarini et al., "Dual Inhibition of Class IA Phosphatidylinositol 3-Kinase and Mammalian Target of Rapamycin as a New Therapeutic Option for T-Cell Acute Lymphoblastic Leukemia," Cancer Res. 69(8): 3250-3528 (2009).
Chiron et al., "Cell-Cycle Reprogramming for PI3K Inhibition Overrides a Relapse-Specific C481S BTK Mutation Revealed by Longitudinal Functional Genomics in Mantle Cell Lymphoma," Cancer Discovery 4:1022-1035 (2014).
Cho et al., "A novel synthesis of benzo[c]phenanthridine skeleton and biological evaluation of isoquinoline derivatives," Chem. Pham. Bull.(Tokyo) 47(6): 900-902 (1999).
Clayton et al., "A crucial role for the p110delta subunit of phosphatidylinositol 3-kinase in B cell development and activation," J. Exp. Med. 196(6): 753-763 (2002).
ClinicalTrials.gov NCT01476657 Study, "A Phase 1 Study of IPI-145 in Patients with Advanced Hematologic Malignancies", Nov. 17, 2011.
ClinicalTrials.GOV Study, "Dose Escalation Study of CAL-101 in Select Relapsed or Refractory Hematologic Malignancies" (2014).
Closse et al., "2,3-dihydrobenzofuran-2-ones: a new class of highly potent antiinflammatory agents," J. Med. Chem. 24 (12): 1465-1471 (1981).
Conte et al., "Inhibition of PI3K Prevent the Proliferation and Differentiation of Human Lung Fibroblasts into Myofibroblasts: The Role of Class I P110 Isoforms," PLOS ONE 6(10) e24663: 1-10 (2011).
Courtney et al., "The PI3K Pathway as Drug Target in Human Cancer," J. Clin. Oncol. 28(6): 1075-1083 (2010).
Cox et al., "Human colorectal cancer cells efficiently conjugate the cyclopentenone prostaglandin, prostaglandin J2, to glutathione," Biochem. Biophys. Acta. 1584(1): 37-45 (2002).
Cui et al., "MicroRNA-155 influences B-cell receptor signaling and associates with aggressive disease in chronic lymphocyte leukemia", Blood. 2014, vol. 124(4), pp. 546-554.
Cushing et al., "PI3Kdelta and PI3Kgamma as Targets for Autoimmune and Inflammatory Diseases,"Chem. J. Med. 55 (20): 8559-8581 (2012).
D'Amore el al., "Clonal Evolution in t(14:18)-Positive Follicular Lymphoma, Evidence for Multiple Common Pathways, and Frequent Parallel Clonal Evolution," Ciin. Cancer Res. 14(22): 7180-7187 (2008).
D'Cruz et al. "Novel Bruton's tyrosine kinase inhibitors currently in development," OncoTargets and Therapy, Mar 5, 2013, vol. 6, pp. 161-176.
Dai et al., "Distinct Roles of Phosphoinositide-3 Kinase and Phospholipase Cgamma2 in B-Cell Receptor-Mediated Signal Transduction," Mol. Cell. Biol. 26(1): 88-99 (2006).
Davids et al., "Decreased mitochondrial apoptotic priming underlies stroma-mediateci treatment resistance in chronic lymphocytic leukemia," Blood 120 (17): 3501-3509 (2012).

(56) References Cited

OTHER PUBLICATIONS

Davies et al., "The Human T3 gamma Chain is Phosphorylated at Serine 126 in Response to T Lymphocyte Activation," J. Biol. Chem. 262(23): 10918-10921 (1997).
Davis et al., "Chronic active B-cell-receptor signalling in diffuse large B-cell lymphoma," Nature 463: 88-92 (2010).
Davis et al., "The preparation of substituted 1(2H)-isoguinolinones from dilithiated 2-methyl-N-arylbenzamides, 2-methyl-N-(arylmethyl)-benzamides, or 2-methylbenzoic acid, 2, 2-dimethylhydrazide," Synthetic Commun. 27(17): 2961-2969 (1997).
De Frias et al., "Akt inhibitors induce apoptosis in chronic lymphocytic leukemia cells," Haematologica 94: 1698-1707 (2009).
De Vos et al., "A Phase 1 Study of the Selective Phosphatidylinositol 3-Kinase-Delta (PI3K delta) Inhibitor, Cal-101 (GS-1101), in Combination with Rituximab anchor Bendamustine in Patients with Previously Treated, Indolent Non-Hodgkin Lymphoma (iNHL)", Blood (ASH) 118(21), p. 1160 (2011).
De Weers et al., "The Bruton's tyrosine kinase gene is expressed throughout B cell differentiation, from early precursor B cell stages preceding immunoglobulin gene rearrangement up to mature B cell stages," Eur. J. Immunol. 23(12): 3109-3114 (1993).
Diederich et al., "In the search for specific inhibitors of human 11beta-hydroxysteroid-dehyrdogenases (11beta-HSDs): chenodeoxycholic acid selectively inhibits 11beta-HSD-I" Eur. J. Endocrinol. 142(2): 200-207 (2000).
Dijksman et al., "271.1: 2-dihydro-2-thianaphthalene derivatives. Part I. Preparation and reactions of 1: 2-dihydro-1-keto-2-thianaphthalenes," J. Chem. Soc. 1213-1218 (1951).
Ding et al., "A combinatorial scaffold approach toward kinase-directed heterocycle libraries," J. Am. Chem. Soc. 124 (8): 1594-1596 (2002).
Ding et al., "A concise and traceless linker startegy toward combinatorial libraries of 2,6,9-substituted purines," J. Org. Chem. 66(24): 8273-8276 (2001).
Ding et al., "Resin-capture and release strategy toward combinatorial libraries of 2,6,9-substituted purines," J. Comb. Chem. 4(2):183-186 (2002).
Donati, "Emerging therapies for neovascular age-related macular degeneration: state of the art," Ophthalmologica 221 (6): 366-377 (2007).
Engelman J. "Targeting PI3K signalling in cancer: opportunities, challenges and limitations", Nature Reviews: Cancer vol. 9 (2009), pp. 550-562.
European Examination Report for EP Application No. 07873406.8 dated Sep. 14, 2011.
European Search Report and Search Opinion for EP Application No. 09700424.6 dated Oct. 26, 2011.
European Search Report for EP Application No. 05857011.0 dated Feb. 4, 2011.
European Search Report for EP Application No. 07754845.1 dated Sep. 20, 2011.
European Search Report for EP Application No. 07873406.8 dated Mar. 1, 2010.
European Search Report for EP Application No. 09700784.3 dated Oct. 28, 2011.
Examination Report for GB Application No. GB 0819947.3 dated Oct. 27, 2010.
Extended European Search Report for EP Application No. 09816603.6 dated Mar. 19, 2012.
Abdel-Moshen, "Synthesis, Reactions and Antimicrobial Activity of 2-Amino-4-(8-quinolinol-5-yl)-1-(p-tolyl)-pyrrole-3-carbonitrile," Bull. Korean Chem. Soc. 26(5): 719-728 (2005).
Abe et al., "T Cell Receptor-mediated Recognition of Self-Ligand Induces Signaling in Immature Thymocytes before Negative Selection," J. Exp. Med. 176(2): 459-468 (1992).
Abraham, T., "Thermally induced intramolecular cycloaddition reaction of N-phenyl-2-phenylethynlbenzamide potential cure reaction for thermosetting polymers," J. Polym. Sci. Polym. Chem. Ed. 20(7): 1953-1957 (1982).

Abrahamian et al., "Immunological and Clinical Profile of Adult Patients with Selective Immunoglobulin Subclass deficiency: response to intravenous immunoglobulin therapy," Clin. Exp. Immunol. 159(3): 344-350 (2010).
American Cancer Society. Non-Hodgkin's Lymphoma. 2014. <http://www.cancer.org/cancer/nonhodgkinlymphoma/detailedguide/non-hodgkin-lymphoma-types-of-non-hodgkin-lymphoma>.
Ameriks and Venable, "Small Molecule Inhibitors of Phosphoinositide 3-Kinase (PI3K) delta and gamma," Current Topics in Medicinal Chemistry 9: 738-753 (2009).
Ames et al., "Heterocyclic Syntheses from o-Haiogeno-acids. Part II. Thienopyridinones and Thienopyranones from 3-Bromothlophen-2- and 4-Bromothiophen-3-carboxylic Acids," J. Chem. Soc., Perkin Trans. 1: 1390-1395 (1975).
Anderson et al., "Paradoxical inhibition of T-cell function in response to CTLA-4 blockade; heterogeneity within the human T-cell population," Nat. Med. 6(2): 211-214 (2000).
Andrews et al., "Effects of the 11 beta-hydroxysteroid dehydrogenase inhibitor carbenoxolone on insulin sensitivity in men with type 2 diabetes," J. Clin. Endocrinol. Metab. 88(1): 285-291 (2003).
Arcaro et al., "Wortmannin is a potent phosphatidylinositol 3-kinase inhibitor: the role of phosphatidylinositol 3,4,5-triphosphate in neutrophil responses," Biochem J. 296(Pt 2): 297-301 (1993).
Arnold et al., "Pyrrolo[2,3-d]pyrimidines containing an extended 5-substituent as potent and selective inhibitors of Ick I," Bioorg. Med. Chem. Lett. 10(19): 2167-2170 (2000).
Augustine et al., "Interleukin 2- and polyomavirus middle T antigen-induced modification of phosphatidylinositol 3-kinase activity in activated T lymphocytes," Mol. Cell. Biol. 11(9): 4431-4440 (1991).
Baggiolini et al., "Inhibition of the phagocytosis-induced respiratory burst by the fungal metabolite wortmannin and some analogues," Exp. Cell. Res. 169(2): 408-418 (1987).
Ballell et al., "New Thiopyrazolo[3,4-d]pyrimidine derivatives as anti-mycobacterial agents," Bioorg. Med. Chem. Lett. 17(6): 1736-1740 (2007).
Banker et al., Modern Pharmaceutics, pp. 451, 596, 3rd ed, Marcel Dekker, New York (1996).
Bansal et al., "The Molecular Biology of Endometrial Cancers and the Implications for Pathogenesis, Classification, and Targeted Therapies," Cancer Control 16(1): 8-13 (2009).
Barber et al., "PI3Kgamma inhibition blocks glomerulonephritis and extends lifespan in a mouse model of systemic lupus," Nat. Med. 11(9): 933-935 (2005).
Barf et al., "Arylsulfonamidothiazoles as a new class of potential antidiabetic drugs. Discovery of potent and selective inhibitors of the 11beta-hydroxysteroid dehydrogenase type 1," J. Med. Chem. 45(18): 3813-3815 (2002).
Barnes et al., "Efficacy and Safety of Inhaled Corticosteroids in Asthma. Report of a Workshop Held in Eze, France Oct. 1992," Am. Rev. Respir. Dis. 148: S1-S26 (1993).
Barnes et al., "Glucocortoid resistance in inflammatory diseases," The Lancet 373 (9768): 1905-1917 (2009).
Bartholomeusz et al., "Targeting the PI3K Signaling Pathway in Cancer Therapy," Expert Opin. Ther. Targets 16(1): 121-130 (2012).
BASOTEST®, Test Kit for the Quantitative Determination of the Degranulation of Basophilic Granulocytes in Heparinized Human Whole Blood, version 04/02, pp. 1-10.
Beeram et al., "Akt-induced endocrine therapy resistance is reversed by inhibition of mTOR signaling," Ann. Oncol. 18 (8): 1323-1328 (2007).
Bell et al., "Glucokinase mutations, insulin secretion, and diabetes mellitus," Annu. Rev. Physiol. 58: 1-186 (1996).
Berndt et al., "The p110delta structure: mechanisms for selectivity and potency of novel PI(3)K inhibitors," Nat. Chem Biol. 6(2): 117-124 (2010).
Bhat et al., "Pyrazolopyrimidine nucleosides. 12. Synthesis and biological activity of certain pyrazolo[3,4-d]pyrimidine nucleosides related to adenosine," J. Med. Chem. 24(10): 1165-1172 (1981).
Bhatt et al., "Dual inhibition of PI3K and mTOR inhibits autocrine and paracrine proliferative loops in PI3K/Akt/mTOR-addicted lymphomas," Blood 115(22):4455-4463 (2010).

(56) References Cited

OTHER PUBLICATIONS

Bi et al., "Proliferative defect and embryonic lethality in mice homozygous for a deletion in the p110alpha subunit of phosphoinositide 3-kinase" J. Biol. Chem. 274(16): 10963-10968 (1999).
Billottet et al., "A selective inhibitor of the p110delta isoform of PI 3-kinase inhibits AML cell proliferation and survival and increases the cytotoxic effects of VP-16," Oncogene 25: 6648-6659 (2006).
Biliottet et al., "Inhibition of Class I Phosphoinositide 3-Kinase Activity Impairs Proliferation and Triggers Apoptosis in Acute Promyelocytic Leukemia without Affecting ATM-Induced Differentiation," Cancer Res. 69(3): 1027-1036 (2009).
Bishop et al., "Generation of monospecific nanomolar tyrosine kinase inhibitors via a chemical genetic approach," J. Am. Chem. Soc. 121(4): 627-631 (1999).
Blunden et al., "Mycotoxins in food," Med. Lab. Sci. 48(4): 271-282 (1991).
Bochner et al., "Immunological aspects of allergic asthma," Annu. Rev. Immunol. 12: 295-335 (1994).
Bohren et al., "Expression, crystallization and preliminary crystallographic analysis of human carbonyl reductase," J. Mol. Biol. 224(5): 659-664 (1994).
Bojarczuk et al., "B-cell receptor pathway inhibitors affect CD20 levels and impair antitumor activity of anti-CD20 monoclonal antibodies" Leukemia 1-5 (2014).
Bone et al., "Phosphoinositide 3-kinase signalling regulates early development and developmental haemopoiesis," J. Cell. Sci. 120(Pt 10): 1752-1762 (2007).
Bouska et al., "Genome-wide copy-number alyses reveal genomic abnormalities involved in transformation of follicular lymphoma," Blood 123 (11): 1681-1690 (2014).
Bowers et al., "A platelet biomarker for assessing phosphoinositide 3-kinase inhibition during cancer chemotherapy," Mol. Cancer. Ther. 6(9): 2600-2607 (2007).
Boyle et al., "Efficacy of the Potent PI3K-delta,gamma Inhibitor IPI-145 in Rat Adjuvant Arthritis," Arthritis & Rheumatism 64(10): 5879 (2012).
Brown et al., "Idelalisib, an ihibitor of phosphatidylinositol 3-kinase p110delta, for relapsed/refractory chronic lympocytic leukemia," Blood 123(22): 3390-3397 (2014).
Brown et al., "Phase I Trial of SAR245408 (S08), a Pan-Phosphatidylionositol 3 Kinase (PI3K) Inhibitor, in Patients with Chronic Lymphocytic Leukemia (CLL) and Lymphoma," Blood (ASH), 118 (21), p. 1153 (2011).
Brzezianska et al., "A Minireview: The Role of MAPK/ERK and PI3K/Akt Pathways in Thyroid Follicular Cell-Derived Neoplasm," Front. Biosci. 16: 422-439 (2011).
Buitenhuis et al., "The role of the PI3K-PKB signaling module in regulation of hematopoiesis," Cell Cycle 8(4): 560-566 (2009).
Burger et al., "High-level expression of the -1-cell chemokines CCL3 and CCL4 by chronic lymphocytic leukemia B cells in nurselike cell cocultures and after BCR stimulation," Blood 113(13): 3050-3058 (2009).
Burger, "Inhibiting B-Cell Receptor Signaling Pathways in Chronic Lymphocytic Leukemia," Curr. Mematol. Malig. Rep. 7(1): 26-33 (2012).
Byrd et al., "Translating PIk-Delta Inhibitors to the Clinic in Chronic Lymphocytic Leukemia: The Story of CAL-101 (GS1101)," ASCO Program Proceedings, pp. 691-694 (2012).
Caira, "Crystalline Polymorphism of Organic Compounds," Topics in Current Chemistry, Springer, Berlin, DE 198: 163-208 (1998).
Calin et al., "A MicroRNA Signature Associated with Prognosis and Progression in Chronic Lymphocytic Leukemia", N Engl J Med, 2005, vol. 353, pp. 1793-801.
Campora et al., "Binuclear complexes of nickel bridged by hydrocarbon ligands. Isocyanide insertion chemistry and amide formation by intramolecular coupling of acyl and imidoyl functionalities," Organometallics 11(1): 11-13 (1992).
Campora et al., "Isocyanide insertion chemistry. Synthesis and structural characterization of bridging imidoyl complexes of nickel and amide formation by intramolecular coupling of acyl and imidoyl functionalities," Organometallics 12(10): 4025-4031 (1993).
Norman, "Selective PI3K-delta Inhibitors, A Review of the Patent Literature," Expert Opinion on Therapeutic Patents 21 (11): 1773-1790 (2011).
Nunes et al., "Signalling through CD28 T-cell activation pathway involves an inositol phospholipid-specific phospholipase C activity," Biochem. J. 293 (pt. 3): 835-842 (1993).
O'Shea et al., "Activation of human peripheral blood T lymphocytes by pharmacological induction of protein-tyrosine phosphorylation," Proc. Natl. Acad. Sci. U.S.A. 89 (21): 10306-10310 (1992).
Oda et al., "PIK3CA Cooperates with Other Phosphatidylinositol 3'-Kinase Pathway Mutations to Effect Oncogenic Transformation," Cancer Res. 68 (19): 8127-8136 (2008).
Office Action dated Dec. 13, 2012 for 7004 US1, U.S. Appl. No. 13/112,611.
Okada et al., "Blockage of chemotactic peptide-induced stimulation of neutrophils by wortmannin as a result of selective inhibition of phosphatidylinositol 3-kinase," J. Biol. Chem. 269 (5): 3563-3567 (1994).
Okada et al., "Essential role of phosphatidylinositol 3-kinase in insulin-induced glucose transport and antilipolysis in rat adipocytes. Studies with a selective inhibitor wortmannin," J. Biol. Chem. 269 (5): 3568-3573 (1994).
Okosun et al., "Integrated genomic analysis identifies recurrent mutations and evolution patterns driving the initiation and progession of follicular lymphoma," Nature Genetics 46(2): 176-181 (2014).
Okosun et al., Supplementary information "Integrated genomic analysis identifies recurrent mutations and evolution patterns driving the initiation and progession of follicular lymphoma," Nature Genetics: doi:10.1038/ng.2856, Feb. 2014.
Oppermann et al., "Forms and functions of human SDR enzymes," Chem. Biol. Interact. 130-132 (1-3): 699-705 (2001).
Oricchio et al., "The Eph-Receptor A7 is a Soluble Tumor Suppressor for Follicular Lymphoma," Cell 147: 554-564 (2011).
Ozaki et al., "Studies on 4(1H)-Quinazolinones. IV. Convenient Syntheses of 12-Methyl-6H-isoquino [2,1-a] quinazolin-6-one and 6-Methyl-13H-quinazolino [3,4-a] quinazolin-13-one," Chem. Pharm. Bull. 32 (6): 2160-2164.
Ozol et al., "Autoxidative transformations of 2-substituted 3-alkyl-4-hydroxy-1-oxo-1, 2-dihydroisoqinolines," Chemistry of Heterocyclic Compounds 14 (6): 644-648 (1978).
Patel, Manish R., "Early Clinical Activity and Pharmacodynamic Effects of Duvelisib, a PI3K-delta, gamma Inhibitor, in Patients with Treatment-Naïve CLL", ASCO Annual Meeting 2015, May 29-Jun. 2, Chicago, IL (poster).
Perez-Blas et al., "Impaired T cell signal transduction through CD28 in a patient with idiopathic thrombocytopenia," Clin. Exp. Immunol. 85 (3): 424-428 (1991).
Persson, "Glucocorticoids for asthma—early contributions," Pulm. Pharmacol. 2 (3): 163-166 (1989).
Petrie et al., "A Novel biotinylated adenylate analogue derived from pyrazolo[3,4-d]pyrimidine for labeling DNA probes," Bioconjug. Chem. 2 (6) 441-446 (1991).
Pharmacyclics Inc. Form 8-K Filing. May 15, 2013. Article retrieved from the Internet: www.sec.gov/Archives/edgar/data/949699/000092189513001115/0000921895-13-001115-index.htm on Dec. 11, 2014.
Pighi et al., "Phospho-proteomic analysis of mantle cell lymphoma cells suggests a pro-survival role of B-cell receptor signaling," Cell Oncol. (Dordr) 34 (2): 141-153 (2011).
Polak et al., "The PI3k/PKB signaling module as key regulator of hematopoiesis: implications for therapeutic strategies in leukemia," Blood 119 (4): 911-923 (2012).
Porta and Figlin, "Phosphaticlyinositol-3-kinase/Akt signaling pathway and kidney cancer, and the therapeutic potential of phosphatidylinositol-3-kinase/Akt inhibitors," J. Urol. 182 (6): 2569-2577 (2009).
Porter et al., "The Potent Phosphoinositide-3-Kinase-(delta,garnma) Inhibitor IPI-145 is Active in Preclinical Models of Arthritis and Well Tolerated in Healthy Adult Subjects," Arthritis & Rheumatism 64(10): s147 (2012) (abstract only).

(56) References Cited

OTHER PUBLICATIONS

Prasad et al., "Phosphatidylinositol (PI) 3-kinase and PI 4-kinase binding to the CD4-p56lck complex: the p56lck SH3 domain binds to PI 3-kinase but not PI 4-kinase," Mol. Cell. Biol. 13 (12): 7708-7717 (1993).
Prasad et al., "Src-homology 3 domain of protein kinase p59fyn mediates binding to phosphatidylinositol 3-kinase in T cells," Proc. Natl. Acad. Sci. U.S.A. 90 (15): 7366-7370 (1993).
Prasad et al., "T-cell antigen CD28 interacts with the lipid kinase phosphatidylinositol 3-kinase by a cytoplasmic Tyr(P)-Met-Xaa-Met motif," Proc. Natl. Acad. Sci. U.S.A. 91(7): 2832-2838 (1994).
Press Release: "Infinity Regains Worldwide Rights to PI3k, FAAH and Early Discovery Programs", Infinity Pharmaceuticals, Jul. 18, 2012.
Pudlo et al., "Synthesis, antiproliferative, and antiviral activity of certain 4-substituted and 4,5-disubstituted 7-[1,3-dihydroxy-2-propoxy)methyl]pyrrolo[2,3-d]pyrimidines," J. Med. Chem. 33 (7): 1984-1992 (1990).
Puri and Gold, "Selective inhibitors of phosphoinositide 3-kinase delta: modulators of B-cell function with potential for treating autoimmune inflammatory disease and B-cell malignancies," Front. Immunol. 3: 256 (2012).
Quiroga et al., "B-cell antigen receptor signaling enhances chronic lymphocytic leukemia cell migration and survival: specific targeting with a novel spleen tyrosine kinase inhibitor, R406," Blood 114 (5): 1029-1037 (2009).
Reif et al., "Divergent regulation of phosphatidylinositol 3-kinase p85alpha and p85beta isoforms upon T cell activation," J. Biol. Chem. 268 (15): 10780-10788 (1993).
Report of the Expert Committee on the Diagnosis and Classification of Diabetes Mellitus, Diabetes Care 2(Suppl. 1): S5-S19 (1992).
Rizzatti et al., "Gene expression profiling of mantle cell lymphoma cells reveals aberrant expression of genes from the PI3K-Akt, WNT and TGFbeta signalling pathways," Brit. J. Haematol. 130 (4): 516-526 (2005).
Robertson, "Eicosanoids and human disease," Harrison's Principles of Internal Medicine, Isselbacher K.J. et al. (eds.), vol. 1, pp. 431-435, McGraw-Hill, New York City (1994).
Roller et al., "Blockade of Phosphatidylinositol 3-Kinase (PI3K)delta or PI3Kgamma Reduces Il-17 and Ameliorates Imiquimod-Induced Psoriasis-like Dermatitis," J. Immunol. 189 (9): 4612-4620 (2012).
Romero et al., "Cloning and expression of the bovine 11b-hydroxysteroid dehydrogenase type-2," J. Steroid Biochem. Mol. Biol. 72 (5): 231-237 (2000).
Rommel et al., "PI3Kdelta and PI3Kgamma: partnersin crime in inflammation in rheumatoid arthritis and beyond?" Nat. Rev. Immunol. 7 (3): 191-201 (2007).
Ross et al., "Comprehensive Analysis of Copy Number and Allele Status Identifies Multiple Chromosome Defects Underlying Follicular Lymphoma Pathogenesis," Clin. Cancer Res. 2007 13(16): 4777-4785 (2007).
Rott et al., "Recent developments in the use of biologics in psoriasis and autoimmune disorders. The role of autoantibodies," BMJ 330 (7493): 716-720 (2005).
Rudelius et al., "Constitutive activation of Akt contributes to the pathogenesis and survival of mantle cell lymphoma," Blood 108 (5): 1668-1676 (2006).
Sail and Chu, "Biology of colorectal cancer," Cancer J. 16 (3): 196-201 (2010).
Salmena et al., "Tenets of PTEN Tumor Suppression," Cell 133 (3): 403-414 (2008).
Sarker et al., "Targeting the PI3K/AKT pathway for the treament of prostate cancer," Clin. Cancer Res. 15 (15): 4799-4805 (2009).
Sasaki et al., "Function of PI3Kgamma in Thymocyte Development, T Cell Activation, and Neutrophil Migration," Science 287 (5455): 1040-1046 (2000).
Schwaenen et al., "Microarray-Based Genomic Profiling Reveals Novel Genomic Aberrations in Follicular Lymphoma Which Associate with Patient Survival and Gene Expression Status," Genes, Chromosomes & Cancer 48: 39-54 (2009).
Schwartz et al., "Quercetin inhibition of the induction and function of cytotoxic T lymphocytes," Immunopharmacology 4 (2): 125-138 (1982).
Schwartz, "A cell culture model for T lymphocyte clonal energy," Science 248 (4961): 1349-1356 (1990).
Seda and Mraz, "B-cell receptor signalling and its crosstalk with other pathways in normal and malignant cells", European Journal of Haematology, 2015, vol. 94 (3) p. 193-205.
Shapiro et al., "A Phase I Dose-Escalation Study of XL147, A PI3K Inhibitor Administered Orally to Patients with Solid Tumors," J. Clin. Oncol. 27 (15s): 146x (suppl Abstr 3500) (2009).
Sharman et al., "A Phase 1 Study of the Selective Phosphatidylinositol 3-Kinase-Delta (PI3K delta) Inhibitor, CAL-101 (GS-1101), in Combination with Rituximab and/or Bendamustine in Patients with Relapsed or Refratory Chronic Lymphocytic Leukemia (CLL)", Blood (ASH), 118(21), pp. 779-780 (2011).
Shibasaki et al., "Different properties of monomer and heterodimer forms of phosphatidylinositol 3-kinases," Biochem. J. 289 (Pt 1): 227-231 (1993).
Kridel et al., "Pathogenesis of follicular lypmhoma," J. of Clinical Investigation 122(10): 3424-3431 (2012).
Kukulski et al., "The P2 receptor antagonist PPADS abrogates LPS-induced neutrophil migration in the murine air pouch via inhibition of MIP-2 and KC production," Molecular Immunol. 47: 833-839 (2010).
Kulkarni et al., "PI3Kbeta plays a critical role in neutrophil activation by immune complexes," Sci. Signal 4 (168): ra 23 (2011).
Kumar et al., "Keten Dithioacetals. Part 11. Reaction of 3-Cyano-4-Methylthio-2(1H)-pyridones with Hydrazine and Guanidine: Synthesis of Novel Substituted and Fused Pyrazolo[4,3-c]pyridone and Pyrido[4,3-d]pyrimidine derivatives," J. Chem. Soc., Perkin Trans. 1, 8: 857-862 (1978).
Kundu et al., "Paliadium-Catalysed Heteroannulation with Terminal Alkynes: a Highly Regio- and Stereoselective Synthesis of (Z)-3-Aryl(alkyl)idene Isoindolin-1-ones" Tetrahedron 56 (27): 4777-4792 (2000).
Kurtova et al., "Diverse marrow stromal cells protect CLL cells from spontaneous and drug-induced apoptosis: development of a reliable and reproducible system to assess stromal cell adhesion-mediated drug resistance," Blood 114 (20): 4441-4450 (2009).
Kwok et al., "The anti-inflammatory natural product parthenolide from the medicinal herb Feverfew directly binds to and inhibits IkB kinase," Chem. Biol. 8 (8): 759-766 (2001).
Lannutti et al., "CAL-101, a p110delta selective phosphatidylinositol-3-kinase inhibitor for the treatment of B-cell malignancies, inhibits PI3K signaling and cellular viability," Blood 117 (2): 591-594 (2011).
Larabi et al., "Crystal Structure and Mechanism of Activation of TANK-Binding Kinase 1," Cell Reports 3 (3): 734-746 (2013).
Ledbetter et al., "CD28 Ligation in T-Cell Activation: Evidence for Two Signal Transduction Pathways," Blood 75 (7): 1531-1539 (1990).
Ledbetter et al., "Crosslinking of surface antigens causes mobilization of intracellular ionized calcium in T lymphocytes," Proc. Natl. Acad. Sci. U.S.A. 84 (5): 1384-1388 (1987).
Lee et al., "All roads lead to mTOR: integrating inflammation and tumor angiogenesis," Cell Cycle 6 (24): 3011-3014 (2007).
Lee et al., "The CD28 Signal Transduction Pathway in T Cell Activation," Advances in Regulation of Cell Growth, vol. 2, pp. 141-160, New York: Raven Press, Ltd. 1991.
Ley et al., "The T cell receptors/CD3 complex arid CD2 stimulate the tyrosine phosphorylation of indistinguishable patterns of polypeptides in the human T leukemic cell line Jurkat," Eur. J. Immunol. 21 (9): 2203-2209 (1991).
Li et al., "Roles of PLC-beta2 and -beta3 and PI3Kgamma in chemoattractant-mediated signal transduction," Science 287 (5455): 1046-1049 (2000).
Liu et al., "Costimulation of T-cell growth," Curr. Opin. Immunol. 4 (3): 265-270 (1992).
Lu et al., "CD28-induced T cell activation. Evidence for a protein-tyrosine kinase signal transduction pathway," J. Immunol. 149 (1): 24-29 (1992).

(56) References Cited

OTHER PUBLICATIONS

Macias-Perez et al., "B-Cell Receptor Pathobiology and Targeting in NHL", Current Oncology Report 14(5), pp. 411-418 (2012).
Majumder et al., "mTOR inhibition reverses Akt-dependent prostate intraepithelial neoplasia through regulation of apoptotic and HIF-1-dependent pathways," Nat. Med. 10 (6): 594-601 (2004).
Mansour et al., "Discovery of a Secreted Tumor Suppressor Provides a Promising Therapeutic Strategy for Follicular Lymphoma," Cancer Cell 20: 559-561 (2011).
Markman et al., "Status of PI3K inhibition and biomarker development in cancer therapeutics," Ann. Oncol. 21 (4): 683-691 (2010).
Martelli et al., "The emerging role of the phosphatidylinositol 3-kinase/Akt/mammalian target of rapamycin signaling network in normal myelopoiesis and leukemogenesis," Biochim. Biophys. Acta. 1803 (9): 991-1002 (2010).
Martin-Sanchez et al., "PI3K Inhibition as a Potential Therapeutic Strategy in Peripheral T-Cell Lymphomas," Blood (ASH Annual Meeting Abstracts) 118: Abstract 3493 (2011).
Martinez et al., "The Molecular Signature of Mantle Cell Lymphoma Reveals Multiple Signals Favoring Cell Survival," Cancer Res. 63: 8226-8232 (2003).
Mattes et al., "DNA sequence selectivity of guanine-N7 alkylation by nitrogen mustards," Nucleic Acids Res. 14 (7): 2971-2987 (1986).
Maxwell et al., "Attenuation of phosphoinositide 3-kinase delta signaling restrains autoimmune disease," J. Autoimmun. 38 (4): 381-391 (2012).
Mayer et al., "Small Molecule Inhibitor of Mitotic Spindle Bipolarity Identified in a Phenotype-Based Screen," Science 286 (5441): 971-974 (1999).
Mazzoletti and Broggini, "PI3K/AKT/mTOR inhibitors in ovarian cancer," Curr. Med. Chem. 17 (36): 4433-4447 (2010).
Meadows et al., "CAL-101, a Potent Selective Inhibitor of the p110delta Isoform of Phosphatidylinositol 3-Kinase, Attenuates Pathway Signaling, Induces Apoptosis, and Overcomes Signals from the Microenvironment in Cellular Models of Hodgkin Lymphoma," Blood (ASH Annual Meeting Abstracts), 116: Abstract 3926 (2010).
MedicineNet.com, Cancer Definition, http://www.medterms.com, 2004.
Medline Plus, Autoimmune Diseases, NIH, 2014.<http://www.nlm.nih.gov/medlineplus/autoimmunediseases.html>.
Mellinghoff et al., "TORward AKTually useful mouse models," Nat. Med. 10 (6): 579-580 (2004).
Merida et al., "IL-2 binding activates a tyrosine-phosphorylated phosphatidylinositol-3-kinase," J. Immunol. 147 (7): 2202-2207 (1991).
Miyaura et al., "Palladium-Catalyzed Cross-Coupling Reactions of Organoboron Compounds," Chem. Rev. 95 (7): 2457-2483 (1995).
Modi et al., "Isoquinolones; part IV-synthesis of methyl, 3-formyl & other 3-substituted N-arylisoquinolones," Indian J. Chem. 18B: 304-306 (1979).
Moon et al., "A Novel Microtubule Destabilizing Entity from Orthogonal Synthesis of Triazine Library and Zebrafish Embryo Screening," J. Am. Chem. Soc. 124 (39): 11608-11609 (2002).
Mosmann et al., "The expanding universe of T-cell subsets: Th1, Th2 and more," Immunology Today 17 (3): 138-146 (1996).
Mraz and Kipps, "MicroRNAs and B cell receptor signaling in chronic lymphocytic leukemia", Leukemia & Lymphoma, Aug. 2013, vol. 54(8), pp. 1836-1839.
Mraz et al., "MicroRNAs in chronic lymphocytic leukemia pathogenesis and disease subtypes", Mar. 2009, vol. 50 (3), pp. 506-509.
Mraz et al., "miR-150 influences B-cell receptor signaling in chronic lymphocytic leukemia by regulating expression of GAB1 and FOXP1", Blood, 2014, vol. 124(1), pp. 84-95.
Musilova and Mraz, "MicroRNAs in B-cell lymphomas: how a complex biology gets more complex", Leukemia (2015), 1-14.

Nakanishi et al., "Cloning and sequence analysis of a cDNA encoding tetrameric carbonyl reductase of pig lung," Biochem. Biophys, Res. Commun. 194 (3): 1311-1316 (1993).
National Cancer Institute. AIDS-Related Lymphoma Treatment. 2015. www.cancer.gov/cancertopics/pdq/treatment/AIDS-related-lymphoma/Patient/page1.
NCBI, Nutritional and Metabolic Diseases, NCBI Bookshelf, 1998. <http://www.ncbi.nlm.nih.gov/books/NBK22259/>.
NCBI, The Nervous System, NCBI Bookshelf, 1998. <http://www.ncbi.nlm.nih.gov/books/NBK22197/>.
Nemazanyi et al., "3-Amino-4-aryl-1(2H)-isoquinolones," Chemistry of Heterocyclic Compounds 27 (3): 307-308 (1991).
Newman et al., "Solid-state analysis of the active pharmaceutical ingredient in drug products," Drug Discov. Today 8 (19): 898-905 (2003).
Nisitani et al., "Posttranscriptional regulation of Bruton's tyrosine kinase expression in antigen receptor-stimulated splenic B cells," PNAS 97 (6): 2737-2742 (2000).
Niswender et al., "Protein engineering of protein kinase a catalytic subunits results in the acquisition of novel inhibitor sensitivity," J. Biol. Chem, 277 (32): 28916-28922 (2002).
Nobel et al., "Purification of full-length recombinant human and rat type 1 11beta-hydroxysteroid dehydrogenases with retained oxidoreductase activities," Protein Expr. Purif. 26 (3): 349-356 (2002).
Sinclair et al., "Phosphatidylinositol-3 Kinase Delta (PI3Kd) Inhibitor AMG 319 is a Potent, Selective and Orally Bioavailable Small Molecule Inhibitor That Suppresses PI3K-Mediated Signaling and Viability in Neoplastic B Cells," Blood (ASH Annual Meeting Abstracts) 118: Abstract 4964 (2011).
Singer et al., "Optimization of in situ Hybridization Using Isotopic and Non-Isotopic Detection Methods," Biotechniques 4(3): 230-250 (1986).
Smith et al., "Expression of Bruton's Agammaglobulinemia Tyrosine Kinase Gene, BTK, is Selectively Down-Regulated in T Lymphocytes and Plasma Cells," J. Immunol. 152 (2): 557-565 (1994).
Soldan et al., "Induction of daunorubicin carbonyl reducing enzymes by daunorubicin in sensitive and resistant pancreas carcinoma cells," Biochem. Pharmacol. 51 (2): 117-123 (1996).
Song et al., "The antagonistic effect of PI3K-gamma inhibitor AS605240 on cardiac hypertrophy and cardiac fibrosis induced by isoproterenol in rats," Sichuan Da Xue Xue Bao Yi Xue Ban 42(1): 471-474 (2011) (abstract only).
Soond et al., "Pi3K p110delta regulates T-cell cytokine production during primary and secondary immune responses in mice and humans," Blood 115 (11): 2203-2213 (2010).
Srinivasan et al., "PI3 Kinase Signals BCR-Dependent Mature B Cell Survival," Cell 139 (3): 573-586 (2009).
Stanoeva et al., "Homophthalic anhydrides and their application to the synthesis of heterocyclic compounds (review)," Chemistry of Heterocyclic Compounds 20 (12): 1305-1315 (1984).
Stone, Richard. "Mast Cell Leukemia and Other Mast Cell Neoplasms." In: Kufe DW, Pollock RE, Weichselbaum RR, et al., editors. Holland-Frei Cancer Medicine. 6th Edition. Hamilton (ON): BC Decker, 2003. Available from: www.ncbi.nlm.nih.gov/books/NBK13427/.
Subramaniam et al., "Targeting Nonclassical Oncogenes for Therapy in T-ALL," Cancer Cell 21 (4): 459-472 (2012).
Sujobert et al., "Essential role for the p110delta isoform in phosphoinositide 3-kinase activation and cell proliferation in acute myeloid leukemia," Blood 106 (3): 1063-1066 (2005).
Supplementary European Examination Report EP Application No. 07754845.1 dated Sep. 20, 2011.
Supplementary European Search Report for EP Application No. 07754845 (4 pages) dated Feb. 24, 2010.
Supplementary European Search Report for EP Application No. 10800175.1 dated Nov. 7, 2012.
Suralkar et al., "In-Vivo Animal Models for Evaluation of Anti-Inflammatory Activity", Pharmainfo Reviews, vol. 6, Issue 2, Mar. 17, 2008.
Sykes et al., "Treatment of severe autoimmune disease by stem-cell transplantation," Nature 35 (7042): 620-627 (2005).

(56) References Cited

OTHER PUBLICATIONS

Sylvester Comprehensive Cancer Center, "Definition: Leukemia, Lymphoma and Myeloma," 2015. sylvester.org/cancer/leukemia-lymphoma-and-myeloma/education/definition.
Takeuchi et al., "Synergistic Augmentation of Rapamycin-Induced Autophagy in Malignant Glioma Cells by Phosphatidylinositol 3-Kinase/Protein Kinase B Inhibitors," Cancer Res. 65 (8): 3336-3346 (2005).
Tanaka et al., "An unbiased cell morphology-based screen for new, biologically active small molecules," PloS Biol. 3 (5): 0764-0776 (2005).
Thompson et al., "Identification of distinct populations of PI-3 kinase activity following T-cell activation," Oncogene 7 (4): 719-725 (1992).
Torbett et al., "A chemical screen in diverse breast cancer cell lines reveals genetic enhancers and suppressors of sensitivty of PI3K isoform-selectiveinhibition," Biochem. J. 415 (1): 97-110 (2008).
Treon et al., "A Prospective Multicenter Study of the Bruton's Tyrosine Kinase Inhibitor Ibrutinib in Patients with Relapsed or Refractory Waldenstrom's Macroglobulinemia," ASH Annual Meeting, Oral Presentation 251, Dec. 9, 2013.
Truitt et al., "Stimulation of CD28 triggers an association between CD28 and phosphatidylinositol 3-kinase in Jurkat T cells," J. Exp. Med. 179 (3): 1071-1076 (1994).
Tyukavkina et al., Bioorganicheskaya Khimiya, Moskva, DROFA, pp. 83-85 (2004).
Uddin et al., "Role of phosphatidylinositol 3'-kinaseIAKT pathway in diffuse large B-cell lymphoma survival," Blood 108 (13): 4178-4166 (2006).
Ugarkar et al., "Adenosine kinase inhibitors. 2. Synthesis, enzyme inhibition, and antiseizure activity of diaryltubercidin analogues," J. Med. Chem. 43 (15): 2894-2905 (2000).
Vandenberghe et al., "Antibody and B7/BB1-mediated ligation of the CD28 receptor induces tyrosine phosphorylation in human T cells," J. Exp. Med. 175 (4): 951-960 (1992).
Vanhaesebroeck et al., "PI3K: From the Bench to the Clinic and Back," Curr. Top. Microbiol. Immunol. 347: 1-19 (2010).
Vara et al., "PI3K/Akt Signalling Pathway and Cancer," Cancer Treat Rev. 30 (2): 193-204 (2001).
Vasilevsky et al., "Study of the Heterocyclization of vic-Substituted Hyrdazides of Acetylenylpyrazolecarboxylic Acids into N-Amino Pyrazolopyridinones," Journal of Heterocyclic Chemistry 39 (6): 1229-1233 (2002).
Vasilevsky et al., "Unexpected results in the heterocyclization of 5-acetylenylpyrazole-4-carboxylic acid hydrazides under the influence of CuCl: Formation of a diazepinone and dehydrociimerization into the corresponding bis(pyrazolo [4,3-d][1,2] diazepinone)," Tetrahedron Lett. 46 (26):4457-4459 (2005).
Venable et al., "Phosphoinositide 3-Kinase Gamma (PI3K$_i$) Inhibitors for the Treatment of Inflammation and Autoimmune Disease", Inflammation & Allergy Drug Discovery, vol. 4, No. 1, pp. 1-15, 2010.
Viardot et al., "Clinicopathologic Correlations of Genomic Gains and Losses in Follicular Lymphoma," Journal of Clinical Oncology 20(23): 4523-4530 (2002).
Vippagunta et al., "Crystalline Solids," Adv. Drug Deliv. Rev. 48 (1): 3-26 (2001).
Vitali et al., "Immunotherapy in rheumatoid arthritis: a review," Int. J. Artif. Organs 16 Suppl. 5: 196-200 (1993).
Vlahos et al., "A specific inhibitor of phosphatidylinositol 3-kinase, 2-(4-morpholinyl)-8-phenyl-4H-1-benzopyran-4-one (LY294002)," J. Biol. Chem. 269 (7): 5241-5248 (1994).
Vogt et al., "Phosphatidylinositol 3-kinase: the oncoprotein," Curr. Top Microbiol. Immunol. 347: 79-104 (2010).
Vogt et al., "Phosphoinositide 3-kinase: from viral oncoprotein to drug target," Virology 344 (1): 131-138 (2006).
Vora et al., "CDK 4/6 Inhibitors Sensitize PIK3CA Mutant Breast Cancer to PI3K Inhibitors," Cancer Cell 26: 136-149 (2014).

Wagner et al., "A First-in-Human Phase 1 Study to Evaluate the Pan-PI3K Inhibitor GDC-0941 Administered QD or BID in Patients with Advanced Solid Tumors," J. Clin. Oncol. 27: 146s (Suppl, Abstr 3501) (2009).
Wahlstrom et al., "Aberrant MAPK and PI3K Signaling Contribute to Chemotherapy Resistance in T Cell Acute Lymphoblastic Leukemia by Altering the Balance of Apoptosis Mediators," Blood (ASH Annual Meeting Abstracts) 118: Abstract 3490 (2011).
Ward et al., "Inhibition of CD28-mediated T cell costimulation by the phosphoinositide 3-kinase inhibitor wortmannin," Eur. J. Immunol. 25 (2): 526-532 (1995).
Ward et al., "Ligation of CD28 receptor by B7 induces formation of D-3 phosphoinositides in T lymphocytes independently of T cell receptor/CD3 activation," Eur. J. Immunol. 23 (10): 2572-2577 (1993).
Ward et al., "Regulation of D-3 phosphoinositides during T cell activation via the T cell antigen receptor/CD3 complex and CD2 antigens," Eur. J. Immunol. 22 (1): 45-49 (1992).
Ward et al., "Regulation of phosphoinositide kinases in T cells, Evidence that phosphatidylinositol 3-kinase is not a substrate for T cell antigen receptor-regulated tyrosine kinases," J. Biol. Chem. 267 (33) 23862-23869 (1992).
Ward et al., "Therapeutic potential of phosphoinositide 3-kinase inhibitors," Chem. Biol. 10 (3): 207-213 (2003).
WebMD, HIV & AIDS Health Center HTLV Type I and Type II. 2014. www.webmd.com/hiv-aids/htlv-type-i-and-type-ii.
WebMD, Chronic Myeloproliferative Disorders. 2014. webmd.com/cancer/tc/chronic-myeloproliferative-disorders-treatment-patient-information-nci-pdq-general-information.
WebMD, Leukemia-Prevention. Cancer Health Center. 2012. www.webmd.com/cancer/tc/leukemia-prevention.
WebMD, Lung Diseases Overview. (2014). <http://www.webmd.com/lung/lung-diseases-overview>.
Extended European Search Report from European Application No. 09700784.3 dated Oct. 28, 2011.
Fajans et al., "Maturity onset diabetes of the young (MODY)," Diabet. Med. 13(9 Suppl 6): S90-S95 (1996).
Feinstein et al., "Regulation of the action of hydrocortisone in airway epithelial cells by 11beta-hydroxysteroid dehydrogenase," Am. J. Respir. Cell. Mol. Biol. 21(3): 403-408 (1999).
Feldman et al., "Active-Site Inhibitors of mTOR Target Rapamycin-Resistant Outputs of mTORC1 and mTORC2," PLoS Biol. 7(2): 371-383 (2009).
Fingl et al., "Chapter 1—General Principles," The Pharmacological Basis of Therapeutics, 5th edition, Goodman and Gilman editors, MacMillan Publishings Co., Inc., New York, pp. 1-46 (1975).
Flinn et al., "Clinical Safety and Activity in a Phase 1 Trial of IPI-145, a Potent Inhibitor of Phosphoinositide-3-Kinase-delta,gamma, in Patients with Advanced Hematologic Malignancies," Blood 120(21), p. 3663 (2012).
Forrest et al., "Carbonyl Reductase," Chem. Biol. Interact. 129(1-2): 21-40 (2000).
Forrest et al., "Induction of a human carbonyl reductase gene located on chromosome 21," Biochem. Biophys. Acta. 1048 (2-3): 149-155 (1990).
Franzen, "The Suzuki, the Heck, and the Stille reaction—three versatile methods for the introduction of new C—C bonds on solid support," Can. J. Chem. 78(7): 957-962 (2000).
Fruman et al., "PI3K[delta] inhibitors in cancer: Rationale and serendipity merge in the clinic," Cancer Discovery 1(7), pp. 565-572 (2011).
Fulci et al., "Quantitative technologies establish a novel microRNA profile of chronic lymphocytic leukemia", Blood, 2007, vol. 109(11), pp. 4944-4951.
Funder et al., "Mineralocorticoid action: target tissue specificity is enzyme, not receptor, mediated," Science 242: 583-585 (1998).
Fung-Leung, W.P., "Phosphoinositide 3-kinase delta (PI3Kdelta in leukocyte signaling and function," Cell Signal. 23 (4): 603-608 (2011).
Furman et al., "CAL-101, An Isoform-Selective Inhibitor of Phosphatidylinositol 3-Kinase P110d, Demonstrates Clinical Activity and Pharmacodynamic Effects in Patients with Relapsed or

(56) References Cited

OTHER PUBLICATIONS

Refractory Chronic Lymphocytic Leukemia" Blood (ASH Annual Meeting Abstracts) 116, Abstract 55 (2010).
Furukawa, T., "Molecular Targeting Therapy for Pancreatic Cancer: Current Knowledge and Perspectives from Bench to Bedside," J. Gastroenterol. 43(12): 905-911 (2008).
Garber et al., "Diversity of gene expression in adenocarcinoma of the lung," Proc. Natl. Acad. Sci. U.S.A. 98(24): 13784-13789 (2001).
Ghigo et al., "PI3K Inhibition in Inflammation: Toward Tailored Therapies for Specific Diseases", BioEssays 32, pp. 185-196 (2010).
Gillespie et al., "Antagonists of the human adenosine A2A receptor. Part 3: Design and synthesis of pyrazolo[3,4-d] pyrimidines, pyrrolo[2,3-d]pyrimidines and 6-arylpurines," Bioorg. Med. Chem. Lett. 18(9): 2924-2929 (2008).
Gonzalez et al., "Protection against daunorubicin cytotoxicity by expression of a cloned human carbonyl reductase cDNA in K562 leukemia cells," Cancer Res. 55(20): 4646-4650 (1995).
Graber et al., "The protein tyrosine kinase inhibitor herbimycin A, but not genistein, specifically inhibits signal transduction by the T cell antigen receptor," Int. Immunol. 4(11): 1201-1210 (1992).
Graham et al., "The TAM family: phosphatidylserinesensing receptor tyrosine kinases gone awry in cancer", Nature Rev Cancer, 2014; vol. 14, pp. 769-785.
Graupera et al., "Angiogenesis selectively requires the p110alpha isoform of PI3K to control endothelial cell migration," Nature 453 (7195): 662-666 (2008).
Gunther et al., "Acute pathological effects on rats of orally administered wortmannin-containing preparations and purified wortmannin from Fusarium oxysporum." Fd. Chem. Toxicol. 27(3): 173-179 (1989).
Gunther et al., "Immunosuppressive effectsof dietary wortmannin on rats and mice," Immunopharmacol. Immunotoxicol. 11(4): 559-570 (1989).
Haase et al., "Detection of viral nucleic acids by in situ hybridization," Methods in Virology 7: 189-226 (1984).
Hall and Kang, "The dual PI3K/mTOR inhibitor NVP-BEZ235 enhances dexamethasone induced apoptosis in models of T-cell ALL with PTEN dysfunction and hyperactivated PI3K/Akt pathway," Cancer Research 73(8): supplement 1, abstract 2757 (2013).
Haluska et al., "The RTK/RAS/BRAF/PI3K Pathways in Melanoma: Biology, Small Molecule Inhibitors, and Potential Applications," Semin. Oncol. 34 (6): 546-554 (2007).
Hanefeld et al., "One-pot synthesis of tetrasubstituted pyrazoles—proof of regiochemistry," J. Chem. Soc., Perkin Trans. 1: 1545-1552 (1996).
Harada et al., "Novel role of phosphatidylinositol 3-kinase in CD28-mediated costirnulation," J. Biol. Chem. 276(12): 9003-9008 (2001).
Harding et al., "CD28-mediated signalling co-stimulates murine T cells and prevents induction of anergy in T-cell clones," Nature 356(6370): 607-609 (1992).
Harris et al., "PI3K isoforms as drug targets in inflammatory diseases: Lessons from pharmacological and genetic strategies," Curr. Opin. in Inv. Drugs 10(11): 1151-1162 (2009).
Hasselblom et al., "High immunohistochemical expression of p-AKT predicts inferior survival in patients with diffuse large B-cell lymphoma treated with immunochemotherapy," Brit. J. Haematol. 149 (4): 550-568 (2010).
Haylock-Jacobs et al., "PI3Kdelta drives the pathogenesis of experimental autoimmune encephalomyelitis by inhibiting effector T cell apoptosis and promoting Th17 differentiation," J. Autoimmun. 36: 278-287 (2011).
Hellwinkel et al., "Heterocyclensynthesen mit MF/A1203-basensystemen; 2-arylbenzofurane and 2,3-diarylisochinolin-1 (2H)-one," Synthesis 1995(9): 1135-1141 (1995).
Henderson et al., "Delineation of a Minimal Region of Deletion at 6q16.3 in Follicular Lymphoma and Construction of a Bacterial Artificial Chromosome Contig Spanning a 6-Megabase Region of 6q16-q21," Genes, Chromosomes & Cancer 40: 60-65 (2004).

Herishanu et al., "The lymph node microenvironment promotes B-cell receptor signaling, NF-kB activation, and tumor proliferation in chronic lymphocytic leukemia," Blood 117(2): 563-574 (2011).
Herman et al., "Molecular Pathways: Targeting the Phosphoinositide 3-Kinase (PI3-Kinase) p110 delta in Chronic Lymphocytic Leukemia" Clin. Cancer Res., ePub Jun. 18, 2012, Aug. 2012, vol. 18, pp. 4013-4018.
Herman et al., "Phosphatidylinositol 3-kinase-delta inhibitor CAL-101 shows promising preclinical activity in chronic lymphocytic leukemia by antagonizing intrinsic and extrinsic cellular survival signals," Blood 116(12): 2078-2088 (2010).
Herman et al., "The role of phosphatidylinositol 3-kinase-delta in the immunomodulatory effects of lenalidomide in chronic lymphocytic leukemia," Blood 117 (16): 4323-4327 (2011).
Herrera et al., "The dual PI3K/mTOR inhibitor BEZ235 is effective in lung cancer cell lines," Anticancer Res. 31(3): 849-854 (2011).
Hickey et al., "BCR-ABL Regulates Phosphatidylinositol 3-Kinase-p110gamma Transcription and Activation and is Required for Proliferation and Drug Resistance," J. Biol. Chem. 281(5): 2441-2450 (2006).
Higgs et al., "Patients with systemic lupus erythematosus, myositis, rheumatoid arthritis and scleroderma share activation of a common type I interferon pathway," Ann. Rheum. Dis. 70: 2029-2036 (2011).
Hirsch et al., "CALming Down T Cell Acute Leukemia," Cancer Cell 21(4): 449-450 (2012).
Hirsch et al., "Central Role for G Protein-Coupled Phosphoinositide 3-Kinase gamma in Inflammation," Science 287 (5455): 1049-1053 (2000).
Hoe et al., "Drugging the p53 pathway: understanding the route to clinical efficacy," Nature Reviews Drug Discovery 13: 217-236 (2014).
Hoellenriegel and Burger, "Phosphoinositide 3'-kinase delta: turning off BCR signaling in Chronic Lymphocytic Leukemia," Oncotarget 2(10): 737-738 (2011).
Hoellenriegel et al., "Phosphoinositide 3'kinase (PI3K) Delta Inhibition with CAL-101 Blocks B-cell Receptor (BCR) Signaling and the Prosurvival Actions of Nurse-Like Cells (NLC) in Chronic Lymphocytic Leukemia (CLL)," (ASH Annual Meeting 2010).
Hoellenriegel et al., "The phosphoinositide 3'-kinase delta inhibitor, CAL-101, inhibits B-cell receptor signaling and chemokine networks in chronic lymphocytic leukemia," Blood 118(13): 3603-3612 (2011).
Honigherg et al., "The Bruton tyrosine kinase inhibitor PCI-32765 blocks B-Cell activation and is efficacious in models of autoimmune disease and B-cell malignancy," PNAS 107(29): 13075-13080 (2010).
Ikeda et al., "PI3K/p110delta is a novel therapeutic target in multiple myeloma," Blood 116(9): 1460-1468 (2010).
Wei et al., "A phosphoinositide 3-kinase-gamma inhibitor, AS605240 prevents bleomycin-induced pulmonary fibrosis in rats," Biochem. Biophy. Res. Comm. 397: 311-317 (2010).
Wen et al., "Current Clinical Development of P13K Pathway Inhibitors in Glioblastoma", Neuro-Oncology 14 (7):819-829, ePub May 22, 2012, 2012.
White et al., "11beta-Hydroxysteroid Dehydrogenase and the Syndrome of Apparent Mineralocorticoid Excess," Endocr. Rev. 18 (1): 135-156 (1997).
Widler et al., "7-alkyl- and 7-Cycloalkyl-5-aryl-pyrrolo[2,3-d]pyrimidines—potent inhibitors of the tyrosine kinase c-Src," Bioorg. Med. Chem. Lett. 11 (6): 849-852 (2001).
Wiesinger et al., "Antiinflammatory activity of the new mould metabolite 11-desacetoxy-wortmannin and of some of its derivates," Experientia 30 (2): 135-136 (1974).
Winkler et al., "PI3K-delta and PI3K-gamma Inhibition by IPI-145 Abrogates Immune Responses and Suppresses Activity in Autoimmune and Inflammatory Disease Models," Chemistry & Biology 20: 1-11 (2013).
Wolff, Burger's Medicinal Chemistry, 5th ed, Part 1, pp. 975-977, John Wiley & Sons (1995).
Wong et al., "Targeting the PI3K signaling pathway in Cancer," Current Opinion in Genetics & Development, vol. 20, (2010), pp. 87-90.

(56) References Cited

OTHER PUBLICATIONS

Woscholski et al., "A comparison of demethoxyviridin and wortmannin as inhibitors of phosphatidylinositol 3-kinase," FEBS Lett. 342 (2): 109-114 (1994).
Woyach et al., "Resistance Mechanisms for the Bruton's Tyrosine Kinase Inhibitor Ibrutinib," N. Engl. J. Med. 370: 2286-2294 (2014).
Wu et al., "Decreased immunological responses by wortmannin-containing rice culture of Fusarium oxysporum and by purified wortmannin in avian species," Immunopharmacol. Immunotoxicol. 14 (4): 913-923 (1992).
Wu et al., "Wortmannin (a mycotoxin) inhibited immune responses in chickens," Poultry Sci. Vo. 71, Suppl 1, pp. 13 (1992).
Wymann et al., "Phosphoinositide 3-kinase g: a key modulator in inflammation and allergy", 2003, Biochem Soc. Transactions. 31, Par I, pp. 275-280.
Yaguchi et al., "Antitumor activity of ZSTK474, a new phosphatidylinositol 3-kinase inhibitor," J. Natl. Cancer Inst. 98 (8): 545-556 (2006).
Yang et al., "A novel activation pathway for mature thymocytes. Costimulation of CD2 (T,p50) and CD28 (T,p44) induces autocrine interleukin 2/interleukin 2 receptor-mediated cell proliferation," J. Exp. Med. 168 (4): 1457-1468 (1988).
Yano et al., "Inhibition of histamine secretion by wortmannin through the blockade of phosphatidylinositol 3-kinase in RBL-2H3 cells," J. Biol. Chem. 268 (34): 25846-25856 (1993).
Yoshida et al., "Quercetin arrests human leukemic T-cells in late G1 phase of the cell cycle," Cancer Res. 52 (23): 6676-6681 (1992).
Zhao and Vogt, "Class I PI3K in oncogenic cellular transformation," Oncogene 27 (41): 5486-5496 (2008).
Zhao et al., "TNF-a promotes LPA1- and LPA3-mediated recruitment of leukocytes in vivo through CXCR2 ligand chemokines," J. Lipid Research 52: 1307-1318 (2011).
Akinleye et. al., "Phosphatidylinositol 3-Kinaase (PI3K) inhibitors as cancer therapeutics", Journal of Hematology & Oncology, Nov. 2013, vol. 6:88 (pp. 1-18).
Ashizawa, Kazuhide, "Science polymorphismand crystallization in pharmaceutical products", Maruzen Planet Co., Sep. 20, 2002, pp. 3-16.
Balakrishnan et al., "Inhibition of PI3K-delta and -y Isoforrns by IPI-145 in Chronic Lymphocytic Leukemia Overcomes Signals From PI3K/AKT/S6 Pathway and Promotes Apoptosis", ASH Annual Meeting, Dec. 2013, Poster 4167.
Buet et al., "Cotargeting signaling pathways driving survival and cell cycle circumvents resistance to Kit inhibitors in leukemia", Blood, vol. 119, No. 18, 3 May 2012, pp. 4228-4241.
CAL-101, PubChem CID 11625818, created date Oct. 26, 2006.
Campbell, et al., "The Potent PI3K-delta Inhibitor, IPI-145, Exhibits Differential Activity in Diffuse Large B-cell Lymphoma (DLBCL) Cell Lines", Dec. 7, 2013, 55th ASH Annual Meeting and Exposition, New Orleans, LA, Poster 1832.
Cao et al., "The BCL2 antagonist ABT-199 triggers apoptosis, and augments ibrutinib and idelalisib mediated cytotoxicity in; CXCR4Wildtype and CXCR4WHIM mutated Watdenstram macroglabulinaemia cells", British Journal of Haematology, vol. 170, online Jan. 12, 2015, pp. 134-138.
Chabner et. al., "Che herapy and the war on cancer", Nature Reviews Cancer, 2005, Nature Publishing Group, vol. 5, pp. 65-72.
Chang et al., "Novel Synthesis and Reactions of 5,7-Dialkyl-4,6-dioxo-4,5,6,7-tetrahydro-isothiazolo[3,4,-d] pyrimidine-3-carbonitriles and 6-Methyl-4-oxo-4H-1-aza-5-oxa-2-thiaindene-3-carbonitrile", Org. Lett. (5)4: 507-510 (2003).
Chang et al., "PI3-Kinase Inhibitors in Chronic Lymphocytic Leukemia", Current Hematologic Malignancy Reports, vol. 9, No. 1, pp. 33-43 (2014).
Chemical Society of Japan ed., Jikken kagaku kouza (zoku), 2. Bunri to seisei (Experimental chemical lecture, second series, 2. Separation and purification), Maruzen Co., Ltd., Jan. 25, 1967, pp. 159-178, 186-187.

Chiron et al., "791 Induction of Early G1-Arrest by CDK4/CDK6 Inhibition Sensitizes Mantle Cell Lymphoma Cells to Selective PI3Kdelta Inhibition by GS-1101 Through Enhancing the Magnitude and Duration of p-AKT Inhibition", American Society of Hematology, Dec. 10, 2013, retrieved from the internet: https://ash.confex.com/ash/2012/webprogram/Paper52021.html.
Choudhary et al., "MCL-1 and BCL-xL-dependent resistance to the BGL-2 inhibitor ABT-199 can be overcome by preventing PI3KJ AKT/mT4R activation in lymphoid malignancies", Cell Death & Disease 2015, vol. 6, 2015, online 15.01.2015, p. e1593.
D'Cruz et. al., "Protein kinase inhibitors against malignant lymphoma", Expert Opinion on Pharmacotherapy, Mar. 2013, Taylor & Francis Group, vol. 14(6), pp. 707-721.
Dinitto et al., "Biochemical and Cellular Characterization of IPI-145, a Potent PI3K-delta,y Inhibitor", PI 3-Kinase and Signaling Interplay with Other Signaling Pathways, Feb. 25, 2013, Keystone, Colorado.
Douglas et al. "Treatment with the Potent PI3K-o,y Inhibitor IPI-145 is Associated with Rapid Decreases in Specific Cytokines, Chemokines and Matrix Metalloproteinases in the Serum of Patients with Chronic Lymphocytic Leukemia and Indolent Non-Hodgkin Lymphoma", 55th ASH Annual Meeting and Exposition, Dec. 7, 2013, New Orleans, LA.
Douglas et al., "Serum Chemokines and Cytokines in CLL Patients Treated with Duvelisib, a PI3K-delta,gamma Inhibitor", American Society of Clinical Oncology (ASCO) Annual Meeting 2015, May 29-Jun. 2, Chicago, IL.
Equivalent Surface Area Dosage Conversion Factors (https://ncifrederick.cancer.gov/lasp/acuc/frederick/Media/Documents/ACUC42.pdf, Aug. 2007).
Flinn et al., "Preliminary Safety and Efficacy of IPI-145 a Potent Inhibitor of Phosphoinositide 3 Kinase-delta, y, in Patients with Relapsed/Refractory CLL/SLL", 12th International Conference on Malignant Lymphoma, Jun. 22, 2013, Lugano, Switzerland.
Flinn et al., "Preliminary Safety and Efficacy of IPI-145, a Potent Inhibitor of Phosphoinositide-3-Kinase-?,?, In Patients With Chronic Lymphocytic Leukemia", Blood, vol. 122, No. 21, Nov. 2013, p. 677.
Flinn et al., "DUO: A Phase 3 Trial of the PI3K-delta,y Inhibitor IPI-145 Versus Ofatumumab in Patients with Relapsed or Refractory Chronic Lymphocytic Leukemia or Small Lymphocytic Lymphoma", American Society of Clinical Oncology (ASCO), Annual Meeting 2014, Jun. 2, Chicago, IL.
Flinn, I., "A Phase 1 Evaluation of Duvelisib (IPI-145), a PI3K-delta, gamma Inhibitor, in Patients with Relapsed/Refractory iNHL", American Society of Hematology Meeting, Dec. 6, 2014.
Flinn, I.W., et al., "Preliminary Evidence of Clinical Activity in a Phase I Study of CAL-101, a Selective Inhibitor of the p1108 Isoform of Phosphatidylinositol 3-Kinase (PI3K), in Patients with Select Hematologic Malignancies," J. Clin. Oncol. 27:156s (Suppl: Abstr 3543) (2009).
Goodman, A., "Encouraging Early Results With Novel Agents in CLL", The ASCO Post, Mar 1, 2014, Reterieved from the internet: URL: http://www.ascopost.com/issues/march-1,-2014/encouraging-early-results-with-novel-agents-in-cll.aspx.
Harb et al., "Combined Pharmacologic Inhibition of Bcl-XI/Bcl-2 and mTORC1/2 Survival Signals Trigger Apoptosis in BCR-ABL1+ in Vitro Models of Blast Crisis Chronic Myelogenous Leukemia (CML-BC), and Primary CD34+35 /CD38− Stem and CD34+ progenitor Cells From CML-BC Patients", Blood, 53rd Ash Annual Meeting and Exposition, San Diego, CA, Dec. 10-13, 2011, Retrieved from the Internet: URL:https://ash.confex.com/ash/2011/Jwebprogram/Paper44381.html.
Horwitz et al. "Preliminary Safety and Efficacy of IPI-145, a Potent Inhibitor of Phosphoninositide-3-Kinase-delta,y, in patients with Relapsed/Refractory Lymphoma", ASCO, Lymphoma, Oral Presentation, Jun. 3, 2011.
Horwitz et al., "Clinical Activity of IPI-145, a Potent inhibitor of Phosphoinositide-3-Kinase-delta,y, in Patients with Relapsed/Refractory T-Cell Lymphoma: Preliminary Results from an Ongoing Phase 1 Study", 6th Annual T-cell Lymphoma Fomm Jan. 23-25, 2014, San Francisco, CA.

(56) References Cited

OTHER PUBLICATIONS

Horwitz et al., "Duvelisib (IPI-145), a Phosphoinositide-3-Kinase-delta, gamrraa Inhibitor, Shows Activity in Patients with Relapsed/Refractory T-Cell Lymphoma," American Society of Hematology Meeting, Dec. 6, 2014.
Horwitz et al., "Preliminary Safety and Efficacy of IPI-145, a potent Inhibitor of Phosphoinositide-3-Kinase-delta,y, in Patients with Relapsed/Refractory Lymphoma", 12th International Conference on Malignant Lymphoma, Jun. 19, 2013, Lugano, Switzerland.
Huang et al., "The Potent PI3K delta,y Inhibitor, IPI-145, Exhibits Preclinical Activity in Murine and Human T-Cell Acute Lymphoblastic Leukemia", 55th ASH Annual Meeting and Exposition, Dec. 7, 2013, New Orleans, LA.
Infinity Pharmaceuticals, Inc., "Infinity Reports Preclinical Data at ASH Annual Meeting in Diffuse Large B-Cell Lymphoma and T-Cell Acute Lymphoblastic Leukemia Suggesting Broad Potential of IPI-145 in Blood Cancers", http://businesswire.com, Dec. 7, 2013, Downloaded from the internet: http://www.businesswire.com/news/home/20131207005015/en/infinity-Reports-Preclinical-Data-ASH-Annual-Meeting.
Leaf, "Why We're Losing the War on Cancer—and How to Win it", Fortune, Mar. 9, 2004, Time Inc., pp. 1-28.
Letai et al., "Antipoptotic BCL-2 is required for maintenance of a model leukemia", Cancer Cell, vol. 6, No. 3, Sep. 1, 2004, pp. 241-249.
Linhua et al., "Efficacy and Mechanisms of Apoptosis Induction by Simultaneous Inhibition of PI3K with GDC-0941 and Blockade of Bcl-2 (ABT-737) or FLT3 (Sorafenib) in AML Cells in the Hypoxic Bone Marrow Microenvironment", Blood, vol. 116, 2010, 777.
Liu et al., "Improved syntheses of alpha-BOC-aminoketones from alpha-BOC-amino-Weinreb amides using a pre-deprotonation protocol", Tetrahedron Letters, vol. 43, Issue 46, 11 Nov. 2002, pp. 8223-8226.
Martin-Sanchez et al., "Simultaneous inhibition of pan-phosphatidylinositol-3-kinases and MEK as a potential therapeutic strategy in peripheral T-cell lymphomas", Haematologica, vol. 98, No. 1, Jan. 2013, pp. 57-64.
Mashkovskiy, Lekarstvennye sredstva, vol. 1, 2001, p. 11.
Milella et al., 566 POSTER Anti-leukemic activity of the novel MEK Inhibitor PD0325901, European Journal of Cancer Supplement, vol. 4, Iss 12, Nov. 1, 2006, p. 112.
Morrison, C., "First P13k inhibitor launches info crowded hematology markets", Nature Biotechnology, vol. 32, No. 10, online Oct. 9, 2014, pp. 963-964.
Muranen et al., "Inhibition of P13K/mTOR Leads to Adaptive Resistance in Matrix-Attached Cancer Cells", Cancer Cell, vol. 21, No. 2, Dec. 20, 2011, pp. 227-239.
Muranen et al., "Promising Rationally Derived Combination Therapy with PI3K and CDK4/6 Inhibitors", Cancer Cell, vol. 26, No. 1, Jul. 14, 2014, pp. 7-9.
Nakai, Yoshinobu et al., New galenical pharmacy, Nanzando Co., Ltd., Apr. 25, 1984, pp. 102-103, 232-233.
Nishigaki, Sadao, Dispensing pharmacy (Principle and Application), Nanzando Co., Ltd., Sep. 20, 1977, pp. 142-145.
O'Brien et al., "Duvelisib (IPI-145), a PI3K-delta,y Inhibitor, is Clinically Active in Patients with Relapsed/Refractory Chronic Lymphocytic Leukemia", 56th ASH Annual Meeting and Exposition, Dec. 7, 2014, San Francisco, CA.
O'Connor, "Adult T-Cell Leukemia/Lymphoma (HTLV-1)", Lymphoma Research Foundation, 2008, pp. 1-4.
Okano, Teisuke, New general remarks of practical pharmacy, 3rd ed., Nankodo Co., Ltd, Apr. 10, 1987, pp. 111.
Okkenhaug, K., "Two Birds with One Stone: Dual p110? and p110? Inhibition", Chemistry and Biology, vol. 20, No. 11, Nov. 1, 2013, pp. 1309-1310.
Oltersdorf et al., "An inhibitor of Bcl-2 family proteins induces regression of solid tumour", Nature, vol. 435, Jun. 2, 2005, pp. 677-681.
Palombella et al., "Development of the Potent PI3K-delta,y Inhibitor IPI-145", Oral Presentation, Keystone, Feb. 25, 2013.
Palombella et al., "Targeting PI3K-delta and PI3K-y in Inflammation", NYAS Jun. 27, 2012.
Patel et al., "Immunopathological aspects of age-related macular degeneration", Seminars in Immunopathology, 2008, vol. 30, No. 2, pp. 97-110.
Patel et al., "Preliminary Safety and Efficacy of IPI-145, a Potent Inhibitor of Phosphoinositide-3-Kinase-δ, γ in Patients with Relapsed/Refractory CLL", American Society of Clinical Oncology (ASCO), Annual Meeting 2013, Jun. 2, Chicago, IL.
Peluso et al., "Duvelisib(IPI-145) Inhibits Malignant B-Cell Proliferation and Disrupts Signaling from the Tumor Microenvironment through Mechanisms That are Dependent on PI3K-delta and PI3K-y", Oral Presentation, 56th ASH Annual Meeting and Exposition, Dec. 7, 2014, San Francisco, CA.
Porcu et al., "Clinical Activity of Duvelisib (IPI-145), a Phosphoinositide-3-Kinase-delta,y Inhibitor, in Patients Previously Treated with Ibrutinib", 56th ASH Annual Meeting and Exposition, Dec. 7, 2014, San Francisco, CA.
Porter et al., "Development of the Potent PI3K-delta,y Inhibitor IPI-145 in Hematologic Malignancies and Inflammatory Disease Indications", 245th National ACS meeting, New Orleans, LA, Apr. 7, 2013.
Qian et al., "Synergy between phosphatidylinositol 3-kinase/Akt pathway and Bcl-xL in the control of apoptosis in adertocarcinoma cells of the lung", Molecular Cancer Therapeutics, vol. 8, No. 1, Jan. 1, 2009, pp. 101-109.
Rahmani et al., "Dual Inhibition of Bcl-2 and Bcl-xL Strikingly Enhances PI3K Inhibition-Induced Apoptosis in Human Myeloid Leukemia Cells through a GSK3- and Bim-Dependent Mechanism", Cancer Research, vol. 73, No. 4, Feb. 2013, pp. 1340-1351.
Roberts et al., "Substantial Susceptibility of Chronic Lymphocytic Leukemia to BCL2 Inhibition: Results of a Phase I Study of Navitoclax in Patients With Relapsed or Refractory Disease", Journal of Clinical Oncology, vol. 30, No. 5, Feb. 10, 2012, pp. 488-496.
Schwamb et al., "B-cell receptor triggers drug sensitivity of primary CLL cells by controlling glucosylation of ceramides", Blood, vol. 120, No. 19, Nov. 8, 2012, pp. 3978-3985.
Seymour et al., "Bcl-2 Inhibitor ABT-199 (GDC-0199) Monotherapy Shows Anti-Tumor Activity Including Complete Remissions in High-Risk Relapsed/Refractory (R/R) Chronic Lyrriphocytic Leukemia (CLL) and Small Lymphocytic Lymphoma (SLL)", Blood, vol. 122, No. 21, Nov. 2013, p. 872.
Simioni et al., "Cytotoxic activity of the novel Akt inhibitor, MK-2206, in T-cell acute lymphoblastic leukemia", Leukemia, Vo. 26, No. 11, Nov. 2012, pp. 2336-2342.
Tong et al., "Perifosine induces protective autophagy and upregulation of ATG5 in human chronic myelogenous leukemia cells in vitro", Acta Pharmacologica Sinica, vol. 33, No. 4, pp. 542-550 (2012).
Vachhani et al., "Rational combination of dual PI3K/mTOR blockade and Bcl-2/-xl inhibition in AML", Physiological Genomics, vol. 46, No. 13, Jul. 1, 2014, pp. 448-456.
Veliz et al., "Treatment of relapsed or refractory chronic lymphocytic leukemia", Cancer Control, 2012, vol. 19, pp. 37-53.
Wagner-Johnston et al., "DYNAMO: A Phase 2 Trial of the PI3K-delta,y Inhibitor IPI-145 in Patients with Refractory Indolent non-Hodgkin Lymphoma", American Society of Clinical Oncology (ASCO), Annual Meeting 2014, Jun. 2, Chicago, IL.
White et al., "The Combination of Duvelisib with Either Dexamethasone or Ibrutinib Prevents mTOR-Dependent Feedback in Aggressive B-Cell Lymphoma Cell Lines", Presented at the AACR Annual Meeting 2016. Apr. 17, 2016. New Orleans, LA.
Winkler et al., "Targeting PI3K-delta,gamma in Inflammatory and Autoimmune Disease", RA Keystone, Jan. 2012, Oral Presentation.
Wullschleger et al., "Quantitative MRI Establishes the Efficacy of PI3K Inhibitor (GDC-0941) Multi-Treatments in Men-deficient Mice Lymphoma", Anticancer Research, vol. 32, No. 2, pp. 415-420 (2012).
Zhu et al., "PI3K inhibition potentiates Bcl-2-dependent apoptosis in renal carcinoma cells", Journal of Cellular and Molecular Medicine, vol. 17, No. 3, Mar. 2013, pp. 377-385.

(56) References Cited

OTHER PUBLICATIONS

Schneider et al, "Molecular mechanisms by which BAY 80/6946 induces apoptosis in breast tumor cells as single agent or in combination," AACR 102nd Annual Meeting of the American Association for Cancer Research, Apr. 2011, Poster & Abstract 3833 (4 pages).

Liu et al, "BAY 80/6946, a highly selective and potent pan-class I PI3K inhibitor, induces tumor apoptosis in vitro and tumor regression in vivo in a subset of tumor models," AACR 101st Annual Meeting of the American Association for Cancer Research, Apr. 2010, Poster & Abstract 4476 (3 pages).

Arteaga, C.L., "Clinical development of phosphatidylinositol-3 kinase pathway inhibitors," in Phosphoinositide 3-kinase in health and disease, Rommel, C. et al (eds), Springer, New York, 2010, vol. 2, pp. 189-208.

Flinn et al, "Clinical Safety and Activity in a Phase 1 Trial of IPI-145, a Potent Inhibitor of Phosphoinositide-3-Kinase-gamma-delta, in Patients with Advanced Hematologic Malignancies," Blood, 2012, vol. 120, 3663 (3 pages).

Flinn et al, poster presented at the ASH annual meeting and exposition, Dec. 10, 2012, Atlanta, Georgia (2 pages).

Cho et al, "Targeting apoptosis in renal cell carcinoma (RCC): In vitro synergy between ABT-737 and inhibition of PI3-Kinase in RCC cell lines," AACR annual meeting, Apr. 2009 (2 pages).

Wilson et al, "The Bruton's Tyrosine Kinase (BTK) Inhibitor, Ibrutinib (PCI-32765), Has Preferential Activity in the ABC Subtype of Relapsed/Refractory De Novo Diffuse Large B-Cell Lymphoma (DLBCL): Interim Results of a Multicenter, Open-Label, Phase 2 Study," Blood, 2012, vol. 120, 686 (4 pages).

Porter et al, "The Potent Phosphoinositide-3-Kinase-(delta,gamma) Inhibitor IPI-145 Is Active in Preclinical Models of Arthritis and Well Tolerated in Healthy Adult Subjects," Acr/Arnp annual meeting, Nov. 2012, Poster & Abstract 338 (6 pages).

Ringshausen et al, "Constitutively activated phosphatidylinositol-3 kinase (PI-3K) is involved in the defect of apoptosis in B-CLL: association with protein kinase C-delta," Blood, 2002, vol. 100, No. 10, pp. 3741-3748.

Herman et al, "Phosphatidylinositol 3-kinase-delta inhibitor CAL-101 shows promising preclinical activity in chronic lymphocytic leukemia by antagonizing intrinsic and extrinsic cellular survival signals," Blood, 2010, vol. 116, No. 12, pp. 2078-2088.

Crombie, J.L. et al. (2019) "A Phase 1 Study of Duvelisib and Venetoclax in Patients with Relapsed or Refractory CLL/SLL" Blood, 134(Suppl. 1):1763, doi.org/10.1182/blood-2019-127343, 5 pages.

Fang, B. et al. (2020) "Inhibition of PI3K by copanlisib exerts potent antitumor effects on Merkel cell carcinoma cell lines and mouse xenografts" Scientific Reports, 10:8867, doi.org/10.1038/s41598-020-65637-2, 13 pages.

Gilead Sciences, Inc. Highlights of Prescribing Information, Full Prescribing Information, and Medication Guide for ZYDELIG®. Revised Oct. 2020; 30 total pages.

\* cited by examiner

| Patient | 1 | 2 | 3 | 4 | 5 | 6 | 7 | 8 | 9 | 10 | 11 | 12 | 13 |
|---|---|---|---|---|---|---|---|---|---|---|---|---|---|
| BAD_chr11 | -0.46 | -0.93 | 0.5 | 0.36 | -1.16 | -0.41 | 0.28 | 1.17 | -0.2 | 0.05 | 1.05 | 0 | 0.44 |
| BAK1_chr6 | -0.44 | -0.33 | -0.32 | -0.42 | -0.87 | -0.51 | -0.2 | 1.14 | 0.02 | -0.66 | 0.45 | 0.05 | 0.2 |
| BAX_chr19 | -0.14 | -0.23 | -0.1 | -0.76 | -0.91 | -0.36 | -0.32 | 1.55 | -0.25 | -0.05 | 0.63 | -0.16 | 0.23 |
| BBC3_chr19 | -0.03 | -0.89 | 0.16 | 1.13 | -0.5 | 0.01 | 1.1 | 1.74 | -0.07 | 1.11 | 0.97 | 1.18 | 2.62 |
| BCL2_chr18 | -0.08 | 0.84 | 0.36 | 0.08 | -0.17 | -0.03 | -0.05 | 2.02 | 0.14 | 0.39 | 1.26 | 0.94 | 0.81 |
| BCL2A1_chr15 | 0.27 | 0.32 | -0.84 | -0.47 | -0.04 | 0.47 | 0.4 | 0.53 | 0.13 | -0.09 | -0.1 | 0.77 | 0.58 |
| BCL2L1_chr20 | -0.42 | -1.29 | -2.84 | 0.9 | -0.48 | 0.13 | -2.83 | -2.18 | -0.99 | -1.4 | -1.3 | -2.05 | -0.85 |
| BCL2L11_chr2 | -0.02 | 0.33 | 0.17 | 0.73 | 0.06 | 0.58 | 0.14 | 0.95 | 0.05 | 0.21 | 0.87 | 1.3 | 0.57 |
| BCL2L2_chr14 | -0.48 | 0.05 | 0.06 | 0.09 | -0.56 | -0.2 | -0.4 | 1.46 | 0.28 | -0.22 | 1.08 | 1.1 | 0.58 |
| BID_chr22 | -0.44 | -0.3 | -0.29 | 0.16 | -0.32 | 0.16 | -0.64 | 0.18 | 0.06 | -0.23 | -0.93 | 0.38 | 0.17 |
| BIK_chr22 | -0.33 | -0.48 | 1.89 | -3.44 | -2.94 | -1.82 | 1.29 | 1.23 | -2.16 | -0.53 | -0.38 | -0.83 | -0.98 |
| BMF_chr15 | -0.37 | 1.16 | 0.53 | 0.47 | -0.29 | 0.39 | -0.04 | 1.73 | 0.65 | 0.37 | 1.61 | 1.31 | 1.17 |
| HRK_chr12 | -0.44 | 2.34 | 1.37 | 0.26 | -0.03 | 0.71 | 0.88 | 3 | 1.99 | 0.5 | 2.1 | 2.48 | 2.6 |
| MCL1_chr1 | 0.07 | 0.25 | -0.02 | -0.15 | -0.18 | -0.17 | -0.13 | 0.67 | -0.16 | -0.16 | 0.19 | 0.18 | 0.2 |
| PMAIP1_chr18 | -0.11 | 2.38 | 1.37 | 2.29 | 0.8 | 1.3 | 1.11 | 1.79 | 0.77 | 0.66 | 1.26 | 1.32 | 1.06 |

FIG. 5A

| Patient | 14 | 15 | 16 | 17 | 18 | 19 | 20 | 21 | 22 | 23 | 24 | 25 | 26 |
|---|---|---|---|---|---|---|---|---|---|---|---|---|---|
| BAD_chr11 | 0.52 | 0.44 | 0.19 | 0.36 | 0.29 | 0.85 | 0.23 | 0.17 | 0.54 | 0.02 | -0.37 | 1.64 | -1.13 |
| BAK1_chr6 | 0.51 | 0.43 | 0.17 | 0.29 | 0.04 | 0.77 | 0.2 | -0.03 | -0.06 | -0.7 | -0.13 | 1.07 | -0.5 |
| BAX_chr19 | 0.43 | 0.16 | 0.11 | -0.32 | -0.27 | 1.2 | 0.71 | -0.11 | 0.21 | -0.72 | 0.41 | 1.01 | -0.88 |
| BBC3_chr19 | 0.85 | 1.37 | 1.49 | 0.9 | 0.28 | 0.98 | 1.88 | 1.69 | 0.61 | -1.91 | 1.09 | 2.06 | 1.62 |
| BCL2_chr18 | 0.89 | 0.73 | 0.33 | 0.71 | 0.6 | 0.41 | 0.4 | 0.98 | 0.33 | -0.85 | 0.6 | 1.94 | 0.49 |
| BCL2A1_chr15 | 0.5 | 0.04 | -0.42 | 1.22 | 0.64 | 0.17 | 0.49 | 0.72 | 0.87 | 0.39 | 0.05 | -0.13 | 1.03 |
| BCL2L1_chr20 | 1.02 | -0.27 | -1.64 | -1.44 | -0.38 | 1.46 | -2.07 | -3.73 | -1.39 | 0.95 | -1.09 | 0.19 | -0.6 |
| BCL2L11_chr2 | 0.69 | 0.82 | 0.34 | 0.91 | 0.94 | 0.4 | 0.19 | 0.77 | 0 | -0.37 | 0.46 | 0.64 | 1.08 |
| BCL2L2_chr14 | 1.06 | 0.63 | 0.64 | 0.52 | 0.3 | 0.5 | 0.56 | 0.73 | 0.44 | -1.84 | 0.76 | 0.79 | -0.07 |
| BID_chr22 | 1.16 | 0.15 | 0.28 | 0.23 | 0.48 | 0.37 | -0.66 | 0.59 | 0 | -0.71 | 0.19 | 0.7 | 0.22 |
| BIK_chr22 | -5.41 | -1.32 | -0.67 | -1.06 | -0.99 | -4.32 | -1.4 | 2.56 | -0.35 | 0.29 | -0.99 | 1.04 | -0.14 |
| BMF_chr15 | 1.37 | 0.95 | 0.7 | 0.63 | 0.41 | 0.8 | 0.32 | 1.03 | 0.01 | -1 | 0.25 | 1.97 | 0.23 |
| HRK_chr12 | 2.54 | 1.82 | 1.63 | 1.06 | 0.79 | 2.4 | 2.58 | 2.64 | 1.64 | -1.61 | 2.15 | 2.14 | 1.3 |
| MCL1_chr1 | 0.57 | 0.22 | -0.26 | 0.21 | 0.35 | 0.1 | -0.24 | 0.48 | -0.3 | -0.68 | 0.32 | -0.41 | 0.65 |
| PMAIP1_chr18 | 1.13 | 0.93 | 0.76 | 1.21 | 0.64 | 0.59 | 1.15 | 1.63 | 0.83 | -0.34 | 1.9 | 1.15 | 2.57 |

FIG. 5B

| Patient | 27 | 28 | 39 | 30 | 31 |
|---|---|---|---|---|---|
| BAD_chr11 | 1.1 | 1.24 | 1.07 | 1.43 | 0.13 |
| BAK1_chr6 | 0.02 | 0.34 | 0.65 | 0.86 | -0.8 |
| BAX_chr19 | -0.32 | 1.18 | 1.6 | 0.81 | -1.23 |
| BBC3_chr19 | 1.16 | 1.14 | 2.23 | 2.13 | -0.94 |
| BCL2_chr18 | 0.21 | 0.82 | 0.92 | 1.49 | -0.25 |
| BCL2A1_chr15 | -0.18 | 1.21 | 1.61 | 0.16 | 0.01 |
| BCL2L1_chr20 | 2.63 | -0.25 | -1.02 | -0.11 | 0.74 |
| BCL2L11_chr2 | 0.7 | 0.12 | -0.13 | 0.77 | 0.45 |
| BCL2L2_chr14 | -0.02 | 0.4 | 0.83 | 1.13 | 0.08 |
| BID_chr22 | -0.56 | 0.35 | 0.02 | 0.09 | -0.05 |
| BIK_chr22 | -0.54 | -1.46 | -1.05 | -0.56 | 0.4 |
| BMF_chr15 | -0.07 | 0.7 | 0.58 | 1.42 | -0.21 |
| HRK_chr12 | 1.51 | 1.46 | 2.17 | 2.22 | 0.68 |
| MCL1_chr1 | -0.34 | 0.38 | -0.1 | 0.01 | -0.03 |
| PMAIP1_chr18 | 1.59 | -0.64 | -0.31 | 1.22 | 0.78 |

FIG. 5C

COMBINATION THERAPIES

This application is a Continuation of U.S. application Ser. No. 14/687,768, filed on Apr. 15, 2015, which claims priority to U.S. Ser. No. 61/980,549, filed Apr. 16, 2014, U.S. Ser. No. 62/042,691 filed Aug. 27, 2014, and U.S. Ser. No. 62/042,681, filed Aug. 27, 2014, the contents of each are incorporated by reference in their entireties.

BACKGROUND

The phosphoinositide 3-kinases (PI3Ks) signaling pathway is one of the most highly mutated systems in human cancers. PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate phosphatidylinositol (3,4,5)-trisphosphate (PIP3), which engages downstream effectors such as those in the AKT/PDK1 pathway, mTOR, the Tec family kinases, and the Rho family GTPases. The class II and III PI3Ks play a key role in intracellular trafficking through the synthesis of phosphatidylinositol 3-bisphosphate (PI(3)P) and phosphatidylinositol (3,4)-bisphosphate (PI(3,4)P2). The PI3Ks are protein kinases that control cell growth (mTORC1) or monitor genomic integrity (ATM, ATR, DNA-PK, and hSmg-1).

There are four mammalian isoforms of class I PI3Ks: PI3K-α, β, δ (class Ia PI3Ks) and PI3K-γ (a class Ib PI3K). These enzymes catalyze the production of PIP3, leading to activation of downstream effector pathways important for cellular survival, differentiation, and function. PI3K-α and PI3K-β are widely expressed and are important mediators of signaling from cell surface receptors. PI3K-α is the isoform most often found mutated in cancers and has a role in insulin signaling and glucose homeostasis (Knight et al. Cell (2006) 125(4):733-47; Vanhaesebroeck et al. Current Topic Microbiol. Immunol. (2010) 347:1-19). PI3K-β is activated in cancers where phosphatase and tensin homolog (PTEN) is deleted. Both isoforms are targets of small molecule therapeutics in development for cancer.

PI3K-δ and -γ are preferentially expressed in leukocytes and are important in leukocyte function. These isoforms also contribute to the development and maintenance of hematologic malignancies (Vanhaesebroeck et al. Current Topic Microbiol. Immunol. (2010) 347:1-19; Clayton et al. J Exp Med. (2002) 196(6):753-63; Fung-Leung Cell Signal. (2011) 23(4):603-8; Okkenhaug et al. Science (2002) 297 (5583):1031-34). PI3K-δ is activated by cellular receptors (e.g., receptor tyrosine kinases) through interaction with the Sarc homology 2 (SH2) domains of the PI3K regulatory subunit (p85), or through direct interaction with RAS.

SUMMARY

The present invention provides, at least in part, compositions and methods comprising a PI3K inhibitor in combination with a Bcl-2 inhibitor. In one embodiment, it has been discovered a combination of a PI3K inhibitor (e.g., Compound 1) and a Bcl-2 inhibitor (e.g., ABT-199 or ABT-263) has a synergistic effect in treating a cancer (e.g., in reducing cancer cell growth or viability, or both). In certain embodiments, the combination of a PI3K inhibitor and a Bcl-2 inhibitor can allow the PI3K inhibitor, the Bcl-2 inhibitor, or both, to be administered at a lower dosage, e.g., a lower dosage than would be required to achieve the same therapeutic effect if the PI3K inhibitor or Bcl-2 inhibitor were administered as a monotherapy. In some embodiments, the combination can allow the PI3K inhibitor, the Bcl-2 inhibitor, or both, to be administered at a lower frequency than if the PI3K inhibitor or Bcl-2 inhibitor were administered as a monotherapy. Such combinations provide advantageous effects, e.g., in reducing (e.g., inhibiting, preventing, delaying, and/or decreasing the likelihood of occurrence of) one or more of: a side effect, toxicity, or resistance (e.g., acquired resistance) that would otherwise be associated with administration of a higher dose of the agent(s), e.g., when the agent is administered as a monotherapy.

In one aspect, provided herein are compositions, e.g., pharmaceutical compositions comprising a PI3K inhibitor (e.g., one or more PI3K inhibitors), or a pharmaceutically acceptable form thereof, in combination with a Bcl-2 inhibitor (e.g., one or more Bcl-2 inhibitors), or a pharmaceutically acceptable form thereof. By "in combination with" it is not intended to imply that the Bcl-2 inhibitor and the PI3K inhibitor must be administered at the same time and/or formulated for delivery together, although these methods of delivery are within the scope of this disclosure.

In some embodiments, the PI3K inhibitor and the Bcl-2 inhibitor are present in a single composition.

In some embodiments, the PI3K inhibitor and the Bcl-2 inhibitor are present in two or more different compositions (e.g., as separate dosage forms). In some embodiments, the PI3K inhibitor and the Bcl-2 inhibitor are formulated for administration via the same administration route. In some embodiments, the PI3K inhibitor and the Bcl-2 inhibitor are formulated for administration via different administration routes.

In some embodiments, the composition (e.g., one or more compositions or dosage forms) comprising the combination of PI3K inhibitor and the Bcl-2 inhibitor) is synergistic, e.g., the combination has a synergistic effect, e.g., a synergistic effect in treating a cancer (e.g., in reducing cancer cell growth or viability, or both). In certain embodiments, the amount or dosage of the PI3K inhibitor, the Bcl-2 inhibitor, or both, present in the composition(s) does not exceed the level at which each agent is used individually, e.g., as a monotherapy. In certain embodiments, the amount or dosage of the PI3K inhibitor, the Bcl-2 inhibitor, or both, present in the composition(s) is lower (e.g., at least 20%, at least 30%, at least 40%, or at least 50%) than the amount or dosage of each agent used individually, e.g., as a monotherapy. In other embodiments, the amount or dosage of the PI3K inhibitor, the Bcl-2 inhibitor, or both, present in the composition(s) that results in a desired effect (e.g., treatment of cancer, achieve inhibition e.g., 50% inhibition, achieve growth inhibition e.g., 50% growth inhibition, achieve a therapeutic effect) is lower (e.g., at least 20%, at least 30%, at least 40%, or at least 50% lower) than the amount or dosage of each agent used individually, e.g., as a monotherapy. In certain embodiments, the frequency of administration of the PI3K inhibitor that achieves a therapeutic effect is lower (e.g., at least 20%, 30%, 40%, or 50% lower), when the PI3K inhibitor is administered in combination with the Bcl-2 inhibitor than when the PI3K inhibitor is administered alone. In some embodiments, the frequency of administration of the Bcl-2 inhibitor that achieves a therapeutic effect is lower (e.g., at least 20%, 30%, 40%, or 50% lower), when the Bcl-2 inhibitor is administered in combination with PI3K inhibitor than when the Bcl-2 inhibitor is administered alone.

In another aspect, featured herein is a method of treating (e.g., inhibiting, reducing, ameliorating, managing, or preventing) a cancer in a subject. The method includes administering to the subject a PI3K inhibitor (e.g., one or more PI3K inhibitors), or a pharmaceutically acceptable form thereof, in combination with a Bcl-2 inhibitor (e.g., one or more Bcl-2 inhibitors), or pharmaceutically acceptable form thereof.

The combination of the PI3K inhibitor and the Bcl-2 inhibitor can be administered together in a single composition or administered separately in two or more different compositions, e.g., pharmaceutical compositions or dosage forms as described herein. The administration of the PI3K inhibitor and the Bcl-2 inhibitor can be in any order. The PI3K inhibitor can be administered concurrently with, prior to, or subsequent to, the Bcl-2 inhibitor. In one embodiment, the Bcl-2 inhibitor is administered to a subject at least 5 minutes, 15 minutes, 30 minutes, 45 minutes, 1 hour, 2 hours, 4 hours, 6 hours, 12 hours, or 24 hours before the PI3K inhibitor (e.g., Compound 1), or a pharmaceutically acceptable form thereof, is administered. In another embodiment, the Bcl-2 inhibitor is administered concurrently with the PI3K inhibitor (e.g., Compound 1), or a pharmaceutically acceptable form thereof, e.g., in a single dosage form or separate dosage forms. In yet another embodiment, the Bcl-2 inhibitor is administered to the subject at least 5 minutes, 15 minutes, 30 minutes, 45 minutes, 1 hour, 2 hours, 4 hours, 6 hours, 12 hours, or 24 hours after the PI3K inhibitor (e.g., Compound 1), or a pharmaceutically acceptable form thereof, is administered. In some embodiments, the PI3K inhibitor and the Bcl-2 inhibitor are administered with a timing that results in both inhibitors being present at therapeutic levels at the same time in the patient.

In some embodiments, the combination of the PI3K inhibitor and the Bcl-2 inhibitor is additive, e.g., the effect of the combination is similar to their individual effects added together.

In some embodiments, the combination of PI3K inhibitor and the Bcl-2 inhibitor) is synergistic, e.g., has a synergistic effect, e.g., a synergistic effect in treating a cancer (e.g., in reducing cancer cell growth or viability, or both).

In some embodiments, the amount or dosage of the PI3K inhibitor, the Bcl-2 inhibitor, or both, used in combination does not exceed the level at which each agent is used individually, e.g., as a monotherapy. In certain embodiments, the amount or dosage of the PI3K inhibitor, the Bcl-2 inhibitor, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the Bcl-2 inhibitor, or both, used in combination that results in treatment of cancer is lower (e.g., at least 20%, at least 30%, at least 40%, or at least 50% lower) than the amount or dosage of each agent used individually, e.g., as a monotherapy. In certain embodiments, the frequency of administration of the PI3K inhibitor, the Bcl-2 inhibitor, or both, used in combination that results in treatment of cancer is lower (e.g., at least 20%, 30%, 40%, or 50% lower), than the frequency of administration of each agent used individually, e.g., as a monotherapy.

The combination of PI3K inhibitor and the Bcl-2 inhibitor can be administered during periods of active disorder, or during a period of remission or less active disease. The combination can be administered before a third treatment or procedure (e.g., radiation or surgery), concurrently with the third treatment, post-treatment, or during remission of the disorder.

In another aspect, featured herein is a method of inhibiting the growth or the viability, or both, of a cancer cell. The method includes contacting the cancer cell with a PI3K inhibitor (e.g., one or more PI3K inhibitors), or a pharmaceutically acceptable form thereof, in combination with a Bcl-2 inhibitor (e.g., one or more Bcl-2 inhibitors), or pharmaceutically acceptable form thereof. In certain embodiments, the method is for use in vitro. In certain embodiments, the method is for use or in vivo, e.g., in an animal subject or as part of a therapeutic protocol.

The contacting of the cell with the PI3K inhibitor and the Bcl-2 inhibitor can be in any order. In certain embodiments, the cell is contacted with the PI3K inhibitor concurrently, prior to, or subsequent to, the Bcl-2 inhibitor. In certain embodiments, the combination of the PI3K inhibitor and the Bcl-2 inhibitor is synergistic, e.g., has a synergistic effect in reducing cancer cell growth or viability, or both. In some embodiments, the amount or dosage of the PI3K inhibitor, the Bcl-2 inhibitor, or both, used in combination does not exceed the level at which each agent is used individually, e.g., as a monotherapy. In certain embodiments, the amount or dosage of the PI3K inhibitor, the Bcl-2 inhibitor, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, the Bcl-2 inhibitor, or both, used in combination that results in a reducing cancer cell growth or viability, or both is lower (e.g., at least 20%, at least 30%, at least 40%, or at least 50% lower) than the amount or dosage of each agent used individually, e.g., as a monotherapy.

In another aspect, the present disclosure provides a synergistic combination of a PI3K inhibitor, or a pharmaceutically acceptable form thereof, and a Bcl-2 inhibitor, or a pharmaceutically acceptable form thereof, for use in treating cancer. In another aspect, the present disclosure provides a synergistic combination of a PI3K inhibitor, or a pharmaceutically acceptable form thereof, and a Bcl-2 inhibitor, or a pharmaceutically acceptable form thereof, for use in a medicament. In another aspect, the present disclosure provides a use of a synergistic combination of a PI3K inhibitor, or a pharmaceutically acceptable form thereof, and a Bcl-2 inhibitor, or a pharmaceutically acceptable form thereof, for treating cancer. In another aspect, the present disclosure provides a use of a synergistic combination of a PI3K inhibitor, or a pharmaceutically acceptable form thereof, and a Bcl-2 inhibitor, or a pharmaceutically acceptable form thereof for the manufacture of a medicament for treating cancer.

Additional embodiments of the compositions and/or methods described herein include one or more of the following:

The compositions described herein can be used, e.g., for treatment of a cancer described herein and/or for inhibiting the growth or viability of a cancer cell in vitro or in vivo.

In certain embodiments, the combination of the PI3K inhibitor and the Bcl-2 inhibitor used in the compositions and methods described herein is synergistic, e.g., as indicated by a combination index value that is less than 1 for the combination of the PI3K inhibitor and the Bcl-2 inhibitor. In certain embodiments, the combination is synergistic as indicated by a combination index value that is less than 0.7 for the combination of the PI3K inhibitor and the Bcl-2 inhibitor. In some embodiments, the combination is synergistic as indicated by a combination index value that is less than 0.5 for the combination of the PI3K inhibitor and the Bcl-2 inhibitor. In some embodiments, the combination is synergistic as indicated by a combination index value that is less than 0.7, 0.6, 0.5, 0.4, 0.3, 0.2, or 0.1 for the combination of the PI3K inhibitor and the Bcl-2 inhibitor. In some embodiments, the combination of the PI3K inhibitor and the Bcl-2 inhibitor used in the compositions and methods described herein is additive, e.g., as indicated by a combination index value that is equal to about 1 for the combination of the PI3K inhibitor and the Bcl-2 inhibitor. In some embodiments, the combination index value is assessed at 50% or more inhibition or growth inhibition. In certain embodiments, the combination index value is assessed at 50% inhibition, e.g., as described herein in the Examples. In some embodiments, the combination index value is assessed at 50% inhibition or growth inhibition, e.g., as described herein in the Examples. In some embodiments, the combination index value is assessed at 85% inhibition or growth inhibition, e.g., as described herein in the Examples. In some embodiments, the combination index value is assessed at 110% growth inhibition, e.g., as described herein in the Examples. In some embodiments, the combination index value is assessed at 140% growth inhibition, e.g., as described herein in the Examples. In some embodiments, the combination index value is assessed at 10%, 20%, 30%, 40%, 50%, 60%, 60%, 70%, 80%, 90%, 100% inhibition. In some embodiments, the combination index value is assessed at 10%, 20%, 30%, 40%, 50%, 60%, 60%, 70%, 80%, 90%, 100%, 110%, 120%, 130%, 140%, or 150% or more growth inhibition. In some embodiments, the combination index value is calculated as described herein.

In other embodiments, the combination of the PI3K inhibitor and the Bcl-2 inhibitor used in the compositions and methods described herein is synergistic, e.g., as indicated by a synergy score value of greater than 1, 2, or 3. In certain embodiments, the combination is synergistic as indicated by a synergy score value that is 1 or more. In certain embodiments, the combination is synergistic as indicated by a synergy score value that is 3 or more. In certain embodiments, the combination is synergistic as indicated by a synergy score value that is 10 or more. In certain embodiments, the combination of the PI3K inhibitor and the second agent used in the compositions and methods described herein is additive, e.g., as indicated by a synergy score value of zero.

In one embodiment, the combination is synergistic as indicated by a synergy score value that is two standard deviations or three standard deviations of the value of the self-crosses, which indicates synergy at a confidence level of 95% or 99%, respectively. In certain embodiments, the synergy score is calculated as described herein.

In some embodiments, the anti-cancer effect provided by the combination of the PI3K inhibitor and the Bcl-2 inhibitor used in the compositions and methods described herein is greater than the anti-cancer effect provided by an agent (e.g., the PI3K inhibitor or the Bcl-2 inhibitor) used individually, e.g., as a monotherapy. In one embodiment, the anti-cancer effect provided by the combination of the PI3K inhibitor and the Bcl-2 inhibitor is greater than the anti-cancer effect provided monotherapy with the same dose of the PI3K inhibitor. In certain embodiments, the anti-cancer effect provided by the combination of the PI3K inhibitor and the Bcl-2 inhibitor is at least 2 fold greater, at least 3 fold greater, at least 5 fold greater, or at least 10 fold greater than the anti-cancer effect provided by an agent used individually, e.g., as a monotherapy (e.g., by a monotherapy with the same dose of the PI3K inhibitor, or by a monotherapy with the same dose of the Bcl-2 inhibitor).

As used herein, a "monotherapy" refers to the use of an agent individually (also referred to herein as alone), e.g., without a second active ingredient to treat the same indication, e.g., cancer. For example, in this context, the term monotherapy includes the use of either the PI3K inhibitor or the Bcl-2 inhibitor individually or alone to treat the cancer.

In some embodiments, the anti-cancer effect provided by the combination of the PI3K inhibitor and the Bcl-2 inhibitor used in the compositions and methods described herein is greater than the anti-cancer effect provided by a monotherapy with the same dose of the PI3K inhibitor. In certain embodiments, the anti-cancer effect provided by the combination is at least 2 fold greater, at least 3 fold greater, at least 5 fold greater, or at least 10 fold greater than the anti-cancer effect provided by the monotherapy with the same dose of the PI3K inhibitor.

In some embodiments, the anti-cancer effect of the combination of the PI3K inhibitor and the Bcl-2 inhibitor used in the compositions and methods described herein is greater than the anti-cancer effect provided by a monotherapy with the same dose of the Bcl-2 inhibitor. In certain embodiments, the anti-cancer effect of the combination of the PI3K inhibitor and the Bcl-2 inhibitor is at least 2 fold greater, at least 3 fold greater, at least 5 fold greater, or at least 10 fold greater than the anti-cancer effect provided by the monotherapy with the same dose of the Bcl-2 inhibitor.

In some embodiments, one or more side effects of the PI3K inhibitor, the Bcl-2 inhibitor, or both, is reduced compared with the side effects of an agent (e.g., the side effects of either the PI3K inhibitor or the Bcl-2 inhibitor) when used individually, e.g., as a monotherapy (e.g., a monotherapy with the PI3K inhibitor, or by a monotherapy with the Bcl-2 inhibitor), e.g., when the monotherapy is administered at a dose that achieves the same therapeutic effect as the combination.

In some embodiments, one or more side effects of the PI3K inhibitor, the Bcl-2 inhibitor, or both is reduced compared with the side effects of each agent when used individually, e.g., as a monotherapy (e.g., a monotherapy with the PI3K inhibitor, or by a monotherapy with the Bcl-2 inhibitor), e.g., when the monotherapy is administered at a dose that achieves the same therapeutic effect as the combination.

In some embodiments, one or more side effects of the compositions or methods described herein is reduced compared with the side effects of a monotherapy comprising either the Bcl-2 inhibitor (or pharmaceutically acceptable form thereof) or the PI3K inhibitor (or pharmaceutically acceptable form thereof), e.g., a monotherapy at a dose that achieves the same therapeutic effect as does the combination.

In some embodiments, said one or more side effects includes a liver enzyme level, e.g., a liver enzyme level indicative of toxicity.

In some embodiments, said one or more side effects include thrombocytopenia.

In some embodiments, said one or more side effects include tumor lysis syndrome.

In some embodiments, the combination of the PI3K inhibitor and the Bcl-2 inhibitor used in the compositions and methods described herein results in a reduction in resistance (e.g., a decrease in a measure of resistance or a decreased likelihood of developing resistance), or a delay in the development of resistance, to at least one of the agents, e.g., resistance (e.g., acquired resistance) to the PI3K inhibitor. In certain embodiments, resistance is assessed at least in part by evaluating minimal residual disease (MRD).

In some embodiments, the combination of the PI3K inhibitor and the Bcl-2 inhibitor used in the compositions and methods described herein results in a reduction in the level of minimal residual disease (MRD) that can be detected. In certain embodiments, the combination of a PI3K inhibitor (e.g. a PI3K inhibitor described herein) and a Bcl-2 inhibitor (e.g., a Bcl-2 inhibitor described herein) is effective to reduce the level of MRD in the subject, e.g., below a level previously measured in the subject (e.g., the level measured before the combination was administered). In certain embodiments, the combination of a PI3K inhibitor and a Bcl-2 inhibitor is effective to reduce the level of MRD in the subject below the level observed during or after treatment with a monotherapy, e.g., a monotherapy comprising either the PI3K inhibitor or the Bcl-2 inhibitor. In certain embodiments, the level of MRD is decreased below the level observed during treatment with a monotherapy comprising the PI3K inhibitor. In certain embodiments, the level of MRD is decreased below the level observed during treatment with a monotherapy comprising the Bcl-2 inhibitor. In certain embodiments, the combination is effective to reduce the level of MRD below a preselected cutoff value (e.g., 1 malignant cell in 100 normal cells, 1 malignant cell in 1000 normal cells, 1 malignant cell in 10,000 normal cells, or 1 malignant cell in 100,000 normal cells). In certain embodiments, the preselected cutoff value is 1 malignant cell in 1,000 or 10,000 normal cells. In some embodiments, a subject exhibits MRD negativity (or is MRD-negative) if the MRD is below a preselected cutoff value (e.g., a preselected cutoff value as described herein). In some embodiments, the level of MRD is not detectable by standard laboratory methodologies.

In another aspect, the invention features a method of treating a cancer in a subject, or a method of decreasing the level of MRD in a subject having a cancer. The method comprises:
  (a) administering to the subject a PI3K inhibitor (e.g., Compound 1), or a pharmaceutically acceptable form thereof, in combination with a Bcl-2 inhibitor (e.g., at least one Bcl-2 inhibitor) (also referred to as "a first treatment");
  (b) monitoring the level of MRD in the subject, e.g., by one or more of the methods described herein or known in the art (e.g., flow cytometry, sequencing, or PCR); and
  (c) if the subject is MRD negative, e.g., for a time period after therapy (e.g., at least 1, 2, 3, 6, 9, 12 months), alter the combination treatment (e.g., reduce the dose or cease the first treatment).

In some embodiments, the method further includes monitoring the subject after altering the combination treatment (e.g., after reducing the dose or ceasing the first treatment), e.g., for a period of at least 6 months, 9 months or 12 months. If the MRD levels increase, e.g., increase above a preselected cutoff value (e.g., a preselected cutoff value as described herein), administer a second treatment. In one embodiment the second treatment is a PI3K inhibitor monotherapy. In another embodiment, the second treatment is a PI3K inhibitor in combination with a Bcl-2 inhibitor (e.g., at least one Bcl-2 inhibitor). In another embodiment, the second treatment is a PI3K inhibitor in combination with a third agent. In yet another embodiment, the second treatment is a PI3K inhibitor in combination a Bcl-2 inhibitor and a third agent.

In another aspect, the invention features a method of treating a cancer in a subject, or a method of decreasing the level of MRD detected in a subject having a cancer. The method comprises:
  (a) administering to the subject a PI3K inhibitor (e.g., Compound 1), or a pharmaceutically acceptable form thereof, in combination with a Bcl-2 inhibitor (e.g., at least one Bcl-2 inhibitor) (also referred to as "a first treatment");
  (b) monitoring the MRD in the subject, e.g., by one or more methods described herein or known in the art (e.g., flow cytometry, sequencing, or PCR); and
  (c) stop administering the first treatment (e.g., the combination) if the level of MRD in the subject is decreases below a preselected cutoff value (e.g., 1 malignant cell in 100 normal cells, 1 malignant cell in 1000 normal cells, or 1 malignant cell in 10,000 normal cells). In some embodiments, the method further comprises (d) monitoring the level of MRD in the subject, e.g., by one or more of the methods described herein or known in the art (e.g., flow cytometry, sequencing, or PCR) and (e) administering a second treatment (e.g., a monotherapy comprising a PI3K inhibitor, or administering a further combination comprising the PI3K inhibitor, or a pharmaceutically acceptable form thereof), if the level of MRD increases, e.g., increase above a preselected cutoff value (e.g., 1 malignant cell in 100 normal cells, 1 malignant cell in 1000 normal cells, or 1 malignant cell in 10,000 normal cells). Optionally, the method comprises repeating steps (b), (c), (d) and (e). In one embodiment the second treatment is a PI3K inhibitor monotherapy. In another embodiment, the second treatment is a PI3K inhibitor in combination with a Bcl-2 inhibitor (e.g., at least one Bcl-2 inhibitor). In another embodiment, the second treatment is a PI3K inhibitor in combination with a third agent. In yet another embodiment, the second treatment is a PI3K inhibitor in combination a Bcl-2 inhibitor and a third agent.

The aforesaid compositions and methods can be used in combination with a monotherapy (e.g., a monotherapeutic administration or dose of the PI3K inhibitor, the Bcl-2 inhibitor or a third agent). In one embodiment, the subject is administered a monotherapy with a PI3K inhibitor, which can be followed with a combination composition or method described herein. For example, if the subject is developing, or is identified as developing, a decreased responsiveness to a first monotherapy, (e.g., with a PI3K inhibitor, Bcl-2 inhibitor, or third agent), any of the combination compositions or methods described herein can be administered. In certain embodiments, the combination compositions or methods described herein improve responsiveness (e.g., as indicated by a decrease in MRD, e.g., a decrease below the level of MRD observed during treatment with the first monotherapy). Alternatively, administration of any of the combination compositions or methods described herein can be followed by administration of a monotherapy, e.g., with a PI3K inhibitor, Bcl-2 inhibitor, or third agent.

In other embodiments, the composition and methods described herein can include further agents or therapies, including but not limited to, chemotherapeutics, radiation or surgery.

In certain embodiments of the compositions and methods described herein, the PI3K inhibitor is a PI3K delta inhibitor. In one embodiment, the PI3K inhibitor is a PI3K delta/gamma dual inhibitor.

In one embodiment, the PI3K inhibitor is chosen from one or more of: Compound 1, AMG-319, GSK 2126458, GSK 1059615, GDC-0032, GDC-0980, GDC-0941, XL147, XL499, XL765, BKM 120, GS1101, CAL 263, SF1126, PX-866, BEZ235, CAL-120, BYL719, RP6503, RP6530, TGR1202, INK1117, PX-886, BAY 80-6946, IC87114, Palomid 529, ZSTK474, PWT33597, TG100-115, GNE-477, CUDC-907, AEZS-136, BGT-226, PF-05212384, LY3023414, PI-103, LY294002, INCB-040093, CAL-130 or wortmannin.

In one embodiment, the PI3K inhibitor is Compound 1, or a pharmaceutically acceptable form thereof. Compound 1 has the following structure:

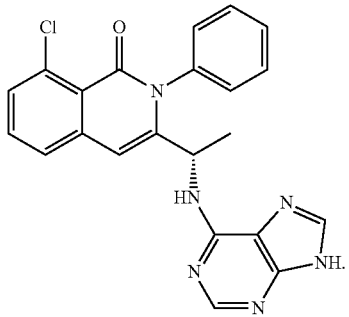

In other embodiments, the PI3K inhibitor is GS1101 (CAL-101), or a pharmaceutically acceptable form thereof.

In one embodiment, the pharmaceutical composition further comprises one or more pharmaceutically acceptable excipients.

In some embodiments of the compositions and methods described herein, the combination of the PI3K inhibitor and the Bcl-2 inhibitor is therapeutically effective (e.g., synergistically effective), in treating a cancer in the subject, e.g., for treatment of a cancer described herein.

In one embodiment, the cancer to be treating using the methods or compositions described herein is of hematopoietic origin. In one embodiment, the cancer is lymphoma or leukemia. In one embodiment, the cancer is B-cell lymphoma, mantle cell lymphoma, non-Hodgkin's lymphoma (e.g., non-Hodgkin's B-cell lymphoma), T-cell lymphoma (e.g., peripheral T-cell lymphoma (PTCL) and cutaneous T-cell lymphoma (CTCL)), cutaneous lymphoma, anaplastic large cell lymphoma, multiple myeloma, myeloma, or plasmacytoma. In one embodiment, the cancer is a multiple myeloma.

In one embodiment, the cancer is chronic lymphocytic leukemia (CLL).

In other embodiments, the cancer has a high level of Bcl-2 expression. In one embodiment, the cancer is a diffuse large B-cell lymphoma with a high level of Bcl-2 expression.

In one embodiment, the cancer is diffuse large B-cell lymphoma, follicular lymphoma, T-cell lymphoma, B-cell lymphoma, mantle cell lymphoma, non-Hodgkin B-cell lymphoma, non-Hodgkin T-cell lymphoma, indolent non-Hodgkin lymphoma, cutaneous lymphoma, anaplastic large cell lymphoma, multiple myeloma, myeloma, or plasmacytoma.

In other embodiments, the cancer is a non-Hodgkin's lymphoma. In certain embodiments, the cancer is a B cell non-Hodgkin's lymphoma. In certain embodiments, the non-Hodgkin's lymphoma is a diffuse large B-cell lymphoma. In certain embodiments, the non-Hodgkin's lymphoma is a diffuse large B-cell lymphoma activated B-cell like or a diffuse large B-cell lymphoma germinal center B-cell-like. In certain embodiments, the cancer is an indolent non-Hodgkin's lymphoma, e.g., a follicular lymphoma. In certain embodiments, the cancer is a mantle cell lymphoma. In certain embodiments, the cancer is a T-cell non-Hodgkin's lymphoma.

In one embodiment, the subject is a mammal, e.g., a human. In one embodiment, the subject is at risk or suffers from a cancer, e.g., a cancer described herein.

In one embodiment, the method delays resistance of the cancer, e.g., to a therapeutic agent, e.g., to the PI3K inhibitor such as Compound 1, or to the Bcl-2 inhibitor. In one embodiment, the method reduces the risk that the cancer becomes resistant, e.g., to a therapeutic agent, e.g., to the PI3K inhibitor such as Compound 1, or to the Bcl-2 inhibitor. In one embodiment, the cancer does not become resistant (e.g., to the PI3K inhibitor) for at least 1, 2, 3, 4, 5, 6, 7, 8, 9, 10, 11, 12, 18, 24, 30, or 36 months. In one embodiment, the method prolongs remission (e.g., complete remission or partial remission) in the subject. In one embodiment, the subject experiences remission (e.g., complete remission or partial remission) for at least 1, 2, 3, 4, 5, 6, 7, 8, 9, 10, 11, 12, 18, 24, 30, or 36 months. In one embodiment, the method increases the likelihood that the subject experiences complete remission. In one embodiment, the subject experiences complete remission. In one embodiment, the method results in a reduction in the level of minimal residual disease (MRD). In one embodiment, the subject has substantially no detectable MRD. In certain embodiments, the subject displays one or more of these characteristics (e.g., remission) after treatment with the PI3K inhibitor and the Bcl-2 inhibitor for a therapeutically effective period of time, e.g., at least 1, 2, 3, or 4 weeks, or 1, 2, 4, 6, 9, or 12 months.

In one embodiment, the subject is resistant or refractive to a treatment, e.g., a treatment with a PI3K inhibitor (e.g., Compound 1 or GS1101). In one embodiment, the subject is identified as having a decreased susceptibility (e.g., resistance or acquired resistance) to a monotherapy treatment with a PI3K inhibitor (e.g., Compound 1 or GS1101), or a pharmaceutically acceptable form thereof.

In some embodiments of the compositions and methods described herein, the PI3K inhibitor and the Bcl-2 inhibitor are the only therapeutically active ingredients for treating a cancer. Additional combinations of three or more agents are encompassed by the methods and compositions described herein.

Additional combinations of three or more agents are encompassed by the methods and compositions described herein.

In some embodiments of the compositions and methods described herein, the PI3K inhibitor and the Bcl-2 inhibitor are in a single dosage form. In other embodiments, the PI3K inhibitor and the Bcl-2 inhibitor are in separate dosage forms.

In some embodiments of the compositions and methods described herein, the combination of the PI3K inhibitor and the Bcl-2 inhibitor is synergistic, e.g., in inhibiting tumor cell growth, viability or both, or in treating a cancer.

In certain embodiments, the Bcl-2 inhibitor is ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, 544563, or a combination or mixture thereof. In one embodiment, the Bcl-2 inhibitor is ABT-199. In one embodiment, the Bcl-2 inhibitor is ABT-263.

In certain embodiments, provided herein is a composition (e.g., a pharmaceutical composition) comprising a PI3K inhibitor (e.g., Compound 1 or GS1101), or a pharmaceutically acceptable form thereof, in combination with ABT-199, or a pharmaceutically acceptable form thereof. The PI3K inhibitor and ABT-199 can be present in a single composition or as two or more different compositions. In some embodiments, the composition (e.g., one or more compositions comprising the combination of PI3K inhibitor and ABT-199) is synergistic, e.g., has a synergistic effect in treating a cancer (e.g., in reducing cancer cell growth or viability, or both, e.g., as described herein). In certain embodiments, the amount or dosage of the PI3K inhibitor, ABT-199, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating (e.g., inhibiting, managing, or preventing) a cancer in a subject comprising administering to the subject a PI3K inhibitor, e.g., one or more PI3K inhibitors (e.g., Compound 1 or GS1101, or both) or a pharmaceutically acceptable form thereof, in combination with ABT-199, or a pharmaceutically acceptable form thereof. In certain embodiments, the combination of the PI3K inhibitor and ABT-199 is synergistic, e.g., has a synergistic effect in treating the cancer (e.g., in reducing cancer cell growth or viability, or both). In some embodiments, the amount or dosage of the PI3K inhibitor, ABT-199, or both, used in combination does not exceed the level at which each agent is used individually, e.g., as a monotherapy. In certain embodiments, the amount or dosage of the PI3K inhibitor, ABT-199, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, ABT-199, or both, used in combination that results in treatment of cancer is lower (e.g., at least 20%, at least 30%, at least 40%, or at least 50% lower) than the amount or dosage of each agent used individually, e.g., as a monotherapy.

In certain embodiments, provided herein is a composition (e.g., a pharmaceutical composition) comprising a PI3K inhibitor (e.g., Compound 1 or GS1101), or a pharmaceutically acceptable form thereof, in combination with ABT-263, or a pharmaceutically acceptable form thereof. The PI3K inhibitor and ABT-263 can be present in a single composition or as two or more different compositions. In some embodiments, the composition (e.g., one or more compositions comprising the combination of PI3K inhibitor and ABT-263) is synergistic, e.g., has a synergistic effect in treating a cancer (e.g., in reducing cancer cell growth or viability, or both, e.g., as described herein). In certain embodiments, the amount or dosage of the PI3K inhibitor, ABT-263, or both, present in the composition(s) is lower (e.g., at least 20%, at least 30%, at least 40%, or at least 50% lower) than the amount or dosage of each agent used individually, e.g., as a monotherapy.

In certain embodiments, provided herein is a method of treating (e.g., inhibiting, managing, or preventing) a cancer in a subject comprising administering to the subject a PI3K inhibitor, e.g., one or more PI3K inhibitors or a pharmaceutically acceptable form thereof, in combination with ABT-263, or a pharmaceutically acceptable form thereof. In certain embodiments, the combination of the PI3K inhibitor and ABT-263 is synergistic, e.g., has a synergistic effect in treating the cancer (e.g., in reducing cancer cell growth or viability, or both). In some embodiments, the amount or dosage of the PI3K inhibitor, ABT-263, or both, used in combination does not exceed the level at which each agent is used individually, e.g., as a monotherapy. In certain embodiments, the amount or dosage of the PI3K inhibitor, ABT-263, or both, used in combination is lower (e.g., at least 20%, at least 30%, at least 40%, or at least 50% lower) than the amount or dosage of each agent used individually, e.g., as a monotherapy. In other embodiments, the amount or dosage of the PI3K inhibitor, ABT-263, or both, used in combination that results in treatment of cancer is lower (e.g., at least 20%, at least 30%, at least 40%, or at least 50% lower) than the amount or dosage of each agent used individually, e.g., as a monotherapy.

In one embodiment, the PI3K inhibitor is chosen from one or more of: Compound 1, AMG-319, GSK 2126458, GSK 1059615, GDC-0032, GDC-0980, GDC-0941, XL147, XL499, XL765, BKM 120 GS1101, CAL 263, SF1126, PX-866, BEZ235, CAL-120, BYL719, RP6503, RP6530, TGR1202, INK1117, PX-886, BAY 80-6946, IC87114, Palomid 529, ZSTK474, PWT33597, TG100-115, GNE-477, CUDC-907, AEZS-136, BGT-226, PF-05212384, LY3023414, PI-103, LY294002, INCB-040093, CAL-130 or wortmannin.

Embodiments relating to dosages of the agents included in the compositions and methods described herein follow. In one embodiment, the PI3K inhibitor, e.g., Compound 1, is administered at a dosage of from about 0.01 mg to about 75 mg daily, and the Bcl-2 inhibitor is administered at a dosage of from about 0.01 to about 1100 mg daily.

In certain embodiments, the amount or dosage of the PI3K inhibitor, the Bcl-2 inhibitor, or both, that is used in the method or composition is lower (e.g., at least 20%, at least 30%, at least 40%, at least 50%, at least 60%, at least 70%, or at least 80% lower) than the amount or dosage of each agent used individually, e.g., as a monotherapy. In other embodiments, the amount or dosage of the PI3K inhibitor, the Bcl-2 inhibitor, or both, present in the composition(s) that results in a desired effect (e.g., treatment of cancer) is lower (e.g., at least 20%, at least 30%, at least 40%, at least 50%, at least 60%, at least 70%, or at least 80% lower) than the amount or dosage of each agent used individually, e.g., as a monotherapy.

In one embodiment, the composition comprises the PI3K inhibitor, or a pharmaceutically acceptable form thereof, at an amount of in the range of from about 0.01 mg to about 75 mg.

In one embodiment, the molar ratio of Compound 1, or a pharmaceutically acceptable form thereof, to the Bcl-2 inhibitor, or a pharmaceutically acceptable form thereof, is in the range of from about 50:1 to about 1:50. In one embodiment, the molar ratio of Compound 1, or a pharmaceutically acceptable form thereof, to the Bcl-2 inhibitor, or a pharmaceutically acceptable form thereof, is in the range of from about 10:1 to about 1:10 or from about 1:3 to about 1:7.

In one embodiment, the composition comprises Compound 1, or a pharmaceutically acceptable form thereof, at an amount in the range of from about 0.01 mg to about 75 mg and the Bcl-2 inhibitor, or a pharmaceutically acceptable form thereof, at an amount of in the range of from about 0.01 mg to about 1100 mg. In one embodiment, the composition comprises ABT-199 at an amount of about 400 mg, about 325 mg, about 150 mg, or about 75 mg.

In some embodiments, the PI3K inhibitor is Compound 1 at a dosage of 25 mg (e.g., 25 mg BID). In certain embodiments, Compound 1 is effective as a monotherapy at a dosage of 25 mg (e.g., 25 mg BID). In certain embodiments, the combination of Compound 1 and the Bcl-2 inhibitor is effective, e.g., in treating a cancer and/or in reducing cancer cell growth or viability, with Compound 1 at a dosage lower than 25 mg (e.g., 25 mg BID). In certain embodiments, the dosage of Compound 1 is 22.5 mg (e.g., 22.5 mg BID), 20 mg (e.g., 20 mg BID), 17.5 mg (e.g., 17.5 mg BID), 15 mg (e.g., 15 mg BID), 12.5 mg (e.g., 12.5 mg BID), 10 mg (e.g., 10 mg BID), 7.5 mg (e.g., 7.5 mg BID), or 5 mg (e.g., 5 mg BID).

In some embodiments, the PI3K inhibitor, e.g., Compound 1, is administered at a dose frequency of twice per day (BID), once per day, once per two days, once per three days, once per four days, once per five days, once per six days, or once per week. In certain embodiments, the combination of the PI3K inhibitor (e.g., Compound 1) and the Bcl-2 inhibitor is effective, e.g., in treating a cancer and/or in reducing cancer cell growth or viability, with the PI3K inhibitor (e.g., Compound 1) administered at a dose frequency of twice per day (BID), once per day, once per two days, once per three days, once per four days, once per five days, once per six days, or once per week.

In some embodiments, the PI3K inhibitor is GS1101 at a dosage of 150 mg (e.g., 150 mg BID). In certain embodiments, GS1101 is effective as a monotherapy at a dosage of 150 mg (e.g., 150 mg BID). In certain embodiments, the combination of GS1101 and the Bcl-2 inhibitor is effective, e.g., in treating a cancer and/or in reducing cancer cell growth or viability, with GS1101 at a dosage lower than 150 mg (e.g., 150 mg BID). In certain embodiments, the dosage of GS1101 is 135 mg (e.g., 135 mg BID), 120 mg (e.g., 120 mg BID), 105 mg (e.g., 105 mg BID), 90 mg (e.g., 90 mg BID), 75 mg (e.g., 75 mg BID), 60 mg (e.g., 60 mg BID), 45 mg (e.g., 45 mg BID), or 30 mg (e.g., 30 mg BID).

In some embodiments, the PI3K inhibitor is GS1101 and is administered at a dose frequency of twice per day, once per day, once per two days, once per three days, once per four days, once per five days, once per six days, or once per week. In certain embodiments, the combination of GS1101 and the Bcl-2 inhibitor is effective, e.g., in treating a cancer and/or in reducing cancer cell growth or viability, with GS1101 administered at a dose frequency of twice per day (BID), once per day, once per two days, once per three days, once per four days, once per five days, once per six days, or once per week.

In some embodiments, the Bcl-2 inhibitor is ABT-199 at a dosage of 400 mg (e.g., 400 mg QID). In certain embodiments, ABT-199 is effective as a monotherapy at a dosage of 400 mg (e.g., 400 mg QID). In certain embodiments, the combination of the PI3K inhibitor and ABT-199 is effective, e.g., in treating a cancer and/or in reducing cancer cell growth or viability, with ABT-199 at a dosage lower than 400 mg (e.g., 400 mg QID). In certain embodiments, the dosage of ABT-199 is 50 to 350 mg (e.g., 50 to 350 mg BID), e.g., 50 to 100 mg (e.g., 50 to 100 mg BID), 100 to 200 mg (e.g., 100 to 200 mg BID), 200 to 300 mg (e.g., 200 to 300 mg BID) or 250 to 350 mg (e.g., 250 to 350 mg BID). In certain embodiments, the dosage of ABT-199 is about 350 mg (e.g., 350 mg QID), 300 mg (e.g., 300 mg QID), 250 mg (e.g., 250 mg QID), 200 mg (e.g., 200 mg QID), 150 mg (e.g., 150 mg QID), 100 mg (e.g., 100 mg QID), or 50 mg (e.g., 50 mg QID).

In some embodiments, the Bcl-2 inhibitor is a Bcl-2 inhibitor (e.g., ABT-199) administered at a dose frequency of four times per day (QID), three times per day, twice per day (BID), once per day, once per two days, once per three days, once per four days, once per five days, once per six days, or once per week. In certain embodiments, the combination of the PI3K inhibitor and Bcl-2 inhibitor (e.g., ABT-199) is effective, e.g., in treating a cancer and/or in reducing cancer cell growth or viability, when the Bcl-2 inhibitor (e.g., ABT-199) administered at a dose frequency of four times per day (QID), three times per day, twice per day (BID), once per day, once per two days, once per three days, once per four days, once per five days, once per six days, or once per week.

In some embodiments, the Bcl-2 inhibitor is ABT-263 at a dosage of 325 mg. In certain embodiments, ABT-263 is effective as a monotherapy at a dosage of 325 mg. In certain embodiments, the combination of the PI3K inhibitor and ABT-263 is effective, e.g., in treating a cancer and/or in reducing cancer cell growth or viability, with ABT-263 at a dosage lower than 325 mg. In certain embodiments, the dosage of ABT-263 is 50 to 300 mg (e.g., 50 to 100 mg, 100 to 200 mg, or 200 to 300 mg). In certain embodiments, the dosage of ABT-263 is about 300 mg, 275 mg, 250 mg, 225 mg, 200 mg, 175 mg, 150 mg, 125 mg, 100 mg, 75 mg, or 50 mg. In certain embodiments, the dosage is for daily administration.

In some embodiments, the Bcl-2 inhibitor is ABT-263 and is administered at a dose frequency of four times per day (QID), three times per day, twice per day (BID), once per day, once per two days, once per three days, once per four days, once per five days, once per six days, or once per week. In certain embodiments, the combination of the PI3K inhibitor and ABT-263 is effective, e.g., in treating a cancer and/or in reducing cancer cell growth or viability, when ABT-263 administered at a dose frequency of four times per day (QID), three times per day, twice per day (BID), once per day, once per two days, once per three days, once per four days, once per five days, once per six days, or once per week.

In one embodiment, the Bcl-2 inhibitor is administered to a subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the Bcl-2 inhibitor is administered concurrently with the PI3K inhibitor (e.g., Compound 1), or a pharmaceutically acceptable form thereof, e.g., in a single dosage form or separate dosage forms. In yet another embodiment, the Bcl-2 inhibitor is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered.

In one embodiment, Compound 1, or a pharmaceutically acceptable form thereof, and the Bcl-2 inhibitor (e.g., ABT-199 or ABT-263), or a pharmaceutically acceptable form thereof, are the only therapeutically active ingredients.

In one embodiment, Compound 1, or a pharmaceutically acceptable form thereof, and the Bcl-2 inhibitor, or a pharmaceutically acceptable form thereof, are in a single dosage form. In one embodiment, Compound 1, or a pharmaceutically acceptable form thereof, and the Bcl-2 inhibitor, or a pharmaceutically acceptable form thereof, are in separate dosage forms. In one embodiment, the molar ratio of Compound 1, or a pharmaceutically acceptable form thereof, to the Bcl-2 inhibitor, or a pharmaceutically acceptable form thereof, is in the range of from about 50:1 to about 1:50. In one embodiment, the molar ratio of Compound 1, or a pharmaceutically acceptable form thereof, to the Bcl-2 inhibitor, or a pharmaceutically acceptable form thereof, is in the range of from about 10:1 to about 1:10 or from about 1:3 to about 1:7.

In one embodiment, Compound 1 is administered at an amount to reach maximum plasma concentration at steady state (Cmaxss) at about 1000 ng/mL to about 5000 ng/mL; and the Bcl-2 inhibitor is administered at an amount to reach Cmaxss at about 0.1 µg/mL to about 1000 µg/mL.

In one embodiment, Compound 1 is administered at an amount to reach an area under the plasma concentration-time curve at steady-state (AUCss) at about 5000 ng/mL*hr to about 10000 ng/mL*hr; and the Bcl-2 inhibitor is administered at an amount to reach an AUCss at about 0.1 ng/mL*hr to about 10000 ng/mL*hr.

In some embodiments, the PI3K inhibitor is Compound 1 and is effective (e.g., therapeutically effective) in the combination at an amount that is decreased by about 1.5 fold to about 50 fold of the amount that is required to achieve the same effect, e.g., the same therapeutic effect, when Compound 1 is administered as a monotherapy. In certain embodiments, the Bcl-2 inhibitor is effective (e.g., therapeutically effective) in the combination at an amount that is decreased by about 1.5 fold to about 50 fold of the amount that is required to achieve the same effect, e.g., the same therapeutic effect, when Compound 1 is administered as a monotherapy.

In some embodiments, the PI3K inhibitor is Compound 1, the Bcl-2 inhibitor is ABT-199 or ABT-263, and the cancer is a diffuse large B-cell lymphoma. In some such embodiments, the molar ratio of Compound 1, or a pharmaceutically acceptable form thereof, to the Bcl-2 inhibitor, or a pharmaceutically acceptable form thereof, is in the range of from about 50:1 to about 1:50.

In some embodiments, the PI3K inhibitor is Compound 1, the Bcl-2 inhibitor is ABT-199 or ABT-263, and the cancer is a follicular lymphoma. In some such embodiments, the molar ratio of Compound 1, or a pharmaceutically acceptable form thereof, to the Bcl-2 inhibitor, or a pharmaceutically acceptable form thereof, is in the range of from about 50:1 to about 1:50.

In some embodiments, the PI3K inhibitor is Compound 1, the Bcl-2 inhibitor is ABT-199 or ABT-263, and the cancer is a T-cell lymphoma. In some such embodiments, the molar ratio of Compound 1, or a pharmaceutically acceptable form thereof, to the Bcl-2 inhibitor, or a pharmaceutically acceptable form thereof, is in the range of from about 50:1 to about 1:50.

In some embodiments, the PI3K inhibitor is Compound 1, the Bcl-2 inhibitor is ABT-199 or ABT-263, and the cancer is mantle cell lymphoma. In some such embodiments, the molar ratio of Compound 1, or a pharmaceutically acceptable form thereof, to the Bcl-2 inhibitor, or a pharmaceutically acceptable form thereof, is in the range of from about 50:1 to about 1:50.

In one embodiment, provided herein is a method of reducing or delaying resistance to a treatment with PI3K inhibitor (e.g., a treatment with one or more PI3K inhibitors described herein) in a subject, or a method of reducing the likelihood for a subject to develop resistance to a treatment with a PI3K inhibitor (e.g., a treatment with one or more PI3K inhibitors described herein), the method comprising:
(a) administering to the subject a therapeutically effective amount of a monotherapy comprising the PI3K inhibitor, or a pharmaceutically acceptable form thereof, for a first period of time;
(b) after the first period of time, administering to the subject a therapeutically effective amount of a combination therapy comprising the PI3K inhibitor in combination with a Bcl-2 inhibitor (e.g., one or more Bcl-2 inhibitors as described herein), for a second period of time; and
(c) optionally repeating steps (a) and (b) one or more times.

In one embodiment, provided herein is a method of reducing or delaying resistance to a treatment with PI3K inhibitor (e.g., a treatment with one or more PI3K inhibitors described herein) in a subject, or a method of reducing the likelihood for a subject to develop resistance to a treatment with a PI3K inhibitor (e.g., a treatment with one or more PI3K inhibitors described herein), the method comprising:
(a) administering to the subject a therapeutically effective amount of a monotherapy comprising the Bcl-2 inhibitor, or a pharmaceutically acceptable form thereof, for a first period of time;
(b) after the first period of time, administering to the subject a therapeutically effective amount of a combination therapy comprising a PI3K inhibitor in combination with the Bcl-2 inhibitor (e.g., one or more Bcl-2 inhibitors as described herein), for a second period of time; and
(c) optionally repeating steps (a) and (b) one or more times.

In certain embodiments, the subject is identified as developing resistance (e.g., acquired resistance) to the monotherapy. In certain embodiments, the subject is identified as developing resistance based on an assessment of MRD. In certain embodiments, the subject is identified as developing resistance if the MRD is above a preselected cutoff value (e.g., 1 malignant cell in 100 normal cells, 1 malignant cell in 1000 normal cells, or 1 malignant cell in 10,000 normal cells). In certain embodiments, the preselected cutoff value is 1 malignant cell in 1000 or 10,000 normal cells. In certain embodiments, the method further comprises assessing MRD, e.g., in step (a) and/or (b).

In certain aspects, this disclosure provides a method of delaying resistance of a subject having a cancer, comprising administering to the subject a synergistic amount of a PI3K inhibitor, or a pharmaceutically acceptable form thereof, and a Bcl-2 inhibitor, or a pharmaceutically acceptable form thereof, thereby delaying resistance (e.g., resistance to the PI3K inhibitor). The method may comprise administering the PI3K inhibitor before the Bcl-2 inhibitor.

The disclosure also provides, in certain aspects, a method of reducing the risk that a cancer becomes resistant to the PI3K inhibitor, comprising administering to a subject having a cancer a synergistic amount of a PI3K inhibitor, or a pharmaceutically acceptable form thereof, and a Bcl-2 inhibitor, or a pharmaceutically acceptable form thereof, thereby reducing the risk that the cancer becomes resistant to the PI3K inhibitor.

The disclosure also provides, in certain aspects, a method of prolonging remission (e.g., complete remission or partial remission) in a subject having a cancer, comprising administering to the subject a synergistic amount of a PI3K inhibitor, or a pharmaceutically acceptable form thereof, and a Bcl-2 inhibitor, or a pharmaceutically acceptable form thereof, thereby prolonging remission in the subject.

The disclosure also provides, in certain aspects, a method of increasing the likelihood that a subject having a cancer experiences complete remission, comprising administering to the subject a synergistic amount of a PI3K inhibitor, or a pharmaceutically acceptable form thereof, and a Bcl-2 inhibitor, or a pharmaceutically acceptable form thereof, thereby increasing the likelihood that the subject experiences complete remission.

The disclosure also provides, in certain aspects, a method of reducing the level of minimal residual disease (MRD) compared to a reference value (e.g., compared to a pre-treatment value or a value obtained during treatment) in a subject having a cancer, comprising administering to the subject a synergistic amount of a PI3K inhibitor, or a pharmaceutically acceptable form thereof, and a Bcl-2 inhibitor, or a pharmaceutically acceptable form thereof, thereby reducing the level of MRD in the subject.

This disclosure further provides methods of assessing a subject's cells, and treating the patient with a combination of a PI3K inhibitor and a Bcl-2 inhibitor.

For instance, in certain aspects, the invention features a method of evaluating the responsiveness of a cancer or tumor, or a subject having a cancer or tumor, to a treatment with a BCR pathway inhibitor (e.g., a treatment with an inhibitor of PI3K, BTK or SYK, alone or in combination). In one embodiment, responsiveness to a PI3K inhibitor is evaluated. The method includes: acquiring a value (e.g., determining one or more of: the presence, absence, amount or level) of an alteration or biomarker chosen from one, two, three, four or all of: an STK11 copy number, TSC1 copy number, TSC2 copy number, a p53 pathway mutation (e.g., a mutation disclosed in Table 20), or MAPK pathway mutation (e.g., a mutation disclosed in Table 18), or any combination thereof (e.g., a dual MAPK/p53 pathway mutation, e.g., a mutation disclosed in Table 18 and a mutation disclosed in Table 20). The method further comprises administering a PI3K inhibitor and a Bcl-2 inhibitor to the subject. In some embodiments, the subject has, or is identified as having, a tumor that is responsive to the PI3K inhibitor. In some embodiments, the subject has, or is identified as having, a tumor that is not responsive to the PI3K inhibitor. In some embodiments, PI3K inhibitor and a Bcl-2 inhibitor are administered to a subject that has, or is identified as having, a tumor that is less responsive, e.g., not responsive to the PI3K inhibitor. In some embodiments, PI3K inhibitor and a Bcl-2 inhibitor are administered to a subject that has, or is identified as having, a tumor that is responsive to the PI3K inhibitor. In some embodiments, PI3K inhibitor and a Bcl-2 inhibitor are administered to a subject that has, or is identified as having, a tumor that is less responsive, e.g., not responsive to the PI3K inhibitor. In some embodiments, co-administration of the Bcl-2 inhibitor improves sensitivity of the tumor to the PI3K inhibitor.

In another aspect, the invention features a method of monitoring a treatment of a subject with a BCR pathway inhibitor (e.g., a treatment with an inhibitor of PI3K, BTK or SYK, alone or in combination). In one embodiment, treatment with a PI3K inhibitor is monitored. The method includes: acquiring, at two or more time intervals, a value (e.g., determining one or more of: the presence, absence, amount or level) of an alteration or biomarker chosen from one, two, three, four or all of: an STK11 copy number, TSC1 copy number, TSC2 copy number, a p53 pathway mutation (e.g., a mutation disclosed in Table 20), or MAPK pathway mutation (e.g., a mutation disclosed in Table 18), or any combination thereof (e.g., a dual MAPK/p53 mutation, e.g., a mutation disclosed in Table 18 and a mutation disclosed in Table 20). The method further comprises administering a PI3K inhibitor and a Bcl-2 inhibitor to the subject.

In another aspect, the invention features a method of treating (e.g., inhibiting, reducing, ameliorating, managing, or preventing) a cancer or tumor in a subject. The method includes: acquiring a value (e.g., determining one or more of: the presence, absence, amount or level) of an alteration or biomarker chosen from one, two, three, four or all of: an STK11 copy number, TSC1 copy number, TSC2 copy number, a p53 pathway mutation (e.g., a mutation disclosed in Table 20), or MAPK pathway mutation (e.g., a mutation disclosed in Table 18), or any combination thereof (e.g., a dual MAPK/p53 mutation, e.g., a mutation disclosed in Table 18 and a mutation disclosed in Table 20), and responsive to said value, administering to the subject a BCR pathway inhibitor, e.g., a PI3K inhibitor (e.g., one or more PI3K inhibitors) and a Bcl-2 inhibitor.

In another aspect, the invention features a method of treating a subject, comprising (i) administering a first treatment comprising a first PI3K inhibitor to the subject (ii) acquiring information regarding the presence or absence of an alteration in a biomarker in one or more samples from the subject, wherein the biomarker is selected from STK11, TSC1, TSC2, TP53, PTEN, CBFA2T3, YWHAE, PER1, GAS7, FSTL3, USP6, MAP2K4, or EGFR; and (iii) continuing administration of the first treatment if the alteration is absent, or administering a second treatment if the alteration is present, wherein the second treatment includes administration of a Bcl-2 inhibitor.

In certain embodiments, the alteration is an STK11, TSC1, TSC2, TP53, PTEN, CBFA2T3, YWHAE, PER1, GAS7, FSTL3, USP6, or MAP2K4 copy number loss (e.g., single copy loss). In some embodiments, the STK11, TSC1, TSC2, TP53, PTEN, CBFA2T3, YWHAE, PER1, GAS7, FSTL3, USP6, or MAP2K4 copy number in a sample taken from the subject after the first treatment is lower than a corresponding STK11, TSC1, TSC2, TP53, PTEN, CBFA2T3, YWHAE, PER1, GAS7, FSTL3, USP6, MAP2K4 copy number in a sample taken from the subject before the first treatment (e.g., there is an STK11 single copy loss).

In another aspect, the present disclosure provides a method of evaluating the responsiveness of a cancer or tumor, or a subject having a cancer or tumor, to a treatment with a BCR pathway inhibitor (e.g., a treatment with an inhibitor of PI3K, BTK or SYK, alone or in combination). In one embodiment, responsiveness to a PI3K inhibitor is evaluated. The method includes: acquiring a value (e.g., determining one or more of: the presence, absence, amount or level) of an anti-apoptotic factor such as Bcl-2.

In another aspect, the invention features a method of monitoring a treatment of a subject with a BCR pathway inhibitor (e.g., a treatment with an inhibitor of PI3K, BTK or SYK, alone or in combination). In one embodiment, treatment with a PI3K inhibitor is monitored. The method includes: acquiring, at two or more time intervals, a value (e.g., determining one or more of: the presence, absence, amount or level) of an anti-apoptotic factor such as Bcl-2.

In another aspect, the invention features a method of treating (e.g., inhibiting, reducing, ameliorating, managing, or preventing) a cancer or tumor in a subject. The method includes: acquiring a value (e.g., determining one or more of: the presence, absence, amount or level) of an anti-apoptotic factor such as Bcl-2.

In certain embodiments, the methods that include acquiring a value of Bcl-2 also include acquiring a value (e.g., determining one or more of: the presence, absence, amount or level) of a pro-apoptotic factor or anti-apoptotic factor. The pro-apoptotic factor can be, e.g., one or more of (e.g., 2, 3, 4, or all of) BMF, BIK, BIM, NOXA, PUMA, and HRK. In some embodiments, an elevated level of Bcl-2 indicates that the cancer is resistant to a PI3K inhibitor. In some embodiments, a normal or reduced level of Bcl-2 indicates that the cancer is responsive to a PI3K inhibitor. In some embodiments, an elevated level of one or more pro-apoptotic factors (e.g., BMF, BIK, BIM, NOXA, PUMA, and HRK) indicates that the cancer is more responsive to a PI3K inhibitor (optionally in combination with a Bcl-2 inhibitor) than a cancer with normal or lowered levels of the pro-apoptotic factor. In some embodiments, the methods involve administering a Bcl-2 inhibitor (e.g., in combination with a PI3K inhibitor) to a subject having elevated Bcl-2 levels. In some embodiments, the methods involve administering a PI3K inhibitor as a monotherapy to a subject having normal or low Bcl-2 levels. In some embodiments, the elevated, normal, or reduced levels of a biomarker are determined with reference to a non-cancerous control value.

The disclosure includes all combinations of any one or more of the foregoing aspects and/or embodiments, as well as combinations with any one or more of the embodiments set forth in the detailed description and examples.

INCORPORATION BY REFERENCE

All publications, patents, and patent applications mentioned in this specification are herein incorporated by reference in their entirety and to the same extent as if each individual publication, patent, or patent application is specifically and individually indicated to be incorporated by reference.

BRIEF DESCRIPTION OF THE DRAWINGS

FIGS. 5A, 5B, and 5C show the change in RNA levels of selected differentially regulated genes in patients treated with Compound 1.

DETAILED DESCRIPTION

1. Definitions

Figure 1:
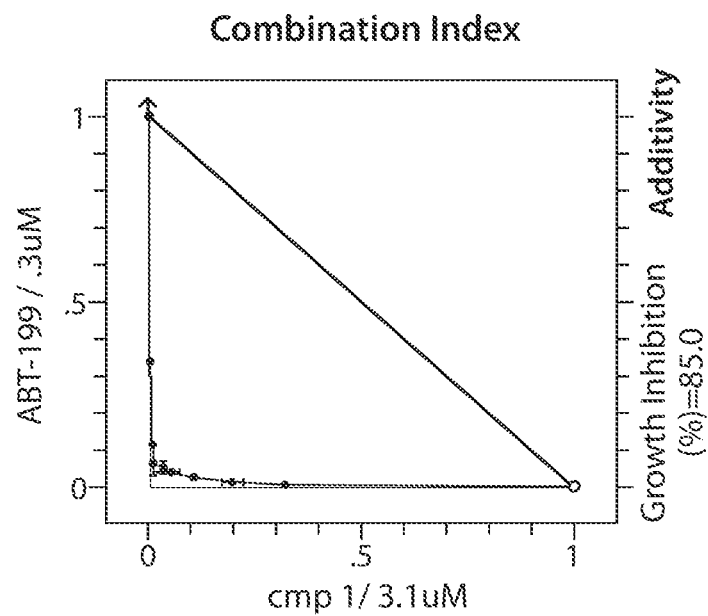
FIG. 1 shows an isobologram depicting the synergistic effect of the combination of Compound 1 and ABT-199 in SU-DHL-4 cell line.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, and unless otherwise indicated, the term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to reduce or inhibit a biological function of a target protein or polypeptide, such as by reducing or inhibiting the activity or expression of the target protein or polypeptide. Accordingly, the terms "antagonist" and "inhibitor" are defined in the context of the biological role of the target protein or polypeptide. An inhibitor need not completely abrogate the biological function of a target protein or polypeptide, and in some embodiments reduces the activity by at least 50%, 60%, 70%, 80%, 90%, 95%, or 99%. While some antagonists herein specifically interact with (e.g., bind to) the target, compounds that inhibit a biological activity of the target protein or polypeptide by interacting with other members of the signal transduction pathway of which the target protein or polypeptide are also specifically included within this definition. Non-limiting examples of biological activity inhibited by an antagonist include those associated with the development, growth, or spread of a tumor, or an undesired immune response as manifested in autoimmune disease.

The term "effective amount" or "therapeutically effective amount" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on, for example, the particular compounds chosen, the dosing regimen to be followed, whether it is administered in combination with other agents, timing of administration, the tissue to which it is administered, and the physical delivery system in which it is carried.

As used herein, a daily dosage can be achieved by a single administration of the targeted dosage amount or multiple administrations of smaller dosage amount(s). For example, a 150 mg daily dosage can be achieved by a single administration of 150 mg of the therapeutic agent per day, two administrations of 75 mg of the therapeutic agent per day, or three administrations of 50 mg of the therapeutic agent per day, or the like.

As used herein, the terms "treatment", "treating", "palliating" and "ameliorating" are used interchangeably herein. These terms refer to an approach for obtaining beneficial or desired results including, but not limited to, therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder.

As used herein, the terms "prevention" and "preventing" are used herein to refer to an approach for obtaining beneficial or desired results including, but not limited to, prophylactic benefit. For prophylactic benefit, the pharmaceutical compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

As used herein, the "aggressiveness" of a tumor or cancer refers to the rate at which the tumor is growing. Thus, a tumor is more aggressive than another tumor or cancer if it is proliferating at a higher rate. Other determinants can be used to measure the level of aggressiveness of a tumor or cancer, for example, based on the appearance of tumor or cancer cells under a microscope to determine the extent to which tumors are differentiated. A well-differentiated tumor tends to be more aggressive than a poorly-differentiated tumor or cancer.

The term "selective inhibition" or "selectively inhibit" as applied to a biologically active agent refers to the agent's ability to selectively reduce the target signaling activity as compared to off-target signaling activity, via direct or indirect interaction with the target. For example, a compound that selectively inhibits one isoform of PI3K over another isoform of PI3K has an activity of at least greater than about 1× against a first isoform relative to the compound's activity against the second isoform (e.g., at least about 2×, 3×, 5×, 10×, 20×, 50×, 100×, 200×, 500×, or 1000×). In certain embodiments, these terms refer to (1) a compound described herein that selectively inhibits the gamma isoform over the alpha, beta, or delta isoform; or (2) a compound described herein that selectively inhibits the delta isoform over the alpha or beta isoform. By way of non-limiting example, the ratio of selectivity can be greater than a factor of about 1, greater than a factor of about 2, greater than a factor of about 3, greater than a factor of about 5, greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by $IC_{50}$. In certain embodiments, the $IC_{50}$ can be measured by in vitro or in vivo assays. In certain embodiments, the PI3K gamma isoform $IC_{50}$ activity of a compound provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM. In certain embodiments, the PI3K delta isoform $IC_{50}$ activity of a compound provided herein can be less than about 1000 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 5 nM, or less than about 1 nM.

"Subject" or "patient" to which administration is contemplated includes, but is not limited to, humans (e.g., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

Combination therapy, or "in combination with" refer to the use of more than one compound or agent to treat a particular disorder or condition. For example, a PI3K inhibitor (e.g., Compound 1) may be administered in combination with at least one additional therapeutic agent (e.g. a Bcl-2 inhibitor). By "in combination with," it is not intended to imply that the PI3K inhibitor and additional therapeutic agent (e.g., the BLC-2 inhibitor) must be administered at the same time and/or formulated for delivery together, although these methods of delivery are within the scope of this disclosure. The PI3K inhibitor, e.g., Compound 1, can be administered concurrently with, prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before), or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after), one or more other additional agents. In certain embodiments, each therapeutic agent will be administered at a dose and/or on a time schedule determined for that particular agent. The other therapeutic agent (e.g., the Bcl-2 inhibitor) can be administered with the PI3K inhibitor (e.g., Compound 1) herein in a single composition or separately in a different composition. Higher combinations, e.g., triple therapy, are also contemplated herein.

The terms "co-administration of" and "co-administering" and their grammatical equivalents, as used herein, encompass administration of two or more agents to subject so that both agents and/or their metabolites are present in the subject at the same or substantially the same time. In one embodiment, co-administration of a PI3K inhibitor with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the PI3K inhibitor, or in some combination thereof. Where the PI3K inhibitor is administered to the patient at repeated intervals, e.g., during a standard course of treatment, the additional agent can be administered prior to, at the same time as, or subsequent to, each administration of the PI3K inhibitor, or some combination thereof, or at different intervals in relation to the PI3K inhibitor treatment, or in a single dose prior to, at any time during, or subsequent to the course of treatment with the PI3K inhibitor. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), essentially concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

As used herein, a "monotherapy" refers to the use of an agent individually (e.g., as a single compound or agent), e.g., without a second active agent to treat the same indication, e.g., cancer. For example, in this context, the term monotherapy includes the use of either the PI3K inhibitor or the second agent individually to treat the cancer.

The term "synergy" or "synergistic" encompasses a more than additive effect of a combination of two or more agents compared to their individual effects. In certain embodiments, synergy or synergistic effect refers to an advantageous effect of using two or more agents in combination, e.g., in a pharmaceutical composition, or in a method of treatment. In certain embodiments, one or more advantageous effects is achieved by using a PI3K inhibitor in combination with a second therapeutic agent (e.g., one or Bcl-2 inhibitors) as described herein.

In some embodiments, the synergistic effect is that a lower dosage of one or both of the agents is needed to achieve an effect. For example, the combination can provide a selected effect, e.g., a therapeutic effect, when at least one of the agents is administered at a lower dosage than the dose of that agent that would be required to achieve the same therapeutic effect when the agent is administered as a monotherapy. In certain embodiments, the combination of a PI3K inhibitor (e.g., Compound 1) and a second agent as described herein (e.g., a Bcl-2 inhibitor as described herein) allows the PI3K inhibitor to be administered at a lower dosage than would be required to achieve the same therapeutic effect if the PI3K inhibitor were administered as a monotherapy. In certain embodiments, the combination of a PI3K inhibitor (e.g., Compound 1) and the Bcl-2 inhibitor allows the Bcl-2 inhibitor to be administered at a lower dosage than would be required to achieve the same therapeutic effect if the Bcl-2 inhibitor were administered as a monotherapy.

In some embodiments, the synergistic effect is a reduction, prevention, delay, or decrease in the occurrence or the likelihood of occurrence of one or more side effects, toxicity, resistance, that would otherwise be associated with administration of at least one of the agents.

In some embodiments, the synergistic effect is a reduction in resistance (e.g., a decrease in a measure of resistance or a decreased likelihood of developing resistance), or a delay in the development of resistance, to at least one of the agents.

In some embodiments, the synergistic effect is a reduction in MRD. In certain embodiments, the combination of a PI3K inhibitor (e.g. a PI3K inhibitor described herein) and a second agent (e.g., a Bcl-2 inhibitor) is effective to reduce the MRD in the subject, e.g., below a level previously measured in the subject (e.g., the level measured before the combination was administered). In certain embodiments, the combination of a PI3K inhibitor and a second agent (e.g., a Bcl-2 inhibitor) is effective to reduce the MRD in the subject below the level observed during or after treatment with a monotherapy, e.g., a monotherapy comprising either the PI3K inhibitor or the second agent (e.g., the Bcl-2 inhibitor). In certain embodiments, the MRD is decreased below the level observed during treatment with a monotherapy comprising the PI3K inhibitor. In certain embodiments, the MRD is decreased below the level observed during treatment with a monotherapy comprising the second agent (e.g., the Bcl-2 inhibitor). In certain embodiments, the combination is effective to reduce the MRD below a preselected cutoff value (e.g., 1 malignant cell in 100 normal cells, 1 malignant cell in 1000 normal cells, or 1 malignant cell in 10,000 normal cells). In certain embodiments, the preselected cutoff value is 1 malignant cell in 1000 or 10,000 normal cells.

In some embodiments, a synergistic effect refers to the combination of a PI3K inhibitor (e.g., Compound 1, or a pharmaceutically acceptable form thereof), and a second therapeutic agent (e.g., one or more the Bcl-2 inhibitor(s), or a pharmaceutically acceptable forms thereof, as described herein), results in a therapeutic effect greater than the additive effect of the PI3K inhibitor and the second agent.

In some embodiments, a synergistic effect means that combination index value is less than a selected value, e.g., for a given effect, e.g., at a selected percentage (e.g., 50%) inhibition or growth inhibition, e.g., as described herein in the Examples. In certain embodiments, the selected value is 1. In certain embodiments, the selected value is 0.7. In certain embodiments, the selected value is 0.5.

In some embodiments, a synergistic effect means that the synergy score is 1 or more. In certain embodiments, the synergy score is greater than 1. In certain embodiments, the synergy score is 3 or more. In certain embodiments, the synergy score is 10 or more.

Combination index (CI) is a score of the potency shifting. Chou et al., Adv Enzyme Regul 1984; 22: 27-55 and in U.S. Patent Publication No. 2013/0295102, the contents of which are incorporated herein by reference. A CI value of greater than 1 indicates antagonistic effect; a CI value of 1.0 is indicative of an additive effect; and a CI value of less than 1 is indicative of a synergistic effect resulting from the combination. The CI value can be determined at various percentages of inhibition or growth inhibition.

The CI can be thought of as an estimate of the fraction of the original (monotherapy) doses of each of two drugs would be needed in combination relative to the single agent doses required to achieve a chosen effect level. For example, when the combination index has a value of 0.1, only about one tenth of the total fractional amounts of the individual agents (expressed as a fraction of the amount of that agent when administered as a monotherapy to achieve a chosen effect) are needed for the combination to reach the same chosen effect level. For example, if a dose of 100 mg/kg of drug A individually or a dose of 200 mg/kg of drug B individually is needed to achieve the chosen effect, and the combination index is 0.1, then approximately 5 mg/kg of drug A and 10 mg/kg of drug B would achieve the chosen effect (one twentieth of the original doses of each of the single agents adds up to a total of one tenth). The doses of the single agents need not be reduced by the same fractional value so long as the sum of their fractional values adds up to the combination index; thus, in this example, a dose of approximately 8 mg/kg of drug A and 4 mg/kg of drug B would also achieve the chosen effect (this is 0.08 times the original dose of drug A and 0.02 times the original dose of drug B; the sum of the fractional amounts (0.08+0.02) is equal to the combination index of 0.1.)

According to one embodiment, synergy score is a measure of the combination effects in excess of Loewe additivity. In one example, synergy score is a scalar measure to characterize the strength of synergistic interaction. The Synergy score can be calculated as:

$$\text{Synergy Score} = \log f_x \log f_y \Sigma \max(0, I_{data})(I_{data} - I_{Loewe})$$

In this example, the fractional inhibition for each component agent and combination point in the matrix is calculated relative to the median of all vehicle-treated control wells. The example Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions at that occur at high activity levels. According to other embodiments, a synergy score can be calculated based on a curve fitting approach where the curvature of the synergy score is extrapolated by introducing a median value and origin value (e.g., a dose zero value).

The synergy score measure can be used for the self-cross analysis. Synergy scores of self-crosses are expected to be additive by definition and, therefore, maintain a synergy score of zero. However, while some self-cross synergy scores are near zero, many are greater suggesting that experimental noise or non-optimal curve fitting of the single agent dose responses are contributing to the slight perturbations in the score. This strategy is cell line-centric, focusing on self-cross behavior in each cell line versus a global review of cell line panel activity. Combinations where the synergy score is greater than the mean self-cross plus two standard deviations or three standard deviations can be considered candidate synergies at 95% and 99% confidence levels, respectively. Additivity should maintain a synergy score of zero, and synergy score of two or three standard deviations indicate synergism at statistically significant levels of 95% and 99%.

Loewe Volume (Loewe Vol) is used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, the Loewe Volume should be assessed to examine if there is any correlation between antagonism and a particular drug target-activity or cellular genotype. This model defines additivity as a non-synergistic combination interaction where the combination dose matrix surface should be indistinguishable from either drug crossed with itself. The calculation for Loewe additivity is:

$$I_{Loewe} \text{ that satisfies } (X/X_I)+(Y/Y_I)=1$$

where $X_I$ and $Y_I$ are the single agent effective concentrations for the observed combination effect I. For example, if 50% inhibition is achieved separately by 1 μM of drug A or 1 μM of drug B, a combination of 0.5 μM of A and 0.5 μM of B should also inhibit by 50%.

As used herein, a daily dosage can be achieved by a single administration of the targeted dosage amount or multiple administrations of smaller dosage amount(s). For example, a 150 mg daily dosage can be achieved by a single administration of 150 mg of the therapeutic agent per day, two administrations of 75 mg of the therapeutic agent per day, or three administrations of 50 mg of the therapeutic agent per day, or the like.

The term "anti-cancer effect" refers to the effect a therapeutic agent has on cancer, e.g., a decrease in growth, viability, or both of a cancer cell. The $IC_{50}$ of cancer cells can be used as a measure the anti-cancer effect.

$IC_{50}$ refers to a measure of the effectiveness of a therapeutic agent in inhibiting cancer cells by 50%.

The term "tumor" refers to any neoplastic cell growth and proliferation, whether malignant or benign, and any pre-cancerous and cancerous cells and tissues. As used herein, the term "neoplastic" refers to any form of dysregulated or unregulated cell growth, whether malignant or benign, resulting in abnormal tissue growth. Thus, "neoplastic cells" include malignant and benign cells having dysregulated or unregulated cell growth.

The term "cancer" includes, but is not limited to, solid tumors and blood born tumors. The term "cancer" refers to disease of skin tissues, organs, blood, and vessels, including, but not limited to, cancers of the bladder, bone or blood, brain, breast, cervix, chest, colon, endometrium, esophagus, eye, head, kidney, liver, lymph nodes, lung, mouth, neck, ovaries, pancreas, prostate, rectum, stomach, testis, throat, and uterus.

Hematopoietic origin refers to involving cells generated during hematopoiesis, a process by which cellular elements of blood, such as lymphocytes, leukocytes, platelets, erythrocytes and natural killer cells are generated. Cancers of hematopoietic origin includes lymphoma and leukemia.

Resistant or refractive refers to when a cancer that has a reduced responsiveness to a treatment, e.g., up to the point where the cancer does not respond to treatment. The cancer can be resistant at the beginning of treatment, or it may become resistant during treatment. The cancer subject may have one or more mutations that cause it to become resistant to the treatment, or the subject may have developed such mutations during treatment. The term "refractory" can refer to a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

"Acquire" or "acquiring" as the terms are used herein, refer to obtaining possession of, determining, or evaluating, a value or information (e.g., one or more of: the presence, absence, amount or level) of an alteration or biomarker, by "directly acquiring" or "indirectly acquiring" the same. "Directly acquiring" means performing a process (e.g., performing a test) to obtain the value or information of the alteration or biomarker. "Indirectly acquiring" refers to receiving the value or information of the alteration or biomarker from another party or source (e.g., a diagnostic provider, a third party clinician or health professional).

"Alteration" of a gene or gene product (e.g., a biomarker gene or gene product) or an "altered gene" or "altered gene product" as used herein, refers to the presence of a mutation (e.g., one or more mutations) within a gene or gene product, which affects the structure, amount or activity of the gene or gene product, as compared to a reference gene or gene product, e.g., a normal or wild-type gene or gene product, or a responder gene or gene product (e.g., a gene or gene product in a responder subject (e.g., a subject in complete or partial cancer remission)). The alteration can be in amount, structure, and/or activity in a cancer tissue or cancer cell, as compared to its amount, structure, and/or activity, in a reference tissue or cell (e.g., a normal or healthy tissue or cell, or a responder tissue or cell (e.g., a tissue or cell from a subject in complete or partial cancer remission)). The alteration can be associated with, or be indicative of, a disease state, such as cancer (e.g., a hematologic malignancy as described herein, e.g., CLL). For example, an alteration which is associated with cancer, or is predictive of responsiveness or non-responsiveness to an anti-cancer therapeutic (e.g., a PI3K inhibitor disclosed herein), can have an altered nucleotide sequence (e.g., a mutation), amino acid sequence, chromosomal translocation, intra-chromosomal inversion, copy number, expression level, protein level, protein activity, or methylation status, in a cancer tissue or cancer cell, as compared to a reference tissue or cell. Exemplary mutations include, but are not limited to, point mutations (e.g., silent, missense, or nonsense), deletions, insertions, inversions, linking mutations, duplications, copy number changes, translocations, inter- and intra-chromosomal rearrangements. Mutations can be present in the coding or non-coding region of the gene (e.g., one or more exons, the 5'- and/or 3'-UTR).

In certain embodiments, the alteration(s) are associated (or not associated) with a phenotype, e.g., a cancerous phenotype (e.g., one or more of cancer risk; cancer progression; responsiveness to a cancer treatment (e.g., complete or partial remission); or decreased responsiveness or non-responsiveness to a cancer treatment (e.g., progressive or stable disease, or resistance, e.g., acquired resistance) to a cancer treatment). In one embodiment, the alteration is associated with, or is, a prognosis-positive predictor or a prognosis-negative predictor (also referred to herein as a "prognosis-positive alteration" or a "prognosis-negative alteration"). In another embodiment, the alteration is associated with, or is, a progression-positive predictor or a progression-negative predictor (also referred to herein as a "progression-positive alteration" or a "progression-negative alteration").

As used herein, the term 'prognosis-positive predictor' refers to any alteration that indicates increased responsiveness (e.g., increased sensitivity) to a PI3K inhibitor. The prognosis-positive predictor can be evaluated relative to a reference value, e.g., a normal or wild-type gene or gene product, or a responder gene or gene product (e.g., a gene or gene product in a responder subject (e.g., a subject in complete or partial cancer remission)). Subjects in complete or partial cancer remission (e.g., CR or PR subjects as described herein) can have one or more prognosis-positive alterations.

The term 'prognosis-negative predictor' refers to any alteration that indicates decreased responsiveness (e.g., sensitivity) to a PI3K inhibitor. The prognosis-negative predictor can be evaluated relative to a reference value, e.g., a reference value disclosed herein. Subjects with progressive disease or stable disease (e.g., PD or SD subjects as described herein) can have one or more prognosis-negative alterations. This term can include a subject who has resistance (e.g., has developed or acquired resistance) to a PI3K inhibitor.

The term 'progression-positive predictor' refers to any alteration that indicates increased progression or increased likelihood of cancer progression. The progression-positive predictor can be evaluated relative to a reference value, e.g., a reference value disclosed herein. Subjects with progressive disease or stable disease (e.g., PD or SD subjects as described herein) can have one or more progression-positive alterations. This term can include a subject who has resistance (e.g., has developed or acquired resistance) to a PI3K inhibitor.

The term 'progression-negative predictor' refers to any alteration that indicates decreased progression or decreased likelihood of cancer progression. The progression-negative predictor can be evaluated relative to a reference value, e.g., a reference value disclosed herein. Subjects in complete or partial cancer remission (e.g., CR or PR subjects as described herein) can have one or more progression-negative alterations.

A "biomarker" or "marker" is a substance, e.g., a gene or gene product (e.g., mRNA or protein) which can be altered (e.g., having an alteration described herein), wherein said alteration is associated with, or is indicative of, a disease state, e.g., a cancer (e.g., a hematological malignancy described herein, e.g., CLL). The alteration can be in amount, structure, and/or activity of the substance (e.g., gene or gene product) in a cancer tissue or cancer cell, as compared to its amount, structure, and/or activity, in a reference sample, e.g., a normal or wild-type gene or gene product, or a responder gene or gene product (e.g., a gene or gene product in a responder subject (e.g., a subject in complete or partial cancer remission). For example, a biomarker described herein which is associated with cancer or predictive of responsiveness to anti-cancer therapeutics can have an altered nucleotide sequence, amino acid sequence, chromosomal translocation, intra-chromosomal inversion, copy number, expression level, protein level, protein activity, or methylation status, in a cancer tissue or cancer cell as compared to a normal, healthy tissue or cell. Furthermore, a "biomarker" includes a molecule whose structure is altered, e.g., mutated (contains an mutation), e.g., differs from the wild type sequence at the nucleotide or amino acid level, e.g., by substitution, deletion, or insertion, when present in a tissue or cell associated with a disease state, such as cancer. In some embodiments, a biomarker can be evaluated individually, or in combinations with one or more other biomarkers.

As used herein, the term 'prognosis-positive biomarker' refers to any biomarker that indicates increased responsiveness (e.g., increased sensitivity) to a PI3K inhibitor. The prognosis-positive biomarker can be evaluated relative to a reference value, e.g., a normal or wild-type gene or gene product, or a responder gene or gene product (e.g., a gene or gene product in a responder subject (e.g., a subject in complete or partial cancer remission)). Subjects in complete or partial cancer remission (e.g., CR or PR subjects as described herein) can have one or more prognosis-positive biomarkers.

The term 'prognosis-negative biomarker' refers to any biomarker that indicates decreased responsiveness (e.g., sensitivity) to a PI3K inhibitor. The prognosis-negative biomarker can be evaluated relative to a reference value, e.g., a reference value disclosed herein. Subjects with progressive disease or stable disease (e.g., PD or SD subjects as described herein) can have one or more prognosis-negative biomarkers. This term can include a subject who has resistance (e.g., has developed or acquired resistance) to a PI3K inhibitor.

The term 'progression-positive biomarker' refers to any biomarker that indicates increased progression or increased likelihood of cancer progression. The progression-positive biomarker can be evaluated relative to a reference value, e.g., a reference value disclosed herein. Subjects with progressive disease or stable disease (e.g., PD or SD subjects as described herein) can have one or more progression-positive biomarker. This term can include a subject who has resistance (e.g., has developed or acquired resistance) to a PI3K inhibitor.

The term 'progression-negative biomarker' refers to any biomarker that indicates decreased progression or decreased likelihood of cancer progression. The progression-negative biomarker can be evaluated relative to a reference value, e.g., a reference value disclosed herein. Subjects in complete or partial cancer remission (e.g., CR or PR subjects as described herein) can have one or more progression-negative biomarkers.

One skilled in the art can recognize that a prognostic biomarker may be used as a diagnostic biomarker or a predictive biomarker, and terms such as 'prognosis-positive', 'prognosis-negative', 'progression-positive' and progression-negative' and the like may refer to biomarkers used in methods involving prediction or diagnosis.

"Copy number loss" as used herein refers to the loss of one or more copies of a DNA sequence from a genome. In some embodiments, the DNA sequence comprises a gene. In some embodiments, the DNA sequence comprises a portion of a gene, e.g., such that loss of the portion reduces or abrogates the gene function. In some embodiments, copy number loss is a result of a deletion, chromosome loss, or chromosome breakage event.

"Responsiveness," to "respond" to treatment, and other forms of this term, as used herein, refer to the reaction of a subject to treatment with a therapeutic, e.g., a PI3K inhibitor, alone or in combination, e.g., monotherapy or combination therapy. In one embodiment, a response to a PI3K inhibitor is determined. Responsiveness to a therapy, e.g., treatment with a PI3K inhibitor alone or in combination, can be evaluated by using any of the alterations/biomarkers disclosed herein and/or comparing a subject's response to the therapy using one or more clinical criteria, such as IWCLL 2008 (for CLL) described in, e.g., Hallek, M. et al. (2008) Blood 111 (12): 5446-5456; RECIST criteria for solid tumors (Response Evaluation Criteria In Solid Tumors), and the like. Additional classifications of responsiveness are provided in Brown, J. R. (2014) Blood, 123(22):3390-3397 and Chesson, B. D. et al. Journal of Clinical Oncology, 30(23):2820-2822.

These criteria provide a set of published rules that define when cancer patients improve ("respond"), stay the same ("stable") or worsen ("progression") during treatments.

In one embodiment, a subject having CLL can be determined to be in complete remission (CR) or partial remission (PR). For example, according to IWCLL 2008, a subject is considered to be in CR if at least all of the following criteria as assessed after completion of therapy are met: (i) Peripheral blood lymphocytes (evaluated by blood and different count) below $4\times10^9$/L (4000 µL); (ii) no hepatomegaly or splenomegaly by physical examination; (iii) absence of constitutional symptoms; and (iv) blood counts (e.g., neutrophils, platelets, hemoglobin) above the values set forth in Hallek, M. et al. supra at page 5451). Partial remission (PR) for CLL is defined according to IWCLL 2008 as including one of: (i) a decrease in number of blood lymphocytes by 50% or more from the value before therapy; (ii) a reduction in lymphadenopathy, as detected by CT scan or palpation; or (iii) a reduction in pretreatment enlargement of spleen or liver by 50% or more, as detected by CT scan or palpation; and blood counts (e.g., neutrophils, platelets, hemoglobin) according to the values set forth in Hallek, M. et al. supra at page 5451).

In other embodiments, a subject having CLL is determined to have progressive disease (PD) or stable disease (SD). For example, according to IWCLL 2008, a subject is considered to be in PD during therapy or after therapy if at least one of the following criteria is met: (i) progression on lymphadenopathy; (ii) an increase in pretreatment enlargement of spleen or liver by 50% or more, or de novo appearance of hepatomegaly or splenomegaly; (iii) an increase in the number of blood lymphocytes by 50% or more with at least 5000 B lymphocytes per microliter; (iv) transformation to a more aggressive histology (e.g., Richter syndrome); or (v) occurrence of cytopenia (neutropenia, anemia or thrombocytopenia) attributable to CLL, as described in Hallek, M. et al. supra at page 5452. Stable disease (SD) for CLL is defined according to IWCLL 2008 as a patient who has not achieved CR or a PR, and who has not exhibited progressive disease, see Hallek, M. et al. supra at page 5452.

In one embodiment, a subject with CLL responds to treatment with a PI3K inhibitor if at least one of the criteria for disease progression according to IWCLL is retarded or reduced, e.g., by about 10%, 20%, 30%, 40%, 50%, 60%, 70%, 80%, 90% or more. In another example, a subject responds to treatment with a PI3K inhibitor, if the subject experiences a life expectancy extension, e.g., extended by about 5%, 10%, 20%, 30%, 40%, 50% or more beyond the life expectancy predicted if no treatment is administered. In another example, a subject responds to treatment with a PI3K inhibitor, if the subject has one or more of: an increased progression-free survival, overall survival or increased time to progression (TTP), e.g., as described in Hallek, M. et al. supra at page 5452.

In another embodiment in solid tumors, a subject responds to treatment with a PI3K inhibitor if growth of a tumor in the subject is retarded about 10%, 20%, 30%, 40%, 50%, 60%, 70%, 80%, 90% or more. In another example, a subject responds to treatment with a PI3K inhibitor, if a tumor in the subject shrinks by about 5%, 10%, 20%, 30%, 40%, 50% or more as determined by any appropriate measure, e.g., by mass or volume. In another example, a subject responds to treatment with a PI3K inhibitor, if the subject experiences a life expectancy extended by about 5%, 10%, 20%, 30%, 40%, 50% or more beyond the life expectancy predicted if no treatment is administered. In another example, a subject responds to treatment with a PI3K inhibitor, if the subject has an increased disease-free survival, overall survival or increased time to progression. Several methods can be used to determine if a patient responds to a treatment including the RECIST criteria, as set forth above.

Chemical Definitions

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds. In one embodiment, a "pharmaceutically acceptable form" includes, but is not limited to, pharmaceutically acceptable salts, isomers, prodrugs and isotopically labeled derivatives of disclosed compounds.

In certain embodiments, the pharmaceutically acceptable form is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts may be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate. Organic bases from which salts may be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a solvate (e.g., a hydrate). As used herein, the term "solvate" refers to compounds that further include a stoichiometric or non-stoichiometric amount of solvent bound by non-covalent intermolecular forces. The solvate may be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, about 3 or about 4, solvent or water molecules. It will be understood that the term "compound" as used herein encompasses the compound and solvates of the compound, as well as mixtures thereof.

In certain embodiments, the pharmaceutically acceptable form is a prodrug. As used herein, the term "prodrug" refers to compounds that are transformed in vivo to yield a disclosed compound or a pharmaceutically acceptable form of the compound. A prodrug may be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, Chp 1, pp 1-12 and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, —NO$_2$, —ONO, or —ONO$_2$ moieties. Prodrugs can typically be prepared using well-known methods, such as those described in *Burger's Medicinal Chemistry and Drug Dis-*

*covery*, 172-178, 949-982 (Manfred E. Wolff ed., 5th ed., 1995), and *Design of Prodrugs* (H. Bundgaard ed., Elsevier, N.Y., 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as $(C_1-C_8)$alkyl, $(C_2-C_{12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug may be formed by the replacement of the hydrogen atom of the alcohol group with a group such as ($C_1$-$C_6$)alkanoyloxymethyl, 1-(($C_1$-$C_6$)alkanoyloxy) ethyl, 1-methyl-1-(($C_1$-$C_6$)alkanoyloxy)ethyl ($C_1$-$C_6$)alkoxycarbonyloxymethyl, N-($C_1$-$C_6$)alkoxycarbonylaminomethyl, succinoyl, ($C_1$-$C_6$)alkanoyl, α-amino($C_1$-$C_4$)alkanoyl, arylacyl and α-aminoacyl, or α-aminoacyl-α-aminoacyl, where each α-aminoacyl group is independently selected from naturally occurring L-amino acids, P(O)(OH)$_2$, —P(O) (O($C_1$-$C_6$)alkyl)$_2$, and glycosyl (the radical resulting from the removal of a hydroxyl group of the hemiacetal form of a carbohydrate).

If a disclosed compound or a pharmaceutically acceptable form of the compound incorporates an amine functional group, a prodrug may be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, a natural α-aminoacyl or natural α-aminoacyl-natural α-aminoacyl, —C(OH)C(O)OY$^1$ wherein Y$^1$ is H, ($C_1$-$C_6$)alkyl or benzyl, —C(OY$^2$)Y$^3$ wherein Y$^2$ is ($C_1$-$C_4$) alkyl and Y$^3$ is ($C_1$-$C_6$)alkyl, carboxy($C_1$-$C_6$)alkyl, amino($C_1$-$C_4$) alkyl or mono-N— or di-N,N—($C_1$-$C_6$)alkylaminoalkyl, —C(Y$^4$)Y$^5$ wherein Y$^4$ is H or methyl and Y$^5$ is mono-N— or di-N,N—($C_1$-$C_6$)alkylamino, morpholino, piperidin-1-yl or pyrrolidin-1-yl.

In certain embodiments, the pharmaceutically acceptable form is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

"Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown may be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that may be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

"Enantiomeric purity" as used herein refers to the relative amounts, expressed as a percentage, of the presence of a specific enantiomer relative to the other enantiomer. For example, if a compound, which can potentially have an (R)- or an (S)-isomeric configuration, is present as a racemic mixture, the enantiomeric purity is about 50% with respect to either the (R)- or (S)-isomer. If that compound has one isomeric form predominant over the other, for example, 80% (S)- and 20% (R)-, the enantiomeric purity of the compound with respect to the (S)-isomeric form is 80%. The enantiomeric purity of a compound may be determined in a number of ways known in the art, including but not limited to chromatography using a chiral support, polarimetric measurement of the rotation of polarized light, nuclear magnetic resonance spectroscopy using chiral shift reagents which include but are not limited to lanthanide containing chiral complexes or the Pirkle alcohol, or derivatization of a compounds using a chiral compound such as Mosher's acid followed by chromatography or nuclear magnetic resonance spectroscopy.

In certain embodiments, the pharmaceutically acceptable form is a tautomer. As used herein, the term "tautomer" is a type of isomer that includes two or more interconvertable compounds resulting from at least one formal migration of a hydrogen atom and at least one change in valency (e.g., a single bond to a double bond, a triple bond to a double bond, or a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers may be reached. Tautomerizations (i.e., the reaction providing a tautomeric pair) may be catalyzed by acid or base, or can occur without the action or presence of an external agent. Exemplary tautomerizations include, but are not limited to, keto-enol; amide-imide; lactam-lactim; enamine-imine; and enamine-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement or enrichment of a hydrogen by deuterium or tritium at one or more atoms in the molecule, or the replacement or enrichment of a carbon by $^{13}C$ or $^{14}C$ at one or more atoms in the molecule, are within the scope of this disclosure. In one embodiment, provided herein are isotopically labeled compounds having one or more hydrogen atoms replaced by or enriched by deuterium. In one embodiment, provided herein are isotopically labeled compounds having one or more hydrogen atoms replaced by or enriched by tritium. In one embodiment, provided herein are isotopically labeled compounds having one or more carbon atoms replaced or enriched by $^{13}C$. In one embodiment, provided herein are isotopically labeled compounds having one or more carbon atoms replaced or enriched by $^{14}C$.

The disclosure also embraces isotopically labeled compounds which are identical to those recited herein, except that one or more atoms are replaced by an atom having an atomic mass or mass number different from the atomic mass or mass number usually found in nature. Examples of isotopes that may be incorporated into disclosed compounds include isotopes of hydrogen, carbon, nitrogen, oxygen, phosphorus, sulfur, fluorine, and chlorine, such as, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^{3}H$ and/or $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

As used herein, and unless otherwise specified, "polymorph" may be used herein to describe a crystalline material, e.g., a crystalline form. In certain embodiments, "polymorph" as used herein are also meant to include all crystalline and amorphous forms of a compound or a salt thereof, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms, as well as mixtures thereof, unless a particular crystalline or amorphous form is referred to. Compounds of the present disclosure include crystalline and amorphous forms of those compounds, including, for example, crystalline forms, polymorphs, pseudopolymorphs, solvates, hydrates, co-crystals, unsolvated polymorphs (including anhydrates), conformational polymorphs, tautomeric forms, disordered crystalline forms, and amorphous forms of the compounds or a salt thereof, as well as mixtures thereof.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of the structure.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

As used herein, a "phosphoinositide 3-kinase (PI3K) inhibitor" or "PI3K inhibitor" refers to an inhibitor of any PI3K. PI3Ks are members of a unique and conserved family of intracellular lipid kinases that phosphorylate the 3'-OH group on phosphatidylinositols or phosphoinositides. The PI3K family includes kinases with distinct substrate specificities, expression patterns, and modes of regulation (see, e.g., Katso et al., 2001, *Annu. Rev. Cell Dev. Biol.* 17, 615-675; Foster, F. M. et al., 2003, *J Cell Sci* 116, 3037-3040). The class I PI3Ks (e.g., p110 α, p110 β, p110 γ, and p110 δ) are typically activated by tyrosine kinases or G-protein coupled receptors to generate PIP5, which engages downstream mediators such as those in the Akt/PDK1 pathway, mTOR, the Tec family kinases, and the Rho family GTPases. The class II PI3Ks (e.g., PI3K-C2α, PI3K-C2β, PI3K-C2γ) and III PI3Ks (e.g., Vps34) play a key role in intracellular trafficking through the synthesis of PI(3)P and PI(3,4)P2. Specific exemplary PI3K inhibitors are disclosed herein.

The class I PI3Ks comprise a p110 catalytic subunit and a regulatory adapter subunit. See, e.g., Cantrell, D. A. (2001) *Journal of Cell Science* 114: 1439-1445. Four isoforms of the p110 subunit (including PI3K-α (alpha), PI3K-β (beta), PI3K-γ (gamma), and PI3K-δ (delta) isoforms) have been implicated in various biological functions. Class I PI3Kα is involved, for example, in insulin signaling, and has been found to be mutated in solid tumors. Class I PI3K-β is involved, for example, in platelet activation and insulin signaling. Class I PI3K-γ plays a role in mast cell activation, innate immune function, and immune cell trafficking (chemokines). Class I PI3K-δ is involved, for example, in B-cell and T-cell activation and function and in Fc receptor signaling in mast cells. In some embodiments provided herein, the PI3K inhibitor is a class I PI3K inhibitor. In some such embodiments, the PI3K inhibitor inhibits a PI3K-α (alpha), PI3K-β (beta), PI3K-γ (gamma), or PI3K-δ (delta) isoform, or a combination thereof.

Downstream mediators of PI3K signal transduction include Akt and mammalian target of rapamycin (mTOR). Akt possesses a pleckstrin homology (PH) domain that binds PIP5, leading to Akt kinase activation. Akt phosphorylates many substrates and is a central downstream effector of PI3K for diverse cellular responses. One important function of Akt is to augment the activity of mTOR, through phosphorylation of TSC2 and other mechanisms. mTOR is a serine-threonine kinase related to the lipid kinases of the PI3K family.

2. Compositions and Methods

B-cell lymphoma 2 (Bcl-2) is a family of proteins that regulates cell death, e.g., by controlling the regulation of mitochondrial membrane and the release of cytochrome c from mitochondria during apoptosis. Bcl-2 plays an important survival role for many cancers, and the overexpression of the Bcl-2 proteins has been associated with tumor initiation, progression, and resistance to certain anticancer therapies.

Damage to the Bcl-2 gene has been identified as a cause of a number of cancers, including melanoma, breast, prostate, chronic lymphocytic leukemia, and lung cancer, and a possible cause of schizophrenia and autoimmunity. It is also a cause of resistance to cancer treatments. Overexpression of anti-apoptotic Bcl-2 members such as Bcl-2, Bcl-xL, and Mcl-1, occurs frequently in cancers, particularly hematological malignancies such as acute myelogenous leukemia (AML), resulting in defective apoptosis leading to enhanced cell survival and drug resistance. Letai A, et al., Cancer Cell 2004; 6:241-9; Oltersdorf T, et al., Nature 2005; 435:677-81; and Letai A., J Clin Invest 2005; 115:2648-55. Several agents have been developed to target these proteins directly, e.g., ABT-737, a BH3 mimetic that binds with high affinity to and antagonizes the functions of Bcl-2 and Bcl-xL but not Mcl-1. Merino et al. Blood 2012 (119) 24; 5807-5816. Preclinical studies demonstrated that ABT-737 induces apoptosis and potentiates the anti-tumor activity of multiple agents in various cancers, including leukemia. Vo, T. T., et al., Cell 151, 344-355 (2012); and Davids, M. S., et al., Blood (2012).

ABT-263, a clinical derivative of ABT-737 is currently undergoing phase I and II clinical evaluation in various tumor types including leukemia.

There is a need for an effective and safe combination therapy of a PI3K inhibitor and a Bcl-2 inhibitor for treating cancers.

Without being bound by theory, this disclosure provides experiments indicating that treating a patient with a PI3K inhibitor induces an apoptotic cascade characterized by up-regulation of the pro-apoptotic factors BMF, BIK, Bcl2L11 (also called BIM), PMAIP1 (also called NOXA), BBC3 (also called PUMA), and HRK (see Example 2). These factors are upstream of, and negatively regulate, the anti-apoptotic factor Bcl-2. This disclosure also provides that Bcl-2 levels rise in some patients treated with a PI3K inhibitor (see Example 2). Taken together, these data indicate that elevated levels of Bcl-2 can prevent the pro-apoptotic factors from successfully initiating apoptosis. These results suggest that inhibiting Bcl-2 will unblock the apoptotic cascade that was initiated by the PI3K inhibitor. Furthermore, experiments in cell lines resistant to a PI3K inhibitor indicate that pro-apoptotic genes promote responsiveness to a PI3K inhibitor (see Example 3). These experiments suggest that a combination therapy with a PI3K-inhibitor and a Bcl-2 inhibitor can produce unexpectedly high efficacy by acting in concert with high levels of pro-apoptotic signaling factors, to trigger apoptosis.Bcl Bcl The experimental results suggest certain therapeutic regimens. For example, according to the non-limiting theory herein, a PI3K inhibitor can be administered to a patient (e.g., as a monotherapy) until rising Bcl-2 levels reduce its efficacy. At that point, a Bcl-2 inhibitor can be administered to counteract the resistance mechanism. In other embodiments, a PI3K inhibitor and a Bcl-2 inhibitor can be administered over the same period, so that Bcl-2 activity can be kept low, thereby preventing resistance from developing. As an additional example, the observation that PI3K inhibitors and Bcl-2 inhibitor show synergistic efficacy indicates that administering both drugs at normal (e.g., monotherapy) levels produces greater efficacy than either agent alone. As still another example, the observation that PI3K inhibitors and Bcl-2 inhibitor show synergistic efficacy suggests that one can lower the dose, frequency, or dose and frequency of one or both of the inhibitors, and still maintain efficacy. Lowering the dose and/or frequency of administration can lower side effects.

In certain embodiments, provided herein are pharmaceutical compositions comprising a PI3K inhibitor, or a pharmaceutically acceptable form thereof, in combination with a Bcl-2 inhibitor, or a pharmaceutically acceptable form thereof. In certain embodiments, the combination is in a therapeutically effective amount. In certain embodiments, the combination is in a synergistically therapeutically effective amount. In certain embodiments, the combination is synergistic. In certain embodiments, the combination has a synergistic effect. In certain embodiments, the combination has a synergistic anti-cancer effect. In certain embodiments, the combination has a synergistic therapeutic effect.

Also provided herein are methods of treating (e.g., inhibiting, managing, or preventing) a cancer in a subject comprising administering to the subject a PI3K inhibitor, or a pharmaceutically acceptable form thereof, in combination with a Bcl-2 inhibitor, or a pharmaceutically acceptable form thereof. In certain embodiments, the combination is synergistic. In certain embodiments, the combination has a synergistic effect. In certain embodiments, the combination has a synergistic anti-cancer effect. In certain embodiments, the combination has a synergistic therapeutic effect. In certain embodiments, the combination is administered in a therapeutically effective amount. In certain embodiments, the combination is administered in a synergistically therapeutically effective amount.

In certain embodiments, the compositions and methods provided herein are utilized where a monotherapy of one of the therapeutic agents is becoming less effective due to drug resistance or where the relatively high dosage of monotherapy lead to undesirable side effects.

Without being limited by a particular theory, recent studies indicate that PI3K inhibitors down-regulate Mcl-1, an event that plays an important role in transformed cell lethality. Balakrishnan et al. (ASH Annual Meeting). 2013; No. 4167. Furthermore, Mcl-1, as well as Bim, which is also regulated by the PI3K pathway, play important roles in determining ABT-737 sensitivity. Merino et al. Blood 2012 (119) 24; 5807-5816. In addition, PI3K activity can lead to inhibition of apoptosis and therefore antagonize the effects of Bcl-2 inhibitors. Michalak et al., BBRC (2005) 331:786-798; Duronio et al., Biochem. J. (2008) 415: 333-344; Franke et al., Oncogene (2003) 22: 8983-8998; Wu et al., Oncogene (2001) 20: 240-251; and Srinivasan et al Cell (2009) 139: 573-586.

These considerations, together with the role of Bcl-2 and Bcl-xL dysregulation in leukemogenesis, raise the possibility that interference with Bcl-2 and Bcl-xL function can be compatible with inhibition of PI3 kinase activity. It has been surprisingly found that the PI3K inhibitors and Bcl-2 inhibitors combinations provided herein exhibit synergistic actions in treating various types of cancers.

PI3K inhibitors that can be used in the compositions and methods provided herein include, but are not limited to, those described in, e.g., WO 09/088990, WO 09/088086, WO 2011/008302, WO 2010/036380, WO 2010/006086, WO 09/114870, WO 05/113556, WO2014072937, WO2014071125; US 2009/0312310, and US 2011/0046165, the entirety of each incorporated herein by reference. Additional PI3K inhibitors that can be used in the compositions and methods provided herein include, but are not limited to, AMG-319, GSK 2126458 (2,4-Difluoro-N-{2-(methyloxy)-5-[4-(4-pyridazinyl)-6-quinolinyl]-3-pyridinyl}benzenesulfonamide), GSK 1059615 (5Z-[[4-(4-pyridinyl)-6-quinolinyl]methylene]-2,4-thiazolidinedione), GDC-0032 (4-[5,6-dihydro-2-[3-methyl-1-(1-methylethyl)-1H-1,2,4-triazol-5-yl]imidazo[1,2-d][1,4]benzoxazepin-9-yl]-α,α-dimethyl-1H-Pyrazole-1-acetamide), GDC-0980 ((S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one), GDC-0941 (2-(1H-indazol-4-yl)-6-((4-(methylsulfonyl)piperazin-1-yl)methyl)-4-morpholinothieno[3,2-d]pyrimidine), XL147 (N-(3-(benzo[c][1,2,5]thiadiazol-5-ylamino)quinoxalin-2-yl)-4-methylbenzenesulfonamide), XL499, XL765 (SAR245409, N-[4-[[[3-[(3,5-dimethoxyphenyl)amino]-2-quinoxalinyl]amino]sulfonyl]phenyl]-3-methoxy-4-methyl-benzamide), PF-4691502 (2-amino-6-(6-methoxypyridin-3-yl)-4-methyl-8-[(1R,4R)-4-(2-hydroxyethoxy)cyclohexyl]-7H,8H-pyrido[2,3-d]pyrimidin-7-one), BKM 120 (buparlisib, 5-(2,6-dimorpholinopyrimidin-4-yl)-4-(trifluoromethyl) pyridin-2-amine), Idelalisib (CAL-101, GS1101, (S)-2-(1-(9H-purin-6-ylamino)propyl)-5-fluoro-3-phenylquinazolin-4(3H)-one), CAL 263, SF1126 (3-[[2-[[5-[[amino (azaniumyl)methylidene]amino]-2-[[4-oxo-4-[4-(4-oxo-8-phenylchromen-2-yl)morpholin-4-ium-4-yl]oxybutanoyl] amino]pentanoyl]amino]acetyl]amino]-4-(1-carboxylatopropylamino)-4-oxobutanoate), PX-866 (sonolisib, [(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5-h]isochromen-10-yl]acetate), BEZ235 (2-methyl-2-(4-(3-methyl-2-oxo-8-(quinolin-3-yl)-2,3-dihydroimidazo[4,5-c]quinolin-1-yl)phenyl)propanenitrile), GS9820 (CAL-120, (S)-2-(1-((9H-purin-6-yl)amino)ethyl)-6-fluoro-3-phenylquinazolin-4(3H)-one), BYL719 ((2S)-1,2-Pyrrolidinedicarboxamide, N1-[4-methyl-5-[2-(2,2,2-trifluoro-1,1-dimethylethyl)-4-pyridinyl]-2-thiazolyl]), RP6503, RP6530, TGR1202 (((S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one)), INK1117 (MLN-1117), PX-866, BAY 80-6946 (2-amino-N-(7-methoxy-8-(3-morpholinopropoxy)-2,3-dihydroimidazo[1,2-c]quinazolin-5-yl)pyrimidine-5-carboxamide), IC87114 (2-((6-amino-9H-purin-9-yl)methyl)-5-methyl-3-o-tolylquinazolin-4(3H)-one), Palomid 529 (3-(4-methoxybenzyloxy)-8-(1-hydroxyethyl)-2-methoxy-6H-benzo[c]chromen-6-one), ZSTK474 (2-(difluoromethyl)-1-(4,6-dimorpholino-1,3,5-triazin-2-yl)-1H-benzo[d] imidazole), PWT33597, TG100-115 (6,7-Bis(3-hydroxyphenyl)pteridine-2,4-diamine), GNE-477 (5-[7-methyl-4-(morpholin-4-yl)-6-[(4-methylsulfonylpiperazin-1-yl)methyl]thieno[3,2-d]pyrimidin-2-yl]pyrimidin-2-amine), CUDC-907 (N-hydroxy-2-(((2-(6-methoxypyridin-3-yl)-4-morpholinothieno[3,2-d]pyrimidin-6-yl)methyl) (methyl)amino)pyrimidine-5-carboxamide), AEZS-136, BGT-226 (8-(6-methoxypyridin-3-yl)-3-methyl-1-(4-(piperazin-1-yl)-3-(trifluoromethyl)phenyl)-1H-imidazo[4,5-c] quinolin-2(3H)-one maleic acid), PF-05212384 (1-(4-(4-(dimethylamino)piperidine-1-carbonyl)phenyl)-3-(4-(4,6-dimorpholino-1,3,5-triazin-2-yl)phenyl)urea), LY3023414, PI-103 (3-[4-(4-morpholinyl)pyrido[3',2':4,5]furo[3,2-d]pyrimidin-2-yl]-phenol), INCB040093, CAL-130 ((S)-2-(1-((2-amino-9H-purin-6-yl)amino)ethyl)-5-methyl-3-(o-tolyl) quinazolin-4(3H)-one), LY294002 (2-Morpholin-4-yl-8-phenylchromen-4-one) and wortmannin.

In one embodiment, the PI3K inhibitor is Idelalisib (GS1101), CAL-130, BKM 120, GDC-0941, PX-866, GDC-0032, BAY 80-6946, BEZ235, BYL719, BGT-226, PF-4691502, GDC-0980, GSK 2126458, PF-05212384, XL765, or XL147.

In certain embodiments, a PI3K inhibitor is a compound that inhibits one or more PI3K isoforms, e.g., alpha, beta, delta, or gamma isoform. In one embodiment, a PI3K inhibitor is a compound that inhibits one or more PI3K isoforms with an $IC_{50}$ of less than about 1000 nM, less than about 900 nM, less than about 800 nM, less than about 700 nM, less than about 600 nM, less than about 500 nM, less than about 400 nM, less than about 300 nM, less than about 200 nM, less than about 100 nM, less than about 75 nM, less than about 50 nM, less than about 25 nM, less than about 20 nM, less than about 15 nM, less than about 10 nM, less than about 10 nM, less than about 5 nM, or less than about 1 nM.

In one embodiment, the PI3K inhibitor is a compound that inhibits alpha, beta, delta and gamma isoforms. In another embodiment, the PI3K inhibitor is a compound that inhibits beta, delta, and gamma isoforms. In another embodiment, the PI3K inhibitor is a compound that inhibits the delta and gamma isoforms.

In certain embodiments, the PI3K inhibitor is a PI3K isoform selective inhibitor. In one embodiment, the PI3K inhibitor is a PI3K alpha selective inhibitor. In another embodiment, the PI3K inhibitor is a PI3K beta selective inhibitor.

In certain embodiments, the PI3K inhibitor is a PI3K delta selective inhibitor. In one embodiment, the PI3K delta selective inhibitor selectively inhibits PI3K delta isoform over PI3K gamma isoform. In one embodiment, the PI3K delta selective inhibitor has a gamma/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has a gamma/delta selectivity ratio in the range of from greater than 1 to about 5, from about 5 to about 10, from about 10 to about 50, from about 50 to about 850, or greater than about 850. In one embodiment, the gamma/delta selectivity ratio is determined by dividing the inhibitor's $IC_{50}$ against PI3K gamma isoform by the inhibitor's $IC_{50}$ against PI3K delta isoform.

In certain embodiments, the PI3K inhibitor is a PI3K delta selective inhibitor. In one embodiment, the PI3K delta selective inhibitor selectively inhibits PI3K delta isoform over PI3K alpha isoform. In one embodiment, the PI3K delta selective inhibitor has an alpha/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has an alpha/delta selectivity ratio in the range of from greater than 1 to about 5, from about 5 to about 10, from about 10 to about 50, from about 50 to about 850, or greater than about 850. In one embodiment, the alpha/delta selectivity ratio is determined by dividing the inhibitor's $IC_{50}$ against PI3K alpha isoform by the inhibitor's $IC_{50}$ against PI3K delta isoform.

In certain embodiments, the PI3K inhibitor is a PI3K delta selective inhibitor. In one embodiment, the PI3K delta selective inhibitor selectively inhibits PI3K delta isoform over PI3K beta isoform. In one embodiment, the PI3K delta selective inhibitor has a beta/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has a beta/delta selectivity ratio in the range of from greater than 1 to about 5, from about 5 to about 10, from about 10 to about 50, from about 50 to about 850, or greater than about 850. In one embodiment, the beta/delta selectivity ratio is determined by dividing the inhibitor's $IC_{50}$ against PI3K beta isoform by the inhibitor's $IC_{50}$ against PI3K delta isoform.

In certain embodiments, the PI3K inhibitor is selective for both gamma and delta. In one embodiment, the PI3K gamma and delta selective inhibitor selectively inhibits PI3K gamma and delta isoforms over PI3K beta isoform. In one embodiment, the PI3K gamma and delta selective inhibitor has a beta/delta selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000 and a beta/gamma selectivity ratio of greater than 1, greater than about 5, greater than about 10, greater than about 50, greater than about 100, greater than about 200, greater than about 400, greater than about 600, greater than about 800, greater than about 1000, greater than about 1500, greater than about 2000, greater than about 5000, greater than about 10,000, or greater than about 20,000. In one embodiment, the PI3K delta selective inhibitor has a beta/delta selectivity ratio in the range of from greater than 1 to about 5, from about 5 to about 10, from about 10 to about 50, from about 50 to about 850, or greater than about 850 and a beta/gamma selectivity ratio in the range of from greater than 1 to about 5, from about 5 to about 10, from about 10 to about 50, from about 50 to about 850, or greater than about 850. In one embodiment, the beta/delta selectivity ratio is determined by dividing the inhibitor's $IC_{50}$ against PI3K beta isoform by the inhibitor's $IC_{50}$ against PI3K delta isoform and the beta/gamma selectivity ratio is determined by dividing the inhibitor's $IC_{50}$ against PI3K beta isoform by the inhibitor's $IC_{50}$ against PI3K gamma isoform.

PI3K delta inhibitors that can be used in the compositions and methods provided herein include, but are not limited to, GSK-2269557 (2-(6-(1H-indol-4-yl)-1H-indazol-4-yl)-5-((4-isopropylpiperazin-1-yl)methyl)oxazole), GS-9820, GS-1101 (5-fluoro-3-phenyl-2-([S)]-1-[9H-purin-6-ylamino]-propyl)-3H-quinazolin-4-one), AMG319, or TGR-1202 (((S)-2-(1-(4-amino-3-(3-fluoro-4-isopropoxyphenyl)-1H-pyrazolo[3,4-d]pyrimidin-1-yl)ethyl)-6-fluoro-3-(3-fluorophenyl)-4H-chromen-4-one)), or a mixture thereof. In one embodiment, the PI3K delta inhibitor is GS1101.

In one embodiment, the PI3K inhibitor is a PI3K inhibitor as described in WO 2005/113556, the entirety of which is incorporated herein by reference. In one embodiment, the PI3K inhibitor is Compound Nos. 113 or 107 as described in WO2005/113556.

In one embodiment, the PI3K inhibitor is a PI3K inhibitor as described in WO2014/006572, the entirety of which is incorporated herein by reference. In one embodiment, the PI3K inhibitor is Compound Nos. A1, A2, B, B1, or B2 as described in WO2014/006572.

In certain embodiments, the PI3K inhibitor is a PI3K delta/gamma dual inhibitor. In one embodiment, the PI3K delta/gamma dual inhibitor has an $IC_{50}$ value against PI3K alpha that is at least 5×, 10×, 20×, 50×, 100×, 200×, 500×, or 1000× higher than its $IC_{50}$ values against delta and gamma.

In certain embodiments, the PI3K inhibitor is Compound 1A of the structure:

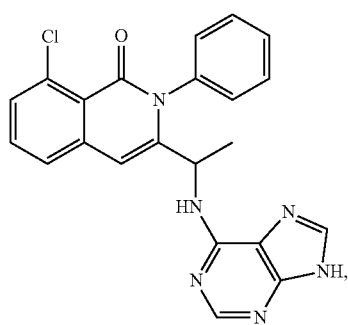

Compound 1A or a pharmaceutically acceptable form thereof.

In certain embodiments, the PI3K inhibitor is Compound 1 of the structure:

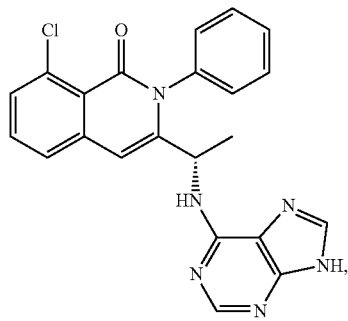 [SMILES: C[C@H](Nc1ncnc2[nH]cnc12)c1cc2cccc(Cl)c2c(=O)n1-c1ccccc1]

Compound 1 or a pharmaceutically acceptable form thereof.

Compound 1A has a chemical name of 3-(1-((9H-purin-6-yl)amino)ethyl)-8-chloro-2-phenylisoquinolin-1(2H)-one. Compound 1 has a chemical name of (S)-3-(1-((9H-purin-6-yl)amino)ethyl)-8-chloro-2-phenylisoquinolin-1(2H)-one. An exemplary method for synthesizing Compound 1A and Compound 1 has been previously described in U.S. Pat. No. 8,193,182, which is incorporated by reference in its entirety. Compound 1 is a PI3K-δ,-γ inhibitor and can be used to treat cancers. See U.S. Pat. No. 8,193,182.

Compound 1 provided herein contains one chiral center, and can exist as a mixture of enantiomers, e.g., a racemic mixture. This application encompasses the use of stereomerically pure forms of such a compound, as well as the use of mixtures of those forms. For example, mixtures comprising equal or unequal amounts of the enantiomers of Compound 1 provided herein may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

In one embodiment, the PI3K inhibitor provided herein is a mixture of Compound 1 and its (R)-enantiomer. In one embodiment, the PI3K inhibitor provided herein is a racemic mixture of Compound 1 and its (R)-enantiomer. In other embodiments, the compound mixture has an (S)-enantiomeric purity of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (R)-enantiomeric purity of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

As used herein, Compound 1 also refers to any crystal form or polymorph of (S)-3-(1-((9H-purin-6-yl)amino)ethyl)-8-chloro-2-phenylisoquinolin-1(2H)-one. In some embodiments, a polymorph of Compound 1, or a pharmaceutically form thereof, disclosed herein is used. Exemplary polymorphs are disclosed in U.S. Patent Publication No. 2012/0184568, which is hereby incorporated by reference in its entirety. In one embodiment, the compound is Form A of Compound 1. In one embodiment, the compound is Form B of Compound 1. In one embodiment, the compound is Form C of Compound 1. In one embodiment, the compound is Form D of Compound 1. In one embodiment, the compound is Form E of Compound 1. In one embodiment, the compound is Form F of Compound 1. In one embodiment, the compound is Form G of Compound 1. In one embodiment, the compound is Form H of Compound 1. In one embodiment, the compound is Form I of Compound 1. In one embodiment, the compound is Form J of Compound 1. In one embodiment, the compound is a mixture of solid forms (e.g., polymorphs and/or amorphous forms) of Compound 1 disclosed herein.

Any of the compounds disclosed herein can be in the form of pharmaceutically acceptable salts, hydrates, solvates, chelates, non-covalent complexes, isomers, prodrugs, isotopically labeled derivatives, or mixtures thereof.

Bcl-2 inhibitors that can be used in the compositions and methods provided herein include, but are not limited to, ABT-199, ABT-263, ABT-737, G3139 (genasense or oblimersen), GX15-070 (obatoclax mesylate), HA14-1, TW-37, sabutoclax, Gossypol (AT-101), antimycin A, and apogossypol. In one embodiment, Bcl-2 inhibitors that can be used in the compositions and methods provided herein include, but are not limited to, those described in, e.g., WO2006/009869, WO2007075387, WO2008024337, WO2008060569, or WO2013110890, the entirety of each incorporated herein by reference.

ABT-737 has the chemical name of (4-[4-[(4'-chloro[1,1'-biphenyl]-2-yl)methyl]-1-piperazinyl]-N-[[4-[[(1R)-3-(dimethylamino)-1-[(phenylthio)methyl]propyl]amino]-3-nitrophenyl]sulfonyl]-benzamide). Bruncko et al. (2007) J. Med. Chem. 50:641-662; U.S. Patent Application Publication No. 2007/0072860.

G3139 (genasense or oblimersen) is an 18-mer phosphorothioate oligodeoxyribonucleotide. R. J. Klasa, et al. (2002) Antisense and Nucleic Acid Drug Development 12:193-213.

GX15-070 (obatoclax mesylate) has a chemical name of (Z)-2-(5-((3,5-dimethyl-1H-pyrrol-2-yl)methylene)-4-methoxy-5H-pyrrol-2-yl)-1H-indole mesylate).

HA14-1 has a chemical name of ((R)-ethyl 2-amino-6-bromo-4-((R)-1-cyano-2-ethoxy-2-oxoethyl)-4H-chromene-3-carboxylate.

TW-37 has the chemical name of [4-[[2-(1,1-Dimethylethyl)phenyl]sulfonyl]phenyl]-2,3,4-trihydroxy-5-[[2-(1-methylethyl)phenyl]methyl]benzamide).

Sabutoclax has the chemical name of ((1R)-[2,2'-Binaphthalene]-5,5'-dicarboxamide, 1,1',6,6',7,7'-hexahydroxy-3,3'-dimethyl-N5,N5'-bis[(2R)-2-phenylpropyl]).

Gossypol (AT-101) has the chemical name of 2,2'-bis-(Formyl-1,6,7-trihydroxy-5-isopropyl-3-methylnaphthalene).

S44563 has the chemical name (R)-3-((4'-chloro-[1,1'-biphenyl]-2-yl)methyl)-N-((4-(((R)-4-(dimethylamino)-1-(phenylthio)butan-2-yl)amino)-3-nitrophenyl)sulfonyl)-2,3,4,4a,5,6-hexahydro-1H-pyrazino[1,2-a]quinoline-8-carboxamide.

Antimycin A has the chemical name of ((2{R},3{S},6{S},7{R},8{R})-3-[(3-formamido-2-hydroxybenzoyl)amino]-8-hexyl-2,6-dimethyl-4,9-dioxo-1,5-dioxonan-7-yl 3-methylbutanoate).

In one embodiment, the Bcl-2 inhibitor is ABT-199. ABT-199 has a chemical name of 4-[4-[[2-(4-chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide, and is of the structure:

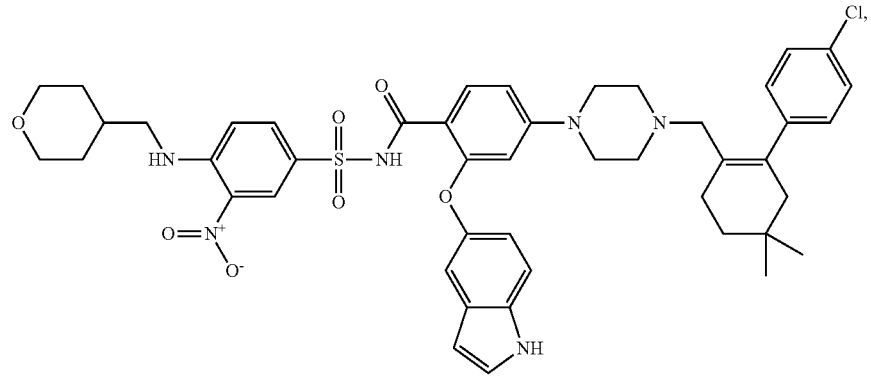 [SMILES: CC1(C)CCC(CN2CCN(c3ccc(C(=O)NS(=O)(=O)c4ccc(NCC5CCOCC5)c([N+](=O)[O-])c4)c(Oc4ccc5[nH]ccc5c4)c3)CC2)=C(c2ccc(Cl)cc2)C1]

as described in U.S. Pat. No. 8,546,399, which is incorporated by reference in its entirety.

In one embodiment, the Bcl-2 inhibitor is ABT-263. ABT-263 has a chemical name of (R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3((trifluoromethyl)sulfonyl)phenyl)sulfonyl)benzamide and is of the structure:

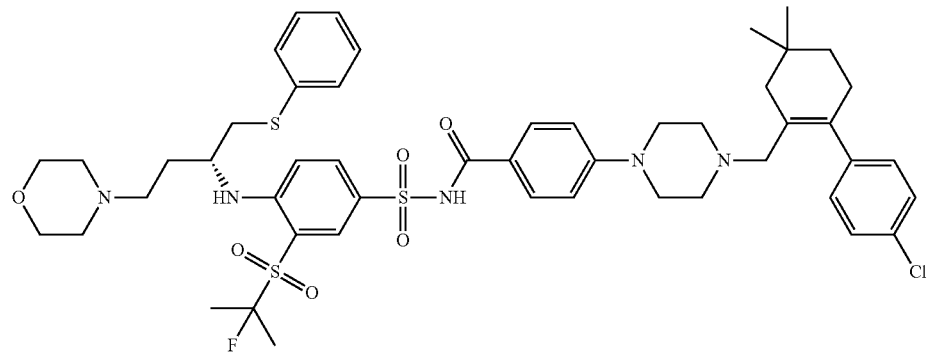 [SMILES: CC1(C)CCC(c2ccc(Cl)cc2)=C(CN2CCN(c3ccc(C(=O)NS(=O)(=O)c4ccc(N[C@H](CCN5CCOCC5)CSc5ccccc5)c(S(=O)(=O)C(C)(C)F)c4)cc3)CC2)C1]

as described in U.S. Pat. No. 7,390,799, which is incorporated by reference in its entirety.

In certain embodiments, provided herein is a pharmaceutical composition comprising a therapeutically effective amount of a PI3K delta selective inhibitor, or a pharmaceutically acceptable form thereof, and a Bcl-2 inhibitor, or a pharmaceutically acceptable form thereof. In one embodiment, the PI3K delta selective inhibitor is GS1101 (CAL-101). In one embodiment, the Bcl-2 inhibitor is ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, or a mixture thereof. In one embodiment, the Bcl-2 inhibitor is ABT-199. In another embodiment, the Bcl-2 inhibitor is ABT-263. In one embodiment, provided herein is a pharmaceutical composition comprising a therapeutically effective amount of GS1101, or a pharmaceutically acceptable form thereof, and ABT-199, or a pharmaceutically acceptable form thereof. In another embodiment, provided herein is a pharmaceutical composition comprising a therapeutically effective amount of GS1101, or a pharmaceutically acceptable form thereof, and ABT-263, or a pharmaceutically acceptable form thereof.

In one embodiment of the compositions and methods described herein, the molar ratio of the PI3K delta inhibitor (e.g., GS1101), or a pharmaceutically acceptable form thereof, to a Bcl-2 inhibitor (e.g., ABT-199 or ABT-263), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, or from about 5:1 to about 1:5. In an embodiment, the PI3K delta inhibitor is GS1101 and the Bcl-2 inhibitor is ABT-199, and the molar ratio of the PI3K delta inhibitor to the Bcl-2 inhibitor is from about 10:1 to about 1:500, from about 1:1 to about 1:50, from about 1:2 to about 1:10, from about 1:3 to about 1:5, from about 1:3 to about 1:1, from about 1:2 to about 1:1, from about 5:1 to about 1:1, from about 2:1 to about 1:1, about 2:1, or about 1.5:1.

In one embodiment, the PI3K delta inhibitor (e.g., GS1101) is administered at an amount to reach maximum plasma concentration at steady state (Cmaxss) at about 1000 ng/mL to about 5000 ng/mL, about 1000 ng/mL to about 4000 ng/mL, about 1000 ng/mL to about 3000 ng/mL, about 1000 ng/mL to about 2500 ng/mL, about 1400 ng/mL to about 2300 ng/mL, about 2000 ng/mL to about 2300 ng/mL, or about 2200 ng/mL; and
    the Bcl-2 inhibitor (e.g., ABT-199 or ABT-263) is administered at an amount to reach Cmaxss at about 0.1 µg/mL to about 1000 µg/mL, about 0.1 µg/mL to about 500 µg/mL, about 0.1 µg/mL to about 250 µg/mL, about 1 µg/mL to about 100 µg/mL, about 1 µg/mL to about 50 µg/mL, about 1 µg/mL to about 25 µg/mL, about 1 µg/mL to about 20 µg/mL, about 1 µg/mL to about 10 µg/mL, about 4 µg/mL, or about 3 µg/mL.

In one embodiment, the PI3K delta inhibitor (e.g., GS1101) is administered at an amount to reach maximum plasma concentration at steady state (Cmaxss) at less than about 5000 ng/mL, less than about 4000 ng/mL, less than about 3000 ng/mL, less than about 2000 ng/mL, less than about 1500 ng/mL, less than about 1000 ng/mL, less than about 500 ng/mL, less than about 100 ng/mL, less than about 50 ng/mL, less than about 25 ng/mL, less than about 10 ng/mL, or less than about 1 ng/mL.

In one embodiment, the Bcl-2 inhibitor (e.g., ABT-199 or ABT-263) is administered at an amount to reach Cmaxss less than about 1000 µg/mL, less than about 500 µg/mL, less than about 100 µg/mL, less than about 50 µg/mL, less than about 10 µg/mL, less than about 5 µg/mL, less than about 4 µg/mL, less than about 3 µg/mL, less than about 2 µg/mL, less than about 1 µg/mL, less than about 0.5 µg/mL, or less than about 0.1 µg/mL.

In one embodiment, the PI3K delta inhibitor (e.g., GS1101) is administered at an amount to reach an area under the plasma concentration-time curve at steady-state (AUCss) at about 5000 ng/mL*hr to about 10000 ng/mL*hr, about 5000 ng/mL*hr to about 9000 ng/mL*hr, about 6000 ng/mL*hr to about 9000 ng/mL*hr, about 6000 ng/mL*hr to about 8000 ng/mL*hr, about 6500 ng/mL*hr to about 7500 ng/mL*hr, or about 7000 ng/mL*hr; and
    the Bcl-2 inhibitor (e.g., ABT-199 or ABT-263) is administered at an amount to reach an AUCss at about 0.1 ng/mL*hr to about 10000 ng/mL*hr, about 1 ng/mL*hr to about 10000 ng/mL*hr, or about 100 ng/mL*hr to about 5000 ng/mL*hr.

In one embodiment, the PI3K delta inhibitor (e.g., GS1101) is administered at an amount to reach an area under the plasma concentration-time curve at steady-state (AUCss) at less than about 10000 ng/mL*hr, less than about 9500 ng/mL*hr, less than about 9000 ng/mL*hr, less than about 8500 ng/mL*hr, less than about 8000 ng/mL*hr, less than about 7000 ng/mL*hr, less than about 6000 ng/mL*hr, less than about 5000 ng/mL*hr, less than about 4000 ng/mL*hr, less than about 3000 ng/mL*hr, less than about 2000 ng/mL*hr, less than about 1000 ng/mL*hr, less than about 500 ng/mL*hr, less than about 100 ng/mL*hr, less than about 10 ng/mL*hr, or less than about 1 ng/mL*hr.

In one embodiment, the composition comprises the PI3K delta inhibitor (e.g., GS1101), or a pharmaceutically acceptable form thereof, at an amount in the range of from about 0.1 mg to about 500 mg, from about 1 mg to about 500 mg, from about 10 mg to about 500 mg, from about 50 mg to about 500 mg, from about 100 mg to about 400 mg, from about 200 mg to about 400 mg, from about 250 mg to about 350 mg, or about 300 mg. In one embodiment, the composition comprises the PI3K delta inhibitor (e.g., GS1101), or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg.

In one embodiment, the composition comprises the PI3K delta inhibitor (e.g., GS1101), or a pharmaceutically acceptable form thereof, at an amount of less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, less than about 30 mg, less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg.

In certain embodiments, provided herein is a pharmaceutical composition comprising a therapeutically effective amount of a PI3K delta/gamma dual inhibitor, or a pharmaceutically acceptable form thereof, and a Bcl-2 inhibitor, or a pharmaceutically acceptable form thereof. In one embodiment, the Bcl-2 inhibitor is ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, or a mixture thereof. In one embodiment, the Bcl-2 inhibitor is ABT-199. In another embodiment, the Bcl-2 inhibitor is ABT-263.

In one embodiment of the compositions and methods described herein, the molar ratio of the PI3K delta/gamma dual inhibitor, or a pharmaceutically acceptable form thereof, to a Bcl-2 inhibitor (e.g., ABT-199 or ABT-263), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, or from about 5:1 to about 1:5. In an embodiment, the PI3K delta/gamma dual inhibitor is Compound 1 and the Bcl-2 inhibitor is ABT-199, and the molar ratio of the PI3K delta/gamma dual inhibitor to the Bcl-2 inhibitor is from about 10:1 to about 1:100, from about 1:1 to about 1:20, from about 1:2 to about 1:5, from about 1:3.5 to about 1:4.5, or about 1:4. In an embodiment, the PI3K delta/gamma dual inhibitor is Compound 1 and the Bcl-2 inhibitor is ABT-263, and the molar ratio of the PI3K delta/gamma dual inhibitor to the Bcl-2 inhibitor is from about 10:1 to about 1:100, from about 1:1 to about 1:20, from about 1:2 to about 1:5, from about 1:3.5 to about 1:4.5, about 1:3, or about 1:4.

In one embodiment, the PI3K delta/gamma dual inhibitor (e.g., Compound 1) is administered at an amount to reach maximum plasma concentration at steady state (Cmaxss) at about 1000 ng/mL to about 5000 ng/mL, about 1000 ng/mL to about 4000 ng/mL, about 1000 ng/mL to about 3000 ng/mL, about 1000 ng/mL to about 2500 ng/mL, about 1400 ng/mL to about 2000 ng/mL, about 1400 ng/mL to about 1500 ng/mL, or about 1487 ng/mL; and the Bcl-2 inhibitor (e.g., ABT-199 or ABT-263) is administered at an amount to reach Cmaxss at about 0.1 µg/mL to about 1000 µg/mL, about 0.1 µg/mL to about 500 µg/mL, about 0.1 µg/mL to about 250 µg/mL, about 1 µg/mL to about 100 µg/mL, about 1 µg/mL to about 50 µg/mL, about 1 µg/mL to about 25 µg/mL, about 1 µg/mL to about 20 µg/mL, about 1 µg/mL to about 10 µg/mL, about 4 µg/mL, or about 3 µg/mL.

In one embodiment, the PI3K delta/gamma dual inhibitor (e.g., Compound 1) is administered at an amount to reach maximum plasma concentration at steady state (Cmaxss) at less than about 5000 ng/mL, less than about 4000 ng/mL, less than about 3000 ng/mL, less than about 2000 ng/mL, less than about 1500 ng/mL, less than about 1000 ng/mL, less than about 500 ng/mL, less than about 100 ng/mL, less than about 50 ng/mL, less than about 25 ng/mL, less than about 10 ng/mL, or less than about 1 ng/mL.

In one embodiment, the Bcl-2 inhibitor (e.g., ABT-199 or ABT-263) is administered at an amount to reach Cmaxss less than about 1000 µg/mL, less than about 500 µg/mL, less than about 100 µg/mL, less than about 50 µg/mL, less than about 10 µg/mL, less than about 5 µg/mL, less than about 4 µg/mL, less than about 3 µg/mL, less than about 2 µg/mL, less than about 1 µg/mL, less than about 0.5 µg/mL, or less than about 0.1 µg/mL.

In one embodiment, the PI3K delta/gamma dual inhibitor (e.g., Compound 1) is administered at an amount to reach an area under the plasma concentration-time curve at steady-state (AUCss) at about 5000 ng/mL*hr to about 10000 ng/mL*hr, about 5000 ng/mL*hr to about 9000 ng/mL*hr, about 6000 ng/mL*hr to about 9000 ng/mL*hr, about 7000 ng/mL*hr to about 9000 ng/mL*hr, about 8000 ng/mL*hr to about 9000 ng/mL*hr, or about 8787 ng/mL*hr; and the Bcl-2 inhibitor (e.g., ABT-199 or ABT-263) is administered at an amount to reach an AUCss at about 0.1 ng/mL*hr to about 10000 ng/mL*hr, about 1 ng/mL*hr to about 10000 ng/mL*hr, or about 100 ng/mL*hr to about 5000 ng/mL*hr.

In one embodiment, the PI3K delta/gamma dual inhibitor (e.g., Compound 1) is administered at an amount to reach an area under the plasma concentration-time curve at steady-state (AUCss) at less than about 10000 ng/mL*hr, less than about 9500 ng/mL*hr, less than about 9000 ng/mL*hr, less than about 8500 ng/mL*hr, less than about 8000 ng/mL*hr, less than about 7000 ng/mL*hr, less than about 6000 ng/mL*hr, less than about 5000 ng/mL*hr, less than about 4000 ng/mL*hr, less than about 3000 ng/mL*hr, less than about 2000 ng/mL*hr, less than about 1000 ng/mL*hr, less than about 500 ng/mL*hr, less than about 100 ng/mL*hr, less than about 10 ng/mL*hr, or less than about 1 ng/mL*hr.

In one embodiment, the PI3K delta/gamma dual inhibitor (e.g., Compound 1) is administered at an amount that is decreased by about 1.5 fold to about 50 fold of the amount when administered alone and the Bcl-2 inhibitor (e.g., ABT-199 or ABT-263) is administered at an amount that is decreased by about 1.1 fold to about 50 fold of the amount when administered alone.

In one embodiment, the PI3K delta/gamma dual inhibitor (e.g., Compound 1) is administered at an amount that is decreased by about 1.5 fold to about 50 fold, about 1.5 fold to about 25 fold, about 1.5 fold to about 20 fold, about 1.5 fold to about 15 fold, about 1.5 fold to about 10 fold, about 2 fold to about 10 fold, about 2 fold to about 8 fold, about 4 fold to about 6 fold, or about 5 fold of the amount when administered alone; and the Bcl-2 inhibitor (e.g., ABT-199 or ABT-263) is administered at an amount that is decreased by about 1.1 fold to about 50 fold, about 1.1 fold to about 40 fold, about 1.1 fold to about 30 fold, about 1.1 fold to about 25 fold, about 1.1 fold to about 20 fold, about 1.1 fold to about 15 fold, about 1.1 fold to about 10 fold of the amount when administered alone.

In one embodiment, the composition comprises the PI3K delta/gamma dual inhibitor, or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg.

In one embodiment, the composition comprises the PI3K delta/gamma dual inhibitor, or a pharmaceutically acceptable form thereof, at an amount of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg.

In certain embodiments, provided herein is a pharmaceutical composition comprising a Compound 1:

Compound 1

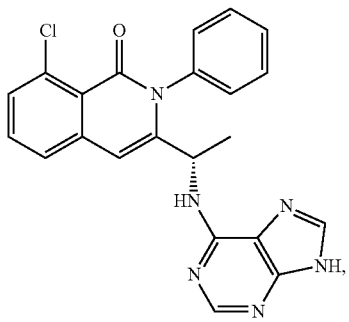

or a pharmaceutically acceptable form thereof, in combination with a Bcl-2 inhibitor, or a pharmaceutically acceptable form thereof.

In some embodiments, the combination is synergistic. In certain embodiments, the combination has a synergistic effect. In certain embodiments, the combination has a synergistic anti-cancer effect. In certain embodiments, the combination has a synergistic therapeutic effect. In certain embodiments, the combination is in a therapeutically effective amount. In certain embodiments, the combination is in a synergistically therapeutically effective amount.

In one embodiment, the Bcl-2 inhibitor is ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, 544563, or a mixture thereof. In one embodiment, the Bcl-2 inhibitor is ABT-199. In another embodiment, the Bcl-2 inhibitor is ABT-263.

In certain embodiments, provided herein is a method of treating (e.g., inhibiting, managing, or preventing) a cancer in a subject comprising administering to the subject Compound 1:

Compound 1

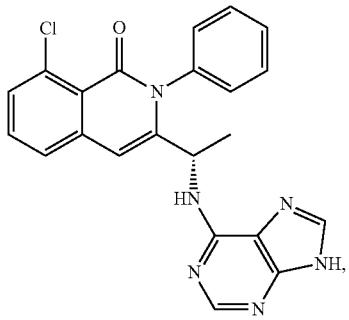

or a pharmaceutically acceptable form thereof, in combination with a Bcl-2 inhibitor, or a pharmaceutically acceptable form thereof.

In some embodiments, the combination is synergistic. In certain embodiments, the combination has a synergistic effect. In certain embodiments, the combination has a synergistic anti-cancer effect. In certain embodiments, the combination has a synergistic therapeutic effect. In certain embodiments, the combination is in a therapeutically effective amount. In certain embodiments, the combination is in a synergistically therapeutically effective amount.

In one embodiment, the Bcl-2 inhibitor is ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol, S44563, or a mixture thereof. In one embodiment, the Bcl-2 inhibitor is ABT-199. In another embodiment, the Bcl-2 inhibitor is ABT-263.

In some embodiments of the compositions and methods described herein, Compound 1, or a pharmaceutically acceptable form thereof, is used in combination with a Bcl-2 inhibitor (e.g., ABT-199 or ABT-263), or a pharmaceutically acceptable form thereof, at certain molar ratios. In one embodiment, provided herein is a pharmaceutical composition comprising Compound 1:

Compound 1

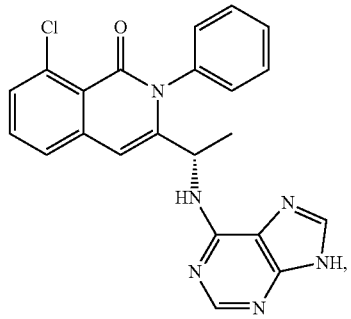

or a pharmaceutically acceptable form thereof, and a Bcl-2 inhibitor, or a pharmaceutically acceptable form thereof, wherein the molar ratio of Compound 1, or a pharmaceutically acceptable form thereof, to a Bcl-2 inhibitor (e.g., ABT-199 or ABT-263), or a pharmaceutically acceptable form thereof, is in the range of from about 1000:1 to about 1:1000.

In one embodiment of the compositions and methods described herein, the molar ratio of Compound 1, or a pharmaceutically acceptable form thereof, to a Bcl-2 inhibitor (e.g., ABT-199 or ABT-263), or a pharmaceutically acceptable form thereof, is in the range of from about 500:1 to about 1:500, from about 400:1 to about 1:400, from about 300:1 to about 1:300, from about 200:1 to about 1:200, from about 100:1 to about 1:100, from about 75:1 to about 1:75, from about 50:1 to about 1:50, from about 40:1 to about 1:40, from about 30:1 to about 1:30, from about 20:1 to about 1:20, from about 10:1 to about 1:10, or from about 5:1 to about 1:5. In some embodiment, the molar ratio of Compound 1, or a pharmaceutically acceptable form thereof, to a Bcl-2 inhibitor (e.g., ABT-199 or ABT-263), or a pharmaceutically acceptable form thereof, is in the range of from about 1:3 to about 1:7 or from about 1:5 to about 1:6. In some embodiments, the molar ratio of Compound 1, or a pharmaceutically acceptable form thereof, to a Bcl-2 inhibitor (e.g., ABT-199 or ABT-263), or a pharmaceutically acceptable form thereof, is from about 10:1 to about 1:100, from about 1:1 to about 1:20, from about 1:2 to about 1:5, from about 1:3.5 to about 1:4.5, about 1:3, or about 1:4. In some embodiment, the molar ratio of Compound 1, or a pharmaceutically acceptable form thereof, to a Bcl-2 inhibitor (e.g., ABT-199 or ABT-263), or a pharmaceutically acceptable form thereof, is about 1:3, about 1:4, about 1:5, about 1:6, or about 1:7.

In one embodiment of the compositions and methods described herein, the weight ratio of Compound 1, or a pharmaceutically acceptable form thereof, to ABT-199, or a pharmaceutically acceptable form thereof, is in the range of from about 7.5-37.5 of Compound 1 to from 40-200 of ABT-199. In one embodiment, the weight ratio is in the range of from about 1:1.1 to about 1:27. In one embodiment, the weight ratio is in the range of from about 1:2.2 to about 1:13.5. In one embodiment, the weight ratio is in the range of from about 1:3.3 to about 1:9.

In one embodiment of the compositions and methods described herein, the weight ratio of Compound 1, or a pharmaceutically acceptable form thereof, to ABT-263, or a pharmaceutically acceptable form thereof, is in the range of from about 7.5-37.5 of Compound 1 to from 32.5-162.5 of ABT-263. In one embodiment, the weight ratio is in the range of from about 1.2:1 to about 1:21. In one embodiment, the weight ratio is in the range of from about 1:1.7 to about 1:10.5. In one embodiment, the weight ratio is in the range of from about 1:2.5 to about 1:7.

In one embodiment, Compound 1 is administered at an amount to reach maximum plasma concentration at steady state (Cmaxss) at about 1000 ng/mL to about 5000 ng/mL, about 1000 ng/mL to about 4000 ng/mL, about 1000 ng/mL to about 3000 ng/mL, about 1000 ng/mL to about 2500 ng/mL, about 1400 ng/mL to about 2000 ng/mL, about 1400 ng/mL to about 1500 ng/mL, or about 1487 ng/mL; and ABT-199 or ABT-263 is administered at an amount to reach Cmaxss at about 0.1 µg/mL to about 1000 µg/mL, about 0.1 µg/mL to about 500 µg/mL, about 0.1 µg/mL to about 250 µg/mL, about 1 µg/mL to about 100 µg/mL, about 1 µg/mL to about 50 µg/mL, about 1 µg/mL to about 25 µg/mL, about 1 µg/mL to about 20 µg/mL, about 1 µg/mL to about 10 µg/mL, about 4 µg/mL, or about 3 µg/mL.

In one embodiment, Compound 1 is administered at an amount to reach an area under the plasma concentration-time curve at steady-state (AUCss) at about 5000 ng/mL*hr to about 10000 ng/mL*hr, about 5000 ng/mL*hr to about 9000 ng/mL*hr, about 6000 ng/mL*hr to about 9000 ng/mL*hr, about 7000 ng/mL*hr to about 9000 ng/mL*hr, about 8000 ng/mL*hr to about 9000 ng/mL*hr, or about 8787 ng/mL*hr; and ABT-199 or ABT-263 is administered at an amount to reach an AUCss at about 0.1 ng/mL*hr to about 10000 ng/mL*hr, about 1 ng/mL*hr to about 10000 ng/mL*hr, or about 100 ng/mL*hr to about 5000 ng/mL*hr.

In some embodiments, the composition comprises Compound 1, or a pharmaceutically acceptable form thereof, and a Bcl-2 inhibitor (e.g., ABT-199 or ABT-263), or a pharmaceutically acceptable form thereof, at certain amounts. In one embodiment, the composition comprises Compound 1, or a pharmaceutically acceptable form thereof, at an amount in the range of from about 0.01 mg to about 75 mg and the Bcl-2 inhibitor (e.g., ABT-199 or ABT-263), or a pharmaceutically acceptable form thereof, at an amount of in the range of from about 0.01 mg to about 1100 mg.

In one embodiment, the composition comprises Compound 1, or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg.

In one embodiment, the composition comprises Compound 1, or a pharmaceutically acceptable form thereof, at an amount of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg.

In one embodiment, the composition comprises the Bcl-2 inhibitor (e.g., ABT-199 or ABT-263), or a pharmaceutically acceptable form thereof, at an amount in the range of from about 0.1 mg to about 800 mg, from about 0.1 mg to about 750 mg, from about 0.1 mg to about 600 mg, from about 1 mg to about 500 mg, from about 1 mg to about 400 mg, from about 10 mg to about 300 mg, from about 50 mg to about 250 mg, from about 50 mg to about 200 mg, from about 50 mg to about 150 mg, from about 50 mg to about 100 mg, from about 50 mg to about 90 mg, or from about 50 mg to about 80 mg.

In one embodiment, the composition comprises the Bcl-2 inhibitor (e.g., ABT-199 or ABT-263), or a pharmaceutically acceptable form thereof, at an amount of less than about 1000 mg, less than about 800 mg, less than about 750 mg, less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, or less than about 25 mg.

In one embodiment, the composition comprises ABT-199, or a pharmaceutically acceptable form thereof, at an amount of less than about 1000 mg, less than about 800 mg, less than about 750 mg, less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, or less than about 25 mg. In one embodiment, the composition comprises ABT-199, or a pharmaceutically acceptable form thereof, at an amount of about 400 mg. In one embodiment, the composition comprises ABT-199, or a pharmaceutically acceptable form thereof, at an amount of about 325 mg. In one embodiment, the composition comprises ABT-199, or a pharmaceutically acceptable form thereof, at an amount of about 250 mg. In one embodiment, the composition comprises ABT-199, or a pharmaceutically acceptable form thereof, at an amount of about 150 mg. In one embodiment, the composition comprises ABT-199, or a pharmaceutically acceptable form thereof, at an amount of about 100 mg, about 90 mg, about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, about 10 mg, or about 5 mg. In one embodiment, the composition comprises ABT-199, or a pharmaceutically acceptable form thereof, at an amount of about 85 mg. In one embodiment, the composition comprises ABT-199, or a pharmaceutically acceptable form thereof, at an amount of about 75 mg. In one embodiment, the composition comprises ABT-199, or a pharmaceutically acceptable form thereof, at an amount of about 50 mg.

In one embodiment, the composition comprises ABT-263, or a pharmaceutically acceptable form thereof, at an amount of less than about 1000 mg, less than about 800 mg, less than about 750 mg, less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, or less than about 25 mg. In one embodiment, the composition comprises ABT-263, or a pharmaceutically acceptable form thereof, at an amount of about 325 mg. In one embodiment, the composition comprises ABT-263, or a pharmaceutically acceptable form thereof, at an amount of about 250 mg. In one embodiment, the composition comprises ABT-263, or a pharmaceutically acceptable form thereof, at an amount of about 150 mg. In one embodiment, the composition comprises ABT-263, or a pharmaceutically acceptable form thereof, at an amount of about 100 mg, about 90 mg, about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, about 10 mg, or about 5 mg. In one embodiment, the composition comprises ABT-263, or a pharmaceutically acceptable form thereof, at an amount of about 85 mg. In one embodiment, the composition comprises ABT-263, or a pharmaceutically acceptable form thereof, at an amount of about 75 mg. In one embodiment, the composition comprises ABT-263, or a pharmaceutically acceptable form thereof, at an amount of about 50 mg.

In certain embodiments, the PI3K inhibitor (e.g., Compound 1 or GS1101), or pharmaceutically acceptable form thereof, and the Bcl-2 inhibitor, or pharmaceutically acceptable form thereof, are in a single dosage form. In other embodiments, the PI3K inhibitor, or pharmaceutically acceptable form thereof, and the Bcl-2 inhibitor, or pharmaceutically acceptable form thereof, are in separate dosage forms.

In certain embodiments, the PI3K inhibitor (e.g., Compound 1), or pharmaceutically acceptable form thereof, and the Bcl-2 inhibitor, or pharmaceutically acceptable form thereof, are the only therapeutically active ingredients of the compositions and methods provided herein. In other embodiments, the compositions and methods provided herein comprise or use at least one more therapeutically active ingredient, e.g., a third agent, e.g., an anti-CD20 antibody.

In one embodiment, a method described herein further comprises administration of an anti-CD20 antibody. In one embodiment, a pharmaceutical composition described herein further comprises an anti-CD20 antibody. In some such embodiments, the anti-CD20 antibody is included in the same dosage form as the PI3K inhibitor and/or second agent. In some such embodiments, the anti-CD20 antibody is in a separate dosage form as the PI3K inhibitor and/or second agent. The anti-CD20 antibody can be administered before, after, or concurrent with the PI3K inhibitor and/or second agent. In certain embodiments, the anti-CD20 antibody is selected from one or more of rituximab, ofatumumab and obinotuzumab.

Cancers

Subjects that can be treated with a pharmaceutical composition as provided herein, according to the methods as provided herein include, but are not limited to, patients that have been diagnosed as having breast cancer such as a ductal carcinoma, lobular carcinoma, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, NK cell leukemia (e.g., blastic plasmacytoid dendritic cell neoplasm), acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer; kidney cancer; thyroid cancer such as papillary, follicular, medullary and anaplastic; lymphoma such as diffuse large B-cell lymphoma, B-cell immunoblastic lymphoma, NK cell lymphoma (e.g., blastic plasmacytoid dendritic cell neoplasm), and Burkitt lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), oligodendroglioma, ependymoma, meningioma, lymphoma, schwannoma, and medulloblastoma; peripheral nervous system (PNS) cancers such as acoustic neuromas and malignant peripheral nerve sheath tumor (MPNST) including neurofibromas and schwannomas, malignant fibrocytoma, malignant fibrous histiocytoma, malignant meningioma, malignant mesothelioma, and malignant mixed Müllerian tumor; oral cavity and oropharyngeal cancers such as, hypopharyngeal cancer, laryngeal cancer, nasopharyngeal cancer, and oropharyngeal cancer; stomach cancers such as lymphomas, gastric stromal tumors, and carcinoid tumors; testicular cancers such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin lymphoma, non-Hodgkin lymphomas carcinoids or carcinoid tumors; rectal cancer; and colon cancer.

In one embodiment, the cancer or disease that may be treated (e.g., inhibited or prevented) by methods, compositions, or kits provided herein includes a blood disorder or a hematologic malignancy. In one embodiment, the cancer or disease that may be treated is an acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphocytic leukemia (ALL), which includes B-lineage ALL and T-lineage ALL, chronic lymphocytic leukemia (CLL), prolymphocytic leukemia (PLL), hairy cell leukemia (HCL) and Waldenstrom's macroglobulinemia (WM); peripheral T cell lymphomas (PTCL), adult T cell leukemia/lymphoma (ATL), cutaneous T-cell lymphoma (CTCL), large granular lymphocytic leukemia (LGF), Hodgkin's disease and Reed-Stemberg disease; acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic andenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenstrom's macroglobulinemia.

In one embodiment, the cancer or disease being treated or prevented, such as a blood disorder or hematologic malignancy, has a high expression level of one or more PI3K isoform(s) (e.g., PI3K-α, PI3K-β, PI3K-δ, or PI3K-γ, or a combination thereof).

In one embodiment, the cancer or disease that may be treated or prevented by methods, compositions, or kits provided herein includes a blood disorder or a hematologic malignancy, including, but not limited to, myeloid disorder, lymphoid disorder, leukemia, lymphoma, myelodysplastic syndrome (MDS), myeloproliferative disease (MPD), mast cell disorder, and myeloma (e.g., multiple myeloma), among others.

In one embodiment, the blood disorder or the hematologic malignancy includes, but is not limited to, acute lymphoblastic leukemia (ALL), T-cell ALL (T-ALL), B-cell ALL (B-ALL), acute myeloid leukemia (AML), chronic lymphocytic leukemia (CLL), chronic myelogenous leukemia (CML), blast phase CML, small lymphocytic lymphoma (SLL), CLL/SLL, blast phase CLL, Hodgkin lymphoma (HL), non-Hodgkin lymphoma (NHL), B-cell NHL, T-cell NHL, indolent NHL (iNHL), diffuse large B-cell lymphoma (DLBCL), mantle cell lymphoma (MCL), aggressive B-cell NHL, B-cell lymphoma (BCL), Richter's syndrome (RS), T-cell lymphoma (TCL), peripheral T-cell lymphoma (PTCL), cutaneous T-cell lymphoma (CTCL), transformed mycosis fungoides, Sézary syndrome, anaplastic large-cell lymphoma (ALCL), follicular lymphoma (FL), Waldenström macroglobulinemia (WM), lymphoplasmacytic lymphoma, Burkitt lymphoma, multiple myeloma (MM), amyloidosis, MPD, essential thrombocytosis (ET), myelofibrosis (MF), polycythemia vera (PV), chronic myelomonocytic leukemia (CMML), myelodysplastic syndrome (MDS), angioimmunoblastic lymphoma, high-risk MDS, and low-risk MDS.

In one embodiment, the cancer is a T-cell lymphoma (e.g., peripheral T-cell lymphoma (PTCL) and cutaneous T-cell lymphoma (CTCL)).

In one embodiment, the cancer is chronic lymphocytic leukemia (CLL).

In other embodiments, the cancer has a high level of Bcl-2 expression. In one embodiment, the cancer is a large cell lymphoma with a high level of Bcl-2 expression.

In one embodiment, the hematologic malignancy is relapsed. In one embodiment, the hematologic malignancy is refractory.

In one embodiment, the cancer or disease is in a pediatric patient (including an infantile patient). In one embodiment, the cancer or disease is in an adult patient. Additional embodiments of a cancer or disease being treated or prevented by methods, compositions, or kits provided herein are described herein elsewhere.

In exemplary embodiments, the cancer or hematologic malignancy is CLL. In exemplary embodiments, the cancer or hematologic malignancy is CLL/SLL. In exemplary embodiments, the cancer or hematologic malignancy is blast phase CLL. In exemplary embodiments, the cancer or hematologic malignancy is SLL.

In exemplary embodiments, the cancer or hematologic malignancy is iNHL. In exemplary embodiments, the cancer or hematologic malignancy is DLBCL. In exemplary embodiments, the cancer or hematologic malignancy is B-cell NHL (e.g., aggressive B-cell NHL). In exemplary embodiments, the cancer or hematologic malignancy is MCL. In exemplary embodiments, the cancer or hematologic malignancy is RS. In exemplary embodiments, the cancer or hematologic malignancy is AML. In exemplary embodiments, the cancer or hematologic malignancy is MM. In exemplary embodiments, the cancer or hematologic malignancy is ALL. In exemplary embodiments, the cancer or hematologic malignancy is T-ALL. In exemplary embodiments, the cancer or hematologic malignancy is B-ALL. In exemplary embodiments, the cancer or hematologic malignancy is TCL. In exemplary embodiments, the cancer or hematologic malignancy is ALCL. In exemplary embodiments, the cancer or hematologic malignancy is leukemia. In exemplary embodiments, the cancer or hematologic malignancy is lymphoma. In exemplary embodiments, the cancer or hematologic malignancy is T-cell lymphoma. In exemplary embodiments, the cancer or hematologic malignancy is MDS (e.g., low grade MDS). In exemplary embodiments, the cancer or hematologic malignancy is MPD. In exemplary embodiments, the cancer or hematologic malignancy is a mast cell disorder. In exemplary embodiments, the cancer or hematologic malignancy is Hodgkin lymphoma (HL). In exemplary embodiments, the cancer or hematologic malignancy is non-Hodgkin lymphoma. In exemplary embodiments, the cancer or hematologic malignancy is PTCL. In exemplary embodiments, the cancer or hematologic malignancy is CTCL (e.g., mycosis fungoides or Sézary syndrome). In exemplary embodiments, the cancer or hematologic malignancy is WM. In exemplary embodiments, the cancer or hematologic malignancy is CML. In exemplary embodiments, the cancer or hematologic malignancy is FL. In exemplary embodiments, the cancer or hematologic malignancy is transformed mycosis fungoides. In exemplary embodiments, the cancer or hematologic malignancy is Sézary syndrome. In exemplary embodiments, the cancer or hematologic malignancy is acute T-cell leukemia. In exemplary embodiments, the cancer or hematologic malignancy is acute B-cell leukemia. In exemplary embodiments, the cancer or hematologic malignancy is Burkitt lymphoma. In exemplary embodiments, the cancer or hematologic malignancy is myeloproliferative neoplasms. In exemplary embodiments, the cancer or hematologic malignancy is splenic marginal zone. In exemplary embodiments, the cancer or hematologic malignancy is nodal marginal zone. In exemplary embodiments, the cancer or hematologic malignancy is extranodal marginal zone.

In one embodiment, the cancer or hematologic malignancy is a B cell lymphoma. In a specific embodiment, provided herein is a method of treating or managing a B cell lymphoma comprising administering to a patient a therapeutically effective amount of a compound provided herein, or a pharmaceutically acceptable derivative (e.g., salt or solvate) thereof. Also provided herein is a method of treating or lessening one or more of the symptoms associated with a B cell lymphoma comprising administering to a patient a therapeutically effective amount of a compound provided herein, or a pharmaceutically acceptable derivative (e.g., salt or solvate) thereof. In one embodiment, the B cell lymphoma is iNHL. In another embodiment, the B cell lymphoma is follicular lymphoma. In another embodiment, the B cell lymphoma is Waldenstrom macroglobulinemia (lymphoplasmacytic lymphoma). In another embodiment, the B cell lymphoma is marginal zone lymphoma (MZL) In another embodiment, the B cell lymphoma is MCL. In another embodiment, the B cell lymphoma is HL. In another embodiment, the B cell lymphoma is aNHL. In another embodiment, the B cell lymphoma is DLBCL. In another embodiment, the B cell lymphoma is Richters lymphoma.

In one embodiment, the cancer or hematologic malignancy is a T cell lymphoma. In a specific embodiment, provided herein is a method of treating (e.g., inhibiting, preventing or managing) a cell lymphoma comprising administering to a patient a composition described herein. Also provided herein is a method of treating (e.g., lessening one or more of the symptoms associated with) a T cell lymphoma comprising administering to a patient a composition described herein. In one embodiment, the T cell lymphoma is peripheral T cell lymphoma (PTCL). In another embodiment, the T cell lymphoma is cutaneous T cell lymphoma (CTCL).

In one embodiment, the cancer or hematologic malignancy is Sézary syndrome. In a specific embodiment, provided herein is a method of treating (e.g., inhibiting, preventing or managing) Sézary syndrome comprising administering to a patient a composition described herein. Also provided herein is a method of treating (e.g., lessening one or more of the symptoms associated with) Sézary syndrome comprising administering to a patient a therapeutically effective amount of a composition described herein. The symptoms associated with Sézary syndrome include, but are not limited to, epidermotropism by neoplastic CD4+ lymphocytes, Pautrier's microabscesses, erythroderma, lymphadenopathy, atypical T cells in the peripheral blood, and hepatosplenomegaly. In one embodiment of the compositions and methods described herein, the dosage (e.g., the therapeutically effective dosage) of Compound 1 included in the combination is about 25 mg to 75 mg of Compound 1, administered twice daily. In other embodiments, the dosage is from about 50 mg to about 75 mg, from about 30 mg to about 65 mg, from about 45 mg to about 60 mg, from about 30 mg to about 50 mg, or from about 55 mg to about 65 mg. In certain embodiments, this dosage is administered twice daily. In one embodiment, the dosage is about 60 mg, administered twice daily.

Methods of Assessing Cancers

Accordingly, the present invention also provides a method of predicting the sensitivity of tumor cell growth to inhibition by a PI3K inhibitor, comprising: assessing the level of a prognosis-positive biomarker expressed by a tumor cell; and predicting the sensitivity of tumor cell growth to inhibition by a PI3K inhibitor, wherein high expression levels of tumor cell prognosis-positive biomarkers correlate with high sensitivity to inhibition by a PI3K inhibitor, or wherein low expression levels of said tumor cell prognosis-positive biomarker correlate with low sensitivity to inhibition by PI3K inhibitors, and treating the tumor with a PI3K inhibitor and a Bcl-2 inhibitor (e.g., if the tumor is predicted to have a low sensitivity to a PI3K inhibitor alone).

The present invention also provides a method of predicting the sensitivity of tumor cell growth to inhibition by a PI3K inhibitor, comprising: assessing the level of a prognosis-negative biomarker expressed by a tumor cell; and predicting the sensitivity of tumor cell growth to inhibition by a PI3K inhibitor, wherein high expression levels of tumor cell prognosis-negative biomarkers correlate with low sensitivity to inhibition by PI3K inhibitors, or wherein low expression levels of said tumor cell prognosis-negative biomarker correlates with high sensitivity to inhibition by a PI3K inhibitor, and treating the tumor with a PI3K inhibitor and a Bcl-2 inhibitor (e.g., if the tumor is predicted to have a low sensitivity to a PI3K inhibitor alone).

The present invention further provides a method for treating a tumor in a patient, comprising the step of administering to the patient a PI3K inhibitor and a Bcl-2 inhibitor, wherein the patient possesses a tumor that has been determined as having high sensitivity to tumor cell growth inhibition by a PI3K inhibitor by assessing the level of at least one prognosis-positive biomarker expressed by a tumor cell from said tumor; and predicting the sensitivity of tumor cell growth to inhibition by a PI3K inhibitor, wherein high expression levels of said tumor cell prognosis-positive biomarker correlate with high sensitivity to inhibition by a PI3K inhibitor; or assessing the level of at least one prognosis-negative biomarker expressed by a tumor cell from said tumor; and predicting the sensitivity of tumor cell growth to inhibition by a PI3K inhibitor, wherein low expression levels of said tumor cell prognosis-negative biomarker correlate with high sensitivity to inhibition by a PI3K inhibitor.

For any given prognosis-positive or prognosis-negative biomarker, the range of expression level between tumor cells that are relatively insensitive to PI3K inhibitors and those that are sensitive, can readily be assessed by one of skill in the art, for example by testing on a panel of tumor cells as described herein, or by testing in tumor biopsies from patients whose tumors display a range of sensitivities to a PI3K inhibitor.

One of skill in the medical arts, particularly pertaining to the application of prognostic tests and treatment with therapeutics, will recognize that biological systems are somewhat variable and not always entirely predictable, and thus many good diagnostic tests or therapeutics are occasionally ineffective. Thus, it is ultimately up to the judgment of the attending physician to determine the most appropriate course of treatment for an individual patient, based upon test results, patient condition and history, and his own experience. There may even be occasions, for example, when a physician will choose to treat a patient with a PI3K inhibitor even when a tumor is not predicted to be particularly sensitive to PI3K inhibitors, based on data from diagnostic tests or from other criteria, particularly if all or most of the other obvious treatment options have failed, or if some synergy is anticipated when given with another treatment. The fact that the PI3K inhibitors as a class of compounds are relatively well tolerated compared to many other anti-cancer compounds, such as more traditional chemotherapy or cytotoxic agents used in the treatment of cancer, makes this a more viable option.

Furthermore, this invention also provides additional methods wherein simultaneous assessment of the expression level in tumor cells of more than one biomarker level is utilized.

Accordingly, the present invention provides a method of predicting the sensitivity of tumor cell growth to inhibition by a PI3K inhibitor, comprising: assessing the level of at least one (or a panel of) prognosis-positive biomarkers expressed by a tumor cell; and predicting the sensitivity of tumor cell growth to inhibition by a PI3K inhibitor, wherein simultaneous high expression levels of all of the assessed tumor cell prognosis-positive biomarkers correlates with high sensitivity to inhibition by a PI3K inhibitor, and treating the tumor with a PI3K inhibitor and a Bcl-2 inhibitor (e.g., if the tumor is predicted to have a low sensitivity to a PI3K inhibitor alone).

The present invention also provides a method of predicting the sensitivity of tumor cell growth to inhibition by a PI3K inhibitor, comprising: assessing the level of one or more (or a panel of) prognosis-negative biomarkers expressed by a tumor cell; and predicting the sensitivity of tumor cell growth to inhibition by a PI3K inhibitor, wherein simultaneous low or undetectable expression levels of all of the assessed tumor cell prognosis-negative biomarkers correlates with high sensitivity to inhibition by a PI3K inhibitor, and treating the tumor with a PI3K inhibitor and a Bcl-2 inhibitor (e.g., if the tumor is predicted to have a low sensitivity to a PI3K inhibitor alone).

The present invention also provides a method of predicting the sensitivity of tumor cell growth to inhibition by a PI3K inhibitor, comprising: assessing the level of one or more prognosis-positive biomarker expressed by a tumor cell; assessing the level of one or more prognosis-negative biomarker expressed by a tumor cell; and predicting the sensitivity of tumor cell growth to inhibition by a PI3K inhibitor, wherein a high ratio of prognosis-positive to prognosis-negative biomarker expression levels correlates with high sensitivity to inhibition by a PI3K inhibitor and treating the tumor with a PI3K inhibitor and a Bcl-2 inhibitor (e.g., if the tumor is predicted to have a low sensitivity to a PI3K inhibitor alone). As used herein, a high ratio of prognosis-positive to prognosis-negative biomarker expression levels means greater than 1:1, preferably greater than 1.1:1, preferably greater than 1.5:1, more preferably greater than 2:1, more preferably greater than 5:1, more preferably greater than 10:1, even more preferably greater than 100:1, or greater than 1,000:1.

In methods of this invention, biomarker expression level can be assessed relative to the biomarker level in non-tumor cells of the same tissue, or another cell or tissue source used as an assay reference. The expression level of a biomarker is considered high if expression level relative to a suitable reference is greater than 1:1, preferably greater than 1.1:1, preferably greater than 1.5:1, more preferably greater than 2:1, more preferably greater than 5:1, more preferably greater than 10:1, even more preferably greater than 100:1, even more preferably greater than 1,000:1, even more preferably greater than 10,000:1, even more preferably greater than 1,000,000:1. The expression level of a biomarker is considered low if expression level relative to a suitable reference is less than 1:1, preferably less than 1:1.1, preferably less than 1:1.5, more preferably less than 1:2, more preferably less than 1:5, more preferably less than 1:10, even more preferably less than 1:100, even more preferably less than 1:1,000, even more preferably less than 1:10,000, even more preferably less than 1:1,000,000.

The present invention further provides a method of predicting the likelihood that a tumor will progress to a more aggressive tumor wherein the tumor is treatable with a PI3K inhibitor, comprising: assessing the level of at least one progression-positive biomarker expressed by a tumor cell from said tumor; and predicting the likelihood that the tumor cell will progress to a more aggressive tumor, wherein high expression levels of said tumor cell progression-positive biomarker correlate with high likelihood that the tumor cell will progress to a more aggressive tumor or wherein low expression levels of said tumor cell progression-positive biomarker correlate with low likelihood that the tumor cell will progress to a more aggressive tumor and treating the tumor with a PI3K inhibitor and a Bcl-2 inhibitor (e.g., if it is determined that there is a high likelihood that the tumor cell will progress to a more aggressive tumor if treated with a PI3K inhibitor alone).

In one embodiment, the PI3K inhibitor is selected from Compound 1, GS1101, BKM 120, GDC-0941, PX-866, GDC-0032, BAY 80-6946, BEZ235, BYL719, BGT-226, PF-4691502, GDC-0980, GSK 2126458, PF-05212384, XL765, or XL147. In some embodiments, the PI3K inhibitor is selected from Compound 1 and GS1101. In some embodiments, the PI3K inhibitor is Compound 1. In one embodiment the tumor or tumor cell is selected from chronic lymphocytic leukemia, non-Hodgkin lymphoma, diffuse large B-cell lymphoma, mantle cell lymphoma, and adult T-cell lymphoma. In certain embodiments, the tumor is selected from chronic lymphocytic leukemia, non-Hodgkin lymphoma and diffuse large B-cell lymphoma. In one embodiment, the PI3K inhibitor is Compound 1 and the tumor or tumor cell is indolent non-Hodgkin lymphoma. In one embodiment the progression-positive biomarker is a genomic alteration in one or more gene in the 6q deletion region. In one embodiment, the progression-positive biomarker is a genomic alteration in an NF-κB pathway gene. In one embodiment, the progression-positive biomarker is a del(6q13-16) or a del(6q23-24). In one embodiment the progression-positive biomarker is a TNFAIP3 mutation or copy number loss. In one embodiment the progression-positive biomarker is an EPHA7 mutation or copy number loss.

The present invention also provides a method of predicting the likelihood that a tumor cell from a tumor will progress to a more aggressive tumor wherein the tumor is treatable with a PI3K inhibitor, comprising: assessing the level of at least one progression-negative biomarker expressed by a tumor cell; and predicting the likelihood that the tumor cell will progress to a more aggressive tumor, wherein high expression levels of said tumor cell progression-negative biomarker correlate with low likelihood that the tumor cell will progress to a more aggressive tumor, or wherein low expression levels of said tumor cell progression-negative biomarker correlates with high sensitivity to inhibition by a PI3K inhibitor and treating the tumor with a PI3K inhibitor and a Bcl-2 inhibitor (e.g., if it is determined that there is a high likelihood that the tumor cell will progress to a more aggressive tumor if treated with a PI3K inhibitor alone). In one embodiment, the PI3K inhibitor is selected from Compound 1, GS1101, BKM 120, GDC-0941, PX-866, GDC-0032, BAY 80-6946, BEZ235, BYL719, BGT-226, PF-4691502, GDC-0980, GSK 2126458, PF-05212384, XL765, or XL147. In some embodiments, the PI3K inhibitor is selected from Compound 1 and GS1101. In certain embodiments, the PI3K inhibitor is Compound 1. In one embodiment the tumor or tumor cell is selected from chronic lymphocytic leukemia, non-Hodgkin lymphoma, diffuse large B-cell lymphoma, mantle cell lymphoma, and adult T-cell lymphoma. In some embodiments, the tumor is selected from chronic lymphocytic leukemia, non-Hodgkin lymphoma and diffuse large B-cell lymphoma. In one embodiment, the PI3K inhibitor is Compound 1 and the tumor or tumor cell is indolent non-Hodgkin lymphoma. In one embodiment the progression-positive biomarker is a genomic alteration in one or more gene in the 6q deletion region. In one embodiment, the progression-positive biomarker is a genomic alteration in an NF-κB pathway gene. In one embodiment, the progression-positive biomarker is a del(6q13-16) or a del(6q23-24). In one embodiment the progression-positive biomarker is a TNFAIP3 mutation or copy number loss. In one embodiment the progression-positive biomarker is an EPHA7 mutation or copy number loss.

In a further aspect, the present invention provides a method for treating a tumor in a patient, comprising the step of administering to the patient a PI3K inhibitor and a Bcl-2 inhibitor, wherein there is a high likelihood that the patient will develop a more aggressive tumor and wherein said likelihood has been determined by:

assessing the level of at least one progression-positive biomarker expressed by a tumor cell from said tumor; and predicting the likelihood that the tumor cell will progress to a more aggressive tumor, wherein high expression levels of said tumor cell progression-positive biomarker correlate with high likelihood that the tumor cell will progress to a more aggressive tumor; or assessing the level of at least one progression-negative biomarker expressed by a tumor cell from said tumor; and predicting the likelihood that the tumor cell will progress to a more aggressive tumor, wherein low expression levels of said tumor cell progression-negative biomarker correlate with high likelihood that the tumor cell will progress to a more aggressive tumor.

In one embodiment, the PI3K inhibitor is selected from Compound 1, GS1101, BKM 120, GDC-0941, PX-866, GDC-0032, BAY 80-6946, BEZ235, BYL719, BGT-226, PF-4691502, GDC-0980, GSK 2126458, PF-05212384, XL765, or XL147. In some embodiments, the PI3K inhibitor is selected from Compound 1 and GS1101. In certain embodiments, the PI3K inhibitor is Compound 1. In one embodiment the tumor or tumor cell is selected from chronic lymphocytic leukemia, non-Hodgkin lymphoma, diffuse large B-cell lymphoma, mantle cell lymphoma, and adult T-cell lymphoma. In some embodiments, the tumor is selected from chronic lymphocytic leukemia, non-Hodgkin lymphoma and diffuse large B-cell lymphoma. In one embodiment, the PI3K inhibitor is Compound 1 and the tumor or tumor cell is indolent non-Hodgkin lymphoma. In one embodiment the progression-positive biomarker is a genomic alteration in one or more gene in the 6q deletion region. In one embodiment, the progression-positive biomarker is a genomic alteration in an NF-κB pathway gene. In one embodiment, the progression-positive biomarker is a del(6q13-16) or a del(6q23-24). In one embodiment the progression-positive biomarker is a TNFAIP3 mutation or copy number loss. In one embodiment the progression-positive biomarker is an EPHA7 mutation or copy number loss.

In the methods of this invention, the level of a prognosis-positive or prognosis-negative biomarker expressed by a tumor cell can be assessed by using any of the standard bioassay procedures known in the art for determination of the level of expression of a gene, including for example ELISA, RIA, immunoprecipitation, immunoblotting, immunofluorescence microscopy, RT-PCR, in situ hybridization, cDNA microarray, or the like, as described in more detail below.

In the methods of this invention, the expression level of a tumor cell prognosis-positive biomarker or prognosis-negative biomarker is preferably assessed by assaying a tumor biopsy. However, in an alternative embodiment, expression level of the tumor cell biomarker can be assessed in bodily fluids or excretions containing detectable levels of biomarkers originating from the tumor or tumor cells. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor prognosis-positive or prognosis-negative biomarkers in such bodily fluids or excretions can sometimes be preferred in circumstances where an invasive sampling method is inappropriate or inconvenient.

In any of the above methods referring to a patient sample, an example of such a sample can be a tumor biopsy.

In one embodiment, the biomarkers provided herein include, but are not limited to, a target biomarker, a signaling pathway biomarker, a protein mutation biomarker, a protein expression biomarker, a gene mutation biomarker, a copy number alteration (CNA) biomarker, a gene expression biomarker, a cytokine biomarker, a chemokine biomarker, a matrix metalloproteinase biomarker, or a biomarker for particular cancer cells. In one embodiment, the biomarker can be used to evaluate the prognosis, and/or sensitivity to a treatment agent, of a particular type of cancer or disease, or of a particular patient or group of patients.

In one embodiment, the prognosis-positive or prognosis-negative biomarker is a genomic alteration. In one embodiment, the genomic alteration is a gene mutation or a copy number alteration. In one embodiment, the gene mutation is a non-dbSNP mutation. In another embodiment, the gene mutation is a single nucleotide polymorphism (SNP) mutation. In one embodiment, the prognosis-negative biomarker is associated with a mutation in one or more of the following genes: ALK, SF3B1, TP53, NOTCH1, MYD88, ATM, XPO1, POT1, NRAS, BCOR, KRAS, MED12, DDX3X, FBXW7, BTK and PLCG2. In one embodiment, the prognosis-negative biomarker is associated with a mutation in one or more of the following genes: SF3B1, TP53, NOTCH1, MYD88, ATM, XPO1, MED12, and FBXW7. In one embodiment, the prognosis-negative biomarker is associated with a chromosome deletion.

In one embodiment, the prognosis-negative biomarker is associated with one or more genomic alterations selected from the group consisting of del(11q21), del(13q14), trisomy 12, del(11q22-23), del(17p13), del(8p), TP53 mutation, TP53 pathway mutation, MAPK pathway mutation, TP53 copy number loss, STK11 copy number loss, TSC1 copy number loss, and TSC2 copy number loss. In one embodiment, the prognosis-negative biomarker is copy number loss in one or more of STK11, TSC1, and TSC2. In one embodiment, the prognosis-negative biomarker is copy number loss in STK11. In one embodiment, the prognosis-negative biomarker is copy number loss in TSC1. In one embodiment, the prognosis-negative biomarker is copy number loss in TSC2. In one embodiment, the prognosis-negative biomarker is copy number loss in STK11 and TSC1. In one embodiment, the prognosis-negative biomarker is copy number loss in STK11 and TSC2. In one embodiment, the prognosis-negative biomarker is TP53 pathway mutation or MAPK pathway mutation or both. In one embodiment, the prognosis-negative biomarker is TP53 pathway and MAPK pathway dual mutation. In one embodiment, the prognosis-negative biomarker is TP53 C141Y mutation. In another embodiment, the prognosis-negative biomarker is ALK E1028D mutation.

In one embodiment, the prognosis-negative biomarker is associated with one or more (e.g., 2, 3, 4, 5, or all) genomic alterations selected from the group consisting of del(11q21), del(13q14), trisomy 12, del(11q22-23), del(17p13), and del(8p).

In an embodiment, the prognosis-negative biomarker is one or more genomic alterations selected from the group consisting of BRAF copy number gain, CTNNB1 copy number gain, FHIT copy number gain, IRF4 copy number gain, MITF copy number gain, MN1 copy number gain, NF2 copy number gain, NF2 copy number loss, RET copy number loss, STK11 copy number loss, TSC2 copy number loss, RB1 loss of heterozygosity.

In an embodiment, the prognosis-positive biomarker is one or more of RANBP17 copy number gain, FGFR3 loss of heterozygosity, GMPS loss of heterozygosity, and WHSC1 loss of heterozygosity.

In one embodiment, the progression-positive or progression-negative biomarker is a genomic alteration. In one embodiment, the genomic alteration is a gene mutation or a copy number alteration. In one embodiment, the gene mutation is a non-dbSNP mutation. In another embodiment, the gene mutation is a single nucleotide polymorphism (SNP) mutation. In one embodiment, the progression-positive biomarker is a genomic alteration in one or more gene in the 6q deletion region. In an embodiment of the invention the progression-positive biomarker is a genomic alteration in an NF-κB pathway gene. In an embodiment, the progression-positive biomarker is a del(6q13-16) or a del(6q23-24). In one embodiment the progression-positive biomarker is a TNFAIP3 mutation or copy number loss. In one embodiment the progression-positive biomarker is an EPHA7 mutation or copy number loss.

In certain aspects provided herein is a method of predicting the sensitivity of tumor cell growth to inhibition by a PI3K inhibitor, comprising: assessing the level of at least one prognosis-positive biomarker expressed by a tumor cell; and predicting the sensitivity of tumor cell growth to inhibition by a PI3K inhibitor, wherein high levels of a prognosis-positive biomarker expression by the tumor cells correlates with high sensitivity to inhibition by a PI3K inhibitor, or wherein low expression levels of said tumor cell prognosis-positive biomarker correlate with low sensitivity to inhibition by PI3K inhibitors, and treating the tumor with a PI3K inhibitor and a Bcl-2 inhibitor.

In certain aspects, provided herein is a method of predicting the sensitivity of tumor cell growth to inhibition by a PI3K inhibitor, comprising: assessing the level of at least one prognosis-negative biomarker expressed by a tumor cell; and predicting the sensitivity of tumor cell growth to inhibition by a PI3K inhibitor, wherein high levels of prognosis-negative biomarker expression by the tumor cell correlates with low sensitivity to inhibition by a PI3K inhibitor, or wherein low expression levels of said tumor cell prognosis-negative biomarker correlates with high sensitivity to inhibition by a PI3K inhibitor, and treating the tumor with a PI3K inhibitor and a Bcl-2 inhibitor.

In certain aspects provided herein is a method for treating a tumor in a patient comprising the step of administering to the patient a PI3K inhibitor, wherein the patient possesses a tumor that has been determined as having high sensitivity to tumor cell growth inhibition by a PI3K inhibitor by (a) assessing the level of at least one prognosis-positive biomarker expressed by a tumor cell from said tumor; and predicting the sensitivity of tumor cell growth to inhibition by a PI3K inhibitor, wherein high expression levels of said tumor cell prognosis-positive biomarker correlate with high sensitivity to inhibition by a PI3K inhibitor; or (b) assessing the level of at least one prognosis-negative biomarker expressed by a tumor cell from said tumor; and predicting the sensitivity of tumor cell growth to inhibition by a PI3K inhibitor, wherein low expression levels of said tumor cell prognosis-negative biomarker correlate with high sensitivity to inhibition by a PI3K inhibitor, and treating the tumor with a PI3K inhibitor and a Bcl-2 inhibitor.

In certain aspects provided herein is a method for treating a tumor in a patient comprising the step of administering to the patient a PI3K inhibitor as a first-line therapy, wherein the patient possesses a tumor that has been determined as having high sensitivity to tumor cell growth inhibition by a PI3K inhibitor by (a) assessing the level of at least one prognosis-positive biomarker expressed by a tumor cell from said tumor; and predicting the sensitivity of tumor cell growth to inhibition by a PI3K inhibitor, wherein high expression levels of said tumor cell prognosis-positive biomarker correlate with high sensitivity to inhibition by a PI3K inhibitor; or (b) assessing the level of at least one prognosis-negative biomarker expressed by a tumor cell from said tumor; and predicting the sensitivity of tumor cell growth to inhibition by a PI3K inhibitor, wherein low expression levels of said tumor cell prognosis-negative biomarker correlate with high sensitivity to inhibition by a PI3K inhibitor, and treating the tumor with a PI3K inhibitor and a Bcl-2 inhibitor.

In some embodiments, the PI3K inhibitor can be selected from Compound 1, GS1101, BKM 120, GDC-0941, PX-866, GDC-0032, BAY 80-6946, BEZ235, BYL719, BGT-226, PF-4691502, GDC-0980, GSK 2126458, PF-05212384, XL765, or XL147.

In some embodiments, the PI3K inhibitor is selected from Compound 1and GS1101.

In some embodiments, the tumor is an acoustic neuroma, adenocarcinoma, adrenal gland cancer, anal cancer, angiosarcoma, benign monoclonal gammopathy, biliary cancer bladder cancer, breast cancer, brain cancer, bronchus cancer, cervical cancer, choriocarcinoma, chordoma, craniopharyngioma, colorectal cancer, epithelial carcinoma, ependymoma, endotheliosarcoma, endometrial cancer, esophageal cancer, Ewing sarcoma, familiar hypereosinophilia, gastric cancer, gastrointestinal stromal tumor (GIST), head and neck cancer, oral cancer, heavy chain disease, hemangioblastoma, inflammatory myofibroblastic tumors, immunocytic amyloidosis, kidney cancer, liver cancer, malignant hepatoma, lung cancer, leiomyosarcoma (LMS), mastocytosis, multiple myeloma (MM), myelodysplastic syndrome (MDS), mesothelioma, neuroblastoma, neurofibroma neuroendocrine cancer, osteosarcoma, ovarian cancer, Paget's disease of the vulva, Paget's disease of the penis, papillary adenocarcinoma, pancreatic cancer, pinealoma, primitive neuroectodermal tumor (PNT), prostate cancer, rhabdomyosarcoma, retinoblastoma, salivary gland cancer, skin cancer, small bowel cancer, soft tissue sarcoma, sebaceous gland carcinoma, sweat gland carcinoma, synovioma, testicular cancer, thyroid cancer, and Waldenstrom's macroglobulinemia.

In some embodiments, the tumor is a myeloid disorder, lymphoid disorder, leukemia, lymphoma, myelodysplastic syndrome (MDS), myeloproliferative disease (MPD), mast cell disorder, or a myeloma.

In some embodiments, the tumor is selected from acute lymphoblastic leukemia, T-cell acute lymphoblastic leukemia, B-cell acute lymphoblastic leukemia, acute myeloid leukemia, chronic lymphocytic leukemia (CLL), chronic myelogenous leukemia, blast phase chronic myelogenous leukemia, small lymphocytic lymphoma (SLL), CLL/SLL, blast phase CLL, Hodgkin lymphoma, non-Hodgkin lymphoma (NHL), B-cell NHL, T-cell NHL, indolent NHL, diffuse large B-cell lymphoma, mantle cell lymphoma, aggressive B-cell NHL, B-cell lymphoma, Richter's syndrome, T-cell lymphoma, peripheral T-cell lymphoma, cutaneous T-cell lymphoma, transformed mycosis fungoides, Sézary syndrome, anaplastic large-cell lymphoma, follicular lymphoma, Waldenström macroglobulinemia, lymphoplasmacytic lymphoma, Burkitt lymphoma, multiple myeloma, amyloidosis, MPD, essential thrombocytosis, myelofibrosis, polycythemia vera, chronic myelomonocytic leukemia, myelodysplastic syndrome, angioimmunoblastic lymphoma, high-risk MDS, and low-risk MDS.

In some embodiments, the tumor is selected from chronic lymphocytic leukemia, non-Hodgkin lymphoma (e.g., indolent Non-Hodgkin lymphoma), diffuse large B-cell lymphoma, mantle cell lymphoma, and adult T-cell lymphoma.

In some embodiments, the prognosis-positive or prognosis-negative biomarker is a genomic alteration.

In some embodiments, the prognosis-positive or prognosis-negative biomarker is selected from a gene mutation, a copy number alteration, a non-dbSNP mutation or an single nucleotide polymorphism (SNP) mutation.

In some embodiments, the prognosis-positive biomarker is associated with a mutation in a gene selected from RANBP17 copy number gain, FGFR3 loss of heterozygosity, GMPS loss of heterozygosity and WHSC1 loss of heterozygosity.

In some embodiments, the prognosis-negative biomarker is associated with a genomic alteration selected from the group consisting of del(11q21), del(13q14), del(8p), trisomy 12, del(11q22-23), del(17p13), TP53 mutation, TP53 pathway mutation, MAPK pathway mutation, TP53 copy number loss, STK11 copy number loss, TSC1 copy number loss, and TSC2 copy number loss.

In some embodiments, the prognosis-negative biomarker is associated with a mutation in a gene selected from SF3B1, TP53, NOTCH1, MYD88, ATM, XPO1, POT1, NRAS, BCOR, KRAS, MED12, DDX3X, FBXW7, BTK and PLCG2.

In some embodiments, the prognosis-negative biomarker is associated with an STK11 copy number loss, a TSC1 or a TSC2 copy number loss.

In certain aspects, provided herein is a method of predicting the likelihood that a tumor will progress to a more aggressive tumor wherein the tumor is treatable with a PI3K inhibitor and a Bcl-2 inhibitor, said method comprising the steps of: assessing the level of at least one progression-positive biomarker expressed by a tumor cell from said tumor; and predicting the likelihood that the tumor cell will progress to a more aggressive tumor, wherein high expression levels of said tumor cell progression-positive biomarker correlate with high likelihood that the tumor cell will progress to a more aggressive tumor or wherein low expression levels of said tumor cell progression-positive biomarker correlate with low likelihood that the tumor cell will progress to a more aggressive tumor.

In certain aspects, provided herein is a method of predicting the likelihood that a tumor will progress to a more aggressive tumor wherein the tumor is treatable with a PI3K inhibitor and a Bcl-2 inhibitor, said method comprising the steps of: assessing the level of at least one progression-negative biomarker expressed by a tumor cell from said tumor; and predicting the likelihood that the tumor cell will progress to a more aggressive tumor, wherein high expression levels of said tumor cell progression-negative biomarker correlate with low likelihood that the tumor cell will progress to a more aggressive tumor or wherein low expression levels of said tumor cell progression-positive biomarker correlate with low likelihood that the tumor cell will progress to a more aggressive tumor.

In certain aspects, provided herein is a method of treating a tumor in a patient, comprising the step of administering to the patient a PI3K inhibitor and a Bcl-2 inhibitor, wherein there is a high likelihood that the patient will develop a more aggressive tumor and wherein said likelihood has been determined by: (a) assessing the level of at least one progression-positive biomarker expressed by a tumor cell from said tumor; and predicting the likelihood that the tumor cell will progress to a more aggressive tumor, wherein high expression levels of said tumor cell progression-positive biomarker correlate with high likelihood that the tumor cell will progress to a more aggressive tumor; or (b) assessing the level of at least one progression-negative biomarker expressed by a tumor cell from said tumor; and predicting the likelihood that the tumor cell will progress to a more aggressive tumor, wherein low expression levels of said tumor cell progression-negative biomarker correlate with high likelihood that the tumor cell will progress to a more aggressive tumor.

In some embodiments, the PI3K inhibitor is selected from Compound 1, GS1101, BKM 120, GDC-0941, PX-866, GDC-0032, BAY 80-6946, BEZ235, BYL719, BGT-226, PF-4691502, GDC-0980, GSK 2126458, PF-05212384, XL765, or XL147.

In any of the aforesaid aspects and embodiments, the tumor is an acoustic neuroma, adenocarcinoma, adrenal gland cancer, anal cancer, angiosarcoma, benign monoclonal gammopathy, biliary cancer bladder cancer, breast cancer, brain cancer, bronchus cancer, cervical cancer, choriocarcinoma, chordoma, craniopharyngioma, colorectal cancer, epithelial carcinoma, ependymoma, endotheliosarcoma, endometrial cancer, esophageal cancer, Ewing sarcoma, familiar hypereosinophilia, gastric cancer, gastrointestinal stromal tumor (GIST), head and neck cancer, oral cancer, heavy chain disease, hemangioblastoma, inflammatory myofibroblastic tumors, immunocytic amyloidosis, kidney cancer, liver cancer, malignant hepatoma, lung cancer, leiomyosarcoma (LMS), mastocytosis, multiple myeloma (MM), myelodysplastic syndrome (MDS), mesothelioma, neuroblastoma, neurofibroma neuroendocrine cancer, osteosarcoma, ovarian cancer, Paget's disease of the vulva, Paget's disease of the penis, papillary adenocarcinoma, pancreatic cancer, pinealoma, primitive neuroectodermal tumor (PNT), prostate cancer, rhabdomyosarcoma, retinoblastoma, salivary gland cancer, skin cancer, small bowel cancer, soft tissue sarcoma, sebaceous gland carcinoma, sweat gland carcinoma, synovioma, testicular cancer, thyroid cancer, and Waldenstrom's macroglobulinemia. In some embodiments, the tumor is a myeloid disorder, lymphoid disorder, leukemia, lymphoma, myelodysplastic syndrome (MDS), myeloproliferative disease (MPD), mast cell disorder, or a myeloma. In some embodiments, the tumor is indolent. In some embodiments, the tumor is selected from acute lymphoblastic leukemia, T-cell acute lymphoblastic leukemia, B-cell acute lymphoblastic leukemia, acute myeloid leukemia, chronic lymphocytic leukemia (CLL), chronic myelogenous leukemia, blast phase chronic myelogenous leukemia, small lymphocytic lymphoma (SLL), CLL/SLL, blast phase CLL, Hodgkin lymphoma, non-Hodgkin lymphoma (NHL), B-cell NHL, T-cell NHL, indolent NHL, diffuse large B-cell lymphoma, mantle cell lymphoma, aggressive B-cell NHL, B-cell lymphoma, Richter's syndrome, T-cell lymphoma, peripheral T-cell lymphoma, cutaneous T-cell lymphoma, transformed mycosis fungoides, Sézary syndrome, anaplastic large-cell lymphoma, follicular lymphoma, Waldenström macroglobulinemia, lymphoplasmacytic lymphoma, Burkitt lymphoma, multiple myeloma, amyloidosis, MPD, essential thrombocytosis, myelofibrosis, polycythemia vera, chronic myelomonocytic leukemia, myelodysplastic syndrome, angioimmunoblastic lymphoma, high-risk MDS, and low-risk MDS.

In some embodiments, the tumor is selected from chronic lymphocytic leukemia, non-Hodgkin lymphoma (e.g., indolent non-Hodgkin lymphoma), diffuse large B-cell lymphoma, mantle cell lymphoma, and adult T-cell lymphoma.

In some embodiments, the progression-positive or progression-negative biomarker is a genomic alteration.

In some embodiments, the progression-positive or progression-negative biomarker is selected from a gene mutation, a copy number alteration, a non-dbSNP mutation or an single nucleotide polymorphism (SNP) mutation.

In some embodiments, the progression-positive biomarker is associated with a mutation in a gene in the 6q deletion region.

In some embodiments, the progression-positive biomarker is a genomic alteration in an NF-κB pathway gene.

In some embodiments, the progression-positive biomarker is a del(6q13-16) or a del(6q23-24).

In some embodiments, the progression-positive biomarker is a TNFAIP3 mutation or copy number loss.

In some embodiments, the progression-positive biomarker is an EPHA7 mutation or copy number loss.

In some aspects, the disclosure provides a method of treating a patient, comprising (i) administering a first treatment comprising a first PI3K inhibitor to the subject (ii) acquiring information regarding an alteration in a biomarker by comparing an assessment of the biomarker in a first sample taken from the subject before the first treatment is administered with an assessment of the biomarker in a second sample taken from the subject after the first treatment is administered, wherein the biomarker is selected from STK11, TSC1, TSC2, TP53, PTEN, CBFA2T3, YWHAE, PER1, GAS7, FSTL3, USP6, MAP2K4, or EGFR, and (iii) continuing administration of the first treatment if the alteration is absent, or administering a second treatment if the alteration is present, wherein the second treatment includes administration of a Bcl-2 inhibitor.

In some aspects, the present disclosure provides a method of determining the further course of treatment for a subject who has undergone a first treatment with a first PI3K inhibitor, the method comprising: (i) acquiring information regarding the presence or absence of an alteration in one or more of STK11, TSC1, TSC2, TP53, PTEN, CBFA2T3, YWHAE, PER1, GAS7, FSTL3, USP6, MAP2K4, or EGFR in one or more samples from the subject; and (ii) selecting the subject for continuation of the first treatment with the first PI3K inhibitor if the alteration is absent and selecting the subject for a second treatment if the alteration is present, wherein the second treatment includes administration of a Bcl-2 inhibitor.

In some aspects, the disclosure provides a method of determining decreased responsiveness, or resistance, of a subject to a first treatment comprising a first PI3K inhibitor, the method comprising (i) acquiring information regarding the presence or absence of an alteration in one or more of STK11, TSC1, TSC2, TP53, PTEN, CBFA2T3, YWHAE, PER1, GAS7, FSTL3, USP6, MAP2K4, or EGFR in one or more samples from the subject; and (ii) determining that the subject shows decreased responsiveness or resistance to the first treatment if the alteration is present, wherein the second treatment includes administration of a Bcl-2 inhibitor.

In any of the above aspects or embodiments, the PI3K inhibitor can be selected from: Compound 1, AMG-319, GSK 2126458, GSK 1059615, GDC-0032, GDC-0980, GDC-0941, XL147, XL499, XL765, BKM 120 GS1101, CAL 263, SF1126, PX-866, BEZ235, CAL-120, BYL719, RP6503, RP6530, TGR1202, INK1117, PX-886, BAY 80-6946, IC87114, Palomid 529, ZSTK474, PWT33597, TG100-115, GNE-477, CUDC-907, AEZS-136, BGT-226, PF-05212384, LY3023414, PI-103, LY294002, INCB-040093, CAL-130 and wortmannin.

The present invention also provides, at least in part, methods (e.g., diagnostic and prognostic methods) for evaluating, e.g., predicting, the responsiveness to a treatment of a cancer with a B-cell receptor (BCR) pathway inhibitor (e.g., a PI3K inhibitor). In one embodiment, it is shown herein that STK11 copy number loss (with or without copy number loss of TSC1, TSC2, or both) is associated with, or is predictive of, decreased responsiveness (e.g., acquired resistance) of a cancer (e.g., chronic lymphocytic leukemia (CLL)) to a PI3K inhibitor (e.g., Compound 1). In other embodiments, it has been discovered that an alteration in the MAP kinase and p53 (MAPK/p53) pathway is associated with, or is predictive of, decreased responsiveness (e.g., acquired resistance) of a cancer (e.g., CLL) to a PI3K inhibitor (e.g., Compound 1). Thus, compositions, methods, and kits for evaluating responsiveness (e.g., acquisition of resistance) to, or monitor, therapy involving PI3K inhibition (including combination therapies); stratify patient populations; identify subjects likely to benefit from such agents, predict a time course of disease or a probability of a significant event in the disease for such subjects, and/or more effectively monitor, treat or prevent a cancer are disclosed. The methods further comprise treating the subject with a PI3K inhibitor and a Bcl-2 inhibitor.

Aspects of the invention disclosed herein are based, at least in part, on the following findings. Additional details are described herein in the Examples.

In experiments described herein, it was found that STK11 copy number loss is associated with or predictive of nonresponsiveness or resistance (e.g., acquired resistance) of a cancer (e.g., a CLL) to a PI3K inhibitor (e.g., Compound 1). Furthermore, in experiments described herein, it was found that a dual alteration in the MAPK/P53 pathway is associated with or predictive of nonresponsiveness or resistance (e.g., acquired resistance) of a cancer (e.g., a CLL) to a PI3K inhibitor (e.g., Compound 1).

In accordance with certain analyses described in the Examples, it was found that copy number loss of STK11 combined with copy number loss of TSC1, TSC2, or both is associated with or predictive of nonresponsiveness or resistance (e.g., acquired resistance) of a cancer (e.g., a CLL) to a PI3K inhibitor (e.g., Compound 1).

Also, in certain analyses described in the Examples, the following relationships were revealed. TSC2 copy number loss was associated with or predictive of nonresponsiveness or resistance (e.g., acquired resistance) of a cancer (e.g., a CLL) to a PI3K inhibitor (e.g., Compound 1). Copy number gain in each of BRAF, CTNNB1, FHIT, IRF4, MITF, MN1, and NF2 was associated with or predictive of nonresponsiveness or resistance (e.g., acquired resistance) of a cancer (e.g., a CLL) to a PI3K inhibitor (e.g., Compound 1). Copy number loss in each of NF2 and RET was associated with or predictive of nonresponsiveness or resistance (e.g., acquired resistance) of a cancer (e.g., a CLL) to a PI3K inhibitor (e.g., Compound 1). Loss of heterozygosity in RB1 was associated with or predictive of nonresponsiveness or resistance (e.g., acquired resistance) of a cancer (e.g., a CLL) to a PI3K inhibitor (e.g., Compound 1). Copy number gain in RANBP17 was associated with responsiveness or lack of resistance (e.g., acquired resistance) of a cancer (e.g., a CLL) to a PI3K inhibitor (e.g., Compound 1). Loss of heterozygosity in each of FGFR3, GMPS, and WHSC1 is associated with or predictive of responsiveness or lack of resistance (e.g., acquired resistance) of a cancer (e.g., a CLL) to a PI3K inhibitor (e.g., Compound 1).

Improved methods for treating a cancer patient with a PI3K inhibitor that incorporate the methods described herein are also provided, whereby patients with high sensitivity to cancer or tumor cell growth inhibition by a PI3K inhibitor are determined by the methods of the present invention. Thus, the present invention further provides a method for treating cancer in a subject, e.g., a patient, comprising the step of administering to the subject a PI3K inhibitor and a Bcl-2 inhibitor, wherein the subject possesses a cancer that has been determined as having high sensitivity to cancer or tumor cell growth inhibition by a PI3K inhibitor by assessing the level of at least one prognosis-positive biomarker in a cancer or tumor cell from said cancer or tumor; and predicting the sensitivity of cancer or tumor cell growth to inhibition by a PI3K inhibitor, wherein detection or an elevated level of said prognosis-positive biomarker correlate with high sensitivity to inhibition by a PI3K inhibitor; or assessing the level of at least one prognosis-negative biomarker in a cancer or tumor cell from said cancer or tumor; and predicting the sensitivity of cancer or tumor cell growth to inhibition by a PI3K inhibitor, wherein the presence or level of the alteration said prognosis-negative biomarker correlate with high sensitivity to inhibition by a PI3K inhibitor.

A further aspect of the invention is a method of treating a cancer or tumor or a metastasis thereof in a subject, comprising the step of administering to the subject a PI3K inhibitor, e.g., as a first-line therapy, wherein the subject possesses a cancer or tumor that has been determined as having high sensitivity to cancer or tumor cell growth inhibition by a PI3K inhibitor by assessing the level of at least one prognosis-positive biomarker by one of the following: assessing the level of at least one prognosis-positive biomarker expressed by a cancer cell from said cancer or tumor; and predicting the sensitivity of cancer or tumor cell growth to inhibition by a PI3K inhibitor, wherein detection or an elevated level of said prognosis-positive biomarker correlate with high sensitivity to inhibition by a PI3K inhibitor; or assessing the presence or an alteration at least one prognosis-negative biomarker in a cancer or tumor cell from said cancer or tumor; and predicting the sensitivity of cancer or tumor cell growth to inhibition by a PI3K inhibitor, wherein low levels of said prognosis-negative biomarker correlate with high sensitivity to inhibition by a PI3K inhibitor; and, if the cancer or tumor cell growth is predicted to have low sensitivity to inhibition by a PI3K inhibitor as a monotherapy, administering to the patient a combination of a PI3K inhibitor and a Bcl-2 inhibitor.

In a further aspect, the present invention provides a method for treating a cancer or tumor in a subject, e.g., a patient, comprising administering to the subject a PI3K inhibitor and a Bcl-2 inhibitor, wherein there is a high likelihood that the patient will develop a more aggressive tumor and wherein said likelihood has been determined by assessing the level of at least one progression-positive biomarker expressed by a tumor cell from said tumor; and predicting the likelihood that the tumor cell will progress to a more aggressive tumor, wherein high expression levels of said tumor cell progression-positive biomarker correlate with high likelihood that the tumor cell will progress to a more aggressive tumor; or assessing the level of at least one progression-negative biomarker expressed by a tumor cell from said tumor; and predicting the likelihood that the tumor cell will progress to a more aggressive tumor, wherein low expression levels of said tumor cell progression-negative biomarker correlate with high likelihood that the tumor cell will progress to a more aggressive tumor.

In certain aspects, the invention features a method of evaluating the responsiveness of a cancer or tumor, or a subject having a cancer or tumor, to a treatment with a BCR pathway inhibitor (e.g., a treatment with an inhibitor of PI3K, BTK or SYK, alone or in combination). In one embodiment, responsiveness to a PI3K inhibitor is evaluated. The method includes: acquiring a value (e.g., determining one or more of: the presence, absence, amount or level) of an alteration or biomarker chosen from one, two, three, four or all of: an STK11 copy number, TSC1 copy number, TSC2 copy number, a p53 pathway mutation (e.g., a mutation disclosed in Table 20), or MAPK pathway mutation (e.g., a mutation disclosed in Table 18), or any combination thereof (e.g., a dual MAPK/p53 pathway mutation, e.g., a mutation disclosed in Table 18 and a mutation disclosed in Table 20). The method further comprises administering a PI3K inhibitor and a Bcl-2 inhibitor to the subject.

In another aspect, the invention features a method of monitoring a treatment of a subject with a BCR pathway inhibitor (e.g., a treatment with an inhibitor of PI3K, BTK or SYK, alone or in combination). In one embodiment, treatment with a PI3K inhibitor is monitored. The method includes: acquiring, at two or more time intervals, a value (e.g., determining one or more of: the presence, absence, amount or level) of an alteration or biomarker chosen from one, two, three, four or all of: an STK11 copy number, TSC1 copy number, TSC2 copy number, a p53 pathway mutation (e.g., a mutation disclosed in Table 20), or MAPK pathway mutation (e.g., a mutation disclosed in Table 18), or any combination thereof (e.g., a dual MAPK/p53 mutation, e.g., a mutation disclosed in Table 18 and a mutation disclosed in Table 20). The method further comprises administering a PI3K inhibitor and a Bcl-2 inhibitor to the subject.

In another aspect, the invention features a method of treating (e.g., inhibiting, reducing, ameliorating, managing, or preventing) a cancer or tumor in a subject. The method includes: acquiring a value (e.g., determining one or more of: the presence, absence, amount or level) of an alteration or biomarker chosen from one, two, three, four or all of: an STK11 copy number, TSC1 copy number, TSC2 copy number, a p53 pathway mutation (e.g., a mutation disclosed in Table 20), or MAPK pathway mutation (e.g., a mutation disclosed in Table 18), or any combination thereof (e.g., a dual MAPK/p53 mutation, e.g., a mutation disclosed in Table 18 and a mutation disclosed in Table 20), and responsive to said value, administering to the subject a BCR pathway inhibitor, e.g., a PI3K inhibitor (e.g., one or more PI3K inhibitors) and a Bcl-2 inhibitor.

In another aspect, the invention features a method of treating a subject, comprising (i) administering a first treatment comprising a first PI3K inhibitor to the subject (ii) acquiring information regarding the presence or absence of an alteration in a biomarker in one or more samples from the subject, wherein the biomarker is selected from STK11, TSC1, TSC2, TP53, PTEN, CBFA2T3, YWHAE, PER1, GAS7, FSTL3, USP6, MAP2K4, or EGFR; and (iii) continuing administration of the first treatment if the alteration is absent, or administering a second treatment if the alteration is present, wherein the second treatment includes administration of a Bcl-2 inhibitor.

In certain embodiments, the alteration is an STK11, TSC1, TSC2, TP53, PTEN, CBFA2T3, YWHAE, PER1, GAS7, FSTL3, USP6, or MAP2K4 copy number loss (e.g., single copy loss). In some embodiments, the STK11, TSC1, TSC2, TP53, PTEN, CBFA2T3, YWHAE, PER1, GAS7, FSTL3, USP6, or MAP2K4 copy number in a sample taken from the subject after the first treatment is lower than a corresponding STK11, TSC1, TSC2, TP53, PTEN, CBFA2T3, YWHAE, PER1, GAS7, FSTL3, USP6, MAP2K4 copy number in a sample taken from the subject before the first treatment (e.g., there is an STK11 single copy loss).

In another aspect, the present disclosure provides a method of evaluating the responsiveness of a cancer or tumor, or a subject having a cancer or tumor, to a treatment with a BCR pathway inhibitor (e.g., a treatment with an inhibitor of PI3K, BTK or SYK, alone or in combination). In one embodiment, responsiveness to a PI3K inhibitor is evaluated. The method includes: acquiring a value (e.g., determining one or more of: the presence, absence, amount or level) of an anti-apoptotic factor such as Bcl-2.

In another aspect, the invention features a method of monitoring a treatment of a subject with a BCR pathway inhibitor (e.g., a treatment with an inhibitor of PI3K, BTK or SYK, alone or in combination). In one embodiment, treatment with a PI3K inhibitor is monitored. The method includes: acquiring, at two or more time intervals, a value (e.g., determining one or more of: the presence, absence, amount or level) of an anti-apoptotic factor such as Bcl-2.

In another aspect, the invention features a method of treating (e.g., inhibiting, reducing, ameliorating, managing, or preventing) a cancer or tumor in a subject. The method includes: acquiring a value (e.g., determining one or more of: the presence, absence, amount or level) of an anti-apoptotic factor such as Bcl-2.

In certain embodiments, the methods that include acquiring a value of Bcl-2 also include acquiring a value (e.g., determining one or more of: the presence, absence, amount or level) of a pro-apoptotic factor or anti-apoptotic factor. The pro-apoptotic factor can be, e.g., one or more of (e.g., 2, 3, 4, or all of) BMF, BIK, BIM, NOXA, PUMA, and HRK. In some embodiments, an elevated level of Bcl-2 indicates that the cancer is resistant to a PI3K inhibitor. In some embodiments, a normal or reduced level of Bcl-2 indicates that the cancer is responsive to a PI3K inhibitor. In some embodiments, an elevated level of one or more pro-apoptotic factors (e.g., BMF, BIK, BIM, NOXA, PUMA, and HRK) indicates that the cancer is more responsive to a PI3K inhibitor (optionally in combination with a Bcl-2 inhibitor) than a cancer with normal or lowered levels of the pro-apoptotic factor. In some embodiments, the methods involve administering a Bcl-2 inhibitor (e.g., in combination with a PI3K inhibitor) to a subject having elevated Bcl-2 levels. In some embodiments, the methods involve administering a PI3K inhibitor as a monotherapy to a subject having normal or low Bcl-2 levels. In some embodiments, the elevated, normal, or reduced levels of a biomarker are determined with reference to a non-cancerous control value.

In some embodiments, acquiring a value comprises acquiring information regarding the presence or absence of an alteration described herein.

In some embodiments, the methods herein comprise comparing an assessment of a biomarker in a first sample taken from the subject before the first treatment is administered with an assessment of the biomarker in a second sample taken from the subject after the first treatment is administered. In an embodiment, the method comprises determining the further course of treatment for the subject. In an embodiment, the method comprises a method of determining decreased responsiveness, or resistance, of the subject to the first treatment.

In some embodiments, the methods herein comprise administering a first treatment comprising a first PI3K inhibitor to the subject and continuing administration of the first treatment if an alteration is absent, or administering a second treatment including a Bcl-2 inhibitor, if the alteration is present. In some embodiments, the methods herein comprise determining the further course of treatment for a subject, e.g., selecting the subject for continuation of the first treatment with the first PI3K inhibitor if the alteration is absent and selecting the subject for a second treatment if the alteration is present, wherein the second treatment includes administration of a Bcl-2 inhibitor. In some embodiments, the methods comprise determining decreased responsiveness, or resistance, of a subject to a first treatment comprising a first PI3K inhibitor. In some embodiments, the methods comprise determining that the subject shows decreased responsiveness or resistance to the first treatment if the alteration is present, wherein the second treatment includes administration of a Bcl-2 inhibitor.

In certain embodiments of the methods above, the alteration is an STK11 copy number loss (e.g., single copy loss). In some embodiments, the STK11 copy number in a sample taken from the subject after the first treatment is lower than the STK11 copy number in a sample taken from the subject before the first treatment (e.g., there is an STK11 single copy loss). In some embodiments, the first treatment with the first PI3K inhibitor (e.g., Compound 1) is a monotherapy in which the first PI3K inhibitor is the only component of the first treatment known to have a substantial therapeutic activity.

In some embodiments of the methods herein, a prognosis-negative biomarker is chosen from one, two, three or all of the following:
 (i) a copy number loss of STK11;
 (ii) a copy number loss of TSC1 or TSC2, or both;
 (iii) a p53 pathway mutation, e.g., TP53 C141Y; or
 (iv) a MAPK pathway mutation.

In some embodiments of the methods herein, a prognosis-negative biomarker is a copy number loss of STK11. In one embodiment, detection of copy number loss of STK11 is indicative of decreased responsiveness of the cancer or tumor, or the subject, to the treatment.

In some embodiments of the methods herein, a prognosis-negative biomarker is a dual MAPK/p53 mutation. In one embodiment, detection of the dual MAPK/p53 mutation is indicative of decreased responsiveness of the cancer or tumor, or the subject, to the treatment.

In some embodiments of the methods herein, a prognosis-negative biomarker is a copy number loss of STK11 in combination with a copy number loss of TSC1, TSC2, or both. In one embodiment, detection of copy number loss of STK11 in combination with a copy number loss of TSC1 is indicative of decreased responsiveness of the cancer or tumor, or the subject, to the treatment. In another embodiment, detection of copy number loss of STK11 in combination with a copy number loss of TSC2 is indicative of decreased responsiveness of the cancer or tumor, or the subject, to the treatment. In yet another embodiment, detection of copy number loss of STK11 in combination with a copy number loss of TSC1 and TSC2 is indicative of decreased responsiveness of the cancer or tumor, or the subject, to the treatment.

In some embodiments of the methods herein, the alteration is a prognosis-negative biomarker or a progression-positive biomarker, or both. In one embodiment, detection of a prognosis-negative biomarker or a progression-positive biomarker, or both, is indicative of decreased responsiveness of the cancer or tumor, or the subject, to the treatment.

In some embodiments of any of the above aspects, the BCR pathway mutation is a mutation disclosed in Table 19. In an embodiment, the p53 pathway mutation is a mutation disclosed in Table 20. In an embodiment, the MAPK pathway mutation is a mutation disclosed in Table 18. In an embodiment, the combination thereof is a dual MAPK/p53 mutation of which a mutation is disclosed in Table 18 and a mutation is disclosed in Table 20.

In some embodiments of any of the above aspects, one, two, three, four, five, six, seven, eight, nine, 10, 11, 12, 13, or all of the following is indicative of decreased responsiveness of the cancer, or the subject, to the treatment:
 (i) a copy number loss (e.g., a single copy loss) of STK11;
 (ii) a copy number loss of TSC1 or TSC2, or both;
 (iii) a copy number loss of TP53;
 (iv) a copy number loss of PTEN;
 (v) a copy number loss of CBFAT2T3;
 (vi) a copy number loss of YWHAE;
 (vii) a copy number loss of PER1;
 (viii) a copy number loss of GAS7;
 (ix) a copy number loss of FSTL3;
 (x) a copy number loss of USP6;
 (xi) a copy number loss of MAP2K4;
 (xii) a BCR pathway mutation;
 (xiii) a p53 pathway mutation, e.g., a mutation listed in Table 20 (e.g., TP53 C141Y); or
 (xiv) a MAPK pathway mutation, e.g., a mutation listed in Table 18.

In some embodiments of any of the methods herein, the alteration or biomarker is a copy number loss (e.g., a single copy loss) of STK11. In one embodiment, detection of copy number loss of STK11 is indicative of decreased responsiveness of the cancer or tumor, or the subject, to the treatment. In some embodiments of any of the above aspects, the alteration or biomarker is a dual MAPK/p53 pathway mutation. In one embodiment the dual mutation includes a mutation listed in Table 18 and/or Table 20. In one embodiment, detection of the dual MAPK/p53 pathway mutation is indicative of decreased responsiveness of the cancer or tumor, or the subject, to the treatment. In some embodiments of any of the above aspects, the alteration or biomarker is a BCR pathway mutation. In one embodiment, detection of a BCR pathway mutation is indicative of decreased responsiveness of the cancer or tumor, or the subject, to the treatment. In some embodiments of any of the above aspects, detection of copy number loss of TP53 is indicative of decreased responsiveness of the cancer or tumor, or the subject, to the treatment. In some embodiments of any of the above aspects, detection of copy number loss of PTEN is indicative of decreased responsiveness of the cancer or tumor, or the subject, to the treatment. In some embodiments of any of the above aspects, detection of copy number loss of CBFAT2T3 is indicative of decreased responsiveness of the cancer or tumor, or the subject, to the treatment. In some embodiments of any of the above aspects, detection of copy number loss of YWHAE is indicative of decreased responsiveness of the cancer or tumor, or the subject, to the treatment. In some embodiments of any of the above aspects, detection of copy number loss of PER1 is indicative of decreased responsiveness of the cancer or tumor, or the subject, to the treatment. In some embodiments of any of the above aspects, detection of copy number loss of GAS7 is indicative of decreased responsiveness of the cancer or tumor, or the subject, to the treatment. In some embodiments of any of the above aspects, detection of copy number loss of FSTL3 is indicative of decreased responsiveness of the cancer or tumor, or the subject, to the treatment. In some embodiments of any of the above aspects, detection of copy number loss of USP6 is indicative of decreased responsiveness of the cancer or tumor, or the subject, to the treatment. In some embodiments of any of the above aspects, detection of copy number loss of MAP2K4 is indicative of decreased responsiveness of the cancer or tumor, or the subject, to the treatment. In some embodiments of any of the above aspects, detection of copy number loss of EGFR is indicative of increased responsiveness of the cancer or tumor, or the subject, to the treatment; or wherein detection of copy number gain of EGFR is indicative of decreased responsiveness of the cancer or tumor, or the subject, to the treatment, or both. In some embodiments of any of the above aspects, detection of copy number loss of EGFR is indicative of increased responsiveness of the cancer or tumor, or the subject, to the treatment, and wherein increased responsiveness is determined using nodal criteria.

In some embodiments of any of the above aspects, the alteration or biomarker is a copy number loss of STK11 in combination with a copy number loss of TSC1, TSC2, or both. In one embodiment, detection of copy number loss of STK11 in combination with a copy number loss of TSC1 is indicative of decreased responsiveness of the cancer or tumor, or the subject, to the treatment. In another embodiment, detection of copy number loss of STK11 in combination with a copy number loss of TSC2 is indicative of decreased responsiveness of the cancer or tumor, or the subject, to the treatment. In yet another embodiment, detection of copy number loss of STK11 in combination with a copy number loss of TSC1 and TSC2 is indicative of decreased responsiveness of the cancer or tumor, or the subject, to the treatment.

In some embodiments of any of the above aspects, no detectable copy number loss of STK11, TSC1, TSC2, TP53, PTEN, CBFA2T3, YWHAE, PER1, GAS7, FSTL3, USP6, or MAP2K4, or no detectable dual MAPK/p53 pathway mutation, or no detectable BCR pathway mutation, is indicative of continued responsiveness to the treatment.

In some embodiments of any of the above aspects, the alteration is a prognosis-negative biomarker or a progression-positive biomarker, or both. In one embodiment, detection of a prognosis-negative biomarker or a progression-positive biomarker, or both, is indicative of decreased responsiveness of the cancer or tumor, or the subject, to the treatment.

In some embodiments of any of the above aspects, no detectable copy number loss of STK11, or no detectable dual MAPK/p53 pathway mutation, is indicative of continued responsiveness to the treatment.

In some embodiments of any of the above aspects, the subject is evaluated prior to undergoing, while undergoing, or after undergoing, treatment with the BCR pathway inhibitor, e.g., the PI3K inhibitor. In another embodiment, the subject is evaluated at at least two time intervals, e.g., prior to undergoing and while undergoing the treatment. In yet another embodiment, the subject is evaluated at at least three time points, e.g., prior to undergoing, while undergoing the treatment, and after undergoing the treatment.

In some embodiments of any of the above aspects, decreased responsiveness of the cancer or tumor, or the subject to the treatment, e.g., over a timecourse of the treatment, is indicative of increased resistance (e.g., acquired resistance) to the treatment, e.g., the PI3K inhibitor. In an embodiment, if the subject is identified as being responsive to the treatment, the treatment is continued. In an embodiment, if the subject is identified as not being responsive to the treatment, the treatment is altered or discontinued, thereby having a first and second treatment.

In some embodiments of the aforesaid methods, responsive to a determination of the value of the alteration or biomarker, the method further includes one, two, three, four, five, six, seven, eight, nine or all of the following:

(i) identifying the subject as being in need of a treatment, e.g., treatment with a PI3K inhibitor (e.g., a first treatment or a second (alternative) treatment);

(ii) identifying the subject as having an increased or a decreased responsiveness to the treatment, e.g., the treatment with the PI3K inhibitor (e.g., a monotherapy with Compound 1);

(iii) identifying the subject as being a responder to the treatment, e.g., identifying the subjects as being in complete remission (CR) or partial cancer remission (PR) (e.g., CR or PR subjects as described herein);

(iv) identifying the subject as being a non-responder to the treatment, e.g., identifying the subjects as having a progressive disease (PD) or stable disease (SD) (e.g., PD or SD subjects as described herein);

(v) identifying the subject as having developed resistance (e.g., partial or complete, acquired resistance) to the treatment, e.g., the PI3K inhibitor (e.g., Compound 1);

(vi) diagnosing and/or prognosing the subject;

(vii) determining a time course of disease progression in the subject;

(viii) determining the time course of acquisition of resistance to the treatment;

(ix) determining a treatment, e.g., selecting or altering the course of, a treatment (e.g., a first treatment), a dose, a treatment schedule or time course, and/or the use of an alternative, second treatment); and/or (x) administering the treatment (e.g., the first treatment or a second (alternative) treatment) to the subject.

In one embodiment of the aforesaid methods, the subject is identified as having decreased responsiveness to the treatment by having at least one progression-positive biomarker. In one embodiment, the progression-positive biomarker is a genomic alteration in an NF-κB pathway gene. In an embodiment, the progression-positive biomarker is a 6q deletion region, e.g., a del(6q13-16) or a del(6q23-24). In one embodiment, the progression-positive biomarker is a TNFAIP3 mutation or copy number loss. In one embodiment, the progression-positive biomarker is an EPHA7 mutation or copy number loss.

In one embodiment, the subject is a mammal, e.g., a human. In one embodiment, the subject is at risk or suffers from a cancer or tumor, e.g., a cancer or tumor described herein.

In one embodiment, the subject shows decreased responsiveness to a PI3K inhibitor (e.g., is resistant or refractive to treatment with a PI3K inhibitor, e.g., Compound 1).

In certain embodiments, the subject is identified as developing resistance (e.g., acquired resistance) to the monotherapy.

In one embodiment, the subject is identified as having a decreased responsiveness (e.g., being resistance or having acquired resistance) to a monotherapy treatment with a PI3K inhibitor (e.g., Compound 1 or GS1101) (referred herein to a "first PI3K inhibitor treatment"). In one embodiment, the subject is identified as having a decreased responsiveness (e.g., being resistance or having acquired resistance) to a monotherapy treatment of a PI3K inhibitor (e.g., Compound 1).

In one embodiment, the subject is identified as having an increased responsiveness to a second treatment, e.g., a treatment comprising a reduced dose of the PI3K inhibitor, or a treatment comprising a combination of the PI3K inhibitor and a Bcl-2 inhibitor. In one embodiment, the dose of the PI3K inhibitor, the Bcl-2 inhibitor, or both, is reduced, e.g., at least 20%, at least 30%, at least 40%, or at least 50%, than the amount or dosage of each agent used individually, e.g., as a monotherapy.

In some embodiments of the methods described herein, the method further includes altering a treatment (e.g., a first treatment), a dose, a treatment schedule or time course, and/or the use of an alternative, second treatment.

In other embodiments of the methods described herein, the method further includes administering the treatment (e.g., the first treatment or a second (alternative) treatment) to the subject.

In other embodiments of the methods described herein, the method further includes administering a combination of the PI3K inhibitor and a Bcl-2 inhibitor in an amount sufficient to treat the cancer, in the subject, e.g., for treatment of a cancer described herein.

Detection of Alterations

The genomic alteration biomarkers provided herein can be detected by the methods known in the art to detect genomic alterations. In one embodiment, the gene mutations or copy number alterations are detected by methods such as CytoScan Microarray (pre- and post-treatment), targeted exome sequencing (pre- and post-treatment), and Sanger sequencing. In one embodiment, the mutation or copy number alteration of STK11 is detected by STK11 FISH Probe or qPCR.

In one embodiment, the biomarkers provided herein can be used to identify, diagnose, predict efficacy, predict long term clinical outcome, predict prognosis, and/or select patients for a treatment described herein. In one embodiment, the biomarkers provided herein can be used for subsets of patients with different prognostic factors.

In the methods of the invention, one can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the tumor cell (e.g. using a labeled antibody which binds specifically with a cell-surface domain of the protein).

Expression of a biomarkers described in this invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a biomarker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

In another embodiment, expression of a biomarker is assessed by preparing mRNA/cDNA (i.e. a transcribed polynucleotide) from cells in a patient sample, and by hybridizing the mRNA/cDNA with a reference polynucleotide which is a complement of a biomarker nucleic acid, or a fragment thereof. cDNA can, optionally, be amplified using any of a variety of polymerase chain reaction methods prior to hybridization with the reference polynucleotide. Expression of one or more biomarkers can likewise be detected using quantitative PCR to assess the level of expression of the biomarker(s).

In all embodiments of the invention, the expression level of a biomarker can be determined with reference to the effect on biomarker expression caused by a mutation or variant in a gene associated with said biomarker. Accordingly, for example, the consequences of a genomic alteration on the expression level of biomarkers referred to in the methods of the invention may be inferred directly from identification of the genomic alteration in the genome of a patient.

As used herein, the mutation can be a point mutation, e.g. SNP, an insertion, a deletion, an amplification, a deletion, a chromosomal translocation, an interstitial deletion, a chromosomal inversion or a loss of heterozygosity.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biomarker nucleic acid. If polynucleotides complementary to or homologous with are differentially detectable on the substrate (e.g. detectable using different chromophores or fluorophores, or fixed to different selected positions), then the levels of expression of a plurality of biomarkers can be assessed simultaneously using a single substrate (e.g. a "gene chip" microarray of polynucleotides fixed at selected positions). When a method of assessing biomarker expression is used which involves hybridization of one nucleic acid with another, it is preferred that the hybridization be performed under stringent hybridization conditions.

When a plurality of biomarkers of the invention are used in the methods of the invention, the level of expression of each biomarker in a patient sample can be compared with the normal level of expression of each of the plurality of biomarkers in non-cancerous samples of the same type, either in a single reaction mixture (i.e. using reagents, such as different fluorescent probes, for each biomarker) or in individual reaction mixtures corresponding to one or more of the biomarkers.

The level of expression of a biomarker in normal (i.e. non-cancerous) human tissue can be assessed in a variety of ways. In one embodiment, this normal level of expression is assessed by assessing the level of expression of the biomarker in a portion of cells which appears to be non-cancerous, and then comparing this normal level of expression with the level of expression in a portion of the tumor cells. Alternately, and particularly as further information becomes available as a result of routine performance of the methods described herein, population-average values for normal expression of the biomarkers of the invention may be used. In other embodiments, the 'normal' level of expression of a biomarker may be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample (e.g. a tumor-associated body fluid) from a test patient and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a biomarker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a biomarker protein include introducing into a patient a labeled antibody directed against the protein or fragment thereof. For example, the antibody can be labeled with a radioactive marker whose presence and location in a patient can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay would involve anchoring the biomarker or probe onto a solid phase support, also referred to as a substrate, and detecting target biomarker/probe complexes anchored on the solid phase at the end of the reaction. In one embodiment of such a method, a sample from a patient, which is to be assayed for presence and/or concentration of biomarker, can be anchored onto a carrier or solid phase support. In another embodiment, the reverse situation is possible, in which the probe can be anchored to a solid phase and a sample from a patient can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of biomarker/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S. and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the biomarker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, J. Mol. Recognit. Winter 11(1-6):141-8; Hage, D. S., and Tweed, S. A. J. Chromatogr B Biomed Sci Appl 1997 October 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of biomarker mRNA can be determined both by in situ and by in vitro formats in a biological sample using methods known in the art. The term "biological sample" is intended to include tissues, cells, biological fluids and isolates thereof, isolated from a patient, as well as tissues, cells and fluids present within a patient. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

An alternative method for determining the level of mRNA biomarker in a sample involves deep sequencing of cDNA generated from RNA. In some embodiments, mRNA is isolated from tumor cells, fragmented, and converted into cDNA libraries, and quantified using next generation sequencing.

As an alternative to making determinations based on the absolute expression level of the biomarker, determinations may be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or prognosis-positive cell-specific genes. This normalization allows the comparison of the expression level in one sample, e.g., a patient sample, to another sample, e.g., a non-tumor sample, or between samples from different sources.

Alternatively, the expression level can be provided as a relative expression level. To determine a relative expression level of a biomarker (e.g. a prognosis-negative biomarker), the level of expression of the biomarker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. One agent for detecting biomarker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab')2 can be used. The term "labeled", with regard to the probe or antibody, is intended to encompass direct labeling of the probe or antibody by coupling (e.g., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin B12, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are 125I and 3H. Standard radioactive isotopic labeling procedures include the chloramine T, lactoperoxidase and Bolton-Hunter methods for 125I and reductive methylation for 3H. The term "detectably-labeled" refers to a molecule labeled in such a way that it can be readily detected by the intrinsic enzymatic activity of the label or by the binding to the label of another component, which can itself be readily detected.

Enzymes suitable for use in this invention include, but are not limited to, horseradish peroxidase, alkaline phosphatase, β-galactosidase, glucose oxidase, luciferases, including firefly and renilla, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

Kits

The invention also encompasses kits for detecting the presence of a biomarker protein or nucleic acid in a biological sample. Such kits can be used to determine if a patient is suffering from or is at increased risk of developing a tumor that is less susceptible to inhibition by PI3K inhibitors. For example, the kit can comprise a labeled compound or agent capable of detecting a biomarker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a biomarker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

Dosing

In one embodiment, ABT-199, or a pharmaceutically acceptable form thereof, is administered at a dosage of at an amount of less than about 1000 mg, less than about 800 mg, less than about 750 mg, less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, or less than about 25 mg daily. In one embodiment, ABT-199, or a pharmaceutically acceptable form thereof, is administered at a dosage of about 325 mg daily. In one embodiment, ABT-199, or a pharmaceutically acceptable form thereof, is administered at a dosage of about 250 mg daily. In one embodiment, ABT-199, or a pharmaceutically acceptable form thereof, is administered at a dosage of about 150 mg daily. In one embodiment, ABT-199, or a pharmaceutically acceptable form thereof, is administered at a dosage of about 100 mg, about 90 mg, about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, about 10 mg, or about 5 mg daily. In one embodiment, ABT-199, or a pharmaceutically acceptable form thereof, is administered at a dosage of about 85 mg daily. In one embodiment, ABT-199, or a pharmaceutically acceptable form thereof, is administered at a dosage of about 75 mg daily. In one embodiment, ABT-199, or a pharmaceutically acceptable form thereof, is administered at a dosage of about 50 mg daily.

In one embodiment, ABT-263, or a pharmaceutically acceptable form thereof, is administered at a dosage of at an amount of less than about 1000 mg, less than about 800 mg, less than about 750 mg, less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, or less than about 25 mg daily. In one embodiment, ABT-263, or a pharmaceutically acceptable form thereof, is administered at a dosage of about 325 mg daily. In one embodiment, ABT-263, or a pharmaceutically acceptable form thereof, is administered at a dosage of about 250 mg daily. In one embodiment, ABT-263, or a pharmaceutically acceptable form thereof, is administered at a dosage of about 150 mg daily. In one embodiment, ABT-263, or a pharmaceutically acceptable form thereof, is administered at a dosage of about 100 mg, about 90 mg, about 85 mg, about 80 mg, about 75 mg, about 70 mg, about 65 mg, about 60 mg, about 55 mg, about 50 mg, about 45 mg, about 40 mg, about 35 mg, about 30 mg, about 25 mg, about 20 mg, about 15 mg, about 10 mg, or about 5 mg daily. In one embodiment, ABT-263, or a pharmaceutically acceptable form thereof, is administered at a dosage of about 85 mg daily. In one embodiment, ABT-263, or a pharmaceutically acceptable form thereof, is administered at a dosage of about 75 mg daily. In one embodiment, ABT-263, or a pharmaceutically acceptable form thereof, is administered at a dosage of about 50 mg daily.

In certain embodiments, provided herein is a method of treating (e.g., inhibiting, managing, or preventing) a cancer in a subject comprising administering to the subject a therapeutically effective amount of a PI3K delta selective inhibitor (e.g., GS1101), or a pharmaceutically acceptable form thereof, and a Bcl-2 inhibitor (e.g., ABT-199 or ABT-263), or a pharmaceutically acceptable form thereof. In certain embodiments, the cancer is diffuse large B-cell lymphoma (activated B-cell-like), diffuse large B-cell lymphoma (germinal center B-cell-like), follicular lymphoma, T-cell lymphoma, mantle cell lymphoma, multiple myeloma.

In some embodiments of the methods described herein, the PI3K delta inhibitor (e.g., GS1101), or a pharmaceutically acceptable form thereof, and the Bcl-2 inhibitor (e.g., ABT-199 or ABT-263), or a pharmaceutically acceptable form thereof, are administered at certain dosages. In one embodiment, provided herein is a method of treating, managing, or preventing a cancer in a subject comprising administering to the subject a therapeutically effective amount of a PI3K delta inhibitor (e.g., GS1101), or a pharmaceutically acceptable form thereof, and a Bcl-2 inhibitor, or a pharmaceutically acceptable form thereof, wherein the PI3K delta inhibitor (e.g., GS1101), or a pharmaceutically acceptable form thereof, is administered at a dosage of in the range of from about 0.01 mg to about 75 mg daily and the Bcl-2 inhibitor (e.g., ABT-199 or ABT-263), or a pharmaceutically acceptable form thereof, is administered at a dosage of in the range of from about 0.01 mg to about 1100 mg daily.

In one embodiment, the PI3K delta inhibitor (e.g., GS1101), or a pharmaceutically acceptable form thereof, is administered at a dosage of in the range of from about 0.1 mg to about 500 mg, from about 1 mg to about 500 mg, from about 10 mg to about 500 mg, from about 50 mg to about 500 mg, from about 100 mg to about 400 mg, from about 200 mg to about 400 mg, from about 250 mg to about 350 mg, or about 300 mg. In one embodiment, the composition comprises the PI3K delta inhibitor (e.g., GS1101), or a pharmaceutically acceptable form thereof, at an amount in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg daily.

In one embodiment, the PI3K delta inhibitor (e.g., GS1101), or a pharmaceutically acceptable form thereof, is administered at a dosage of less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, less than about 30 mg, less than, less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg daily.

In certain embodiments, provided herein is a method of treating, managing, or preventing a cancer in a subject comprising administering to the subject a PI3K delta/gamma dual inhibitor, or a pharmaceutically acceptable form thereof, in combination with a Bcl-2 inhibitor (e.g., ABT-199 or ABT-263), or a pharmaceutically acceptable form thereof, wherein the cancer is diffuse large B-cell lymphoma (activated B-cell-like), diffuse large B-cell lymphoma (germinal center B-cell-like), follicular lymphoma, T-cell lymphoma, mantle cell lymphoma, or multiple myeloma. In certain embodiments, In some embodiments of the methods described herein, the PI3K delta/gamma dual inhibitor, or a pharmaceutically acceptable form thereof, and the Bcl-2 inhibitor (e.g., ABT-199 or ABT-263), or a pharmaceutically acceptable form thereof, are administered at certain dosages. In one embodiment, provided herein is a method of treating (e.g., inhibiting, managing, or preventing) a cancer in a subject comprising administering to the subject a PI3K delta/gamma dual inhibitor, or a pharmaceutically acceptable form thereof, and a Bcl-2 inhibitor, or a pharmaceutically acceptable form thereof, wherein the PI3K delta/gamma dual inhibitor, or a pharmaceutically acceptable form thereof, is administered at a dosage of in the range of from about 0.01 mg to about 75 mg daily and the Bcl-2 inhibitor (e.g., ABT-199 or ABT-263), or a pharmaceutically acceptable form thereof, is administered at a dosage of in the range of from about 0.01 mg to about 1100 mg daily.

In one embodiment, the PI3K delta/gamma dual inhibitor, or a pharmaceutically acceptable form thereof, is administered at a dosage of in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg daily.

In one embodiment, the PI3K delta/gamma dual inhibitor, or a pharmaceutically acceptable form thereof, is administered at a dosage of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg daily.

In certain embodiments, provided herein is a method of treating (e.g., inhibiting, managing, or preventing) a cancer in a subject comprising administering to the subject a therapeutically effective amount of Compound 1, or a pharmaceutically acceptable form thereof, and a Bcl-2 inhibitor, or a pharmaceutically acceptable form thereof, wherein the cancer is Diffuse large B-cell lymphoma (activated B-cell-like), Diffuse large B-cell lymphoma (germinal center B-cell-like), Follicular lymphoma, T-cell lymphoma, Mantle cell lymphoma, Multiple myeloma. In one embodiment, the Bcl-2 inhibitor is ABT-199. In another embodiment, the Bcl-2 inhibitor is ABT-263.

In some embodiments of the methods described herein, Compound 1, or a pharmaceutically acceptable form thereof, and the Bcl-2 inhibitor (e.g., ABT-199 or ABT-263), or a pharmaceutically acceptable form thereof, are administered at certain dosages. In one embodiment, provided herein is a method of treating, managing, or preventing a cancer in a subject comprising administering to the subject a therapeutically effective amount of Compound 1:

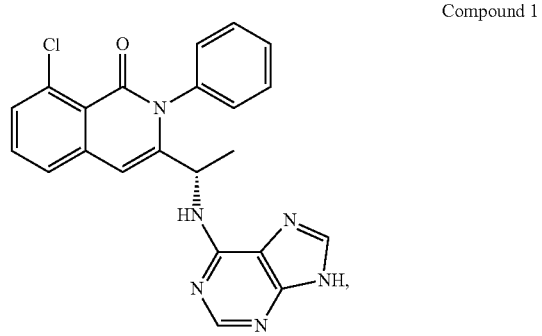 [SMILES: C[C@H](Nc1ncnc2[nH]cnc12)c1cc2cccc(Cl)c2c(=O)n1-c1ccccc1]

Compound 1 or a pharmaceutically acceptable form thereof, and a Bcl-2 inhibitor, or a pharmaceutically acceptable form thereof, wherein Compound 1, or a pharmaceutically acceptable form thereof, is administered at a dosage of in the range of from about 0.01 mg to about 75 mg daily and the Bcl-2 inhibitor (e.g., ABT-199 or ABT-263), or a pharmaceutically acceptable form thereof, is administered at a dosage of in the range of from about 0.01 mg to about 1100 mg daily.

In one embodiment, Compound 1, or a pharmaceutically acceptable form thereof, is administered at a dosage of in the range of from about 0.1 mg to about 75 mg, from about 1 mg to about 75 mg, from about 5 mg to about 75 mg, from about 5 mg to about 60 mg, from about 5 mg to about 50 mg, from about 5 mg to about 30 mg, from about 5 mg to about 25 mg, from about 10 mg to about 25 mg, or from about 10 mg to about 20 mg daily.

In one embodiment, Compound 1, or a pharmaceutically acceptable form thereof, is administered at a dosage of less than about 25 mg, less than about 20 mg, less than about 19 mg, less than about 18 mg, less than about 17 mg, less than about 16 mg, less than about 16 mg, less than about 15 mg, less than about 14 mg, less than about 13 mg, less than about 12 mg, less than about 11 mg, or less than about 10 mg daily.

In one embodiment, the Bcl-2 inhibitor (e.g., ABT-199 or ABT-263), or a pharmaceutically acceptable form thereof, is administered at a dosage of in the range of from about 0.1 mg to about 800 mg, from about 0.1 mg to about 750 mg, from about 0.1 mg to about 600 mg, from about 1 mg to about 500 mg, from about 1 mg to about 400 mg, from about 10 mg to about 300 mg, or from about 50 mg to about 250 mg daily.

In one embodiment, the Bcl-2 inhibitor (e.g., ABT-199 or ABT-263), or a pharmaceutically acceptable form thereof, is administered at a dosage of less than about 1000 mg, less than about 800 mg, less than about 750 mg, less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, or less than about 25 mg daily.

In one embodiment of the methods provided herein, ABT-199, or a pharmaceutically acceptable form thereof, is administered at a dosage of less than about 1000 mg, less than about 800 mg, less than about 750 mg, less than about 500 mg, less than about 400 mg, less than about 350 mg, less than about 300 mg, less than about 250 mg, less than about 200 mg, less than about 150 mg, less than about 100 mg, less than about 75 mg, less than about 50 mg, or less than about 25 mg daily. In one embodiment, ABT-199, or a pharmaceutically acceptable form thereof, is administered at a dosage of about 325 mg daily. In one embodiment, ABT-199, or a pharmaceutically acceptable form thereof, is administered at a dosage of about 400 mg daily. In one embodiment, ABT-199, or a pharmaceutically acceptable form thereof, is administered at a dosage of about 250 mg daily. In one embodiment, ABT-199, or a pharmaceutically acceptable form thereof, is administered at a dosage of about 150 mg daily. In one embodiment, ABT-199, or a pharmaceutically acceptable form thereof, is administered at a dosage of about 100 mg daily, about 90 mg daily, about 85 mg daily, about 80 mg daily, about 75 mg daily, about 70 mg daily, about 65 mg, about 60 mg daily, about 55 mg daily, about 50 mg daily, about 45 mg daily, about 40 mg daily, about 35 mg daily, about 30 mg daily, about 25 mg daily, about 20 mg daily, about 15 mg daily, about 10 mg daily, or about 5 mg daily. In one embodiment, ABT-199, or a pharmaceutically acceptable form thereof, is administered at a dosage of about 75 mg daily. In one embodiment, the composition comprises ABT-199, or a pharmaceutically acceptable form thereof, at an amount of about 55 mg. In one embodiment, ABT-199, or a pharmaceutically acceptable form thereof, is administered at a dosage of about 50 mg daily.

In one embodiment of the methods provided herein, ABT-263, or a pharmaceutically acceptable form thereof, is administered at a dosage of less than about 1000 mg, less than about 800 mg, less than about 750 mg, less than about 500 mg, less than about 400 mg, less than about 350 mg, less than about 325 mg, less than about 300 mg, less than about 250 mg, less than about 200 mg, less than about 150 mg, less than about 100 mg, less than about 75 mg, less than about 50 mg, or less than about 25 mg daily. In one embodiment, ABT-263, or a pharmaceutically acceptable form thereof, is administered at a dosage of about 325 mg daily. In one embodiment, ABT-263, or a pharmaceutically acceptable form thereof, is administered at a dosage of about 250 mg daily. In one embodiment, ABT-263, or a pharmaceutically acceptable form thereof, is administered at a dosage of about 150 mg daily. In one embodiment, ABT-263, or a pharmaceutically acceptable form thereof, is administered at a dosage of about 100 mg daily, about 90 mg daily, about 85 mg daily, about 80 mg daily, about 75 mg daily, about 70 mg daily, about 65 mg, about 60 mg daily, about 55 mg daily, about 50 mg daily, about 45 mg daily, about 40 mg daily, about 35 mg daily, about 30 mg daily, about 25 mg daily, about 20 mg daily, about 15 mg daily, about 10 mg daily, or about 5 mg daily. In one embodiment, ABT-263, or a pharmaceutically acceptable form thereof, is administered at a dosage of about 75 mg daily. In one embodiment, the composition comprises ABT-263, or a pharmaceutically acceptable form thereof, at an amount of about 55 mg. In one embodiment, ABT-263, or a pharmaceutically acceptable form thereof, is administered at a dosage of about 50 mg daily.

As used herein, a daily dosage can be achieved by a single administration of the targeted dosage amount or multiple administrations of smaller dosage amount(s). For example, a 150 mg daily dosage can be achieved by a single administration of 150 mg of the therapeutic agent per day, two administrations of 75 mg of the therapeutic agent per day, or three administrations of 50 mg of the therapeutic agent per day.

In one embodiment, the Bcl-2 inhibitor (e.g., ABT-199 or ABT-263), or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks before the PI3K inhibitor (e.g., Compound 1), or a pharmaceutically acceptable form thereof, is administered. In another embodiment, the Bcl-2 inhibitor (e.g., ABT-199 or ABT-263), or a pharmaceutically acceptable form thereof, is administered concurrently with the PI3K inhibitor (e.g., Compound 1), or a pharmaceutically acceptable form thereof, in a single dosage form or separate dosage forms. In yet another embodiment, the Bcl-2 inhibitor (e.g., ABT-199 or ABT-263), or a pharmaceutically acceptable form thereof, is administered to the subject at least 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, 12 weeks, or 16 weeks after the PI3K inhibitor (e.g., Compound 1), or a pharmaceutically acceptable form thereof, is administered. In one embodiment, the Bcl-2 inhibitor is ABT-199. In another embodiment, the Bcl-2 inhibitor is ABT-263.

In certain embodiments, the PI3K inhibitor (e.g., Compound 1), or a pharmaceutically acceptable form thereof, and the Bcl-2 inhibitor (e.g., ABT-199 or ABT-263), are administered via a same route, e.g., both are administered orally. In other embodiments, the PI3K inhibitor (e.g., Compound 1), or a pharmaceutically acceptable form thereof, and the Bcl-2 inhibitor (e.g., ABT-199 or ABT-263), are administered via different routes, e.g., one is administered orally and the other is administered intravenously. In one embodiment, the PI3K inhibitor (e.g., Compound 1) is administered orally once per day and ABT-199 is administered orally once per day. In one embodiment, the PI3K inhibitor (e.g., Compound 1) is administered orally once per day and ABT-263 is administered orally once per day.

Methods for monitoring minimal residual disease negativity (MRD) are known in the art. See, e.g., Zhou, J. et al., Blood, 2007, 110: 1607-1611 (Prepublished online May 7, 2007. doi: 10.1182/blood-2006-09-045369). Such methods include DNA based tests or RNA based tests. In certain embodiments, MRD is monitored using flow cytometry, sequencing, or PCR.

In some embodiments, the compositions and methods described herein are effective to reduce MRD.

In some embodiments, the methods described herein include selecting a subject for treatment with the combination of a PI3K inhibitor and a Bcl-2 inhibitor. In certain embodiments, the subject (e.g., a patient with a cancer, e.g., a cancer described herein) is selected for treatment with the combination based on the MRD in the subject. In certain embodiments, the selection is based on the presence of an MRD above a preselected level (e.g., 1 malignant cell in 100 normal cells, 1 malignant cell in 1000 normal cells, or 1 malignant cell in 10,000 normal cells).

In some embodiments, the methods described herein further comprise monitoring the MRD in a subject, e.g., evaluating MRD at at least one, two, three, four, five, six, nine months after initiating, continuing or ceasing treatment (e.g., PI3K inhibitor monotherapy or Bcl-2 inhibitor monotherapy, or a combination therapy disclosed herein).

In some embodiments, the combination of a PI3K inhibitor (e.g. a PI3K inhibitor described herein) and a Bcl-2 inhibitor (e.g., a Bcl-2 inhibitor described herein) is effective to reduce the MRD in the subject, e.g., below a level previously measured in the subject (e.g., the level measured before the combination treatment). In certain embodiments, the combination of a PI3K inhibitor and a Bcl-2 inhibitor is effective to reduce the MRD in the subject below the level observed during or after treatment with a monotherapy, e.g., a monotherapy comprising either the PI3K inhibitor or the Bcl-2 inhibitor. In certain embodiments, the MRD is decreased below the level observed during treatment with a monotherapy comprising the PI3K inhibitor.

In certain embodiments, the combination is effective to reduce the MRD below a preselected cutoff value (e.g., 1 malignant cell in 100 normal cells, 1 malignant cell in 1000 normal cells, or 1 malignant cell in 10,000 normal cells). In certain embodiments, the preselected cutoff value is 1 malignant cell in 1000 normal cells. In those embodiments where the MRD is below a preselected cutoff value (e.g., preselected cutoff value as described herein), the treatment (e.g., PI3K inhibitor monotherapy or Bcl-2 inhibitor monotherapy, or a combination therapy disclosed herein) can be altered or discontinued. If upon monitoring the MRD (at at least one, two, three, four, five, six, nine months after altering or discontinuing the therapy), the MRD levels are increased above a preselected cutoff (e.g., a preselected cutoff as described herein), a second treatment can be initiated (e.g., PI3K inhibitor monotherapy or Bcl-2 inhibitor monotherapy, a combination therapy disclosed herein, or a combination with a third agent).

In some embodiments provided herein is a method of treating cancer in a subject, the method comprising (i) administering to the subject a monotherapy (e.g., a monotherapy comprising a PI3K inhibitor or a second therapeutic agent as described herein) and monitoring the MRD in the subject, and (ii) if the MRD increases above a preselected cutoff value (e.g., 1 malignant cell in 100 normal cells, 1 malignant cell in 1000 normal cells, or 1 malignant cell in 10,000 normal cells), administering to the subject a PI3K inhibitor in combination with a Bcl-2 inhibitor. In certain embodiments, the combination is effective to reduce the MRD, e.g. to reduce the MRD below the cutoff value. In certain embodiments, the preselected cutoff value is 1 malignant cell in 1000 or 10,000 normal cells.

In certain embodiments, provided herein is a method of increasing the depth of response resulting in minimal residual disease (MRD) negativity in a subject diagnosed with a cancer comprising: (a) administering to the subject a therapeutically effective amount of a PI3K inhibitor (e.g., Compound 1), and a Bcl-2 inhibitor, or a pharmaceutically acceptable form thereof; (b) monitoring the amount of MRD negativity in the subject, e.g., by methods such as flow cytometry, sequencing, or PCR, and administering a monotherapy comprising the PI3K inhibitor, or a pharmaceutically acceptable form thereof, to the subject if the amount of MRD negativity in the subject represents greater than 1 malignant cell in 1000 normal cells; and (c) monitoring the amount of MRD negativity, e.g., by methods such as flow cytometry, sequencing, or PCR in the subject receiving the monotherapy, and administering a second combination therapy comprising the PI3K inhibitor, or a pharmaceutically acceptable form thereof, and a Bcl-2 inhibitor, or a pharmaceutically acceptable form thereof. In one embodiment, the Bcl-2 inhibitor is ABT-199, ABT-263, ABT-737, G3139 (genasense or oblimersen), GX15-070 (obatoclax mesylate), HA14-1, TW-37, sabutoclax, Gossypol (AT-101), antimycin A, apogossypol to the subject if the amount of MRD negativity in the subject is at least 0.001%.

In certain embodiments, the combination therapy provided herein leads to the reduction or diminishment of one or more undesirable side effects associated with the monotherapy of either the PI3K inhibitor or the Bcl-2 inhibitor. For example, monotherapy of a Bcl-2 inhibitor (e.g., ABT-199 at a dose such as 1200 mg) can cause tumor lysis syndrome. As such, a dose reduction of ABT-199 can diminish the undesirable side effects associated with monotherapy of a Bcl-2 inhibitor.

A PI3K inhibitor and a Bcl-2 inhibitor can have synergistic effects. The synergistic effect can be measured by timing, e.g., by a delay in the development of resistance, to at least one of the agents, or an increased in the period of remission. The synergistic effect can also be measured in the quality of remission, e.g., the synergistic effect can be a reduction in resistance (e.g., a decrease in a measure of resistance or a decreased likelihood of developing resistance), an increased likelihood of experiencing complete remission, or a reduction in the levels of MRD (e.g., to below detectable levels).

More specifically, provided herein (among other things) are methods of delaying resistance of a subject, or prolonging remission (e.g., complete remission or partial remission) of a subject, to a PI3K inhibitor, e.g., Compound 1 or CAL-101, to a Bcl-2 inhibitor, e.g., ABT-199 or ABT-263, or both of a PI3K inhibitor and a Bcl-2 inhibitor. In some embodiments, the method comprises administering a combination of a PI3K inhibitor (e.g., Compound 1 or CAL-101) and a Bcl-2 inhibitor (e.g., ABT-199 or ABT-263). Both agents may be administered to the subject before the subject develops resistance to one or both of the PI3K inhibitor or the Bcl-2 inhibitor, or after the subject develops resistance to the PI3K inhibitor or the Bcl-2 inhibitor. In some embodiments, once the subject becomes resistant to a first agent (e.g., the PI3K inhibitor or Bcl-2 inhibitor), the first agent is withdrawn. In other embodiments, once the subject becomes resistant to a first agent (e.g., the PI3K inhibitor of Bcl-2 inhibitor), the first agent is continued.

In some embodiments, the patient has elevated Bcl-2 levels, e.g., in the cancer cell. In some embodiments, the patient has elevated levels of a Bcl-2 family members such as NOXA, BMF, BIM, PUMA, and HRK, e.g., in the cancer cell. Increased levels of Bcl-2 or its family member may be measured, e.g., by measuring DNA copy number, RNA levels or protein levels. In some embodiments, the level of Bcl-2 or its family member are increased by at least 25%, 50%, 75%, 2-fold, 3-fold, 5-fold, or 10-fold over levels before treatment began (e.g., treatment with the PI3K inhibitor).

In certain embodiments, the subject is not resistant to a PI3K inhibitor (e.g., Compound 1 or CAL-101). In some embodiments, the subject is not resistant to a Bcl-2 inhibitor (e.g., ABT-199 or ABT-263). In certain embodiments, the subject has previously been administered a PI3K inhibitor (e.g., Compound 1 or CAL-101) as a monotherapy or in combination with an agent other than a Bcl-2 inhibitor. In some embodiments, the subject has previously been administered a Bcl-2 inhibitor (e.g., ABT-199 or ABT-263) as a monotherapy or in combination with an agent other than a PI3K inhibitor. In some embodiments, the subject has a cancer, e.g., a cancer described herein. In certain embodiments, in accordance with the method, resistance is delayed compared to the time in which resistance generally develops when the subject is treated with any of the agents or inhibitors alone as monotherapy. In some embodiments, the resistance is delayed by at least 2 weeks, e.g., at least 2 weeks, 4 weeks, 1 month, 2 months, 3 months, 4 months, 5 months, 6 months, 8 months, 10 months, 12 months, 1 year, 2 years, 4 years, 6 years, 8 years, or more. In some embodiments, in accordance with the method, remission (e.g., complete remission or partial remission) is prolonged compared to the time in which remission generally lasts when the subject is treated with any of the agents or inhibitors alone as monotherapy. In certain embodiments, remission (e.g., complete remission or partial remission) is prolonged by at least 2 weeks, e.g., at least 2 weeks, 4 weeks, 1 month, 2 months, 3 months, 4 months, 5 months, 6 months, 8 months, 10 months, 12 months, 1 year, 2 years, 4 years, 6 years, 8 years, or more.

Provided herein is also a method of reducing, e.g., overcoming resistance of a subject to a PI3K inhibitor (e.g., Compound 1 or CAL-101), comprising administering the PI3K inhibitor as a monotherapy to the subject until development of resistance in the subject to the PI3K inhibitor, and subsequently administering a Bcl-2 inhibitor (e.g., ABT-199 or ABT-263) to the subject. In some cases, the method comprises continuing administration of the PI3K inhibitor (e.g., at the same dosage, lower dosage, or higher dosage) to the subject in combination with the Bcl-2 inhibitor. In other cases, the method comprises discontinuing administration of the PI3K inhibitor upon commencing administration of the Bcl-2 inhibitor. For example the administration of the PI3K inhibitor is stopped before administration of the Bcl-2 inhibitor commences. In other examples, the dosage of the PI3K inhibitor is decreased, e.g., gradually, upon commencing administration of the Bcl-2 inhibitor.

4. Formulations

The formulations or compositions described herein can include a PI3K inhibitor (e.g., one or more PI3K inhibitors as described herein) and/or one or more additional agents (e.g., a Bcl-2 inhibitor, e.g., one or more Bcl-2 inhibitors) as described herein. In certain embodiments, the PI3K inhibitor (e.g., one or more PI3K inhibitors as described herein) and the additional agent(s) are included in the same dosage form. In certain embodiments, the PI3K inhibitor (e.g., one or more PI3K inhibitors as described herein) and the second agent (e.g., a Bcl-2 inhibitor, e.g., one or more Bcl-2 inhibitors) are included in separate dosage forms.

Pharmaceutical compositions may be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which may be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein may be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, N.Y., 1990; Katzung, ed.,

*Basic and Clinical Pharmacology*, Twelfth Edition, McGraw Hill, 2011; Goodman and Gilman, eds., *The Pharmacological Basis of Therapeutics*, Tenth Edition, McGraw Hill, 2001; *Remingtons Pharmaceutical Sciences,* 20th Ed., Lippincott Williams & Wilkins, 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of the PI3K inhibitor (e.g., one or more PI3K inhibitors, e.g., Compound 1 and/or GS1101) or another agent (e.g., the Bcl 2 inhibitor, e.g., one or more Bcl 2 inhibitors as described herein) provided a pharmaceutical composition disclosed herein or administered in a method disclosed herein is less than about 100%, about 90%, about 80%, about 70%, about 60%, about 50%, about 40%, about 30%, about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, about 2%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v or v/v.

In some embodiments, the concentration of the PI3K inhibitor (e.g., one or more PI3K inhibitors, e.g., Compound 1 and/or GS1101) or another agent (e.g., the Bcl 2 inhibitor, e.g., one or more Bcl 2 inhibitors as described herein) provided a pharmaceutical composition disclosed herein or administered in a method disclosed herein is greater than about 90%, about 80%, about 70%, about 60%, about 50%, about 40%, about 30%, about 20%, about 19.75%, about 19.50%, about 19.25%, about 19%, about 18.75%, about 18.50%, about 18.25%, about 18%, about 17.75%, about 17.50%, about 17.25%, about 17%, about 16.75%, about 16.50%, about 16.25%, about 16%, about 15.75%, about 15.50%, about 15.25%, about 15%, about 14.75%, about 14.50%, about 14.25%, about 14%, about 13.75%, about 13.50%, about 13.25%, about 13%, about 12.75%, about 12.50%, about 12.25%, about 12%, about 11.75%, about 11.50%, about 11.25%, about 11%, about 10.75%, about 10.50%, about 10.25%, about 10%, about 9.75%, about 9.50%, about 9.25%, about 9%, about 8.75%, about 8.50%, about 8.25%, about 8%, about 7.75%, about 7.50%, about 7.25%, about 7%, about 6.75%, about 6.50%, about 6.25%, about 6%, about 5.75%, about 5.50%, about 5.25%, about 5%, about 4.75%, about 4.50%, about 4.25%, about 4%, about 3.75%, about 3.50%, about 3.25%, about 3%, about 2.75%, about 2.50%, about 2.25%, about 2%, about 1.75%, about 1.50%, about 1.25%, about 1%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, about 0.0009%, about 0.0008%, about 0.0007%, about 0.0006%, about 0.0005%, about 0.0004%, about 0.0003%, about 0.0002%, or about 0.0001%, w/w, w/v, or v/v.

In some embodiments, the concentration of the PI3K inhibitor (e.g., one or more PI3K inhibitors, e.g., Compound 1 and/or GS1101) or another agent (e.g., the Bcl 2 inhibitor, e.g., one or more Bcl 2 inhibitors as described herein) provided a pharmaceutical composition disclosed herein or administered in a method disclosed herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, or approximately 1% to approximately 10%, w/w, w/v or v/v.

In some embodiments, the concentration of the PI3K inhibitor (e.g., one or more PI3K inhibitors, e.g., Compound 1 and/or GS1101) or another agent (e.g., the Bcl 2 inhibitor, e.g., one or more Bcl 2 inhibitors as described herein) provided a pharmaceutical composition disclosed herein or administered in a method disclosed herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, or approximately 0.1% to approximately 0.9%, w/w, w/v or v/v.

In some embodiments, the amount of Compound 1 or one or more of the therapeutic agent disclosed herein is equal to or less than about 10 g, about 9.5 g, about 9.0 g, about 8.5 g, about 8.0 g, about 7.5 g, about 7.0 g, about 6.5 g, about 6.0 g, about 5.5 g, about 5.0 g, about 4.5 g, about 4.0 g, about 3.5 g, about 3.0 g, about 2.5 g, about 2.0 g, about 1.5 g, about 1.0 g, about 0.95 g, about 0.9 g, about 0.85 g, about 0.8 g, about 0.75 g, about 0.7 g, about 0.65 g, about 0.6 g, about 0.55 g, about 0.5 g, about 0.45 g, about 0.4 g, about 0.35 g, about 0.3 g, about 0.25 g, about 0.2 g, about 0.15 g, about 0.1 g, about 0.09 g, about 0.08 g, about 0.07 g, about 0.06 g, about 0.05 g, about 0.04 g, about 0.03 g, about 0.02 g, about 0.01 g, about 0.009 g, about 0.008 g, about 0.007 g, about 0.006 g, about 0.005 g, about 0.004 g, about 0.003 g, about 0.002 g, about 0.001 g, about 0.0009 g, about 0.0008 g, about 0.0007 g, about 0.0006 g, about 0.0005 g, about 0.0004 g, about 0.0003 g, about 0.0002 g, or about 0.0001 g.

In some embodiments, the concentration of the PI3K inhibitor (e.g., one or more PI3K inhibitors, e.g., Compound 1 and/or GS1101) or another agent (e.g., the Bcl 2 inhibitor, e.g., one or more Bcl 2 inhibitors as described herein) provided a pharmaceutical composition disclosed herein or administered in a method disclosed herein is more than about 0.0001 g, about 0.0002 g, about 0.0003 g, about 0.0004 g, about 0.0005 g, about 0.0006 g, about 0.0007 g, about 0.0008 g, about 0.0009 g, about 0.001 g, about 0.0015 g, about 0.002 g, about 0.0025 g, about 0.003 g, about 0.0035 g, about 0.004 g, about 0.0045 g, about 0.005 g, about 0.0055 g, about 0.006 g, about 0.0065 g, about 0.007 g, about 0.0075 g, about 0.008 g, about 0.0085 g, about 0.009 g, about 0.0095 g, about 0.01 g, about 0.015 g, about 0.02 g, about 0.025 g, about 0.03 g, about 0.035 g, about 0.04 g, about 0.045 g, about 0.05 g, about 0.055 g, about 0.06 g, about 0.065 g, about 0.07 g, about 0.075 g, about 0.08 g, about 0.085 g, about 0.09 g, about 0.095 g, about 0.1 g, about 0.15 g, about 0.2 g, about 0.25 g, about 0.3 g, about 0.35 g, about 0.4 g, about 0.45 g, about 0.5 g, about 0.55 g, about 0.6 g, about 0.65 g, about 0.7 g, about 0.75 g, about 0.8 g, about 0.85 g, about 0.9 g, about 0.95 g, about 1 g, about 1.5 g, about 2 g, about 2.5 g, about 3 g, about 3.5 g, about 4 g, about 4.5 g, about 5 g, about 5.5 g, about 6 g, about 6.5 g, about 7 g, about 7.5 g, about 8 g, about 8.5 g, about 9 g, about 9.5 g, or about 10 g.

In some embodiments, the amount of Compound 1 or one or more of the therapeutic agent disclosed herein is in the range of about 0.0001 to about 10 g, about 0.0005 to about 9 g, about 0.001 to about 8 g, about 0.005 to about 7 g, about 0.01 to about 6 g, about 0.05 to about 5 g, about 0.1 to about 4 g, about 0.5 to about 4 g, or about 1 to about 3 g.

Formulations for Oral Administration

In some embodiments of the methods described herein, PI3K inhibitor (e.g., one or more PI3K inhibitors) and/or another agent (e.g., the Bcl-2 inhibitor, e.g., one or more Bcl-2 inhibitors as described herein) is administered orally. In certain embodiments of the compositions described herein, PI3K inhibitor (e.g., Compound 1) and/or another agent (e.g., the Bcl-2 inhibitor, e.g., one or more Bcl-2 inhibitors as described herein) is formulated for oral administration. Some embodiments pertaining to such methods and compositions include the following.

In some embodiments, provided herein are pharmaceutical compositions for oral administration containing a compound as disclosed herein, and a pharmaceutical excipient suitable for oral administration. In some embodiments, provided herein are pharmaceutical compositions for oral administration containing: (i) an effective amount of a disclosed compound; optionally (ii) an effective amount of one or more second agents; and (iii) one or more pharmaceutical excipients suitable for oral administration. In some embodiments, the pharmaceutical composition further contains: (iv) an effective amount of a third agent.

In some embodiments, the pharmaceutical composition can be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more ingredients. In general, the pharmaceutical compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. In some embodiments, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein can be combined with various sweetening or flavoring agents, coloring matter or dyes and, for example, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least about 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of glycerides, vegetable oils, hydrogenated vegetable oils, fatty acids and sterols; oil-soluble vitamins/vitamin derivatives; and mixtures thereof. Within this group, non-limiting examples of lipophilic surfactants include glycerol fatty acid esters, propylene glycol fatty acid esters, and mixtures thereof, or are hydrophobic transesterification products of a polyol with at least one member of vegetable oils, hydrogenated vegetable oils, and triglycerides.

In one embodiment, the pharmaceutical composition can include a solubilizer to ensure good solubilization and/or dissolution of a compound as provided herein and to minimize precipitation of the compound. This can be especially important for pharmaceutical compositions for non-oral use, e.g., pharmaceutical compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methyl pyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject using conventional techniques, such as distillation or evaporation. Thus, if present, the solubilizer can be in a weight ratio of about 10%, 25%, 50%, 100%, or up to about 200% by weight, based on the combined weight of the drug, and other excipients. If desired, very small amounts of solubilizer can also be used, such as about 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, oils, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Examples can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

In one embodiment, the therapeutic agent (e.g., Compound 1 or Bcl-2 inhibitor) can be formulated for oral dosing in phosal, propylene glycol, polyethylene glycol, and ethanol. In one embodiment, the Bcl-2 inhibitor (e.g., ABT-199 or ABT-263) can be formulated for oral dosing in phosal, propylene glycol, polyethylene glycol, and ethanol. For example, the formulation can comprise of 60% phosal 50 propylene glycol (PG), 30% polyethylene glycol (PEG) 400 and 10% ethanol.

5. Dosage

The PI3K inhibitor (e.g., Compound 1 or GS1101) or another agent (e.g., a Bcl-2 inhibitor) disclosed herein may be delivered in the form of pharmaceutically acceptable compositions which comprise the PI3K inhibitor (e.g., (e.g., Compound 1 or GS1101) described herein and/or one or more additional therapeutic agents, formulated together with one or more pharmaceutically acceptable excipients. In some instances, the PI3K inhibitor (e.g., Compound 1 or GS1101) or one or more of the other agents are administered in separate pharmaceutical compositions and may (e.g., because of different physical and/or chemical characteristics) be administered by different routes (e.g., one therapeutic is administered orally, while the other is administered intravenously). In other instances, the PI3K inhibitor (e.g., Compound 1 or GS1101) or one or more of the other agents disclosed herein may be administered separately, but via the same route (e.g., both orally or both intravenously). In still other instances, the PI3K inhibitor (e.g., Compound 1 or GS1101) or one or more of the other agents disclosed herein may be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of Compound 1 described herein and/or a therapeutic agent will be that amount of the compound which, in some embodiments, may be the lowest dose effective to produce a therapeutic effect. Such an effective dose will generally depend upon the factors described herein. Generally, doses of Compound 1 or the therapeutic agent described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg per day. An exemplary dosage is about 10 to 30 mg per day. In some embodiments, for a 70 kg human, a suitable dose would be about 0.05 to about 7 g/day, such as about 0.05 to about 2.5 g/day. Actual dosage levels of the active ingredients in the pharmaceutical compositions described herein may be varied so as to obtain an amount of the active ingredient which is effective to achieve the desired therapeutic response for a particular patient, composition, and mode of administration, without being toxic to the patient. In some instances, dosage levels below the lower limit of the aforesaid range may be more than adequate, while in other cases still larger doses may be employed without causing any harmful side effect, e.g., by dividing such larger doses into several small doses for administration throughout the day.

In some embodiments, the compounds may be administered daily, every other day, three times a week, twice a week, weekly, or bi-weekly. The dosing schedule can include a "drug holiday," e.g., the drug may be administered for two weeks on, one week off, or three weeks on, one week off, or four weeks on, one week off, etc., or continuously, without a drug holiday. The compounds may be administered orally, intravenously, intraperitoneally, topically, transdermally, intramuscularly, subcutaneously, intranasally, sublingually, or by any other route.

In some embodiments, Compound 1 or the therapeutic agent described herein may be administered in multiple doses. Dosing may be about once, twice, three times, four times, five times, six times, or more than six times per day. Dosing may be about once a month, about once every two weeks, about once a week, or about once every other day. In another embodiment, Compound 1 as disclosed herein and another therapeutic agent are administered together from about once per day to about 6 times per day. In another embodiment, the administration of Compound 1 as provided herein and a therapeutic agent continues for less than about 7 days. In yet another embodiment, the administration continues for more than about 6 days, about 10 days, about 14 days, about 28 days, about two months, about six months, or about one year. In some cases, continuous dosing is achieved and maintained as long as necessary.

Administration of the pharmaceutical compositions as disclosed herein may continue as long as necessary. In some embodiments, an agent as disclosed herein is administered for more than about 1, about 2, about 3, about 4, about 5, about 6, about 7, about 14, or about 28 days. In some embodiments, an agent as disclosed herein is administered for less than about 28, about 14, about 7, about 6, about 5, about 4, about 3, about 2, or about 1 day. In some embodiments, a therapeutic agent as disclosed herein is administered chronically on an ongoing basis, e.g., for the treatment of chronic effects.

Since Compound 1 described herein may be administered in combination with one or more therapeutic agent, the doses of each agent or therapy may be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When Compound 1 provided herein, is administered in a pharmaceutical composition that comprises one or more therapeutic agents, and the agent has a shorter half-life than Compound 1, unit dose forms of the agent and Compound 1 may be adjusted accordingly.

6. Kits

In some embodiments, provided herein are kits. The kits may include a pharmaceutical composition as described herein, in suitable packaging, and written material that can include instructions for use, discussion of clinical studies, listing of side effects, and the like. Such kits may also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information may be based on the results of various studies, for example, studies using experimental animals involving in vivo models and studies based on human clinical trials.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, . . . etc. . . . Second Week, Monday, Tuesday, . . . " etc. Other variations of memory aids will be readily apparent. A "daily dose" may be a single tablet or capsule or several tablets or capsules to be taken on a given day.

The kit may contain a PI3K inhibitor (e.g., one or more PI3K inhibitors, e.g., Compound 1 or GS1101) in combination with another agent (e.g., a Bcl-1 inhibitor, e.g., one or more Bcl-1 inhibitors as described herein). In some embodiments, the PI3K inhibitor and the other agent are provided as separate pharmaceutical compositions in separate containers within the kit. In some embodiments, the PI3K inhibitor as disclosed herein and the other agent are provided as a single pharmaceutical composition within a container in the kit. Suitable packaging and additional articles for use (e.g., measuring cup for liquid preparations, foil wrapping to minimize exposure to air, and the like) are known in the art and may be included in the kit. In other embodiments, kits may further comprise devices that are used to administer the active agents. Examples of such devices include, but are not limited to, syringes, drip bags, patches, and inhalers. Kits described herein may be provided, marketed and/or promoted to health providers, including physicians, nurses, pharmacists, formulary officials, and the like. Kits can also, in some embodiments, be marketed directly to the consumer.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules may be removed from the blister pack by manually applying pressure on the recesses whereby an opening is formed in the sheet at the place of the recess. The tablet or capsule can then be removed via said opening.

Kits may further comprise pharmaceutically acceptable vehicles that may be used to administer one or more active agents. For example, if an active agent is provided in a solid form that must be reconstituted for parenteral administration, the kit can comprise a sealed container of a suitable vehicle in which the active agent may be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water may be added (e.g., about 5%) in the pharmaceutical arts as a means of simulating long-term storage in order to determine characteristics such as shelf-life or the stability of formulations over time. Anhydrous pharmaceutical compositions and dosage forms may be prepared using anhydrous or low moisture containing ingredients and low moisture or low humidity conditions. For example, pharmaceutical compositions and dosage forms which contain lactose may be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous pharmaceutical compositions may be packaged using materials known to prevent exposure to water such that they may be included in suitable formulary kits. Examples of suitable packaging include, but are not limited to, hermetically sealed foils, plastic or the like, unit dose containers, blister packs, and strip packs.

EXAMPLES

Example 1

Combination Studies

The effect of the combination of Compound 1 and various Bcl-2 inhibitors are studied using methods known in the art. Provided below is an example where Compound 1 in combination with one or more Bcl-2 inhibitor was examined in 20 cell lines.

The method is described as follows. Cells are thawed from a liquid nitrogen preserved state. Once cells have been expanded and divide at their expected doubling times, screening begins. Cells are seeded in growth media in either black 1536-well or 384-well tissue culture treated plates. Cells are then equilibrated in assay plates via centrifugation and placed in incubators attached to the Dosing Modules at 37° C. for 24 hours before treatment. At the time of treatment, a set of assay plates (which do not receive treatment) are collected and ATP levels are measured by adding ATPLite (Perkin Elmer). These Tzero ($T_0$) plates are read using ultra-sensitive luminescence on Envision plate readers (Perkin Elmer). Treated assay plates are incubated with compound for 72 hours. After 72 hours, plates are developed for endpoint analysis using ATPLite. All data points are collected via automated processes, quality controlled and analyzed using Zalicus software. Assay plates are accepted if they pass the following quality control standards: relative luciferase values are consistent throughout the entire experiment, Z-factor scores are greater than 0.6, untreated/vehicle controls behave consistently on the plate.

Inhibition (I) is defined as $$I = (1 - T/V) * 100\%$$

where T is treated cell count and V is untreated (vehicle) cell count (at 72 hours). I ranges from 0% (when T=V) to 100% (when T=0). The $IC_{50}$ value is defined as the drug concentration needed to inhibit 50% of the cell growth compared to growth of the vehicle treated cells (the drug concentration which gives I=50%). The measure of effect in the experiment can be the inhibition of cellular response relative to the untreated level (vehicle alone). For untreated vehicle and treated levels V and T, a fractional inhibition I=1-T/V is calculated. The inhibition ranges from 0% at the untreated level to 100% when T=0. Inhibition levels are negative for agents that actually increase levels. Other effect measures, such as an activity ratio r=TN may be more appropriate for some assays. When activity ratios (e.g., fold increase over stimulated control) are being used, the effect can be measured using an induction I=ln(T/V). With this definition, all effect expressions are the same as for inhibition.

Growth Inhibition (GI) is used as a measure of cell viability. The cell viability of vehicle is measured at the time of dosing (T0) and after 72 hours (T72). A GI reading of 0% represents no growth inhibition—T72 compound-treated and T72 vehicle signals are matched. A GI reading of 100% represents complete growth inhibition—T72 compound-treated and T0 vehicle signals are matched. Cell numbers have not increased during the treatment period in wells with GI 100% and may suggest a cytostatic effect for compounds reaching a plateau at this effect level. A GI reading of 200% represents complete death of all cells in the culture well. Compounds reaching an activity plateau of GI 200% are considered cytotoxic. GI is calculated by applying the following test and equation:

$$\text{If } T < V_0: 100 * \left(1 - \frac{T - V_0}{V_0}\right)$$

$$\text{If } T \geq V_0: 100 * \left(1 - \frac{T - V_0}{V - V_0}\right)$$

where T is the signal measure for a test article, V is the vehicle-treated control measure, and $V_0$ is the vehicle control measure at time zero. This formula is derived from the Growth Inhibition calculation used in the National Cancer Institute's NCI-60 high-throughput screen.

Combination analysis data were collected in a 6×6 dose matrix. Synergy is calculated by comparing a combination's response to those of its single compound, against the drug-with-itself dose-additive reference model. Deviations from dose additivity may be assessed visually on an isobologram or numerically with a Combination Index (CI). See Tables below for CI at 50% inhibition and CI at 50% growth inhibition. Additive effect is CI=1.0. Synergistic effect is CI<1. Antagonistic effect is CI>1.0.

Potency shifting was evaluated using an isobologram, which demonstrates how much less drug is required in combination to achieve a desired effect level, when compared to the single agent doses needed to reach that effect. The isobologram was drawn by identifying the locus of concentrations that correspond to crossing the indicated inhibition level. This is done by finding the crossing point for each single agent concentration in a dose matrix across the concentrations of the other single agent. Practically, each vertical concentration $C_Y$ is held fixed while a bisection algorithm is used to identify the horizontal concentration $C_X$ in combination with that vertical dose that gives the chosen effect level in the response surface $Z(C_X,C_Y)$. These concentrations are then connected by linear interpolation to generate the isobologram display. For synergistic interactions, the isobologram contour fall below the additivity threshold and approaches the origin, and an antagonistic interaction would lie above the additivity threshold. The error bars represent the uncertainty arising from the individual data points used to generate the isobologram. The uncertainty for each crossing point is estimated from the response errors using bisection to find the concentrations where $Z-\sigma_Z(C_X,C_Y)$ and $Z+\sigma_Z(C_X,C_Y)$ cross $I_{cut}$, where $\sigma_Z$ is the standard deviation of the residual error on the effect scale.

To measure combination effects in excess of Loewe additivity, a scalar measure to characterize the strength of synergistic interaction termed the Synergy Score is devised. The Synergy Score is calculated as:

$$\text{Synergy Score} = \log f_X \log f_Y \Sigma \max(O, I_{data})(I_{data} - I_{Loewe})$$

The fractional inhibition for each component agent and combination point in the matrix is calculated relative to the median of all vehicle-treated control wells. The Synergy Score equation integrates the experimentally-observed activity volume at each point in the matrix in excess of a model surface numerically derived from the activity of the component agents using the Loewe model for additivity. Additional terms in the Synergy Score equation (above) are used to normalize for various dilution factors used for individual agents and to allow for comparison of synergy scores across an entire experiment. The inclusion of positive inhibition gating or an $I_{data}$ multiplier removes noise near the zero effect level, and biases results for synergistic interactions that occur at high activity levels. Combinations where the synergy score is greater than the mean self-cross plus two standard deviations or three standard deviations can be considered candidate synergies at 95% and 99% confidence levels, respectively. Additivity should maintain a synergy score of zero, and synergy score of two or three standard deviations indicate that the combination is synergistic at statistically significant levels of 95% and 99%.

The Synergy Score measure was used for the self-cross analysis. Synergy Scores of self-crosses are expected to be additive by definition and, therefore, maintain a synergy score of zero. However, while some self-cross synergy scores are near zero, many are greater suggesting that experimental noise or non-optimal curve fitting of the single agent dose responses are contributing to the slight perturbations in the score. This strategy was cell line-centric, focusing on self-cross behavior in each cell line versus a global review of cell line panel activity.

Loewe Volume (Loewe Vol) is used to assess the overall magnitude of the combination interaction in excess of the Loewe additivity model. Loewe Volume is particularly useful when distinguishing synergistic increases in a phenotypic activity (positive Loewe Volume) versus synergistic antagonisms (negative Loewe Volume). When antagonisms are observed, as in the current dataset, the Loewe Volume should be assessed to examine if there is any correlation between antagonism and a particular drug target-activity or cellular genotype. This model defines additivity as a non-synergistic combination interaction where the combination dose matrix surface should be indistinguishable from either drug crossed with itself. The calculation for Loewe additivity is:

$$I_{Loewe} \text{ that satisfies } (X/X_I)+(Y/Y_I)=1$$

where XI and YI are the single agent effective concentrations for the observed combination effect I. For example, if 50% inhibition is achieved separately by 1 μM of drug A or 1 μM of drug B, a combination of 0.5 μM of A and 0.5 μM of B should also inhibit by 50%.

Results

The $CI_{50}$ values for growth inhibition and inhibition in Tables 1-6 are categorized as follows: S=0.1 to <0.5, T=0.5 to <0.7, U=0.7 to <1, and W=≥1. The synergy score values for growth inhibition and inhibition are categorized as follows: A1=0.0001 to <1, A2=1 to <3, A3=3 to <10, and A4=≥10.

The types of cell lines tested are diffuse large B-cell lymphoma (DLBCL) activated B-cell-like (ABC), DLBCL germinal center B-cell-like (GCB), follicular lymphoma, mantle cell lymphoma, multiple myeloma, and T-cell lymphoma. These cell lines may have different genomic profiles and thus, a combination of Compound 1 and a therapeutic agent can have different synergistic effects on these cell lines. Data show that a combination of a gamma-selective and a delta-selective compound provides a synergistic effect in various types of cell lines.

Diffuse Large B-Cell Lymphoma (Activated B-Cell-Like)

Cell lines related to diffuse large B-cell lymphoma (DLBCL) activated B-cell-like (ABC) were exposed to a combination of Compound 1 and a Bcl-2 inhibitor. These cell lines include HBL-1, OCI-Ly3, TMD8, and U2832. The results are shown in Table 1 below.

TABLE 1

| therapeutic agent | Cell Line | Synergy score growth inhibition | $CI_{50}$ growth inhibition | Synergy score inhibition | $CI_{50}$ inhibition |
|---|---|---|---|---|---|
| ABT-199 | HBL-1 | A3 | T | A2 | U |
| ABT-199 | OCI-Ly3 | A3 | S | A2 | T |
| ABT-199 | U-2932 | A3 | S | A2 | S |
| ABT-199 | TMD8 | A3 | S | A3 | S |
| ABT-263 | OCI-Ly3 | A3 | U | A1 | W |
| ABT-263 | HBL-1 | A3 | S | A2 | U |
| ABT-263 | U-2932 | A3 | T | A2 | T |
| ABT-263 | TMD8 | A3 | S | A2 | T |

Diffuse Large B-Cell Lymphoma (Germinal Center B-Cell-Like)

Figure 4:
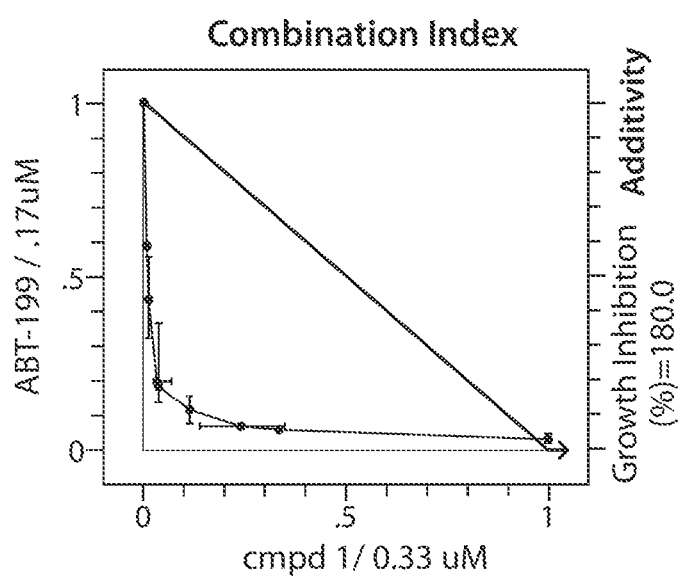
FIG. 4 shows an isobologram depicting the synergistic effect of the combination of Compound 1 and ABT-199 in DoHH-2 cell line.

Cell lines related to DLBCL germinal center B-cell-like (GCB) were exposed to a combination of Compound 1 and a Bcl-2 inhibitor. These cell lines include DOHH-2, Farage, OCI-Ly7, SU-DHL-10-epst, and SU-DHL-4-epst. For example, FIG. 1 (at 85% growth inhibition) and FIG. 4 (at 180% growth inhibition) show isobolograms depicting the synergistic effect of the combination of Compound 1 and ABT-199 in SU-DHL-4 and DoHH-2 cell lines, respectively. The results are shown in Table 2 below.

TABLE 2

| therapeutic agent | Cell Line | Synergy score growth inhibition | CI$_{50}$ growth inhibition | Synergy score inhibition | CI$_{50}$ inhibition |
|---|---|---|---|---|---|
| ABT-199 | OCI-Ly7 | A1 | | A1 | |
| ABT-199 | SU-DHL-10-epst | A1 | W | A1 | W |
| ABT-199 | Farage | A2 | W | A1 | |
| ABT-199 | DOHH-2 | A4 | S | A3 | S |
| ABT-199 | SU-DHL-4-epst | A4 | S | A3 | S |
| ABT-263 | OCI-Ly7 | A1 | W | A1 | |
| ABT-263 | Farage | A3 | T | A2 | T |
| ABT-263 | SU-DHL-10-epst | A3 | U | A2 | U |
| ABT-263 | SU-DHL-4-epst | A4 | T | A3 | S |
| ABT-263 | DOHH-2 | A4 | S | A3 | S |

Follicular Lymphoma

Figure 3:
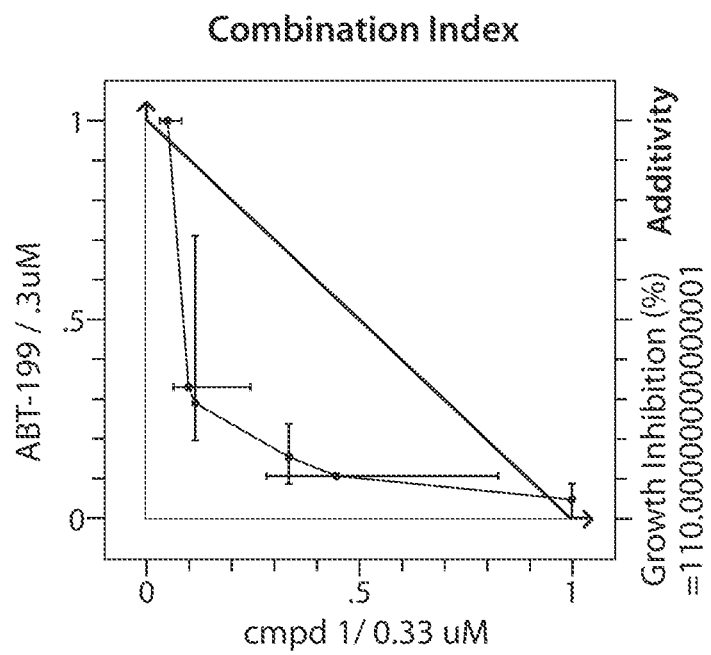
FIG. 3 shows an isobologram depicting the synergistic effect of the combination of Compound 1 and ABT-199 in WSU-NHL cell line.

Cell lines related to follicular lymphoma were exposed to a combination of Compound 1 and a Bcl-2 inhibitor. These cell lines include Karpas-422, RL, and WSU-NHL. For example, FIG. 3 (at 110% growth inhibition) shows an isobologram depicting the synergistic effect of the combination of Compound 1 and ABT-199 in WSU-NHL cell line. The results are shown in Table 3 below.

TABLE 3

| therapeutic agent | Cell Line | Synergy score growth inhibition | CI$_{50}$ growth inhibition | Synergy score inhibition | CI$_{50}$ inhibition |
|---|---|---|---|---|---|
| ABT-199 | RL | A3 | U | A1 | W |
| ABT-199 | KARPAS-422 | A3 | T | A2 | U |
| ABT-199 | WSU-NHL | A3 | T | A2 | S |
| ABT-263 | RL | A3 | U | A1 | U |
| ABT-263 | WSU-NHL | A4 | T | A3 | S |
| ABT-263 | KARPAS-422 | A4 | S | A3 | T |

T-Cell Lymphoma

Cell lines related to T-cell lymphoma were exposed to a combination of Compound 1 and a Bcl-2 inhibitor. The cell line includes HH and Karpas-299. The results are shown in Table 4 below.

TABLE 4

| therapeutic agent | Cell Line | Synergy score growth inhibition | CI$_{50}$ growth inhibition | Synergy score inhibition | CI$_{50}$ inhibition |
|---|---|---|---|---|---|
| ABT-199 | KARPAS-299 | A1 | | A1 | |
| ABT-199 | HH | A2 | S | A1 | T |
| ABT-263 | KARPAS-299 | A1 | | A1 | |
| ABT-263 | HH | A3 | U | A2 | S |

Mantle Cell Lymphoma

Figure 2:
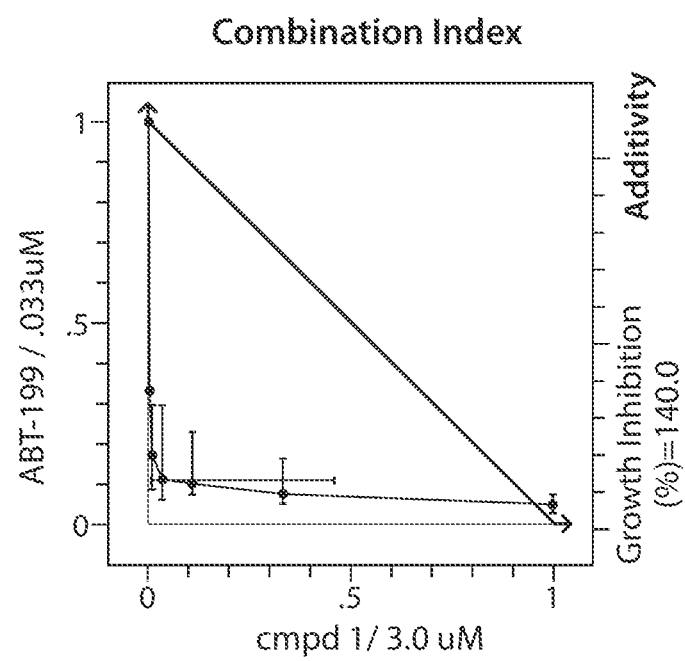
FIG. 2 shows an isobologram depicting the synergistic effect of the combination of Compound 1 and ABT-199 in Mino cell line.

Cell lines related to mantle cell lymphoma were exposed to a combination of Compound 1 and a Bcl-2 inhibitor. These cell lines include GRANTA-519, Jeko-1 and Mino. For example, FIG. 2 (at 140% growth inhibition) shows an isobologram depicting the synergistic effect of the combination of Compound 1 and ABT-199 in Mino cell line. The results are shown in Table 5 below.

TABLE 5

| therapeutic agent | Cell Line | Synergy score growth inhibition | CI$_{50}$ growth inhibition | Synergy score inhibition | CI$_{50}$ inhibition |
|---|---|---|---|---|---|
| ABT-199 | GRANTA-519 | A2 | T | A1 | W |
| ABT-199 | Jeko-1 | A2 | S | A2 | S |
| ABT-199 | Mino | A4 | S | A3 | S |
| ABT-263 | GRANTA-519 | A3 | S | A1 | W |
| ABT-263 | Mino | A3 | S | A2 | T |
| ABT-263 | Jeko-1 | A3 | S | A3 | S |

Multiple Myeloma

Cell lines related to multiple myeloma were exposed to a combination of Compound 1 and a Bcl-2 inhibitor. These cell lines include NCI-H929, OMP-2, and RPMI-8226. The results are shown in Table 6 below.

TABLE 6

| therapeutic agent | Cell Line | Synergy score growth inhibition | CI$_{50}$ growth inhibition | Synergy score inhibition | CI$_{50}$ inhibition |
|---|---|---|---|---|---|
| ABT-199 | NCI-H929 | A2 | U | A1 | U |
| ABT-199 | RPMI-8226 | A2 | W | A1 | |
| ABT-199 | OPM-2 | A2 | U | A1 | |
| ABT-263 | NCI-H929 | A2 | U | A2 | T |
| ABT-263 | OPM-2 | A3 | T | A2 | U |
| ABT-263 | RPMI-8226 | A3 | T | A2 | U |

Example 2

Gene Expression in Compound 1-Treated RR/CLL Subjects

Objectives of this experiment were to characterize the mechanism of action of Compound 1 in CLL patients and support rational combinations of Compound 1 with a second therapeutic agent.

RNAseq technology was used to measure gene expression changes in peripheral blood in patients treated with Compound 1. The patients were treated as part of a clinical trial (identifier NCT01476657) which is a phase 1 study in patients with advanced hematologic malignancies. Briefly, RNA was extracted from 200 ul of blood using TRI reagent, followed by RNA purification using a Zymo-Spin column. Timepoints were taken at baseline and cycle 1 day 8 (C1D8), which is 7 days of Compound 1 treatment. Expression was quantified using both FPKM and VOOM methods. Filters were used to prioritize genes identified during this analysis.

Figure 6A:
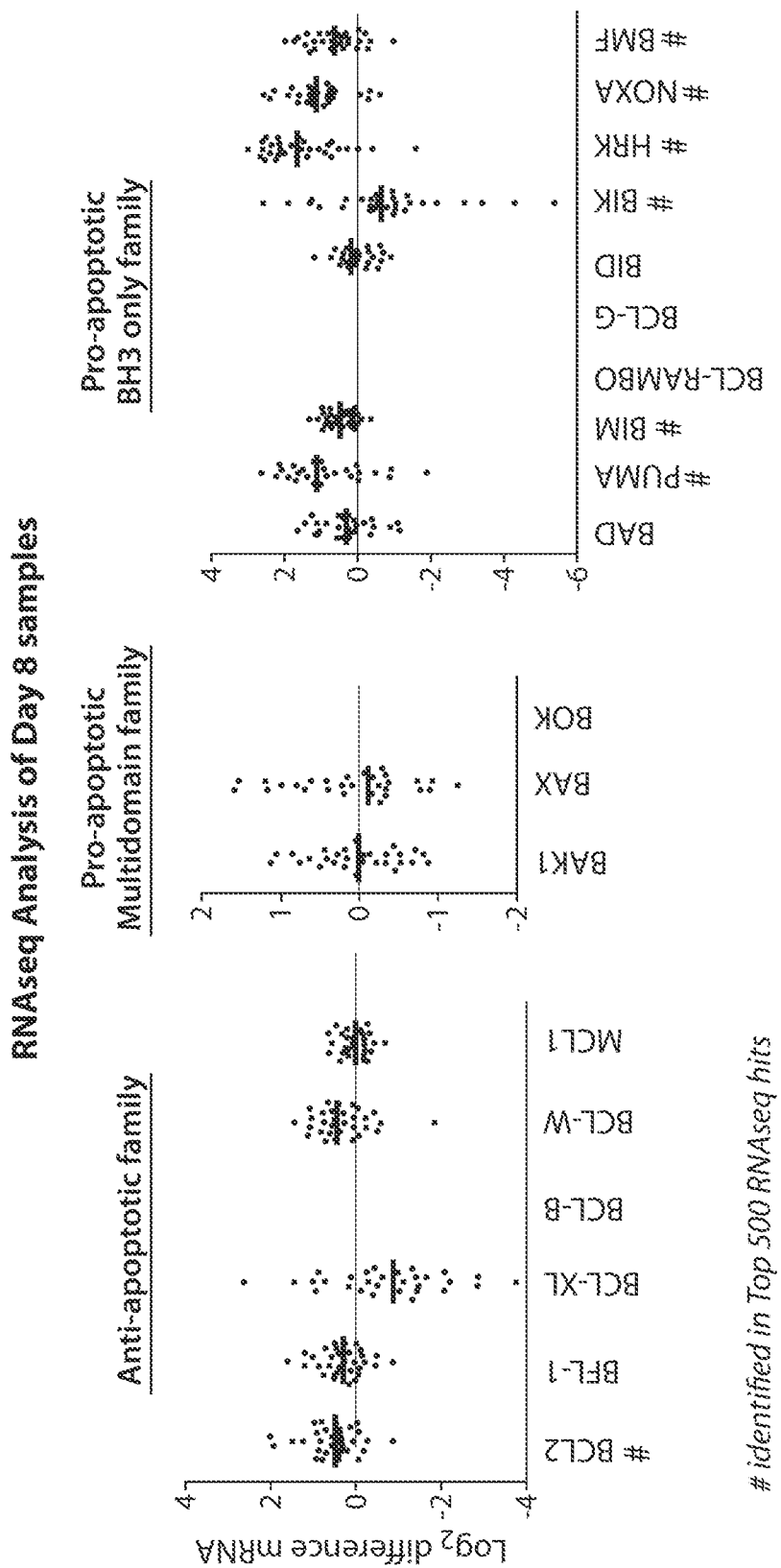
FIG. 6A is a graphical representation of the change in RNA levels of selected genes in patients treated with Compound 1 after 8 days.
Figure 6B:
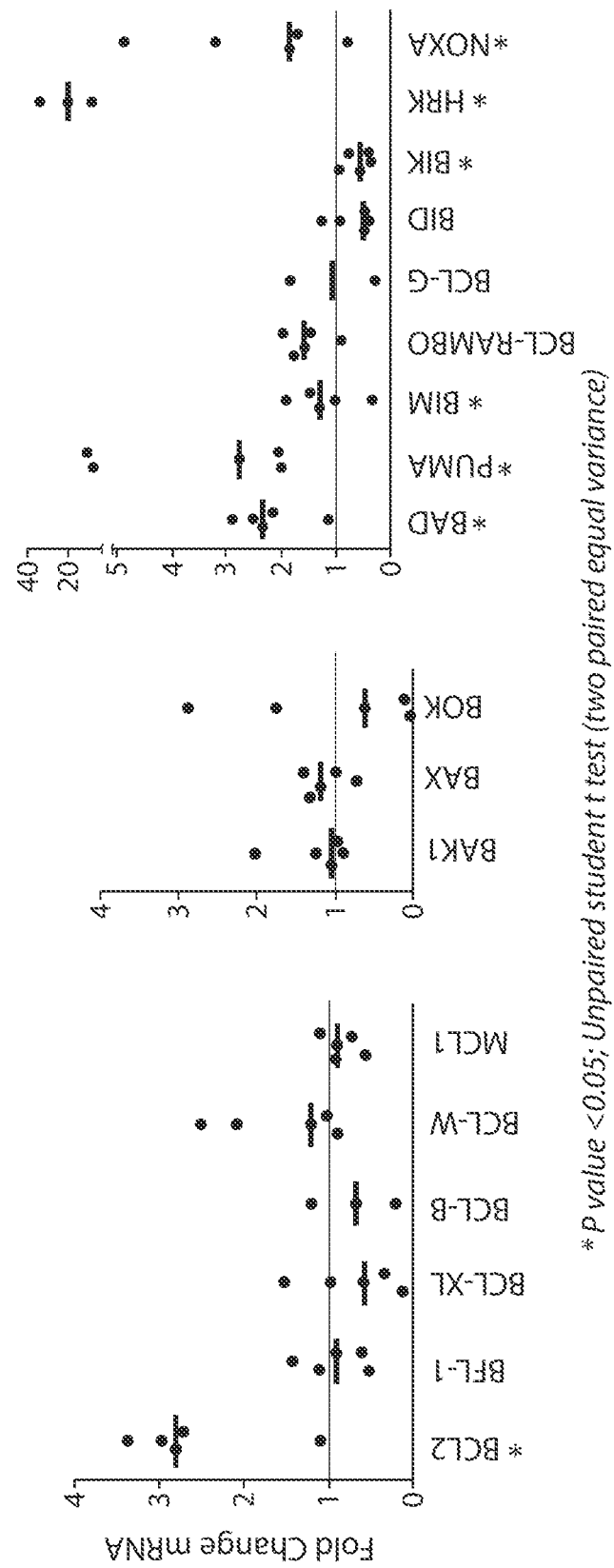
FIG. 6B is a graphical representation of the change in RNA levels of selected genes in patients treated with Compound 1 after 28 days.

The experiment indicated that about 500 genes exhibit consistent changes across the population. The most notable pattern was increased expression of multiple pro-apoptotic BH3 only genes as well as increased expression of the anti-apoptotic gene Bcl-2. Several Bcl-2 family genes were significantly changed. There were also notable changes of gene expression in several B-cell receptor pathway genes. BclThese results show that BIK is downregulated, while Bcl2, BMF, Bcl2L11 (also called BIM), PMAIP1 (also called NOXA), BBC3 (also called PUMA), and HRK are up-regulated in Compound 1-treated patients. Expression levels of selected genes from this study are shown in FIGS. 5A, 5B, and 5C. FIG. 6 uses a graph format to visualize several apoptotic genes examined in the study, and illustrates increased levels of at least NOXA, BMF, BIM, Bcl-22, PUMA, and HRK after 8 and 28 days after treatment with Compound 1.

Figure 7:
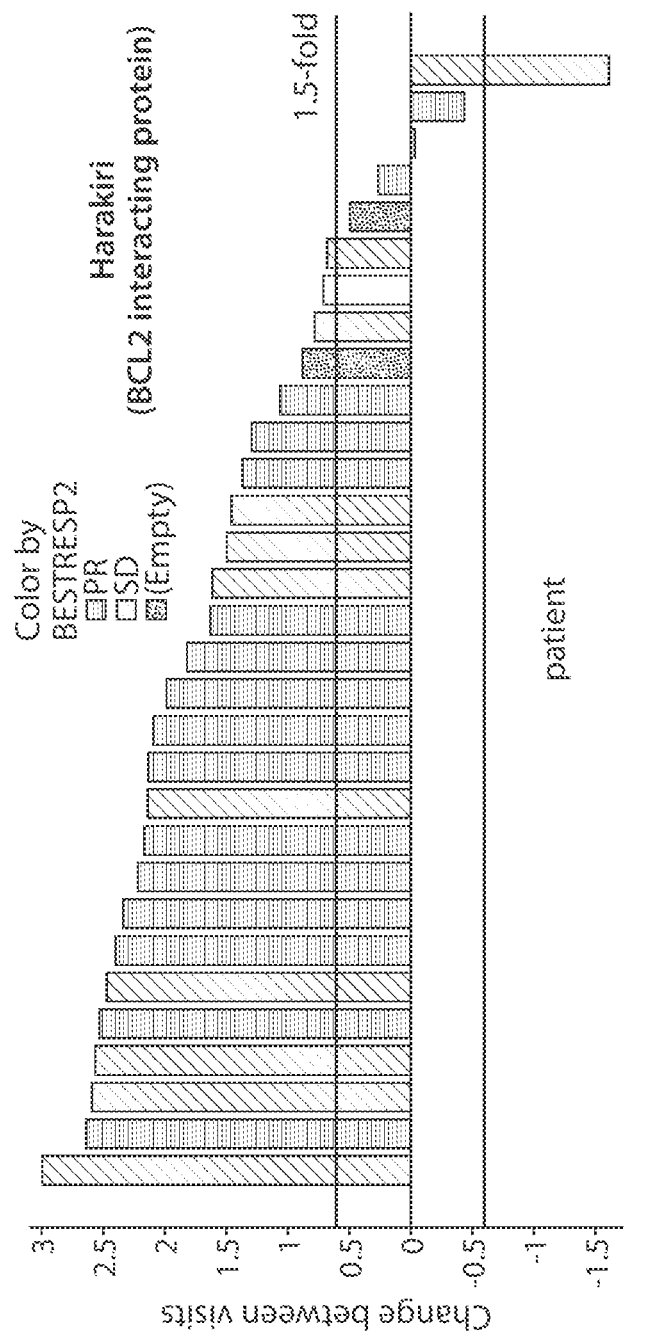
FIG. 7 is a graph showing the fold change in Harakiri expression level in partial remission and stable disease patients after 7 days of Compound 1 treatment.

Levels of one of these Bcl-2 family members, HRK, are explored in more detail in FIG. 7. In many of the patients having stable disease (SD) or partial remission (PR), the HRK expression level increased at least 1.5 fold after 7 days of Compound 1 treatment. These results indicate that increased HRK expression is characteristic of patients that are treated with Compound 1. These effects are seen broadly, in patients that respond to Compound 1 and patients that do not respond. These data suggests that cancer cells respond to Compound 1 treatment by upregulating harakiri, which pushes the balance of cell signaling towards apoptosis.

While not wishing to be bound by theory, this experiment provides a rationale for a combination treatment with a PI3K inhibitor such as Compound 1 with a Bcl-2 inhibitor. First, increased expression of the pro-survival protein Bcl-2 can contribute to resistance to PI3K inhibitor treatment. Accordingly, administering a Bcl-2 inhibitor can overcome this resistance mechanism by allowing the cell to enter the apoptosis pathway.

These data also indicates that cancer cells respond to Compound 1 treatment by upregulating at least five pro-apoptotic genes, e.g., inhibitors of Bcl-2, e.g., BIM, BMF, HRK, NOXA, and PUMA. Without wishing to be bound by theory, this up-regulating of pro-apoptotic genes can tip the balance of cell signaling towards apoptosis. However, elevated levels of Bcl-2 can prevent these pro-apoptotic factors from successfully initiating apoptosis. Thus, by treating this cancer with a Bcl-2 inhibitor, one can unblock the apoptosis pathway, leading to death of the cancer cell. Furthermore, the elevated levels of pro-apoptotic factors suggests that Compound 1-treated cells would be more sensitive than untreated cells to a pro-apoptotic therapeutic such as a Bcl-2 inhibitor. Consequently, a combination therapy with a PI3K-inhibitor such as Compound 1 and a Bcl-2 inhibitor can produce unexpectedly high efficacy by acting in concert with high levels of pro-apoptotic signaling factors, to trigger apoptosis.

In some embodiments, the methods of treatment described herein comprise administering a combination of a PI3K inhibitor and a modulator of, e.g., inhibitor of, the apoptotic signaling pathway. Without being bound by theory, Compound 1 can enhance the expression of key pro-apoptotic factors in CLL cells, but apoptosis can be blocked through a concomitant up-regulation of the anti-apoptotic protein, Bcl-2. Inhibition of Bcl-2 by ABT-199 in this setting can tip the balance toward apoptosis promoting tumor cell death. The translational and ex-vivo experiments provided herein support that a combination of Compound 1 and ABT-199 can provide synergistic effects in subjects.

Example 3

Gene Expression in SU-DHL-4 DLBCL Cell Line

While Example 2 described the effects of Compound 1 on a patient population including responders and non-responders, this Example focuses on cells that are resistant to compound 1.

Experiments were performed to examine the pathway and gene expression alterations in a cell line resistant to PI3K inhibitors. SU-DHL-4 is a DLBCL cell line. SU-DHL-4 cells resistant to Compound 1 were generated by culturing the cells in the presence of Compound 1 or DMSO as a control for 8 weeks. Cells were subcloned under selective pressure from the drug, seeding at densities of 3 cells per well, 1 cell per well, or 0.3 cell per well. Parental, DMSO-treated, and Compound 1-resistant clones were selected for expansion. Five clones from each group were expanded. Cells were harvested for various assays, including CellTiter-Glo® assays, PD, RNA analysis, DNA analysis, and short tandem repeat (STR) fingerprinting. A CTG assay was performed to confirm that cells were resistant to Compound 1 at the time of sample collection, whereas control cells (DMSO treated) were still resistant to Compound 1.

Specific resistance was successfully created, as shown in Table 7 below.

TABLE 7

| Clones | AVG Cpnd 1 IC50 (nM) | AVG IBR IC50 (nM) |
|---|---|---|
| Control | 241 ± 17 | 447 ± 49 |
| Cpnd 1 resistant | 5420 ± 1079 | 697 ± 115 |
| IBR resistant | 805 ± 339 | 3531 ± 568 |

The gene expression pattern of Compound 1 resistant cell clones was determined by RNASeq analysis, e.g., as described in Wong et al. Nature Reviews Genetics 10.1 (2009):57-63, incorporated herein by reference. Briefly, FKPM values (Fragments Per Kilobase Of Exon Per Million Fragments Mapped) were generated and filtered by processing the raw values, normalizing, and filtering the normalized values. This analysis revealed differential gene expression unique and common to Compound 1-resistant and ibrutinib-resistant clones. Specifically, 280 genes were differentially regulated in the Compound 1-resistant cells, 190 genes were differentially regulated in the ibrutinib-resistant cells, and 98 genes were differentially regulated in both the Compound 1-resistant cells and the ibrutinib-resistant cells.

Next, the genes identified in this experiment were grouped into pathways. 51 apoptotic pro-apoptotic genes (GeneGo Pathway ID GO:0006915) were differentially regulated in the Compound 1-resistant cells. This observation support the idea that promoting apoptosis (for instance, using a Bcl-2 inhibitor) can improve cell-killing of Compound 1-resistant cells.

In this experiment, Bcl-2 was not strongly upregulated or downregulated in the Compound 1-resistant cells. This result indicates that Bcl-2 remains a viable drug target even in Compound 1-resistant cells. Without wishing to be bound by theory, this finding supports the methods described herein involving treating a cancer, such as a PI3K-resistant cancer, with a Bcl-2 inhibitor.

It was also observed that harakiri (HRK) mRNA levels decreased in the Compound 1-resistant cells (as well as in ibrutinib-resistant cells). While not wishing to be bound by theory, this finding suggests that low levels of the pro-apoptotic protein HRK contribute to Compound 1 resistance. This finding is in agreement with the data in Example 2 showing that HRK expression rises in Compound 1-treated patients, including patients who respond to the treatment. Thus, high HRK expression is characteristic of cancers that respond to Compound 1 treatment, and low HRK expression is characteristic of at least a subset of cancers that do not respond to Compound 1 treatment. This result supports the rational combination of a PI3K inhibitor and a Bcl-2 inhibitor, for instance in patients that have a response (e.g., a partial or complete response) to the PI3K inhibitor.

Example 4

STK11 Copy Number Loss in Patient with CLL

A patient diagnosed with CLL was treated by a monotherapy of Compound 1 (25 mg bid) in a clinical trial. Serum samples of the patient were collected at various points in the treatment. The copy number of STK11 in the serum samples was determined by CytoScan (Affymetrix). The results are described below:

At C1D1 (cycle 1, day 1), Absolute lymphocyte count (ALC)=257, wild-type STK11 was detected;
At C3D1 (cycle 3, day 1), patient achieved partial response;
At C5D1 (cycle 5, day 1), ALC=134, STK11 copy loss was detected;
After C7 (cycle 7), patient progressed.

The result indicates that STK11 copy number loss can be acquired and can be a contributing factor in acquired resistance to the treatment of Compound 1.

Example 5

Genomic Profiling Protocol

Genomic DNA can be profiled by one or more of CytoScan microarray analysis, targeted NexGen Sequencing and Sanger Sequencing. The protocols for these methods are described herein. CytoScan microarray analysis on genomic DNA can be used to determine copy number alterations (CNAs), such as copy number loss or gain. NexGen Sequencing on genomic DNA can be used to determine gene mutations. Sanger sequencing on genomic DNA can be used to determine IgHV mutation status. Results from genomic DNA profiling were used to assess whether genomic alterations in individuals treated with Compound 1 predict responsiveness or resistance to treatment with Compound 1 and whether genomic alterations occur with acquired resistance.

Preparation of DNA Sample

Peripheral whole blood samples were collected from CLL patients being treated with Compound 1. Genomic DNA was extracted from Cycle 1 Day 1 blood samples of 43 CLL patients, using QIAamp DNA Blood Midi kit (Qiagen, cat #51185) according to the manufacturer's protocol.

CytoScan Array Data Analysis

CytoScan array analysis allows for genome-wide identification of copy number changes. The CytoScan HD array has 750,000 SNP probes and 1.9 million non-polymorphic probes, providing even copy number coverage across the genome. The CytoScan HD array also has intragenic coverage of 36,000 RefSeq genes.

Genomic DNA samples were applied for hybridization to Affymetrix CytoScan HD arrays according to the manufacturer's manual. CEL files were analyzed using Affymetrix software for initial quality control, followed by the use of Nexus 7.5 software (BioDiscovery, Inc.) for copy number and allelic analysis. Following the profiling of copy number variations (CNVs) in each sample, Nexus 7.5 software was used to identify the CNVs that are significantly different between patients who responded to treatment with Compound 1 and patients who did not (differential frequency>25%; p<0.05). Copy number variances were initially assessed with Nexus default setting (500 kb minimum LOH) for the first set of 43 samples. In order to efficiently utilize allele information, the segmentation window was changed to minimum LOH at 2 kb. Furthermore, gains that are not covered by an allelic event were filtered out. The cancer-related genes were annotated based on the Cancer Gene Census database. Association between CNVs and clinical features were assessed by Fisher's exact test.

Targeted NexGen Sequencing and Data Analysis

Protocols for NexGen sequencing and hybrid capture are described in Gnirke et al. (Nat Biotechnol. 27(2): 182-189, 2009). In these experiments, hybrid capture approach was used with the OncoGxOne leukemia/lymphoma panel (GeneWiz) containing 374 genes, including all 4 PI3K isoforms, BTK, and PLCγ. Illumina HiSeq sequencing was used.

Agilent SureSelect solutions were used for the targeted DNA capture of a panel of genes. According to the manufacturer's protocol, DNA-Seq libraries were constructed and sequenced on Illumina HiSeq 2500 using 100 bp paired-end reads. FASTQ files were aligned by the OSA algorithm in Omicsoft Array Studio to generate BAM files with default parameter setting. Non-synonymous mutations including single-nucleotide variations (SNVs), insertions/deletions (InDels) and stop codon gain/loss were detected by Array Studio's mutation calling algorithm with the mutational allelic frequency (MAF) threshold set to be above 0.1. Detected SNVs were annotated with RefSeq gene model along with the Single Nucleotide Polymorphism Database (dbSNP), Catalogue Of Somatic Mutations In Cancer (COSMIC), and ClinVar databases to highlight the known germline polymorphisms and the clinically relevant somatic mutations. The putative somatic mutations were determined by eliminating the SNVs that are known human single-nucleotide polymorphisms (SNPs) archived in dbSNP and ClinVar and that were detected in normal control samples. KEGG and MetoCore Pathway Database was used to define the signaling pathways that are significantly enriched with the genes that have somatic mutations as detected in the CLL patients of this study (p<0.05). Association between mutations and clinical features were assessed by Fisher's exact test.

Example 6

Baseline Mutation Frequency in CLL

Using the targeted NexGen sequencing method described previously, the baseline mutation frequency of CLL patients in the Compound 1-treated patient population was determined, prior to treatment of the patients with Compound 1 (Table 8). Many genes that were previously described in the literature as being commonly mutated in CLL were found to be mutated in the Compound 1-treated population, suggesting that the Compound 1-treated population is similar to what has been described for CLL (Landau et al. Cell 152, 714, 2013). The TP53 mutation rate was twice what has been previously reported. This suggests that the Compound 1-treated population has more aggressive disease than previously published cohorts.

TABLE 8

Comparison of Compound 1-treated baseline mutation frequency with literature.

| Gene | Landau et al. (%) N = 160 | Compound 1-treated (%) N = 55 |
| --- | --- | --- |
| SF3B1 | 14 | 9(5/55) |
| TP53 | 13 | 24 (13/55) |
| NOTCH1 | 10 | 20 (11/55) |
| MYD88 | 8 | 5 (3/55) |
| ATM | 8 | 11(6/55) |
| XPO1 | 4 | 9(5/55) |
| POT1 | 3 | 0 |
| NRAS | 3 | 0 |
| BCOR | 3 | 0 |
| KRAS | 2 | 0 |
| MED12 | 2 | 5(3/55) |
| DDX3X | 2 | 0 |
| FBXW7 | 3 | 2 (1/55) |

In addition, it was found that the average number of baseline mutations per patient was relatively similar among patients who show a complete or partial response to Compound 1 treatment, compared to non-responders (e.g., patients with stable disease or progressive disease). The average number of baseline mutations per patient was also relatively similar among R/R and Tx-naïve patients. Thus, the difference between a mutation profile predictive of response and a mutation profile predictive of non-response seems not to be the total number of mutations, but the identity of the mutations.

Example 7

Baseline Copy Number Changes in CLL

Using the CytoScan array analysis, a genome-wide scan for baseline copy number changes in the Compound 1-treated patient population was performed, prior to treatment of the patients with Compound 1. Copy number losses were in association with del(11q), del(13q), and del(17p). In particular, genetic changes observed at baseline included del(13q14), and del(11q22-23), del(17p13). Del(8p) was also observed in the R/R population (6.5%) but not the Tx-naïve population. Also, copy number gain was observed in association with trisomy 12. In summary, a copy gain at chromosome 12, trisomy 12; a copy loss at chromosome 11q22-23, del(11q22-23); a copy loss at chromosome 13q14, del(13q14); and a copy loss at chromosome 17p, del(17p) were observed.

Example 8

Copy Number Alterations in CLL

Using the CytoScan microarray analysis for genome wide as described above, copy number alterations and losses of heterozygosity were compared between responders and non-responders to treatment with Compound 1. This analysis was performed in the same CLL patient population as was assessed at baseline in Examples 6 and 7. Tumor response to drug is defined by SD/PD (Stable Disease/Progressive Disease, i.e., non-responders) and CR/PR (Complete Remission/Partial Remission, i.e., responders). Also included in the responder group were PR patients with lymphocytosis. See Brown, J. R. (2014) Blood, 123(22):3390-3397 and Chesson, B. D. et al. Journal of Clinical Oncology, 30(23): 2820-2822 for additional information regarding classifications of patient responsiveness.

The genes for which differences between groups were significant included BRAF, CTNNB1, FHIT, IRF4, MITF, MN1, NF2, RET, STK11, TSC2, RB1, RANBP17, FGFR3, GMPS, and WHSC1. Summaries of genetic alterations (500 kb minimum LOH) that were high in the SD/PD group or low in the SD/PD group are provided in Tables 9 and 10 respectively.

TABLE 9

Summary of Changes High in SD/PD group

| High in SD/PD | Count of Region |
| --- | --- |
| Allelic Imbalance | 2 |
| CN Gain | 30 |
| CN Loss | 37 |
| LOH | 66 |
| Total | 135 |

TABLE 10

Summary of Changes Low in SD/PD groups

| Low in SD/PD | Count of Region |
| --- | --- |
| CN Gain | 6 |
| CN Loss | 6 |
| LOH | 56 |
| Total | 68 |

Table 11 shows copy number alterations for cancer genes with a higher frequency in SD/PD (i.e., non-responder) patients compared with CR/PR (i.e., responder) patients. BRAF, CTNNB1, FHIT, IRF4, MITF, MN1, and NF2 had increased frequency of copy number gain in SD/PD patients relative to CR/PR patients. NF2, RET, STK11, and TSC2 had increased frequency of copy number loss in SD/PD patients relative to CR/PR patients. RB1 showed a higher frequency of loss of heterozygosity in SD/PD patients relative to CR/PR patients.

The results presented in Table 10 indicate that copy number gain in each of BRAF, CTNNB1, FHIT, IRF4, MITF, MN1, and NF2 is associated with or predictive of nonresponsiveness or resistance (e.g., acquired resistance) of a cancer (e.g., a CLL) to a PI3K inhibitor (e.g., Compound 1). The results presented in Table 10 also indicate that copy number loss in each of NF2, RET, STK11, and TSC2 is associated with or predictive of nonresponsiveness or resistance (e.g., acquired resistance) of a cancer (e.g., a CLL) to a PI3K inhibitor (e.g., Compound 1). The results presented in Table 10 further suggest loss of heterozygosity in RB1 is associated with or predictive of nonresponsiveness or resistance (e.g., acquired resistance) of a cancer (e.g., a CLL) to a PI3K inhibitor (e.g., Compound 1).

TABLE 11

Cancer genes with higher frequency in SD/PD

| CN gain | CN loss | LOH |
| --- | --- | --- |
| BRAF | NF2 | RB1 |
| CTNNB1 | RET | |
| FHIT | STK11 | |
| IRF4 | TSC2 | |
| MITF | | |
| MN1 | | |
| NF2 | | |

Table 12 shows copy number alterations for cancer genes with a lower frequency in SD/PD patients compared with CR/PR patients. Copy number gain in RANBP17 had a lower frequency in SD/PD (i.e., non-responder) patients compared with CR/PR (i.e., responder) patients. Also, loss of heterozygosity in FGFR3, GMPS, and WHSC1 had a lower frequency in SD/PD (i.e., non-responder) patients compared with CR/PR (i.e., responder) patients.

These results presented in Table 12 indicate that copy number gain in RANBP17 is associated with responsiveness or lack of resistance (e.g., acquired resistance) of a cancer (e.g., a CLL) to a PI3K inhibitor (e.g., Compound 1). These results presented in Table 12 also indicate that loss of heterozygosity in each of FGFR3, GMPS, and WHSC1 is associated with or predictive of responsiveness or lack of resistance (e.g., acquired resistance) of a cancer (e.g., a CLL) to a PI3K inhibitor (e.g., Compound 1).

TABLE 12

Cancer genes w/Lower frequency in SD/PD

| CN gain | CN loss | LOH |
|---|---|---|
| RANBP17 | | FGFR3 |
| | | GMPS |
| | | WHSC1 |

In order to get more specific LOH calls and increase confidence of copy number calling, the CNV data was analyzed with a different segmentation window (minimum LOH is 2kb).

Table 13 shows copy number alterations for cancer genes with a higher frequency of loss in SD/PD patients compared with CR/PR patients (>25% frequency difference, p<0.05). Loss of CBFA2T3, YWHAE, TP53, PER1 and GAS7 are accompanied with an allelic event (allele imbalance or loss of heterozygosity); while only copy number loss was found in STK11, FSTL3 and USP6. Among all patients, loss of YWHAE, STK11, TP53, FSTL3 and USP6 are significantly more frequent in SD/PD patients compared with CR/PR patients. Within the refractory/relapsed cohort (R/R), loss of STK11, TP53,PER1,GAS7 and FSTL3 occur more significantly in SD/PD patients compared to CR/PR patients.

The results presented in Table 13 indicate loss of YWHAE, STK11,TP53,FSTL3 and USP6 are associated with or predictive of nonresponsiveness or resistance (e.g., acquired resistance) of a cancer (e.g., a CLL) for all patients to a PI3K inhibitor (e.g., Compound 1). The results presented in Table 13 further suggest loss of STK11,TP53, PER1,GAS7 and FSTL3 is associated with or predictive of nonresponsiveness or resistance (e.g., acquired resistance) of a cancer (e.g., a CLL) among refractory or relapsed patients to a PI3K inhibitor (e.g., Compound 1).

Table 14 shows copy number alterations for cancer genes with a differential frequency of loss in nodal responders compared to nodal nonresponders (>25% frequency difference, p<0.05). For these three cancer genes, copy number loss was identified without coverage of an allelic event. TSC1 and NF2 are more frequently loss in nodal nonresponders compared to nodal responders, whereas EGFR loss is found significantly frequently lost in nodal responders.

The results presented in Table 14 indicate that loss of EGFR is associated with or predictive of responsiveness or lack of resistance (e.g., acquired resistance) of a cancer (e.g., a CLL) for all patients to a PI3K inhibitor (e.g., Compound 1).

TABLE 13

Cancer genes w/higher frequency in SD/PD

| Loss | Chr | Allelic Event | Fisher's exact (all patients n = 56) | Fisher's exact (R/R only n = 46) |
|---|---|---|---|---|
| CBFA2T3 | 16q24 | Yes | 0.174 | 0.1378 |
| YWHAE | 17p13 | Yes | 0.0459* | 0.0626 |
| STK11 | 19p13 | | 0.0459* | 0.0042** |
| TP53 | 17p13 | Yes | 0.0371* | 0.0274* |
| PER1 | 17p13 | Yes | 0.0696 | 0.0274* |
| GAS7 | 17p13 | Yes | 0.0696 | 0.0274* |
| FSTL3 | 19p13 | | 0.006** | 0.0022** |
| USP6 | 17p13 | | 0.0459* | 0.0626 |
| MAP2K4 | 17p12 | | 0.0696 | 0.0274* |

TABLE 14

Cancer genes w/differential frequency between nodal responders and nodal nonresponders

| Loss | Higher Frequency | Fisher's exact |
|---|---|---|
| TSC1 | Non-responder | 0.09 |
| NF2 | Non-responder | 0.057 |
| EGFR | Responder | 0.035* |

Figure 13A:
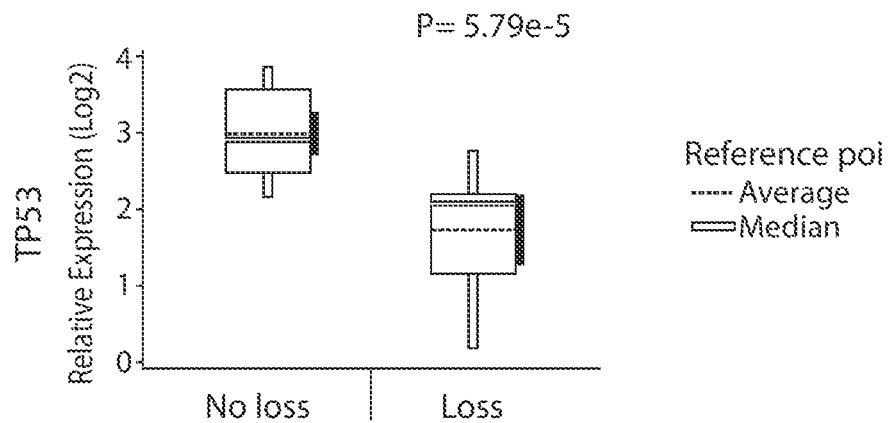
FIG. 13A is a graph depicting relative expression of TP53 (RNA levels) in patients with no loss or with a loss in TP53 copy number.
Figure 13B:
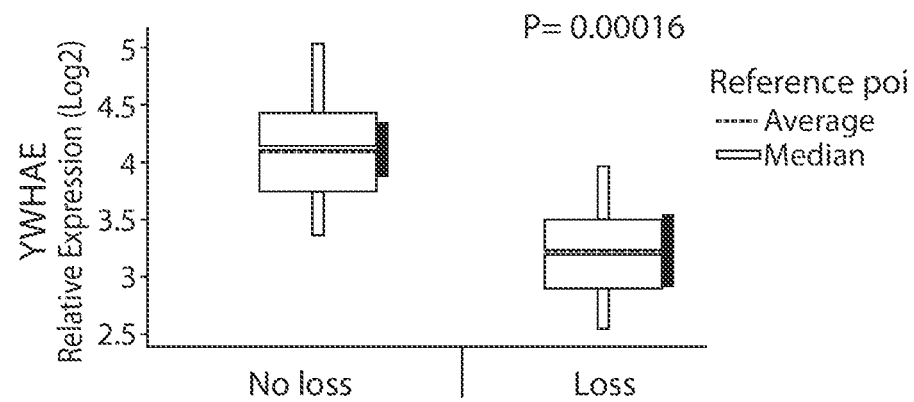
FIG. 13B is a graph depicting relative expression of YWHAE (RNA levels) in patients with no loss or with a loss in YWHAE copy number.
Figure 13C:
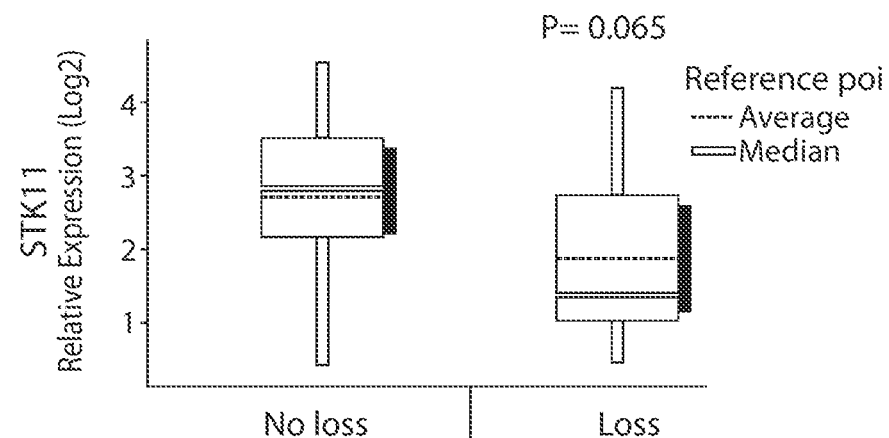
FIG. 13C is a graph depicting relative expression of STK11 (RNA levels) in patients with no loss or with a loss in STK11 copy number.

Validation of copy number losses of several genes was performed by RNAseq, e.g., as described in Wong et al. Nature Reviews Genetics 10.1(2009):57-63, incorporated herein by reference. The relative expression levels of TP53, YWHAE, and STK11 are reduced in patients having a loss in copy number, compared to patients with no loss in copy number, as shown in FIGS. 13A, 13B, and 13C.

Example 10

Relationship Between Mutational and Copy Number Variation Frequencies and Responses The relationship between certain genetic alterations (e.g., exonic deletions) and patient responsiveness to Compound 1 was analyzed.

Figure 8:
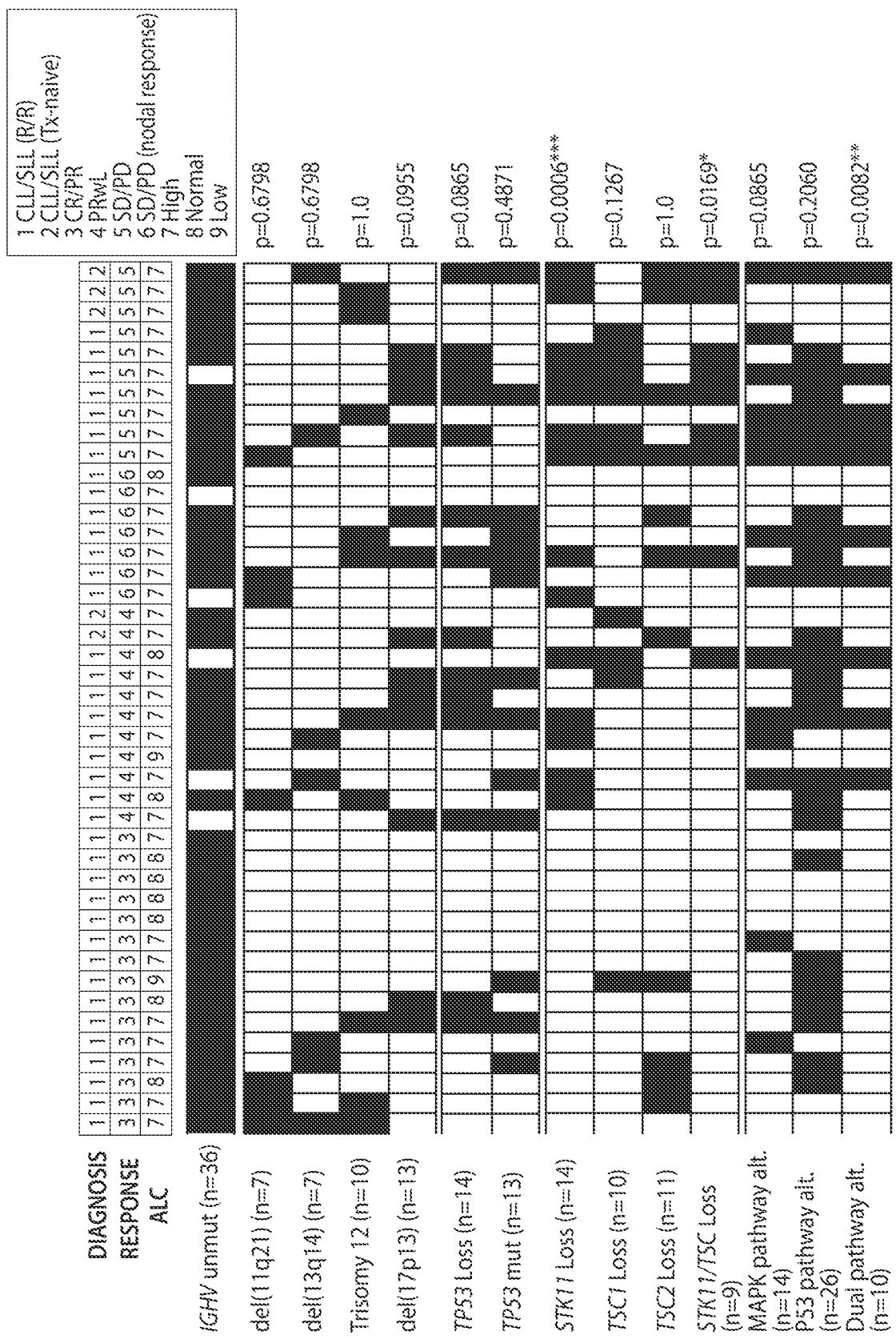
FIG. 8 is a graphical representation of the relationship between mutations and responses to Compound 1. Each column represents a patient. Each row represents a mutation. The diagnosis is coded as 1: CLL/SLL (R/R), or 2: CLL/SLL (treatment-naïve). R/R refers to a patient that has relapsed or is refractory to treatment. Tx näve refers to a patient that is treatment näve, e.g., has not been previously administered Compound 1. The response is coded as 3: CR/PR, 4: PRwL, 5: SD/PD, or 6: SD/PD (nodal response). The ALC is coded as 7: high, 8: normal, or 9: low. PR refers to partial remission, SD refers to stable disease, PD refers to progressive disease, and CR refers to complete remission

The results are shown in FIG. 8. The genes that belonged to the MAPK pathway and the p53 pathway were determined based on pathway identities from KEGG.

The results indicate that STK11 copy number loss is associated with or predictive of nonresponsiveness or resistance (e.g., acquired resistance) of a cancer (e.g., a CLL) to a PI3K inhibitor (e.g., Compound 1).

In addition, the results indicate that a dual pathway alteration (a mutation in both MAPK and p53 pathways) is associated with or predictive of nonresponsiveness or resistance (e.g., acquired resistance) of a cancer (e.g., a CLL) to a PI3K inhibitor (e.g., Compound 1). Genes in the MAPK and p53 pathways that were frequently mutated are indicated in Tables 18 and 20 below.

Furthermore, the results indicate that copy number loss of STK11 combined with copy number loss of TSC1, TSC2, or both (shown as "STK11/TSC loss" in FIG. 8) is associated with or predictive of nonresponsiveness or resistance (e.g., acquired resistance) of a cancer (e.g., a CLL) to a PI3K inhibitor (e.g., Compound 1).

Mutations in TP53 were further characterized, by determining the frequency of TP35 mutations in responders versus non-responders. Specifically, Table 15 below shows that TP53 alterations, including loss of TP53 and TP53 mutations, were more common in non-responders than responders. Thus, loss of TP53 correlated with a poorer prognosis.

TABLE 15

| Genetic alterations | CR/PR (n = 32) | SD/PD (n = 23) | P value (Fisher's exact) |
|---|---|---|---|
| Loss of TP53 | 6 | 11 | 0.0368* |
| TP53 mutation | 6 | 7 | 0.34 |
| Both | 3 | 5 | 0.2573 |
| Any TP53 alterations | 9 | 13 | 0.0511 |

Figure 9:
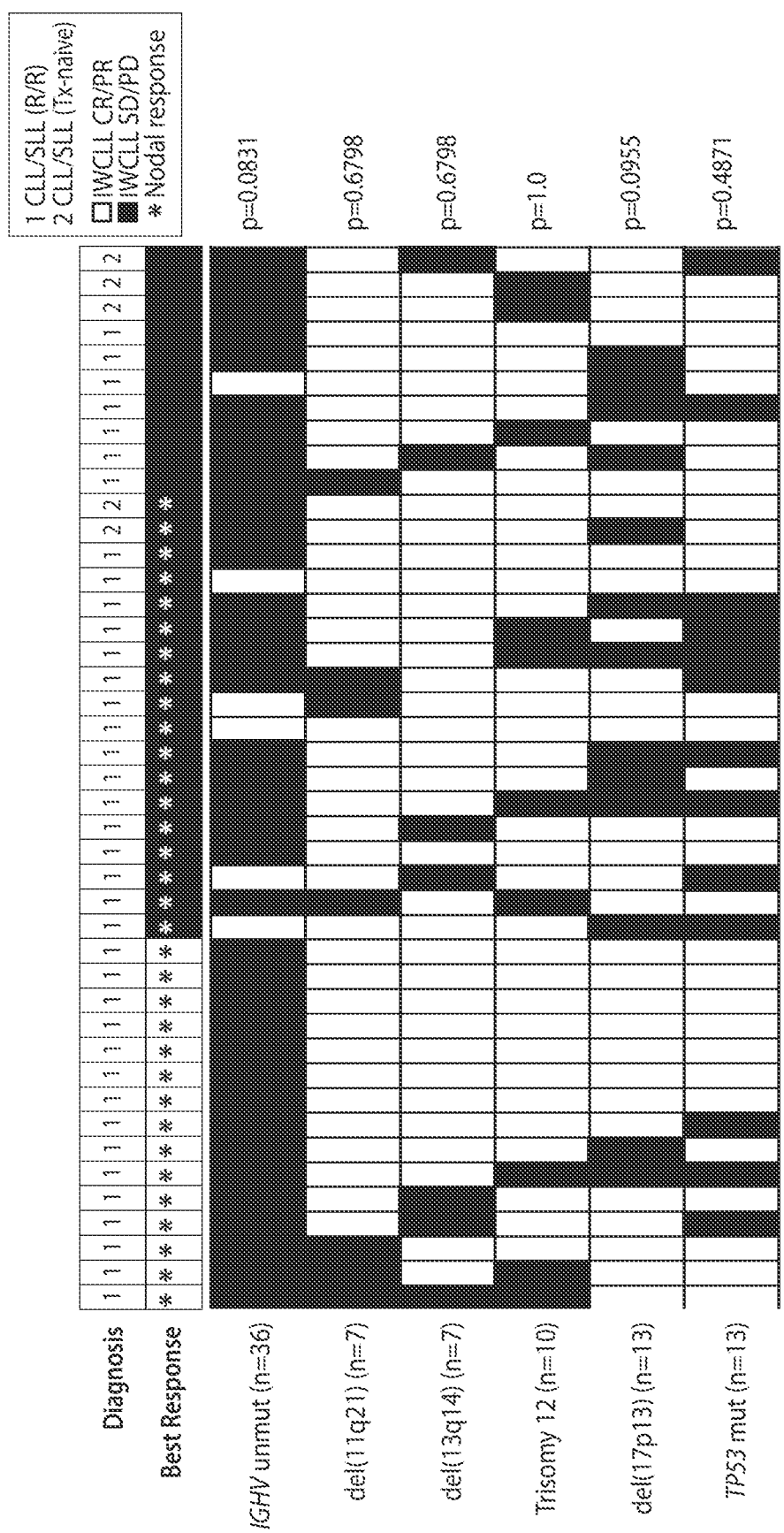
FIG. 9 is a graphical representation of the relationship between mutations and responses to Compound 1. Each column represents a patient. Each row represents a mutation. The diagnosis is coded as 1: CLL/SLL (R/R), or 2: CLL/SLL (treatment-naïve). The response is coded as IWCLL complete remission or partial remission (CR/PR) or IWCLL stable disease or progressive disease (SD/PD). Nodal responses are indicated with an asterisk (*).
Figure 10:
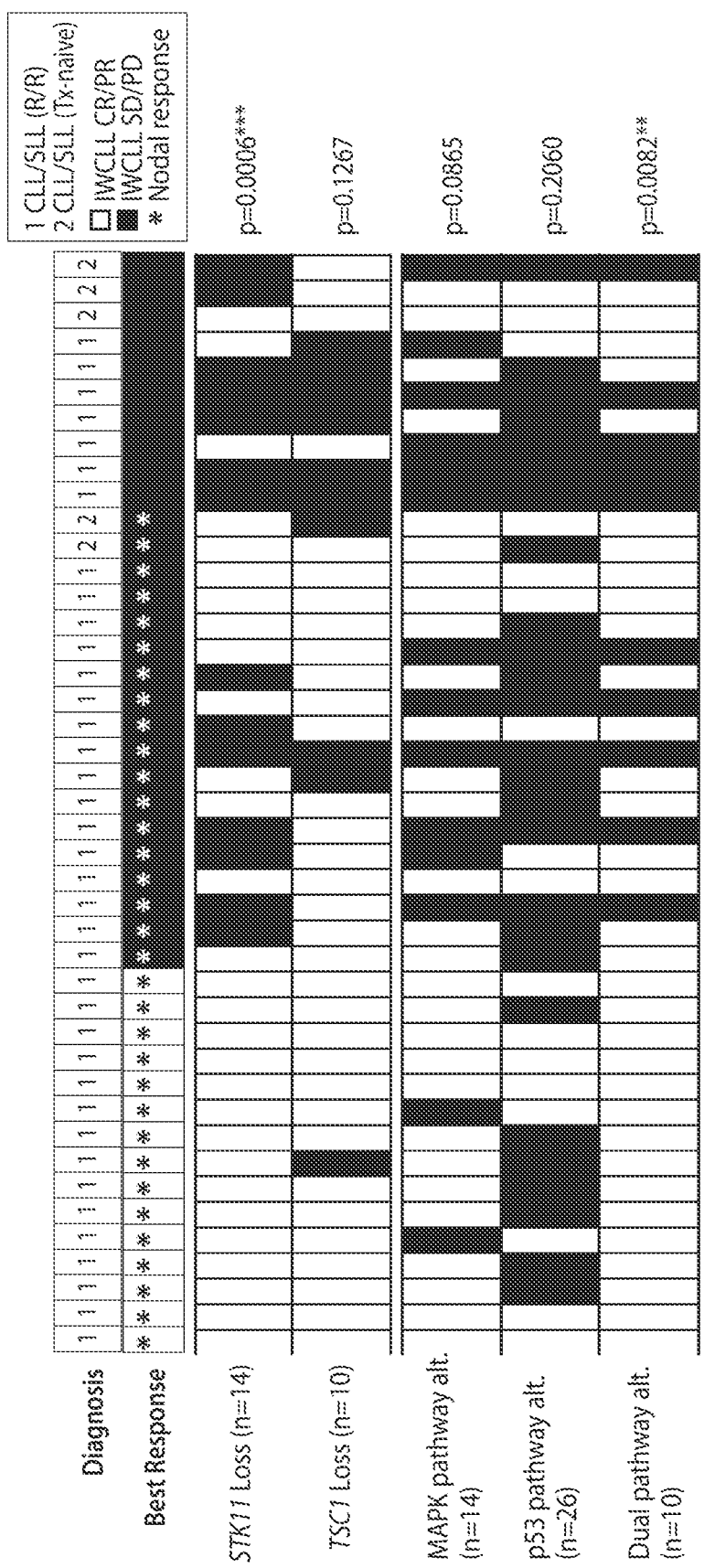
FIG. 10 is a graphical representation of the relationship between mutations and responses to Compound 1. The diagnosis and response is coded as in FIG. 9.

FIGS. 9 and 10 show the results of a re-analysis of the same data that were used in the analysis presented in Example 9, except that PR patients with lymphocytosis were classified as non-responders, whereas such patients were classified as responders in Example 9.

The results of the re-analysis confirmed that STK11 copy number loss is associated with or predictive of nonresponsiveness or resistance (e.g., acquired resistance) of a cancer (e.g., a CLL) to a PI3K inhibitor (e.g., Compound 1). Furthermore, the results confirmed that a dual pathway alteration (a mutation in both MAPK and p53 pathways) and mutation of BCR pathway is associated with or predictive of nonresponsiveness or resistance (e.g., acquired resistance) of a cancer (e.g., a CLL) to a PI3K inhibitor (e.g., Compound 1).

Figure 11:
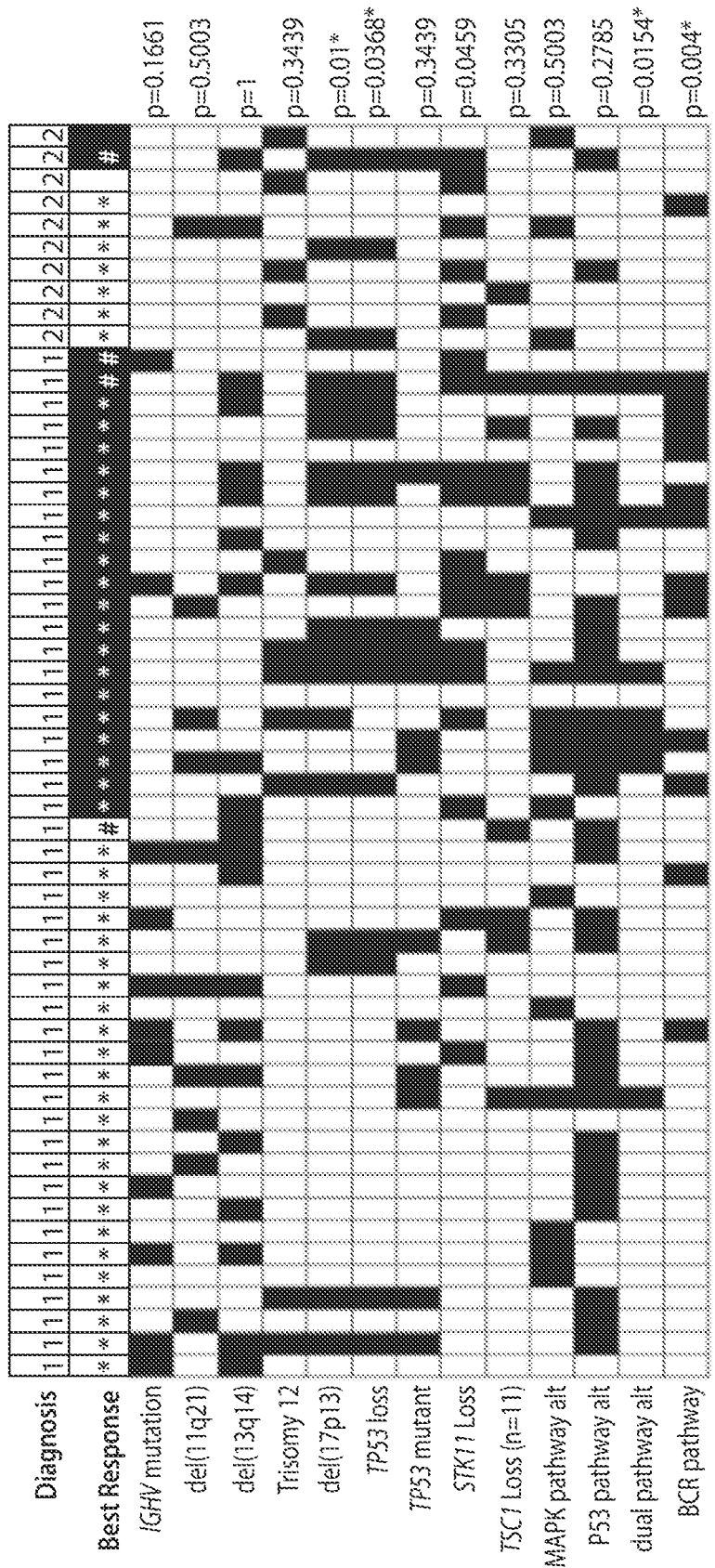
FIG. 11 is a graphical representation of the relationship between mutations and responses to Compound 1. The diagnosis and response is coded as in FIG. 9. Nodal responses are indicated with an asterisk (*). A non-assessable nodal response is indicated by a (#).
Figure 12:
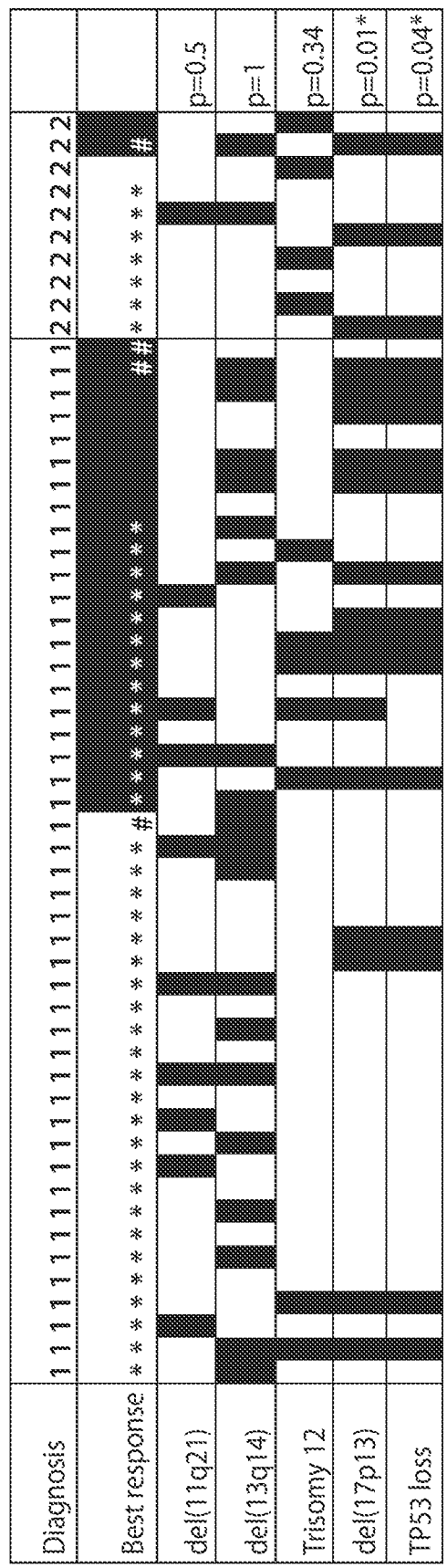
FIG. 12 is a graphical representation of the relationship between CLL common copy number variations (CNVs) and responses to Compound 1. The diagnosis and response is coded as in FIG. 10.

FIG. 11 shows additional results of an analysis of relationships between mutations and copy number variations and responses. Correlations between CLL common CNVs and response to Compound 1 are shown in FIG. 12.

Example 11

Additional Data Regarding CNVs and Mutations in CLL Patients

Using the methods described in the Examples above, CNVs that are more frequently present in non-responders versus responders to Compound 1 were determined. The results are shown in Table 16.

TABLE 16

CNVs that are more frequently present in Compound 1 non-responders.

| Region | Chromosome location | Gene | Event |
|---|---|---|---|
| chr19: 1,205,798-1,228,434 | 19p13.3 | STK11 | Copy number loss |
| chr9: 135,766,735-135,820,020 | 9q34.13 | TSC1 | Copy number loss |
| chr16: 2,097,990-2,138,713 | 16p13.3 | TSC2 | Copy number loss |

In total 140 genes were detected with baseline mutations in Compound 1-treated CLL patients (Table 17).

TABLE 17

List of genes that have mutations detected in Compound 1-treated CLL patients

| GeneName | Refseq ID |
|---|---|
| ABCA13 | NM_152701 |
| ABCA7 | NM_019112 |
| ADAMTSL3 | NM_207517 |
| AKAP8 | NM_005858 |
| ALK | NM_004304 |
| ARID1A | NM_006015 |
| ARID1B | NM_020732 |
| ASXL1 | NM_015338 |
| ATM | NM_000051 |
| ATR | NM_001184 |
| ATRX | NM_000489 |
| Bcl11A | NM_022893 |
| Bcl2 | NM_000633 |
| BCR | NM_004327 |
| BIRC3 | NM_001165 |
| BRAF | NM_004333 |
| BTG1 | NM_001731 |
| BTK | NM_001287344 |
| CARD11 | NM_032415 |
| CBFA2T3 | NM_005187 |
| CBL | NM_005188 |

TABLE 17-continued

List of genes that have mutations detected in Compound 1-treated CLL patients

| GeneName | Refseq ID |
|---|---|
| CCND3 | NM_001287427 |
| CCT6B | NM_006584 |
| CD36 | NM_001001548 |
| CDC73 | NM_024529 |
| CDH1 | NM_004360 |
| CDH11 | NM_001797 |
| CIC | NM_015125 |
| CIITA | NM_001286402 |
| COL4A2 | NM_001846 |
| CREBBP | NM_004380 |
| CSMD1 | NM_033225 |
| CSMD3 | NM_198123 |
| DAXX | NM_001141969 |
| DCHS1 | NM_003737 |
| DEK | NM_003472 |
| DIS3 | NM_014953 |
| DNM2 | NM_001005361 |
| DNMT1 | NM_001130823 |
| DPYD | NM_000110 |
| DST | NM_001144769 |
| EP300 | NM_001429 |
| EPHB1 | NM_004441 |
| EPHB2 | NM_004442 |
| ERBB4 | NM_005235 |
| ETV6 | NM_001987 |
| FAT2 | NM_001447 |
| FAT4 | NM_024582 |
| FBXO11 | NM_001190274 |
| FBXW7 | NM_033632 |
| FGFR1 | NM_001174064 |
| FGFR2 | NM_022970 |
| FGFR4 | NM_213647 |
| FLT3 | NM_004119 |
| FOXO1 | NM_002015 |
| FTCD | NM_006657 |
| FUBP1 | NM_003902 |
| FUS | NM_004960 |
| GNAQ | NM_002072 |
| GNAS | NM_001077490 |
| GRM8 | NM_001127323 |
| H3F3A | NM_002107 |
| HLF | NM_002126 |
| HNF1A | NM_000545 |
| HOXC13 | NM_017410 |
| HRAS | NM_176795 |
| IDH1 | NM_001282387 |
| JAK3 | NM_000215 |
| KIT | NM_000222 |
| LPHN3 | NM_015236 |
| LRP1B | NM_018557 |
| LRRK2 | NM_198578 |
| MAF | NM_001031804 |
| MAGI1 | NM_015520 |
| MALT1 | NM_006785 |
| MAP2K1 | NM_002755 |
| MAP3K1 | NM_005921 |
| MDM2 | NM_002392 |
| MED12 | NM_005120 |
| MEF2B | NM_001145785 |
| MKL1 | NM_001282662 |
| MSH2 | NM_000251 |
| MSH6 | NM_000179 |
| MTOR | NM_004958 |
| MYC | NM_002467 |
| MYD88 | NM_001172567 |
| NCOA2 | NM_006540 |
| NCOR1 | NM_006311 |
| NF1 | NM_001042492 |
| NIN | NM_020921 |
| NKX2-1 | NM_003317 |
| NOTCH1 | NM_017617 |
| NOTCH2 | NM_024408 |
| NSD1 | NM_022455 |
| NTRK1 | NM_002529 |
| NTRK3 | NM_001007156 |

TABLE 17-continued

List of genes that have mutations detected in Compound 1-treated CLL patients

| GeneName | Refseq ID |
|---|---|
| NUMA1 | NM_001286561 |
| NUP214 | NM_005085 |
| NUP98 | NM_016320 |
| OGT | NM_181672 |
| PCDH15 | NM_001142771 |
| PCLO | NM_033026 |
| PCM1 | NM_006197 |
| PCSK7 | NM_004716 |
| PDE4DIP | NM_014644 |
| PDGFRA | NM_006206 |
| PDGFRB | NM_002609 |
| PER1 | NM_002616 |
| PKHD1 | NM_138694 |
| PLCG2 | NM_002661 |
| PML | NM_033238 |
| PMS2 | NM_000535 |
| PRDM16 | NM_022114 |
| PRKDC | NM_006904 |
| PTCH1 | NM_001083602 |
| PTPRD | NM_002839 |
| PTPRT | NM_133170 |
| RALGDS | NM_006266 |
| RB1 | NM_000321 |
| RELN | NM_005045 |
| RNF213 | NM_001256071 |
| ROBO2 | NM_001290040 |
| RYR1 | NM_000540 |
| SETD2 | NM_014159 |
| SF3B1 | NM_012433 |
| SH2B3 | NM_005475 |
| SMARCA4 | NM_001128844 |
| STAT6 | NM_001178078 |
| SUZ12 | NM_015355 |
| SYNE1 | NM_182961 |
| TAL1 | NM_003189 |
| TCF3 | NM_003200 |
| TET1 | NM_030625 |
| TET2 | NM_001127208 |
| TLL2 | NM_012465 |
| TNFAIP3 | NM_001270508 |
| TP53 | NM_001276696 |
| TRIP11 | NM_004239 |
| XPO1 | NM_003400 |
| ZRSR2 | NM_005089 |

Frequently altered signaling pathways in Compound 1 non-responders and the involved genes and mutation sites are shown in Table 18, Table 29 and Table 20.

In the MAPK and ERBB signaling pathways, 16 genes were frequently mutated: BIRC3, BRAF, CBL, ERBB4, FGFR1, FGFR2, FGFR4, FLT3, HRAS, MAP2K1, MAP3K1, MTOR, MYC, NF1, NTRK1, PDGFRA and PDGFRB. See Table 18.

In the BCR pathway, 7 genes were frequently mutated: Bcl2, BTK, CARD11, MALT1, MTOR, MYD88 AND PLCG2. See Table 19.

In the p53 signaling and cell cycle pathways 12 genes were frequently mutated: ATM, ATR, CCND3, MYC, CREBBP, EP300, FBXW7, MDM2, PRKDC, RB1, TP53 and XPO1. See Table 20.

In addition, mutations in the JAK/STAT, NF-κB, and apoptosis pathways are enriched in IWCLL non-responders.

Figure 14:
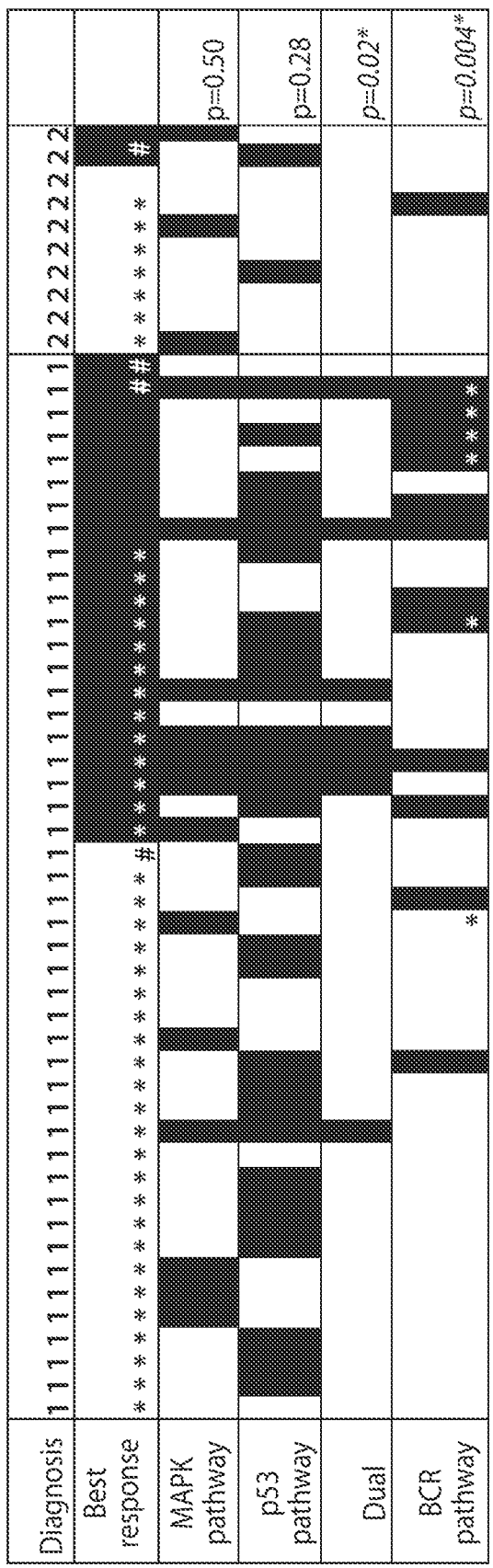
FIG. 14 is a graphical representation of the relationship between and responses to Compound 1 and alterations in various pathways. "Dual" in this figure refers to dual p53 and MAPK pathways. The diagnosis and response is coded as in FIG. 9.

FIG. 14 shows relationships between response and alterations in genes of various pathways, including the MAPK pathway p53 pathway, dual p53 and MAPK pathways, and BCR pathway.

TABLE 18

The frequently mutated MAPK pathway genes and mutation sites in Compound 1 non-responders.

| Pathway | GeneName | Refseq ID | Chromosome | Position | Reference Allele | Mutation Allele | AAMutation |
|---|---|---|---|---|---|---|---|
| MAPK | BIRC3 | NM_001165 | 11 | 102201966 | G | G-AATC | E440DEL |
| | BRAF | NM_004333 | 7 | 140534536 | G | C | S126C |
| | CBL | NM_005188 | 11 | 119155775 | C | G | P510A |
| | ERBB4 | NM_005235 | 2 | 212295820 | C | A | M831I |
| | ERBB4 | NM_005235 | 2 | 212989562 | C | T | R50H |
| | ERBB4 | NM_005235 | 2 | 213403221 | T | A | S12C |
| | FGFR1 | NM_001174064 | 8 | 38272320 | C | T | D642N |
| | FGFR2 | NM_022970 | 10 | 123310807 | G | C | Y207* |
| | FGFR4 | NM_213647 | 5 | 176520277 | A | C | H399P |
| | FGFR4 | NM_213647 | 5 | 176517445 | T | G | L49R |
| | FLT3 | NM_004119 | 13 | 28623641 | T | G | N306H |
| | HRAS | NM_176795 | 11 | 533509 | C | T | D132N |
| | MAP2K1 | NM_002755 | 15 | 66727455 | G | T | K57N |
| | MAP2K1 | NM_002755 | 15 | 66782068 | C | G | N345K |
| | MAP3K1 | NM_005921 | 5 | 56168815 | G | T | A557S |
| | MTOR | NM_004958 | 1 | 11204742 | C | T | R1612Q |
| | MTOR | NM_004958 | 1 | 11301623 | C | T | A510T |
| | MYC | NM_002467 | 8 | 128750680 | A | C | T73P |
| | NF1 | NM_001042492 | 17 | 29557906 | A | C | N1054H |
| | NTRK1 | NM_002529 | 1 | 156836766 | G | A | E142K |
| | PDGFRA | NM_006206 | 4 | 55139810 | G | A | A491T |
| | PDGFRA | NM_006206 | 4 | 5512932 | G | A | E156K |
| | PDGFRB | NM_002609 | 5 | 149510109 | G | A | L454F |

TABLE 19

The frequently mutated BCR pathway genes and mutation sites in Compound 1 non-responders.

| Pathway | GeneName | Refseq ID | Chromosome | Position | Reference Allele | Mutation Allele | AAMutation |
|---|---|---|---|---|---|---|---|
| BCR | Bcl2 | NM_000633 | 18 | 60985508 | G | T | A131D |
| | BTK | NM_001287344 | X | 100611164 | C | A | C481F |
| | BTK | NM-001287344 | X | 100611164 | C | G | C481S |
| | CARD11 | NM_032415 | 7 | 2959106 | G | A | R804C |
| | MALT1 | NM_006785 | 18 | 56411677 | A | G | K621E |
| | MALT1 | NM_006785 | 18 | 56414750 | G | A | M717I |
| | MTOR | NM_004958 | 1 | 11204742 | C | T | R1612Q |
| | MTOR | NM_004958 | 1 | 11301623 | C | T | A510T |
| | MYC | NM_002467 | 8 | 128750680 | A | C | T73P |
| | MYD88 | NM_001172567 | 3 | 38182025 | G | T | V217F |
| | MYD88 | NM_001172567 | 3 | 38182337 | C | T | P266L |
| | PLCG2 | NM_002661 | 16 | 81973605 | T | G | M1141R |
| | PLCG2 | NM_002661 | 16 | 81953154 | C | T | S707F |

TABLE 20

The frequently mutated p53/cell cycle pathway genes and mutation sites in Compound 1 non-responders.

| Pathway | Gene Name | Refseq ID | Chromosome | Position | Reference Allele | Mutation Allele | AAMutation |
|---|---|---|---|---|---|---|---|
| p53/Cell cycle | ATM | NM_000051 | 11 | 108196836 | G | A | G2287R |
| | ATM | NM_000051 | 11 | 108129788 | A | A-TTTGTAAAAG | I818DEL |
| | ATM | NM_000051 | 11 | 108200967 | T | A | L2445Q |
| | ATM | NM_000051 | 11 | 108164152 | G | T | R1575L |
| | ATM | NM_000051 | 11 | 108186596 | T | C | L2018S |
| | ATM | NM_000051 | 111 | 108115724 | A | G | H291R |
| | ATR | NM_001184 | 3 | 142274725 | T | A | K779* |
| | ATR | NM_001184 | 3 | 142274853 | C | A | G736V |
| | CCND3 | NM_001287427 | 6 | 41904413 | G | A | P149S |
| | CCND3 | NM_001287427 | 6 | 41903707 | G | A | P234S |
| | CREBBP | NM_004380 | 16 | 3795324 | T | A | M1290L |
| | EP300 | NM_001429 | 22 | 41574510 | T | T-CAG | L2265DEL |
| | EP300 | NM_001429 | 22 | 41513811 | C | G | P239A |
| | FBXW7 | NM_033632 | 4 | 153253763 | T | A | K324* |
| | MDM2 | NM_002392 | 12 | 69233526 | T | G | L464R |
| | MDM2 | NM_002392 | 12 | 69233160 | A | G | K342R |
| | MDM2 | NM_002392 | 12 | 69233130 | G | A | R332H |
| | MDM2 | NM_002392 | 12 | 69233252 | G | A | V373M |
| | PRKDC | NM_006904 | 8 | 48855869 | T | C | N289S |
| | PRKDC | NM_006904 | 8 | 48761821 | C | G | V2391L |
| | PRKDC | NM_006904 | 8 | 48691647 | T | C | R3832G |
| | PRKDC | NM_006904 | 8 | 48767904 | G | A | R2213* |
| | RB1 | NM_000321 | 13 | 48878084 | C | C-GCCGCCGCT | T12DEL |
| | RB1 | NM_000321 | 13 | 49039396 | G | C | S794T |
| | TP53 | NM_001276696 | 17 | 7578199 | A | C | V178G |
| | TP53 | NM_001276696 | 17 | 7578196 | A | T | V179E |
| | TP53 | NM_001276696 | 17 | 7578211 | C | A | R174L |
| | TP53 | NM_001276696 | 17 | 7578437 | G | A | Q126* |
| | TP53 | NM_001276696 | 17 | 7578508 | C | T | C102Y |
| | TP53 | NM_001276696 | 17 | 7577114 | C | T | C236Y |
| | TP53 | NM_001276696 | 17 | 7578221 | T | T-TC | R209DEL |
| | TP53 | NM_001276696 | 17 | 7578394 | G | C | H140R |
| | TP53 | NM_001276696 | 17 | 7578272 | G | A | H154Y |
| | TP53 | NM_001276696 | 17 | 7578554 | A | C | Y87D |
| | TP53 | NM_001276696 | 17 | 7578394 | T | C | H140R |
| | TP53 | NM_001276696 | 17 | 7578484 | G | G-A | S110DEL |
| | TP53 | NM_001276696 | 17 | 7578263 | G | C | R157G |
| | TP53 | NM_001276696 | 17 | 7577144 | A | G | L226P |
| | TP53 | NM_001276696 | 17 | 7577123 | A | T | V233E |
| | XPO1 | NM_003400 | 2 | 61719472 | C | T | E571K |

Example 12

PTEN is a Biomarker for Compound 1 Resistance

Figure 15:
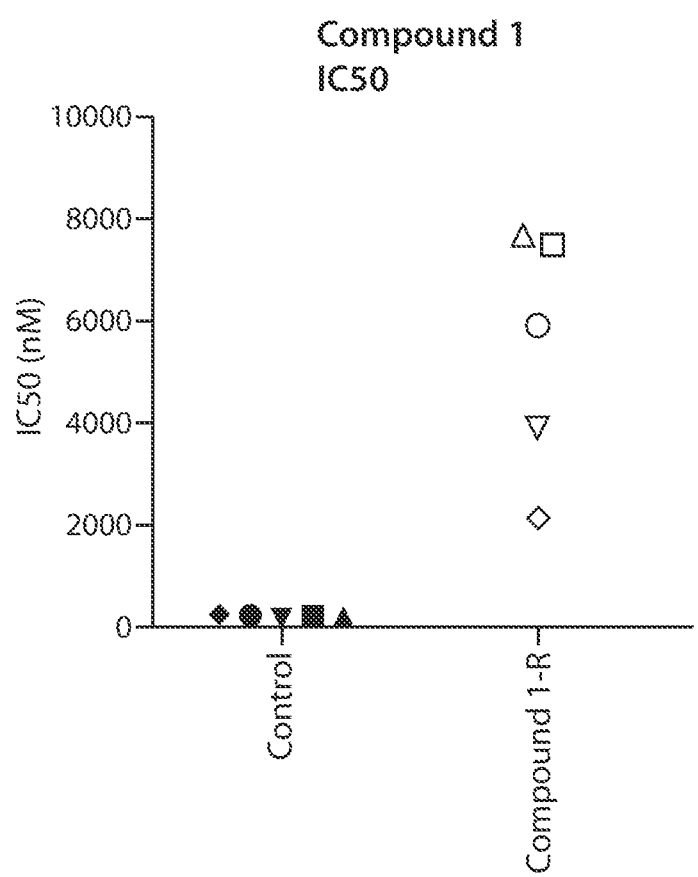
FIG. 15 is a graph showing the IC50 for Compound 1 inhibition of several cell clones.
Figure 16:
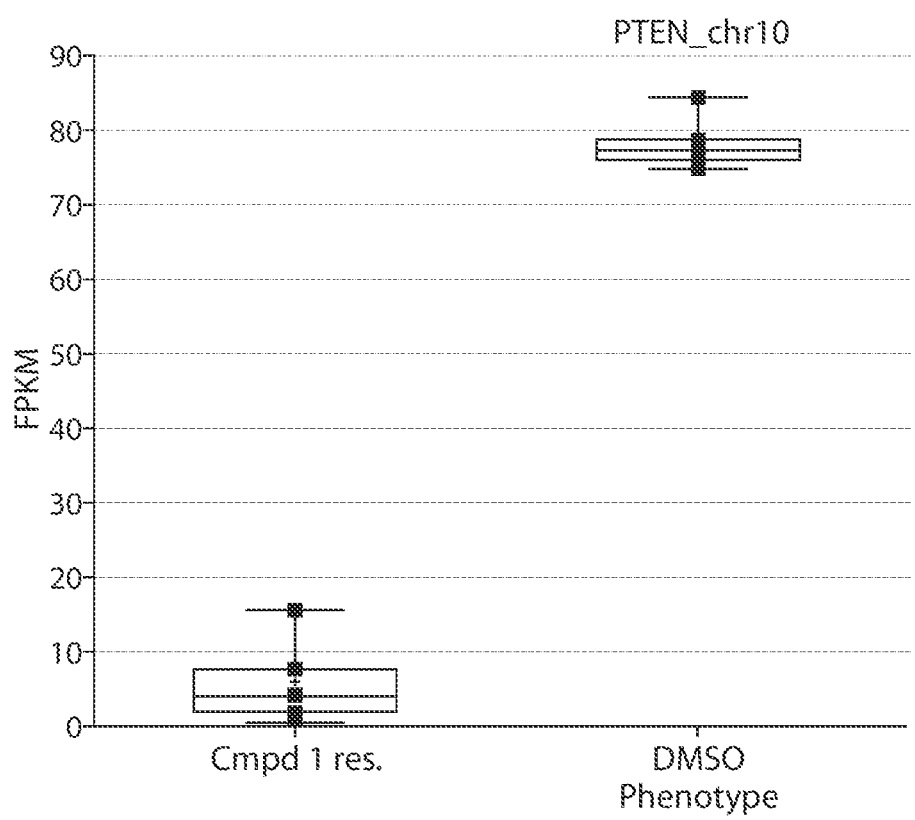
FIG. 16 is a graph showing the PTEN RNA expression level in DMSO control treated cells or cells resistant to Compound 1. FPKM refers to fragments per kilobase of exon per million fragments mapped.

Experiments were performed to assess the expression of PTEN in cells that were resistant to Compound 1. Compound 1 resistant cells were generated by culturing cells in the presence of Compound 1 or DMSO as a control for 8 weeks. Cells were subcloned under selective pressure from the drug, seeding at densities of 3 cells per well, 1 cell per well, or 0.3 cell per well. Parental, DMSO-treated, and Compound 1-resistant (also referred to as Compound 1-R) clones were selected for expansion. Five clones from each group were expanded. Cells were harvested for various assays, including CTG (CellTiter-Glo, Promega, an assay that measures ATP levels as a surrogate for cell number in order to observe cell viability and changes in proliferation rate), PD (pharmacodynamic), RNA analysis, DNA analysis, and short tandem repeat (STR) fingerprinting. A CTG assay was performed to confirm that cells were resistant to Compound 1 at the time of sample collection. As shown in FIG. 15 and Table 21, the average IC50 for Compound 1 inhibition of the resistant cells was higher than the control cells. RNA-seq experiments were also performed on the samples from DMSO control and Compound 1 resistant cells. Five clones of each—DMSO-treated control cells that are not resistant to Compound 1, and Compound 1 resistant cells—were tested. As shown in FIG. 16, there was a substantial downregulation in PTEN expression in Compound 1 resistant cell clones, but not in the DMSO control-treated cell clones. This downregulation in PTEN expression was seen at the RNA level as well as the protein level. See, e.g., FIG. 16. These results show that PTEN is a biomarker for Compound 1 resistance, where low PTEN levels correlate with resistance.

TABLE 21

| Clones | AVG Compound 1 IC50 (nM) |
|---|---|
| Control | 241 ± 17 |
| Compound 1 resistant | 5420 ± 1079 |

EQUIVALENTS

While this invention has been disclosed with reference to specific aspects, it is apparent that other aspects and variations of this invention can be devised by others skilled in the art without departing from the true spirit and scope of the invention. The appended claims are intended to be construed to include all such aspects and equivalent variations.

What is claimed:

1. A method of treating a hematological cancer in a human subject in need thereof, comprising administering to the subject a combination of (S)-3-(1-((9H-purin-6-yl)amino)ethyl)-8-chloro-2-phenylisoquinolin-1(2H)-one (Compound 1), or a pharmaceutically acceptable salt or hydrate thereof, and ABT-199, or a pharmaceutically acceptable salt thereof; wherein Compound 1, or a pharmaceutically acceptable salt or hydrate thereof, is administered at a dose of about 15 mg to about 75 mg;

wherein ABT-199, or a pharmaceutically acceptable salt thereof, is administered at a dose of about 10 mg to about 400 mg; and wherein the hematological cancer is selected from the group consisting of chronic lymphocytic leukemia (CLL), small lymphocytic lymphoma (SLL), CLL/SLL, indolent NHL (iNHL), diffuse large B-cell lymphoma (DLBCL), mantle cell lymphoma (MCL), T-cell lymphoma (TCL), peripheral T-cell lymphoma (PTCL), cutaneous T-cell lymphoma (CTCL), follicular lymphoma (FL), and Richter's syndrome.

2. The method of claim 1, wherein Compound 1 is at an amount sufficient to reach maximum plasma concentration at steady state (Cmaxss) at about 1000 ng/mL to about 5000 ng/mL; and the Bcl-2 inhibitor is administered at an amount to reach Cmaxss at about 0.1 µg/mL to about 1000 µg/mL.

3. The method of claim 1, wherein Compound 1 is at an amount sufficient to reach an area under the plasma concentration-time curve at steady state (AUCss) at about 5000 ng/mL*hr to about 10000 ng/mL*hr; and the Bcl-2 inhibitor is administered at an amount to reach an AUCss at about 0.1 ng/mL*hr to about 10000 ng/mL*hr.

4. The method of claim 1, wherein the cancer is a diffuse large B-cell lymphoma (DLBCL).

5. The method of claim 1, wherein the cancer is an indolent non-Hodgkin's lymphoma (iNHL).

6. The method of claim 1, wherein the cancer is a follicular lymphoma (FL).

7. The method of claim 1, wherein the cancer is a mantle cell lymphoma (MCL).

8. The method of claim 1, wherein the cancer is a T-cell lymphoma.

9. The method of claim 1, wherein the cancer is chronic lymphocytic leukemia (CLL).

10. The method of claim 1, wherein the hematological cancer is small lymphocytic lymphoma (SLL).

11. The method of claim 1, wherein the hematological cancer is CLL, SLL, CLL/SLL, or Richter's syndrome.

12. The method of claim 1, wherein CLL, SLL, or CLL/SLL is relapsed or refractory CLL, SLL, or CLL/SLL.

13. The method of claim 1, wherein Compound 1, or a pharmaceutically acceptable salt or hydrate thereof, is administered at a dose of about 25 mg.

14. The method of claim 1, wherein Compound 1, or a pharmaceutically acceptable salt or hydrate thereof, is administered BID.

15. The method of claim 13, wherein Compound 1, or a pharmaceutically acceptable salt or hydrate thereof, is administered BID.

16. The method of claim 1, wherein ABT-199, or a pharmaceutically acceptable salt thereof, is administered at once per day.

* * * * *